(12) United States Patent
Ricks et al.

(10) Patent No.: US 6,521,622 B1
(45) Date of Patent: Feb. 18, 2003

(54) FUNGICIDAL HETEROCYCLIC AROMATIC AMIDES AND THEIR COMPOSITIONS, METHODS OF USE AND PREPARATION

(75) Inventors: Michael J. Ricks, Indianapolis, IN (US); William H. Dent, III, Indianapolis, IN (US); Richard B. Rogers, Zionsville, IN (US); Chenglin Yao, Westfield, IN (US); Bassam S. Nader, Fishers, IN (US); John L. Miesel, Indianapolis, IN (US); Gina M. Fitzpatrick, Westfield, IN (US); Kevin G. Meyer, Zionsville, IN (US); Noormohamed M. Niyaz, Carmel, IN (US); Irene M. Morrison, Indianapolis, IN (US); Robert P. Gajewski, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/620,662

(22) Filed: Jul. 20, 2000

Related U.S. Application Data

(60) Provisional application No. 60/144,676, filed on Jul. 20, 1999.

(51) Int. Cl.$^7$ ............. C07D 405/12; A01N 43/24; A01N 43/40; A01N 43/54; A01N 43/707
(52) U.S. Cl. ............. 514/252.01; 514/255.05; 514/269; 514/336; 514/362; 514/369; 514/372; 514/376; 514/380; 514/386; 514/397; 514/407; 514/422; 514/444; 514/450; 514/238; 514/298; 514/316; 514/319; 514/406; 546/291; 548/60; 548/265; 548/267; 549/60; 549/265; 549/267
(58) Field of Search ............. 514/252.01, 255.05, 514/269, 336, 362, 369, 372, 376, 380, 386, 397, 407, 422, 444, 450; 544/238, 298, 316, 319, 406; 546/291; 548/175, 188, 213, 225, 243, 311.1, 365.1; 549/517, 60, 265, 267

(56) References Cited

U.S. PATENT DOCUMENTS 3,228,950 A    1/1966   Renk et al. .............. 260/295

FOREIGN PATENT DOCUMENTS

| CH | 415630 | 6/1966 |
|---|---|---|
| EP | 0198382 | 10/1986 |
| EP | 0235470 | 9/1987 |
| EP | 0544151 | 6/1993 |
| EP | 0661269 | 7/1995 |
| EP | 0693477 | 1/1996 |
| EP | 0 661 269 | 3/1997 |
| EP | 0816331 | 1/1998 |
| EP | 0846685 | 6/1998 |
| EP | 0891975 | 1/1999 |
| GB | 1373314 | 11/1974 |
| JP | 7-233165 | * 9/1995 |
| JP | 07233165 | 9/1995 |
| WO | WO 9637472 | 11/1996 |
| WO | WO 97/08135 | 3/1997 |
| WO | WO 99/11127 A1 | * 3/1999 |
| WO | WO 99/40081 | * 8/1999 |
| WO | WO 0076979 | 12/2000 |

OTHER PUBLICATIONS

Barrow, et al., "Antimycins, Inhibitors of ATP–Citrate Lyase, from a Streptomyces sp.", Journal of Antibiotics, vol. 50, No. 9, pp. 729 (1997).

Budavari, et al., "The Merck Index", Twelfth Edition, Merck and Co., Whitehouse Station, N.J., pp. 120 (1996).

Shimano, et al., "Total Synthesis of the Antifungal Dilactones UK–2A and UK–3A: The Determination of their Relative and Absolute Configurations, Analog Synthesis and Antifungal Activities," Tetrahedron Letters, vol. 54, pp. 12745–12774 (1998).

Ueki, et al., "UK–3A, a Novel Antifungal Antibiotic from Streptomyces sp. 517–02: Fermentation, Isolation, Structural Elucidation and Biological Properties," Journal of Antibiotics, vol. 50, No. 7, pp. 551 (1997).

Ueki, et al., "UK–2A, B, and D, Novel Antifungal Antibiotic form Streptomyces sp. 517–02. I. Fermentation, Isolation, and Biological Properties," Journal of Antibiotics, vol. 49, No. 7, pp. 639 (1996).

Hanafi, et al., "UK–2A, B, C and D, Novel Antifungal Antibiotic from Streptomyces sp. 517–02," Journal of Antibiotics, vol. 49, No. 12, pp. 1226 (1996).

Shimano, et al., "Enantioselective Total Synthesis of the Antifungal Dilactone, UK–2A: The Determination of the Relative and Absolute Configurations," Tetrahedron Letters vol. 39, pp. 4363–4366 (1998).

* cited by examiner

Primary Examiner—Mukund J. Shah
Assistant Examiner—Thomas McKenzie
(74) Attorney, Agent, or Firm—Carl D. Corvin

(57) ABSTRACT

Heterocyclic aromatic amides having a hydroxy group adjacent to the amide functionality are useful as antifungal agents, particularly for plants.

34 Claims, No Drawings

FUNGICIDAL HETEROCYCLIC AROMATIC AMIDES AND THEIR COMPOSITIONS, METHODS OF USE AND PREPARATION

PRIORITY CLAIM

This application claims a priority based on provisional application No. 60/144,676 which was filed in the U.S. Patent and Trademark Office on Jul. 20, 1999, the entire disclosure of which is hereby incorporated by reference.

BACKGROUND OF THE INVENTION

1. Field of the Invention

The present invention relates to the field of fungicidal compositions and methods. More particularly, the present invention concerns novel fungicidal heterocyclic aromatic amides and methods involving application of fungicidally effective amounts of such compounds to the locus of a plant pathogen. The present invention also concerns methods useful in the preparation of heterocyclic aromatic amides and their fungicidal compositions.

2. Description of the Prior Art

A variety of antifungal compositions and methods are well known in the art. Antimycin, for example, has been identified as a naturally occurring substance produced by Streptomyces spp. with antibiotic properties (Barrow, C. J.; et al., *Journal of Antibiotics*, 1997, 50(9), 729). These substances have also been found to be effective fungicides (*The Merck Index*, Twelfth Edition, S. Budavari, Ed., Merck and Co., Whitehouse Station, N.J., 1996, p.120). WO 97/08135 describes acylaminosalicylic acid amides which are useful as pesticides. EP-A-O-661269 discloses substituted heterocyclic carboxylic acid amides useful as medical drugs. JP-A-7-233165 discloses antifungal dilactones having 3-hydroxypyridinecarboxyl groups with antimycotic action. The iso-butyryl, tigloyl, iso-valeryl and 2-methylbutyryl derivatives of these latter compounds are further described in the following references: *Tetrahedron* 1998, 54, 12745–12774; *J. Antibiot.* 1997, 50(7), 551; *J. Antibiot.* 1996, 49(7), 639; *J. Antibiot.* 1996, 49(12), 1226; and *Tetrahedron Lett.* 1998, 39, 4363–4366.

However, there has remained a need for new fungicides. The present invention provides fungicides which have a high residual activity, greater activity at lower application rates, curative activity, and a broader spectrum of efficacy.

SUMMARY OF THE INVENTION

Briefly describing one aspect of the present invention, there are provided compounds comprising heterocyclic aromatic amides (HAA) of the Formula I:

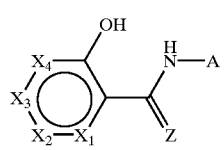

Formula I wherein $X_1-X_4$, Z, and A are hereafter defined. The invention also encompasses hydrates, salts and complexes thereof.

The present invention also provides fungicidal compositions comprising the HAA in combination with phytologically acceptable carriers and/or diluents. Methods for the use of the heterocyclic aromatic amide compounds and compositions are also disclosed.

It is an object of the present invention to provide HAA and compositions thereof which are effective as antifungal agents.

Another object of the present invention is to provide methods for the control and/or prevention of fungal infestations, which methods include the application of HAA and compositions containing same.

Further objects and advantages of the present invention will be apparent from the description which follows.

GENERAL SCOPE OF THE INVENTION

The present invention relates to various HAA compounds which are active as antifungal agents. Also included are formulations including the HAA compounds, and methods of using the HAA compounds and formulations. The methods of preparing the HAA compounds are also encompassed by the present invention and their method of preparation and use as fungicides.

HAA Compounds

The novel antifungal HAA compounds of the present invention are described by the following Formula I:

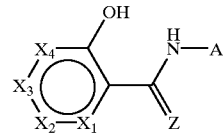

Formula I wherein:

a.

represents a 5- or 6-membered heterocyclic aromatic ring in which
(i) each of $X_1-X_4$ is independently O, S, NR', N, CR" or a bond;
(ii) no more than one of $X_1-X_4$ is O, S or NR';
(iii) no more than one of $X_1-X_4$ is a bond;
(iv) when any one of $X_1-X_4$ is S, O or NR', one of the adjacent $X_1-X_4$ must represent a bond; and
(v) at least one of $X_1-X_4$ must be O, S, NR' or N;
wherein
R' is H, $C_1-C_3$ alkyl, $C_2-C_3$ alkenyl, $C_2-C_3$ alkynyl, hydroxy, acyloxy, $C_1-C_6$ alkoxymethyl, $CHF_2$, cyclopropyl or $C_1-C_4$ alkoxy; and R" is independently H, halogen, cyano, hydroxy, $C_1-C_3$ alkyl, $C_1-C_3$ haloalkyl, cyclopropyl, $C_1-C_3$ alkoxy, $C_1-C_3$ haloalkoxy, $C_1-C_3$ alkylthio, aryl, $C_1-C_3$ NHC(O)alkyl, NHC(O)H, $C_1-C_3$ haloalkylthio, $C_2-C_4$ alkenyl, $C_2-C_4$ haloalkenyl, $C_2-C_4$ alkynyl, $C_2-C_4$ haloalkynyl or nitro wherein adjacent R" substituents may form a ring or adjacent R' and R" substituents may form a ring;

b) Z is O, S or $NOR_z$, in which $R_z$ is H or $C_1-C_3$ alkyl; and c) A represents
(i) $C_1-C_{14}$ alkyl, $C_2-C_{14}$ alkenyl, or $C_2-C_{14}$ alkynyl, all of which may be branched or unbranched, unsubstituted or substituted with halogen, hydroxy, nitro, aroyl, aryloxy, $C_1$–$C_8$ acyloxy, $C_1$–$C_6$ alkylthio, arylthio, aryl, heteroaryl, heteroarylthio, heteroaryloxy, $C_1$–$C_6$ acyl, $C_1$–$C_6$ haloalkyl, $C_1$–$C_6$ alkoxy or $C_1$–$C_6$ haloalkoxy, (ii) $C_3$–$C_{14}$ cycloalkyl, containing 0–3 heteroatoms and 0–2 unsaturations, which may be unsubstituted or substituted with halogen, hydroxy, $C_1$–$C_6$ alkyl, $C_1$–$C_6$ haloalkyl, cyano, nitro, aroyl, aryloxy, heteroaryloxy, $C_1$–$C_6$ alkylthio, arylthio, heteroarylthio, $C_1$–$C_6$ alkoxy, $C_1$–$C_6$ haloalkoxy, $C_1$–$C_8$ acyloxy, aryl, heteroaryl, $C_1$–$C_6$ acyl, carboaryloxy, carboheteroaryloxy, $C_1$–$C_6$ carboalkoxy or amido unsubstituted or substituted with one or two $C_1$–$C_6$ alkyl groups, (iii) $C_1$–$C_{14}$ bi- or tricyclic ring system, containing 0–3 heteroatoms and 0–2 unsaturations, which may be unsubstituted or substituted with halogen, hydroxy, $C_1$–$C_6$ alkyl, $C_1$–$C_6$ haloalkyl, cyano, nitro, aroyl, aryloxy, heteroaryloxy, $C_1$–$C_6$ alkylthio, arylthio, heteroarylthio, $C_1$–$C_6$ alkoxy, $C_1$–$C_6$ haloalkoxy, $C_1$–$C_8$ acyloxy, aryl, heteroaryl, $C_1$–$C_6$ acyl, carboaryloxy, carboheteroaryloxy, $C_1$–$C_6$ carboalkoxy or amido unsubstituted or substituted with one or two $C_1$–$C_6$ alkyl groups, (iv) aryl or heteroaryl, which may be unsubstituted or substituted with nitro, $C_1$–$C_6$ alkyl, $C_1$–$C_6$ haloalkyl, $C_3$–$C_6$ cycloalkyl, $C_2$–$C_6$ alkenyl, $C_2$–$C_6$ alkynyl, aryl, heteroaryl, halogen, hydroxy, $C_1$–$C_6$ alkoxy, $C_1$–$C_6$ haloalkoxy, carboaryloxy, carboheteroaryloxy, $C_1$–$C_6$ carboalkoxy or amido unsubstituted or substituted with one or two $C_1$–$C_6$ alkyl groups, $C_1$–$C_6$ alkylthio, $C_1$–$C_6$ alkylsulfonyl, $C_1$–$C_6$ alkylsulfinyl, $C_1$–$C_6$ OC(O)alkyl, OC(O)aryl, $C_3$–$C_6$ OC(O)cycloalkyl, $C_1$–$C_6$ NHC(O)alkyl, $C_3$–$C_6$ NHC(O) cycloalkyl, NHC(O)aryl, NHC(O) heteroaryl, $C_3$–$C_6$ cycloalkylthio, $C_3$–$C_6$ cycloalkylsulfonyl, $C_3$–$C_6$ cycloalkylsulfinyl, aryloxy, heteroaryloxy, heteroarylthio, heteroarylsulfinyl, heteroarylsulfonyl, arylthio, arylsulfinyl, arylsulfonyl, C(O)$R_Y$, C(NO$R_X$)$R_Y$, in which any alkyl or cycloalkyl containing substituent may be substituted with one or more halogens and in which any aryl or heteroaryl containing substituent may also be unsubstituted or substituted with halogen, cyano, nitro, aroyl, aryloxy, aryl, heteroaryl, $C_1$–$C_6$ acyl, $C_1$–$C_6$ haloalkyl, $C_1$–$C_6$ alkoxy, $C_1$–$C_6$ haloalkoxy, $C_1$–$C_6$ carboalkoxy or amido unsubstituted or substituted with one or two $C_1$–$C_6$ alkyl groups, where $R_Y$ and $R_X$ are independently H, $C_1$–$C_6$ alkyl, $C_2$–$C_6$ alkenyl, $C_3$–$C_6$ cycloalkyl, aryl or heteroaryl, and (v)

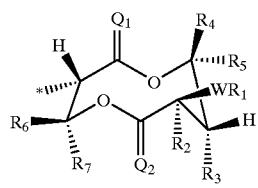

where *=point of attachment
in which
$Q_1$, $Q_2$ are O or S;
W is O, $CH_2$, CH$R_6$, or a bond;
$R_1$ is $C_1$–$C_8$ alkyl, $C_2$–$C_8$ alkenyl, $C_2$–$C_8$ alkynyl, $C_3$–$C_8$ cycloalkyl, aryl or heteroaryl;

$R_2$ is H, $C_1$–$C_3$ alkyl, $C_2$–$C_5$ alkenyl or $C_2$–$C_5$ alkynyl;
$R_3$ is H, $R_1$, OR$_1$, OC(O)$R_1$, OC(O)OR$_1$ or OC(O)NR$_1$R$_6$;
$R_4$ and $R_5$ are independently H, $C_1$–$C_6$ alkyl, or $C_2$–$C_6$ alkenyl, provided that the sum of carbons for $R_4$ plus $R_5$ is six or less, and further provided that $R_4$ and $R_5$ may be joined into a $C_3$–$C_6$ ring;
$R_6$ and $R_7$ are independently H, C1–C6 alkyl, C3–C6 cycloalkyl, C2–C5 alkenyl or C2–C5 alkynyl provided that at least one of R6 and R7 is H;
with the proviso that when

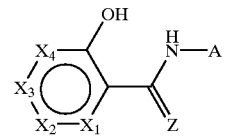

is

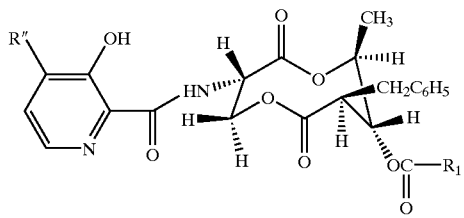

wherein
R″ is H or OCH$_3$, then
$R_1$ is not $C_1$–$C_8$ alkyl or $C_2$–$C_8$ alkenyl.

The terms alkyl, alkenyl, alkynyl and the like, as used herein, include within their scope both straight and branched groups; the terms alkenyl, alkenylene and the like are intended to include groups containing one or more double bonds; and the terms alkynyl, alkynylene and the like are intended to include groups containing one or more triple bonds. Cycloalkyl, as used herein, refers to $C_3$–$C_{14}$ cycloalkyl groups containing 0–3 heteroatoms and 0–2 unsaturations. Bi- or tricyclic ring systems refers to $C_6$–$C_{14}$ aliphatic ring systems containing 0–3 heteroatoms and 0–2 unsaturations. The foregoing terms further contemplate either substituted or unsubstituted forms. Unless specifically defined otherwise, a substituted form refers to substitution with one or more groups selected from halogen, hydroxy, cyano, nitro, aroyl, aryloxy, aryl, arylthio, heteroaryl, heteroaryloxy, heteroarylthio, $C_1$–$C_8$ acyl, $C_1$–$C_6$ haloalkyl, $C_1$–$C_6$ alkoxy, $C_1$–$C_6$ haloalkoxy, $C_1$–$C_6$ alkylthio, $C_1$–$C_6$ haloalkylthio, carboaryloxy, carboheteroaryloxy, $C_1$–$C_6$ carboalkoxy or amido unsubstituted or substituted with one or two $C_1$–$C_6$ alkyl groups. All of the above terms and definitions assume that the rules of chemical bonding and strain energy are satisfied.

The term aryl as used herein refers to a substituted phenyl or naphthyl group. The term heteroaryl refers to any 5 or 6 membered aromatic ring containing one or more heteroatoms; these heteroaromatic rings may also be fused to other aromatic systems. The foregoing terms further contemplate either substituted or unsubstituted forms. A substituted form refers to substitution with one or more groups selected from nitro, $C_1$–$C_6$ alkyl, $C_1$–$C_6$ haloalkyl, $C_3$–$C_6$ cycloalkyl, $C_2$–$C_6$ alkenyl, $C_2$–$C_6$ alkynyl, aryl, heteroaryl, halogen, hydroxy, $C_1$–$C_6$ alkoxy, $C_1$–$C_6$ haloalkoxy, $C_1$–$C_6$ alkylthio, $C_1$–$C_6$ alkylsulfonyl, $C_1$–$C_6$ alkylsulfinyl, $C_1$–$C_6$ OC(O)

alkyl, OC(O)aryl, $C_3$–$C_6$ OC(O)cycloalkyl, $C_1$–$C_6$ NHC(O) alkyl, $C_3$–$C_6$ NHC(O)cycloalkyl, NHC(O)aryl, NEC(O) heteroaryl, $C_3$–$C_6$ cycloalkylthio, $C_3$–$C_6$ cycloalkylsulfonyl, $C_3$–$C_6$ cycloalkylsulfinyl, aryloxy, heteroaryloxy, heteroarylthio, heteroarylsulfinyl, heteroarylsulfonyl, arylthio, arylsulfinyl, arylsulfonyl, C(O)$R_Y$, C(NOR$_X$)$R_Y$ where $R_Y$ and $R_X$ are independently H, $C_1$–$C_6$ alkyl, $C_2$–$C_6$ alkenyl, $C_3$–$C_6$ cycloalkyl, aryl or heteroaryl in which any alkyl or cycloalkyl containing substituent may be substituted with one or more halogens and provided that the rules of chemical bonding and strain energy are satisfied.

The terms halogen and halo as used herein include chlorine, bromine, fluorine and iodine. The terms haloalkyl and the like refer to groups substituted with one or more halogen atoms.

The term Me as used herein refers to a methyl group. The term Et refers to an ethyl group. The term Pr refers to a propyl group. The term Bu refers to a butyl group. The term EtOAc refers to ethyl acetate.

The term alkoxy as used herein refers to a straight or branched chain alkoxy group. The term haloalkoxy refers to an alkoxy group substituted with one or more halogen atoms.

The term heteroatom as used herein refer to O, S and N.

The preferred 5- or 6-membered heterocyclic aromatic rings of the formula

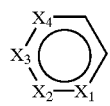

include the appropriate isomers of pyridine, pyridazine, pyrimidine, pyrazine, pyrrole, pyrazole, imidazole, furan, thiophene, oxazole, isoxazole, thiazole, isothiazole, and thiadiazole. The most preferred heterocyclic aromatic rings are pyridine, pyrimidine, pyrazine, pyridazine, thiazole, isothiazole, and oxazole. Particularly preferred compounds of Formula I are based upon 2-amido-3-hydroxypyridine, 2-amido-3-hydroxy-4-methoxypyridine, 2-amido-3-hydroxypyrazine, and 4-amido-5-hydroxypyrimidine.

It will be appreciated that certain combinations of substituent groups for compounds which fall within the definitions given herein will be impossible to prepare for steric and/or chemical reasons. Such compounds are not included within the scope of the invention.

Various hydrates, salts and complexes of compounds of Formula I can be made in the conventional ways. For example, salts may be formed by replacing the hydroxyl hydrogen atom with a cation, for example $NH_4^+$, $^+N(Bu)_4$, $K^+$, $Na^+$, $Ca^{2+}$, $Li^+$, $Mg^{2+}$, $Fe^{2+}$, $Cu^{2+}$, etc. These derivatives are also useful in accordance with the present invention.

Throughout this document, all temperatures are given in degrees Celsius (°C.) and all percentages are weight percentages, unless otherwise stated. The term ppm refers to parts per million. The term psi refers to pounds per square inch. The term m.p. refers to melting point. The term b.p. refers to boiling point.

Preparation of Compounds

The compounds of this invention are made using well known chemical procedures. The required starting materials are commercially available or readily synthesized utilizing standard procedures.

General Preparation of Pyridine-2-Carboxamides

The desired HAAs (2) are prepared by reacting the appropriate ortho-hydroxyheteroaromatic carboxylic acid (1) with an amine in the presence of a coupling reagent (phosgene or 1-[3-dimethylaminopropyl]-3-ethylcarbodiimide hydrochloride [EDCI]) plus 1-hydroxybenzotriazole (HOBt) or 1-hydroxy-7-azabenzotriazole (HOAt) and an acid scavenger, e.g. N-methylmorpholine (NMM), triethylamine, 4-(dimethylamino)pyridine (DMAP), or diisopropylethylamine) (Scheme 1). In some cases acid chlorides with protected hydroxy groups such as (3) could be reacted with the appropriate amine to give the intermediate amides (4). Removal of the protecting groups via hydrogenation in the presence of a palladium (Pd) catalyst gives the desired product (2X).

Scheme 1

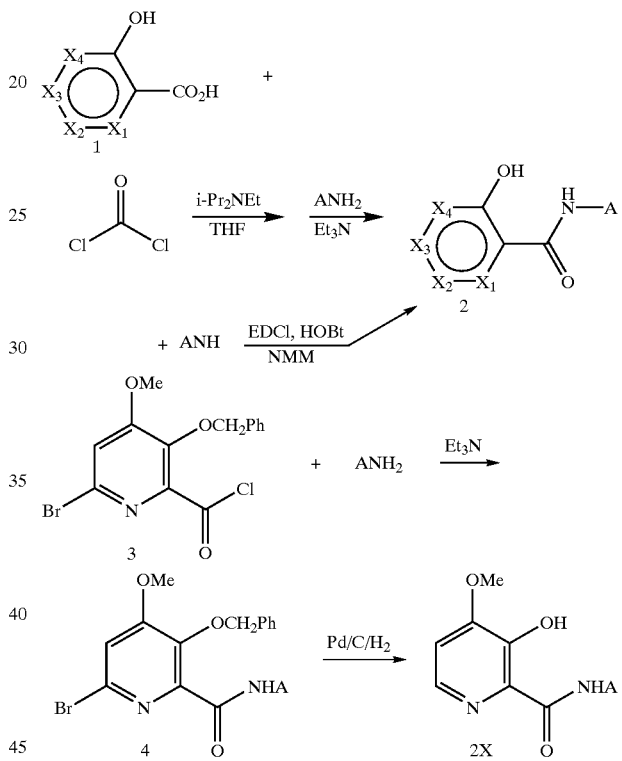

Preparation of the Ortho-Hydroxyheteroaromatic Carboxylic Acids 1

Preparation of carboxylic acids 1 ($X_1$=N, $X_2$=$X_3$=CH, $X_4$=independently C—Me, C—SMe, C—Cl) is shown in Scheme 2. Reaction of 3-hydroxy-2-bromopyridine (5) with 2-(trimethylsilyl)ethoxymethyl chloride (SEM-Cl) using potassium tert-butoxide as the base in a 1:1 mixture of dimethylformamide (DMF)—tetrahydrofuran (THF) gave the desired ether 6. Deprotonation of 6 with lithium diisopropylamide (LDA) followed by condensation with the appropriate electrophile (iodomethane, dimethyldisulfide, or hexachloroethane) gave the 4-substituted pyridine 7. Bromine/lithium exchange between 7 and n-butyllithium (n-BuLi) followed by carboxylation with carbon dioxide ($CO_2$) and acid hydrolysis gave the necessary 4-substituted-3-hydroxypicolinic acid 1X.

Scheme 2

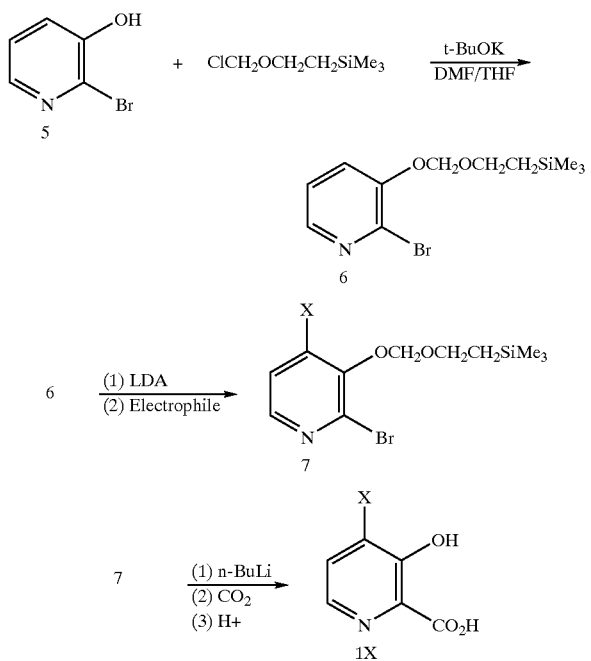

Alternatively, 3-hydroxypyridine (8) could be condensed with SEM-Cl to give 9 (Scheme 3). Deprotonation of 9 with tert-butyllithium (t-BuLi) followed by condensation with N-fluorobenzensulfonimide gave the 4-fluoro derivative 10. Condensation of 10 with sodium ethoxide gave the diether 11. Deprotonation of 11 with t-BuLi followed by carboxylation and acid hydrolysis gave the desired 4-ethoxypyridine 1X (X=OEt).

Scheme 3

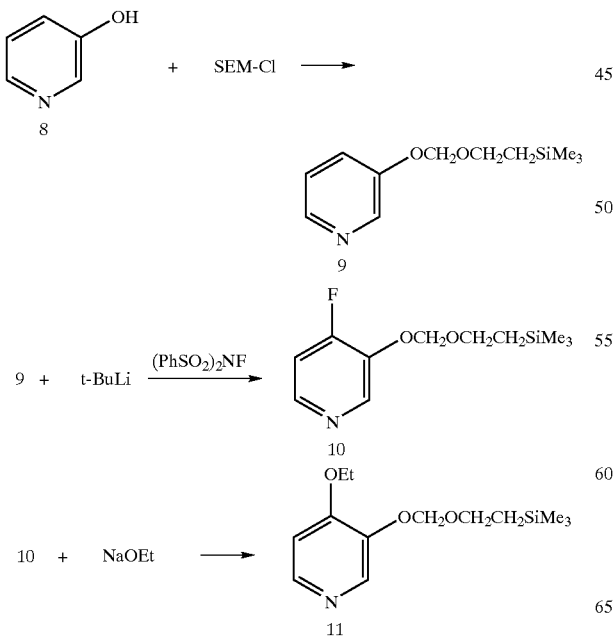

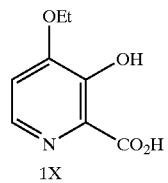

The preparation of acid chloride 3 is outlined in Scheme 4. Thus, 3-hydroxypicolinic acid (12) was converted to the methyl ester 13 in refluxing methanol using boron trifluoride as catalyst. 13 was then brominated using bromine in aqueous base to give the dibromide 14. The benzyl ether 15 was then prepared by condensation of 14 with benzyl chloride in the presence of sodium hydride. Careful methanolysis of 15 in methanol/potassium carbonate gave the 4-methoxypicolinic acid derivative 16. Conversion of 16 to the acid chloride 3 was accomplished with oxalyl chloride using benzene as a solvent and a catalytic amount of DMF.

Scheme 4

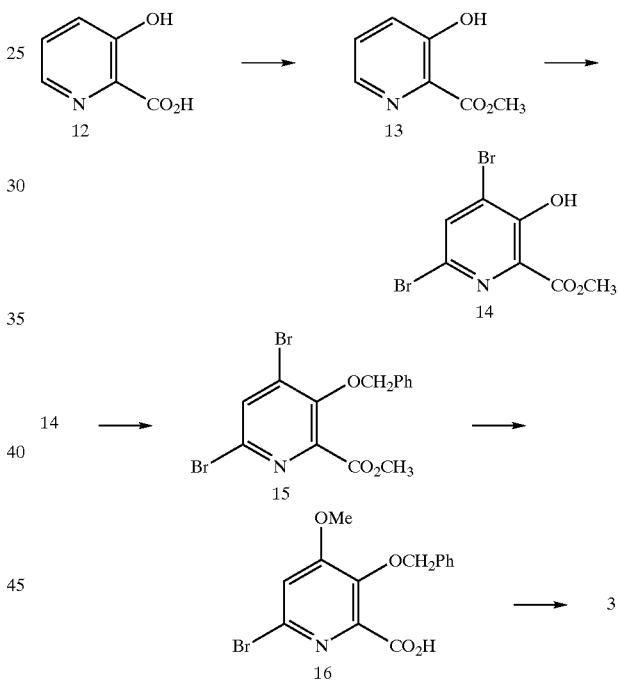

Preparation of 4-Ethoxy-3-Hydroxypicolinic Acid (1, $X_1$=N, $X_2$=$X_3$=H, $X_4$=COEt) (See Schemes 1 and 3)

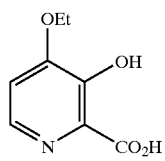

a. Preparation of 3-(2-(trimethylsilyl) ethoxymethoxy)-pyridine (9)

To a stirred mixture of DMF (100 mL) and THF (100 mL), was added solid potassium tert-butoxide (17.96 g, 0.16 mol). After all of the solid had dissolved, the solution was cooled to ≦5° C. and 3-hydroxypyridine (14.25 g, 0.15 mol)

was added all at once. After stirring for 10 minutes, the mixture was cooled to −10° C. and SEM-Cl, 25 g, 0.15 mol) was added dropwise at such a rate that the internal temperature remained at ≦−5° C. After the addition was complete, the mixture was stirred at 0° C. for 1 hour, then at room temperature for 2 hours. The mixture was poured into water (600 mL), then extracted with ether (3×150 mL). The ether extracts were combined, washed sequentially with 2N NaOH (100 mL), water (50 mL), and saturated NaCl solution (100 mL), dried (MgSO$_4$) and concentrated to give a brown liquid. Distillation gave the desired ether 9 as a colorless liquid (20.8 g), b.p. 95–99° C. @ 0.03 mm Hg.

b. Preparation of 4-fluoro-3-(2-(trimethylsilyl)ethoxymethoxy)pyridine (10)

To a stirred solution of 9 (12.39 g, 0.055 mol) in ether (200 mL) cooled to ≦−70° C. under an atmosphere of argon was slowly added t-BuLi (40 mL, 1.5 M pentane solution). During the addition, the reaction temperature was maintained at ≦−68° C. After the addition was complete the mixture was stirred an additional 60 minutes at ≦−70° C., then transferred via cannula to a stirred solution of N-fluorobenzenesulfonimide (18.92 g) in dry THF (200 mL) which was also cooled to ≦−70° C. under argon. After the addition was complete, the cooling bath was removed and the reaction mixture was allowed to warm up to room temperature. Water (100 mL) was added and the organic phase was separated, dried (MgSO$_4$) and concentrated to give a brown oil. Chromatography (silica gel, hexane-acetone, 9:1) gave the desired product 10 as an orange oil (7.5 g) which contained about 15% starting material. This crude mixture was used directly in the next reaction.

c. Preparation of 4-ethoxy-3-(2-(trimethylsilyl)ethoxymethoxy)pyridine (11)

To a stirred solution of sodium ethoxide (0.9 g, 13 mmol) in ethanol (10 mL) was added all at once 10 (1.07 g, 4.4 mmol). The resulting mixture was stirred at room temperature for 48 hours, then poured into water (100 mL). The resulting mixture was extracted with ether (3×50 mL). The ether extracts were combined, dried (MgSO$_4$) and concentrated. The resulting amber oil was chromatographed (silica gel, hexane-acetone, 4:1) to give 11 as a yellow oil (0.6 g).

d. 4-Ethoxy-3-hydroxypyridine-2-carboxylic Acid (1, X$_1$=N, X$_2$=X$_3$=CH, X$_4$=COEt)

A stirred solution of 11 (2.9 g) in THF (50 mL) under an argon atmosphere was cooled to ≦−70 ° C. To this was slowly added t-BuLi (8 mL, 1.5M pentane solution) while keeping the reaction temperature at ≦−66 ° C. After the addition was complete, the mixture was stirred at ≦−70 ° C. for 45 minutes and then poured into a slurry of crushed dry ice in ether. The resulting mixture was stirred until it reached room temperature, then the solvents were evaporated. THF (25 mL) and 4N HCl (15 mL) were added to the residue and the resulting mixture was stirred at room temperature for two hours. At the end of this period, the insoluble material was filtered, washed with a small volume of THF and air dried to give the title compound as a white solid (1.05 g).
Preparation of 6-Bromo-3-Benzyloxy-4-Methoxypyridine-2-Carboxylic Acid (16) and Its Acid Chloride (3) (See Scheme 4)

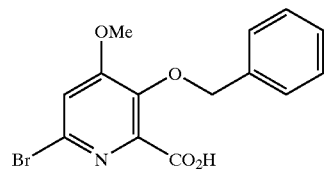

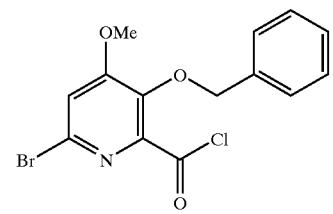

a. Preparation of methyl 4,6-dibromo-3-hydroxypyridine-2-carboxylate (14)

To a 2 L, 3-necked flask equipped with a dropping funnel and a mechanical stirrer, was added water (800 mL) and methyl 3-hydroxypyridine-2-carboxylate (15.3 g). To this stirred solution was slowly added bromine (32 g). As the reaction progressed, a solid separated from solution and the reaction mixture became difficult to stir. After the addition was complete, the mixture was vigorously stirred until the bromine color disappeared. $^1$H-NMR (CDCl$_3$) of a small sample of the crude product showed that it was about a 3:1 mixture of mono to dibrominated product. Sodium carbonate (31.8 g) was carefully added to the reaction mixture and then additional bromine (12 g) was added dropwise. After the bromine color had disappeared, the reaction mixture was adjusted to approximately pH 5 with conc. HCl, and the resulting mixture was extracted with CH$_2$Cl$_2$ (3×150 mL). The organic extracts were combined, dried (MgSO$_4$) and concentrated to give an orange solid (14 g). This material could be recrystallized from methylcyclohexane (after charcoal treatment) to give 14 as a white solid, m.p. 181–183° C.

b. Preparation of methyl 4,6-dibromo-3-benzyloxypyridine-2-carboxylate (15)

To a stirred mixture of sodium hydride (0.6 g) in DMF (50 mL) was slowly added 14 (7.1 g). After the addition was complete, the mixture was stirred at room temperature for 15 minutes, then benzyl chloride (3.05 g) was added all at once. The mixture was then heated at 90° C. for six hours, cooled, poured into water (500 mL) and extracted with ether (2×200 mL). The ether extracts were combined, washed with 2N NaOH (50 mL), dried (MgSO$_4$) and the solvent was evaporated to give 15 as a light yellow solid (8.3 g). Recrystallization from a small volume of methanol gave an analytical sample, m.p. 75–76° C.

c. 6-Bromo-3-benzyloxy-4-methoxypyridine-2-carboxylic Acid (16)

A vigorously stirred mixture of 15 (25.5 g), potassium carbonate (75 g) and methanol (300 mL) was heated at reflux for 30 hours. The mixture was cooled, poured into water (800 mL), and the pH adjusted to 2 by the addition of conc. HCl. The resulting mixture was extracted with CH$_2$Cl$_2$ (3×150 mL). The organic extracts were combined, dried (MgSO$_4$) and the solvent was evaporated to give a nearly colorless oil (20.5 g) which slowly solidified upon standing. This was recrystallized from methanol (125 mL)/water (40 mL) to give the desired acid 16 (11.6 g), m.p. 134–135° C.

d. Preparation of 6-bromo-3-benzyloxy-4-methoxypyridine-2-carbonyl Chloride (3)

To a stirred mixture of 16 (2.54 g., 7.5 mmol) in benzene (30 mL) containing DMF (3 drops) was added oxalyl chloride (1.90 g, 15 mmol) in one portion. After gas evolution had ceased (about 45 min.), the now homogeneous solution was stirred an additional 15 min., then the solvent was evaporated. 1,2-dichloroethane (30 mL) was added and again the solvent was evaporated to give a quantitative yield of 3 as a nearly colorless oil. This material was dissolved in $CH_2Cl_2$ (10 mL) or THF (10 mL) and used directly in subsequent coupling reactions.

6-bromo-3-hydroxyoicolinic Acid (17)

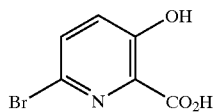

17

To a mechanically stirred solution of methyl 3-hydroxypicolinate (30.6 g) in water (800 mL) was slowly added bromine (32 g) over a 30 minute period. After the addition was complete, stirring was continued for an additional hour. Ether (300 mL) was added and stirring continued until all the solids had dissolved. The organic layer was separated and the aqueous phase extracted with ether (200 mL). The organic phases were combined, dried ($MgSO_4$) and the solvent evaporated to give 32.8 g of methyl 6-bromo-3-hydroxypicolinate as an off-white solid. Recrystallization from methanol/water gave an analytical sample, m.p. 115–117° C.

To a stirred solution of this ester (2.32 g) in THF (15 mL) was added all at once a solution of $LiOH.H_2O$ (1 g) in water (7 mL). The resulting mixture was stirred for 2 hours at room temperature then poured into water (100 mL). The pH was adjusted to approximately 3 with 1N HCl, then the mixture was extracted with $CH_2Cl_2$ (3×100 mL). The organic extract was dried ($MgSO_4$), filtered and concentrated to give 2.0 g of a white solid, whose $^1$H-NMR and MS were consistent with the desired title acid 17.

3-Benzyloxy-6-methoxypicolinic Acid (18)

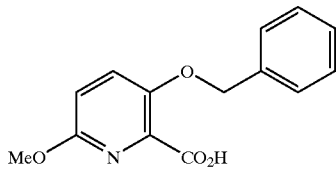

18

A solution of methyl 3-benzyloxypicolinate (4.86 g) and 3-chloroperoxybenzoic acid (5.75 g, 60% peracid) in $CH_2Cl_2$ (100 mL) was stirred at room temperature for 40 hours. The reaction mixture was then extracted with 5% sodium bisulfite solution (100 mL) then with 0.5N NaOH solution (150 mL). After drying ($MgSO_4$), the solvent was evaporated to give 4.9 g of methyl 3-benzyloxypicolinate-1-oxide as a white solid. Recrystallization from methylcyclohexane/toluene gave a crystalline solid, m.p. 104–106° C.

A solution of this compound (16.1 g) in acetic anhydride (80 mL) was stirred and heated in an oil bath at 125° C. for 3 hours. The excess acetic anhydride was removed on a rotary evaporator and the residue taken up in methanol (200 mL). Conc. sulfuric acid (1 mL) was added and the resulting mixture heated at reflux for 90 minutes. The solvent was evaporated then saturated sodium bicarbonate added to the residue. The resulting mixture was extracted with $CH_2Cl_2$ (3×100 mL). The organic fractions were combined, dried ($MgSO_4$) and the solvent evaporated to give 15.5 g of methyl 3-benzyloxy-6-hydroxypicolinate as a yellow solid. Recrystallization from toluene gave a pale yellow solid, m.p. 91–92° C.

To a stirred solution of this compound (10.25 g) in toluene (125 mL), warmed in an oil bath at 60° C., was added silver carbonate (16.6 g), then methyl iodide (8.52 g). The resulting mixture was stirred and heated for 3 hours at 60° C. After cooling, the mixture was filtered through Celite® and the solvent evaporated to give a yellow oil. Silica gel chromatography (4:1 hexane/acetone) gave a nearly colorless oil, whose $^1$H-NMR and MS data were consistent with methyl 3-benzyloxy-6-methoxypicolinate. Hydrolysis of this ester to the title acid 18 was accomplished with $LiOH.H_2O$ as described above for related esters.

4-Hydroxypyrimidine-5-carboxylic Acid (19).

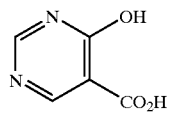

19

Ethyl 4-hydroxypyrimidine-5-carboxylate can be prepared following the procedure of M. Pesson et al., *Eur. J. Med. Chem.— Chim. Ther.* 1974, 9, 585. A solution of this ester (500 mg, 3 mmol) in THF (10 mL) and MeOH (5 mL) was treated with $LiOH.H_2O$ (373 mg, 8.9 mmol) and stirred overnight. The mixture was quenched with conc. HCl (1 mL) and extracted with EtOAc (2×20 mL). The combined organic extract was dried ($MgSO_4$) and concentrated to give 260 mg of the title compound 19 as an orange solid, m.p. 220° C. (dec).

4-Hydroxy-2-methylpyrimidine-5-carboxylic Acid (20)

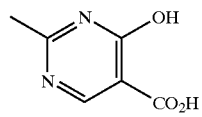

20

Ethyl 4-hydroxy-2-methylpyrimidine-5-carboxylate was prepared following the procedure of Geissman et al., *J. Org. Chem.,* 1946, 11, 741. A solution of this ester (750 mg, 4.11 mmol) in THF (10 mL) and MeOH (5 mL) was treated with $LiOH.H_2O$ (431 mg, 10.3 mmol) and stirred overnight. The mixture was quenched with conc. HCl (1 mL) and extracted with EtOAc (2×20 mL). The combined organic extract was dried ($MgSO_4$) and concentrated to give 155 mg of the title compound 20 as a white solid, m.p. 180° C. (dec).

5,6-Dichloro-3-hydroxypyrazine-2-carboxylic Acid (21)

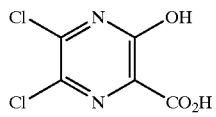

Methyl 3-amino-5,6-dichloropyrazine-2-carboxylate (5.0 g, 23 mmol) was stirred in conc. sulfuric acid (140 mL) and cooled to 0° C. Sodium nitrite was added slowly, maintaining the temperature close to 0° C. After an additional 30 minutes at 0° C., the mixture was allowed to warm to ambient temperature and stirred for 3 hours. The mixture was poured into 500 g of ice, resulting in bubbling and foaming. After 30 minutes, the mixture was extracted 3 times with EtOAc. The combined organic extract was dried (MgSO$_4$), filtered and concentrated. The yellow solid which was left was washed with water and air-dried, to leave 5.0 g of a yellow solid, m.p. 114–116° C., whose $^{13}$C-NMR spectrum was consistent with the methyl ester of the title compound.

This solid (5.0 g) was treated with 1N NaOH (20 mL) and the mixture heated at 90° C. for 1.5 hours. After allowing to cool, the mixture was acidified with conc. HCl, then extracted 3 times with EtOAc. Drying (MgSO$_4$), filtration and concentration afforded 0.48 g of a dark yellow solid, whose $^1$H-NMR and MS spectra were consistent with the title acid 21.

6-Chloro-3-hydroxy-5-methoxypyrazine-2-carboxylic Acid (22)

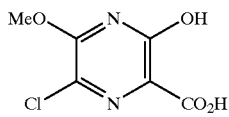

A stirred mixture of methyl 3-amino-5,6-dichloropyrazine-2-carboxylate (5.0 g, 23 mmol) and sodium methoxide (3.6 g, 67.5 mmol) in absolute MeOH (50 mL) was heated at reflux for 2 hours, then allowed to cool and acidified with conc. HCl. The precipitate was collected by filtration, washed with water and air-dried to afford 3.6 g of a brown solid. Recrystallization from hexane-EtOAc (1:1) afforded 2.6 g of a pale yellow solid whose spectra were consistent with methyl 3-amino-6-chloro-5-methoxypyrazine-2-carboxylate.

This compound (1 g, 4.6 mmol) was taken up in conc. sulfuric acid, cooled to 0° C., and treated slowly with sodium nitrite (0.5 g, 6.9 mmol). After 30 minutes at 0° C., the mixture was poured into 300 g of ice/water, resulting in foaming. Stirring was continued for 30 minutes, then the solid was collected by filtration and washed with water. The wet solid was taken up in EtOAc, dried (MgSO$_4$), filtered and concentrated. This gave 0.95 g of an off-white solid, m.p. 180–182° C., whose NMR spectra were consistent with methyl 6-chloro-3-hydroxy-5-methoxypyrazine-2-carboxylate.

This solid (0.9 g, 4.1 mmol) was treated with 1N NaOH (60 mL), and the mixture was stirred for 1 hour, then acidified with conc. HCl. The precipitate was collected by filtration and washed with water, then was dissolved in EtOAc, dried (MgSO$_4$), filtered and concentrated. This afforded 0.62 g of a pale yellow solid, m.p. 170–173° C., whose spectra were consistent with the desired title acid 22.

4-Hydroxyisothiazole-3-carboxylic Acid (23)

This acid was obtained following the procedure shown in Scheme 5.

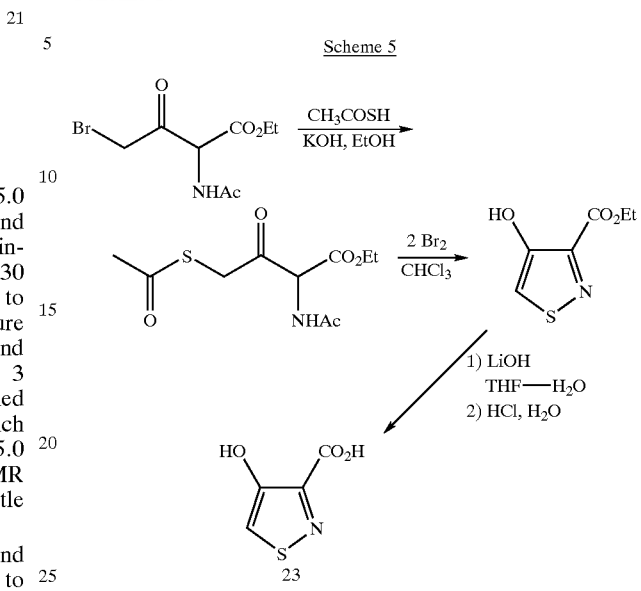

Thus, to a stirred solution of solid KOH (88%, 6.98 g, 0.11 mol) in 75 mL of EtOH in a flask flushed with nitrogen was added thiolacetic acid (8.36 g, 0.11 mol) washed in with 25 mL of EtOH. The mixture was stirred under nitrogen for 5 minutes in the stoppered flask. To this was added 0.1 mol of the crude bromo compound (freshly prepared according to M. Hatanaka and T. Ishimaru, *J. Med. Chem.*, 1973, 16, 798). The flask was flushed with nitrogen and stoppered. The mixture was stirred in an ambient water bath for 3 hours, then was poured into 300 mL CH$_2$Cl$_2$ and 1000 mL water. The aqueous layer was extracted four times with 200 mL of CH$_2$Cl$_2$. The combined organic extracts were washed with 100 mL of cold water and saturated salt solution and dried. The crude mixture was filtered and concentrated. The resulting oil was chromatographed on silica gel, using diethyl ether as eluent, to give 13 g of a light yellow oil which solidified on standing to a gummy solid. Spectral data were consistent with ethyl 2-acetylamino-4-acetylthio-3-oxobutanoate.

To a rapidly stirred solution of this compound (12.95 g) in 450 mL of chloroform, cooled in an ice bath to below 5° C., bromine (15.8 g, 2 equivalents) in 50 mL of chloroform was added dropwise over 45 minutes. Stirring was continued in the ice bath for an additional 45 minutes, and then at ambient temperature for 30 hours. Then the mixture was washed with 200 mL of water, followed by another 100 mL of water. The combined aqueous washes were re-extracted with 100 mL of chloroform. The combined chloroform solutions were washed with saturated salt solution and dried over MgSO$_4$. The solution was filtered and concentrated to a crude oil. This was chromatographed on silica gel using a serial gradient from petroleum ether-CH$_2$Cl$_2$ (3:1) to CH$_2$Cl$_2$, to give first 0.79 g of ethyl 5-bromo-4-hydroxyisothiazole-3-carboxylate, and then 3.40 g of ethyl 4-hydroxyisothiazole-3-carboxylate as colorless crystals, m.p. 44–7° C., consistent by MS and $^1$H-NMR.

To 710 mg of the latter ester in 30 mL of THF was added 370 mg of LiOH.H$_2$O (2.2 equivalents) in 10 mL of water. The mixture was stirred for 3 hours at ambient temperature, then cooled in the refrigerator. The precipitated solid was collected by filtration to give 710 mg of the dilithium salt of the carboxylic acid. This salt was taken up in 7 mL of water, cooled in an ice bath, and taken to pH 1 by addition of 2N HCl. The resulting solution was extracted three times with 50 mL of EtOAc. The combined extracts were washed with 5 mL of brine and dried ($Na_2SO_4$), filtered, and the filtrate placed in the refrigerator. The chilled solution was re-filtered and the filtrate concentrated to give 230 mg of a colorless solid, m.p. 185–89° C., whose $^1$H-NMR and $^{13}$C-NMR spectra were consistent with the title compound 23.

3-Benzyloxy-1-methylpyrazole-4-carboxylic Acid (24) and 5-benzyloxy-1-methylpyrazole-4-carboxylic Acid (25)

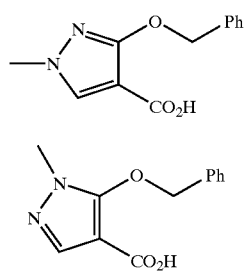

A mixture of ethyl 3-hydroxy-1-methylpyrazole-4-carboxylate and ethyl 5-hydroxy-1-methylpyrazole-4-carboxylate (obtained by the procedure of Y. Wang, et al., Zhejiang Gongxueyuan Xuebao, 1994, 2, 67), was benzylated according to the procedure of S. Yamamoto, et al., Japanese Patent JP 62148482, 1987, and the mixture was separated by column chromatography, using 3:1 hexanes:EtOAc as the eluent, to provide ethyl 3-benzyloxy-1-methylpyrazole-4-carboxylate and ethyl 5-benzyloxy-1-methylpyrazole-4-carboxylate, which were pure by $^1$H-NMR.

Ethyl 3-benzyloxy-1-methylpyrazole-4-carboxylate (283 mg, 1.08 mmol) in THF (10 mL), MeOH (2 mL), and water (5 mL) was treated with LiOH.$H_2O$ (91 mg, 2.17 mmol) and stirred overnight. The mixture was quenched with conc. HCl (1 mL) and extracted with EtOAc (2×20 mL). The combined organic layers were dried ($MgSO_4$) and concentrated to give a white solid (227 mg), m.p. 169–172° C., whose spectra were consistent with 3-benzyloxy-1-methylpyrazole-4-carboxylic acid (24).

Ethyl 5-benzyloxy-1-methylpyrazole-4-carboxylate (755 mg, 2.9 mmol) was likewise hydrolyzed using LiOH.$H_2O$ (243 mg, 5.8 mmol) in THF (20 mL), MeOH (4 mL), and water (10 mL), to afford 608 mg of 5-benzyloxy-1-methyl-4-carboxylic acid (25) as a white solid, m.p. 117–122° C.

Preparation of Other Heteroaromatic Carboxylic Acids

4-Hydroxynicotinic acid was prepared by the procedure of M. Mittelbach et al., Arch. Pharm. (Weinheim, Germany) 1985, 318, 481–486. 2-Hydroxy-6-methylnicotinic acid can be prepared following the method of A. Dornow, Chem. Ber. 1940, 73, 153. 4,6-Dimethyl-2-hydroxynicotinic acid can be prepared following the method of R. Mariella and E. Belcher, J. Am. Chem. Soc., 1951, 73, 2616. 5-Chloro-2-hydroxy-6-methylnicotinic acid can be prepared by the procedure of A. Cale et. al., J. Med. Chem., 1989, 32, 2178. 2,5-Dihydroxynicotinic acid can be prepared by the method of P. Nantka-Namirski and A Rykowski, Chem. Abstr., 1972, 77, 114205. 3-Hydroxyisonicotinic acid was prepared according to the method of J. D. Crum and C. H. Fuchsman, J. Heterocycl. Chem. 1966, 3, 252–256. 3-Hydroxypyrazine-2-carboxylic acid can be prepared according to the method of A. P. Krapcho et al., J. Heterocycl. Chem. 1997, 34, 27. 5,6-Dimethyl-1-3-hydroxypyrazine-2-carboxylic acid can be prepared by hydrolysis of the corresponding ethyl ester, whose synthesis is described by S. I. Zavyalov and A. G. Zavozin, Izv. Akad. Nauk SSSR, 1980, (5), 1067–1070. 4-Hydroxypyridazine-3-carboxylic acid was prepared by the method of I. Ichimoto, K. Fujii, and C. Tatsumi, Agric. Biol. Chem. 1967, 31, 979. 3,5-Dihydroxy-1,2,4-triazine-6-carboxylic acid was prepared by the method of E. Falco, E. Pappas, and G. Hitchings, J. Am. Chem. Soc., 1956, 78, 1938. 5-Hydroxy-3-methylthio-1,2,4-triazine-6-carboxylic acid was prepared following the method of R. Barlow and A. Welch, J. Am. Chem. Soc., 1956, 78, 1258. Hydroxyisothiazole-, hydroxyisoxazole-, and hydroxypyrazole-carboxylic acids were prepared by the method of T. M. Willson et al., Bioorg. Med. Chem. Lett., 1996, 6, 1043. 3-Hydroxy-1,2,5-thiadiazole-4-carboxylic acid was prepared by the method of J. M. Ross et al., J. Am. Chem. Soc., 1964, 86, 2861. 3-Hydroxyisoxazole-4-carboxylic acid was obtained following the procedure described by K. Bowden et al., J. Chem. Soc. (C), 1968, 172. 3-Hydroxy-1-phenylpyrazole-4-carboxylate was generated in accordance with the method of A. W. Taylor and R. T. Cook, Tetrahedron, 1987, 43, 607. 3-Benzyloxyquinoline-2-carboxylic acid was prepared following the procedure of D. L. Boger and J. H. Chen, J. Org. Chem. 1995, 60, 7369–7371.

General Preparation of the Intermediate Amines and Anilines

The synthesis of cyclic, acyclic and benzylamines was carried out by the reduction of the corresponding oximes either by use of metal hydrides or dissolving metal reactions as is illustrated by R. O. Hutchins and M. K. Hutchins in Comprehensive Organic Synthesis; B. M. Trost, Ed.; Pergamon Press: Oxford, 1991; Vol 8, p. 65; or J. W. Huffman in Comprehensive Organic Synthesis; B. M. Trost, Ed.; Pergamon Press: Oxford, 1991; Vol 8, p. 124. Alternatively, these amines could be prepared directly from the requisite ketones and aldehydes via a Leuckart reaction as exemplified by R. Carlson, T. Lejon, T. Lunstedt and E. LeClouerec, Acta Chem. Scand. 1993, 47, 1046. The anilines in general were prepared by catalytic reduction of the corresponding nitroaromatics using Pd on charcoal or sulfided platinum on charcoal as catalysts. Such procedures are well documented as in, for example, R. L. Augustine, Catalytic Hydrogenation, Marcel Decker, Inc., New York, 1965.

The amines 49, which are 9-membered dilactone ring systems, were prepared according to the procedures of M. Shimano, N. Kamei, T. Shibata, K. Inoguchi, N. Itoh, T. Ikari and H. Senda, Tetrahedron, 1998, 54, 12745, or by modifications of these procedures. Such a modification is shown in Scheme 6. Thus, 26 (from the above reference) was reduced with lithium borohydride and the resulting primary alcohol capped with triisopropylsilane (TIPS) to give 27. The free hydroxyl group of 27 was reacted with 1-bromo-2-methyl-2-propene followed by catalytic reduction of the double bond to give 28. Selective removal of the para-methoxybenzyl (PMB) blocking group followed by condensation with N-t-BOC-O-benzyl-L-serine gave 29. Removal of the TIPS group followed by oxidation of the resultant hydroxy group gave 30. This material (30) was subsequently converted to the amine 31 using procedures described in the above reference.

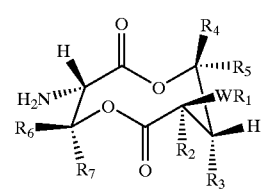

Scheme 6
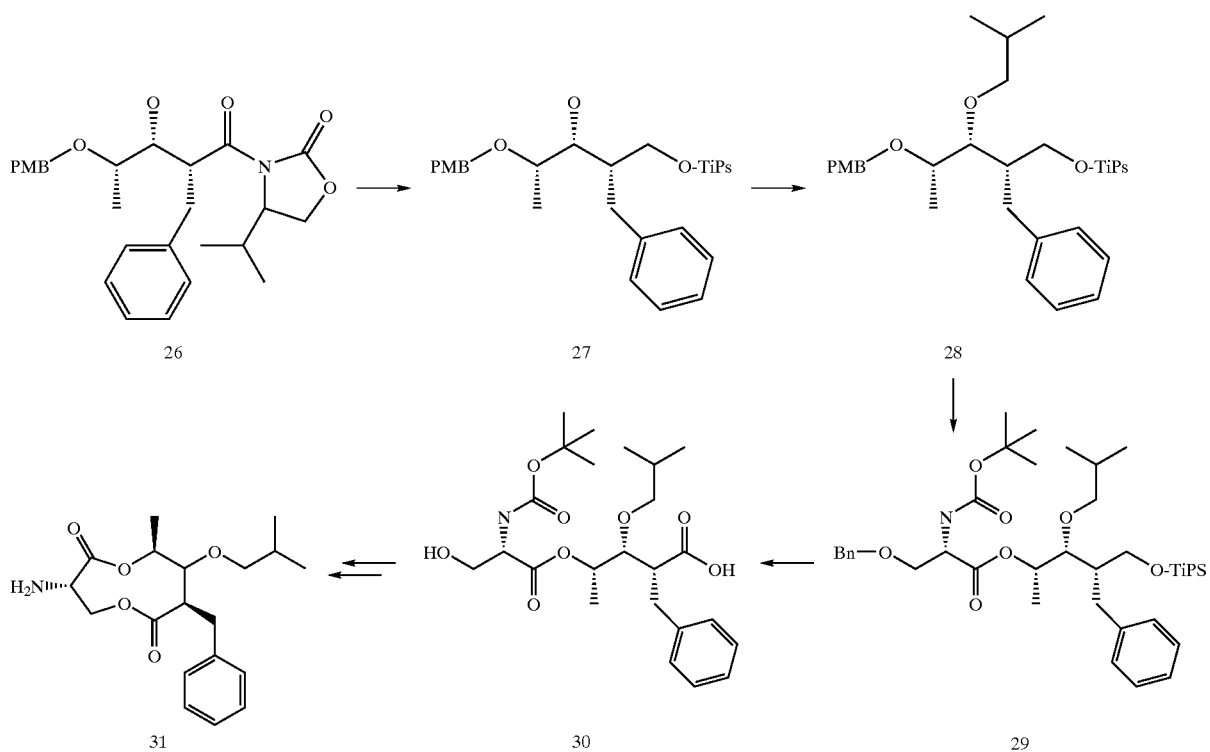
In a similar manner, the syntheses of aminodilactones 38 and 48, which lack the exocyclic ester functionality, are outlined in Schemes 7 and 8, repectively.
Scheme 7
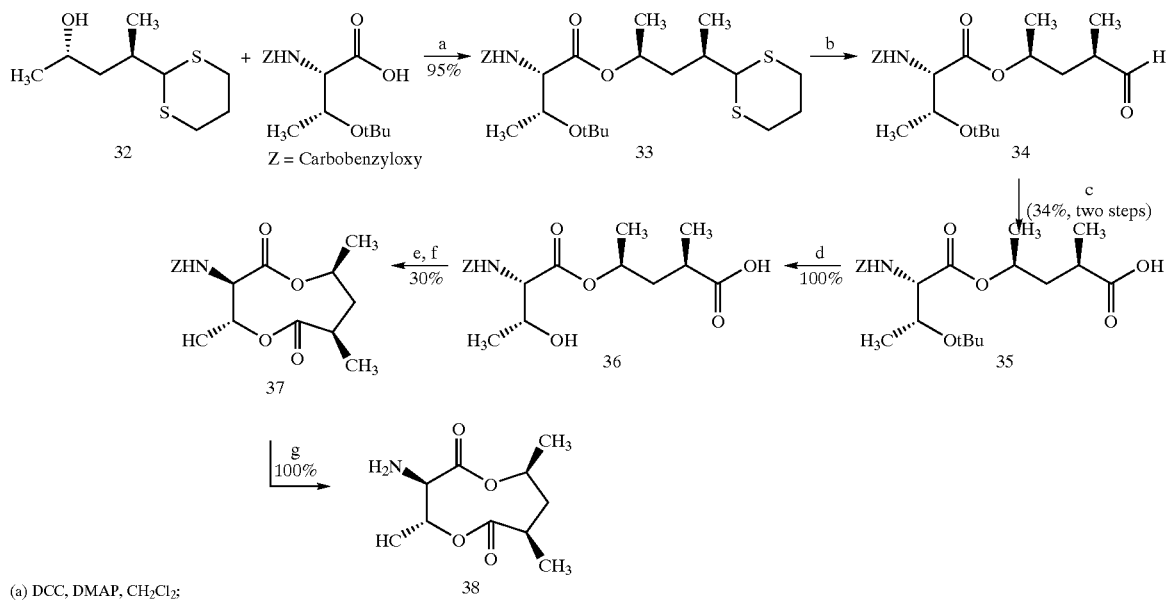
(a) DCC, DMAP, CH$_2$Cl$_2$;
(b) (CF$_3$CO$_2$)$_2$IPh, CH$_3$CN/H$_2$O;
(c) CrO$_3$, AcOH, Pyr;
(d) CF$_3$CO$_2$H;
(e) Aldrithiol-2, Ph$_3$P, Benzene;
(f) 1.0 M AgClO$_4$, toluene, CH$_3$CN;
(g) Pd (black), CH$_3$OH Scheme 8

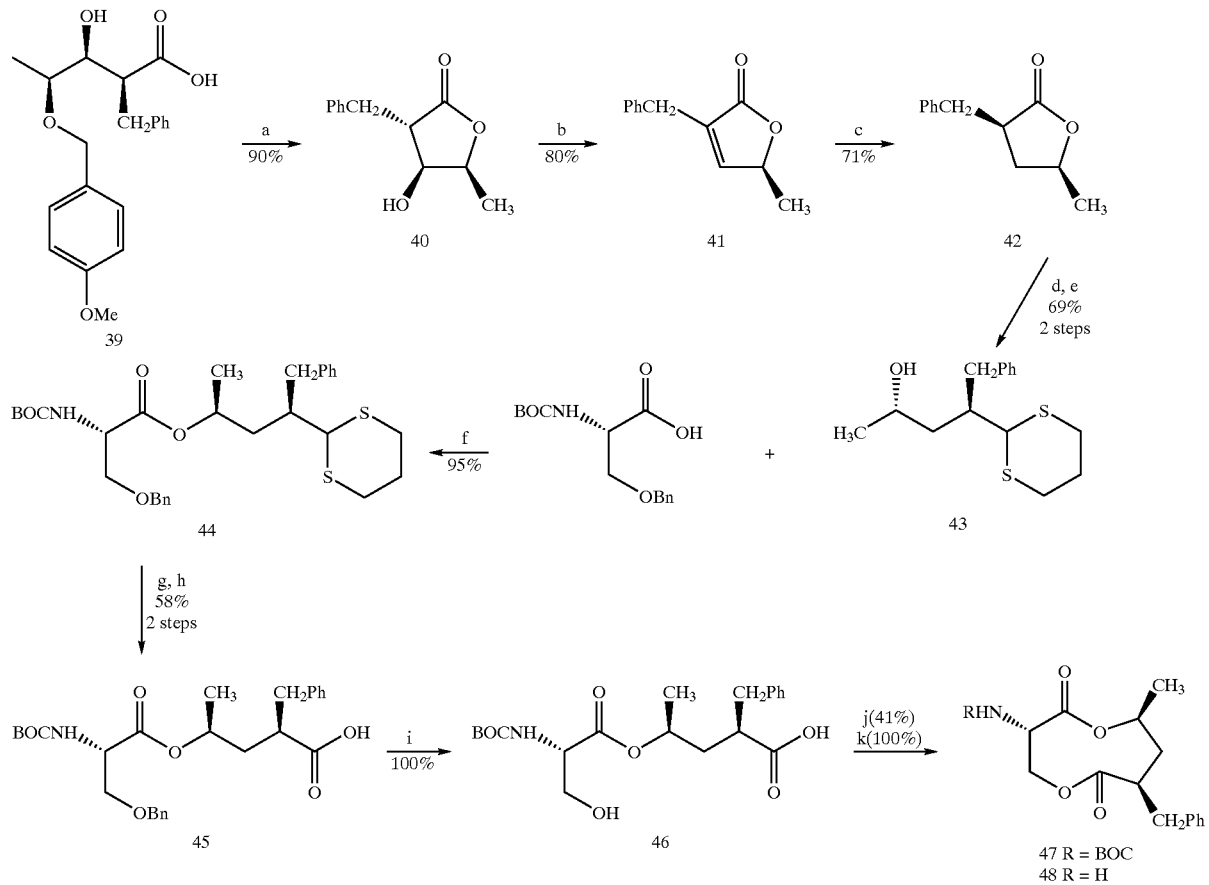

(a) H₂, 10% Pd/C, CH₃OH, HCl; (b) pTsCl, Et₃N, DMAP, CH₂Cl₂; (c) H₂, 10% Pd/C, EtOAc; (d) DIBAL-H, Et₂O; (e) 1,3-propanethiol, BF₃OEt₂, CH₂Cl₂; (f) EDCl, DMAP, DMF; (g) (CF₃CO₂)₂IPH, CH₃CN, H₂O; (h) CrO₃, AcOH, pyr; (i) H₂, 10% Pd/C, EtOAc; (j) DIAD, PPh₃, Benzene; (k) CF₃CO₂H Preparation of 27 (See Scheme 6)

To a solution of lithium borohydride (2.0M in THF, 7.5 mL, 15 mmol) in 7.5 mL dry THF was added 0.1 mL trimethyl borate. This mixture was cooled under nitrogen atmosphere to −30° C. To this solution was added dropwise a solution of compound 26 (4.58 g, 10 mmol) in 10 mL THF over a 10 min period. The solution was stirred at −30° C. for 1 hr, then at 0° C. for 5 hrs. Saturated ammonium chloride solution (10 mL) was added dropwise, the mixture was stirred for 10 min, and the phases were separated. The aqueous phase was extracted with EtOAc (2×25 mL), and the combined organic phases were washed with saturated brine, dried over sodium sulfate, and evaporated to dryness. The crude product was chromatographed to give 2.1 g white solid. A sample recrystallized from hexane-EtOAc gave fine white needles, m.p. 91–93° C. $[\alpha]_D^{25}$=+31.9° (C=1.04, CHCl₃). This diol (2.04 g, 6.22 mmol) was dissolved in 4 mL dry DMF and imidazole (680 mg, 10 mmol) was added. The solution was cooled in an ice-bath, and then triisopropylchlorosilane (1.39 mL, 6.5 mmol) was added over 2 min. The mixture was stirred at room temperature for 4 hr. then poured into ice-water, and extracted with 20% ether in hexanes (3×15 mL). The combined organic phases were washed with brine, dried, and filtered through a short plug of silica gel, which was washed with 20 mL of the same solvent. The solvent was evaporated to give 2.77 g of compound 27 as a pale viscous oil, which was very pure by ¹H-NMR.

Preparation of 28 (See Scheme 6)

Sodium hydride (60% oil dispersion, 400 mg, 10 mmol) was charged to a 50 mL flask and washed three times with hexanes. DMF (15 mL) was added and the suspension was stirred as compound 27 (2.53 g, 5.19 mmol) in 5 mL dry DMF was added dropwise over 15 min. The reaction was stirred for 15 min and then cooled to below 10° C. and 1-bromo-2-methyl-2-propene (1 mL, 10 mmol) was added over 5 min, followed by stirring for 2 hr at room temperature. The mixture was partitioned between hexanes/ice-cold ammonium chloride solution, worked up as in preparation of 27, and the crude product was chromatographed to give 2.20 g of colorless oil which was pure by ¹H-NMR and elemental analysis. This material (2.38 g, 4.4 mmol) was dissolved in 50 mL of EtOAc in a 100 mL Morton flask under nitrogen. 150 mg of 5% Pt on carbon was added, and the mixture was stirred under 1 atmosphere of hydrogen for 20 min. The catalyst was removed by filtration, and the solvent was evaporated to give 2.35 g of 28 as a colorless oil which was pure by ¹H-NMR.

Preparation of 29 (See Scheme 6)

To a 50 mL flask equipped with magnetic stirring was charged a solution of ether 28 (2.0 g, 3.68 mmol) in 40 mL CH₂Cl₂ and 2 mL water. This was stirred under nitrogen and cooled in an ice-bath at <10° C. as 2,3-dichloro-5,6-dicyano-1,4-benzoquinone (DDQ) (920 mg, 4.05 mmol) was added in one portion. The ice-bath was removed, and the mixture was stirred for 1 hr. at room temperature. The gold suspension was suction filtered, the cake was washed with 2×10 mL $CH_2Cl_2$, and the filtrates were extracted with 0.2N NaOH (2×25 mL). The organic layer was dried and concentrated to give a pale oil, which was purified by chromatography to give 1.53 g of colorless oil which was pure by elemental analysis. This was dissolved in 25 mL $CH_2Cl_2$ and stirred in an ice-bath under nitrogen as DMAP (854 mg, 7 mmol), EDCI (1.34 g, 7 mmol), and N-t-BOC-O-benzyl-L-serine (2.07 g, 7 mmol) were added sequentially. The cooling bath was removed, and the mixture was stirred for 2 hr at room temperature. It was then poured into a rapidly stirring mixture of 50 mL of ice-cold 0.5N HCl and 20 mL of $CH_2Cl_2$ and stirred for 10 min. The phases were separated and the aqueous phase was extracted with 1×10 mL $CH_2Cl_2$; then, the combined organic phases were dried and concentrated to give a pale oil. This was chromatographed to give 2.30 g of 29 as a nearly colorless heavy oil. TLC and $^1$H-NMR appeared quite pure.

Preparation of 30 (See Scheme 6)

Silyl ether 29 was dissolved in 7 mL dry pyridine and cooled in an ice bath. HF-pyridine complex (4.5 mL) was added over a 1 min period and the solution was stirred at room temperature for 17 hr, then heated to 50° C. for 4.5 hr, when conversion stopped. The mixture was poured into ice-water and extracted with 3×50 mL ether. The combined organic phases were washed with water, 1N HCl, then dried and concentrated to give an oil. This was chromatographed to give 1.23 g of desired alcohol as a viscous oil, as well as 365 mg of recovered 29. The alcohol (1.14 g, 2.10 mmol) was dissolved in 10 mL DMF, and pyridinium dichromate (3.76 g, 10 mmol) was added. After 21 hours, the mixture was poured into ice-water, 1N HCl was added until the pH was below three, and then solid sodium bisulfite was added until the orange color was discharged. The aqueous phase was extracted with ether (3×50 mL). The organics were combined, washed, dried ($Na_2SO_4$), and concentrated. The residue was chromatographed to give 811 mg of viscous oil which was pure enough to carry on. The acid was dissolved in 30 mL of EtOAc and 200 mg of Pearlman's catalyst was added. The slurry was shaken under 50 psi of hydrogen pressure for 4 hr, 300 mg fresh catalyst was added, and shaking was continued for 2 hrs. It was then filtered and the solvent was evaporated to give 30 as a viscous gum which was pure enough for further use.

Threoninedithiane 33 (See Scheme 7)

Pentyldithiane 32 (Hirai, *Heterocyles* 1990, 30(2, Spec. Issue), 1101) (200 mg, 0.97 mmol) was dissolved in 10 mL of $CH_2Cl_2$ at room temperature. N-(Z)-O-t-Butyl-(L)-threonine (900 mg, 2.91 mmol) was added followed by DMAP (36 mg, 0.29 mmol). To this mixture was added dropwise a solution of dicyclohexyl carbodiimide (DCC) (1M in $CH_2Cl_2$, 2.9 mL, 2.9 mmol) followed by stirring at room temperature overnight. The reaction was diluted with 50 mL of ether ($Et_2O$), filtered and concentrated. The resulting residue was applied to a small (4") silica gel gravity column and eluted with 4:1 hexanes/EtOAc. The eluent collected from the silica gel column was further purified by radial chromatography using 4:1 hexanes/EtOAc as the eluent. Product fractions were evaporated and kept under high vacuum (45° C. @ 0.1 torr) to constant weight to give 500 mg of a nearly colorless heavy oil identified as dithiane 33 (TLC $R_f$=0.32, $^1$H-NMR).

Threoninecarboxylic Acid 35 (See Scheme 7)

Threoninedithiane 33 (500 mg, 1.01 mmol) was dissolved in 10 mL of a 9:1 $CH_3CN/H_2O$ mixture at room temperature. [Bis(trifluoroacetoxy)iodo]benzene (650 mg, 1.50 mmol) was added and the reaction was stirred for 10 min. Saturated $NaHCO_3$ was added (20 mL) and the solution was extracted with $Et_2O$ (3×20 mL). The ethereal layer was dried over $MgSO_4$, filtered, and concentrated. The aldehyde 34 was sufficiently pure (TLC, GC/MS) for use directly in the next reaction. The crude aldehyde was taken up in 15 mL (4.95 mmol) of $CrO_3$ reagent (made from 1 g $CrO_3$, 30 mL of $CH_3CO_2H$ and 1 mL pyridine) and stirred at room temperature overnight. The solution was diluted with 30 mL cold water and extracted with $Et_2O$ (3×30 mL). The organic layer was washed with 30 mL brine, dried over $MgSO_4$, filtered, and concentrated. The residue was purified via radial chromatography using 2:1 heptane/EtOAc containing 2% $CH_3CO_2H$ as the eluent. The carboxylic acid 35 (120 mg) was quite pure by TLC and $^1$H-NMR.

Threoninehydroxycarboxylic Acid 36 (See Scheme 7)

Threoninecarboxylic acid 35 (137 mg, 0.324 mmol) was stirred in 3 mL of trifluoroacetic acid for 10 min and the mixture was concentrated on a rotary evaporator. The residue was dried under high vacuum (0.05 mm) overnight. The hydroxyacid 36 (119 mg) was used directly in the next step.

N-Cbz-Threoninebislactone 37 (See Scheme 7)

Threoninehydroxycarboxylic acid 36 (119 mg, 0.324 mmol) was dissolved in 1 mL benzene and Aldrithiol™-2 was added (85 mg, 0.39 mmol) followed by triphenylphosphine (0.39 mmole, 101 mg) and the reaction was stirred overnight. The crude thioester was diluted with 15 mL of $CH_3CN$. A separate flask equipped with a reflux condenser was charged with 1.2 mL (1.16 mmol) of a 1.0 M $AgClO_4$ solution in toluene, followed by 32 mL of $CH_3CN$. This solution was heated to a reflux rate of 5–10 drops per second (oil bath ~160° C.). The thioester solution was then added dropwise via an addition funnel at the top of the condenser over 2 hr. The mixture was refluxed an additional 30 min, cooled and concentrated. The residue was diluted with 10 mL 0.5 M KCN and extracted with benzene (3×20 mL). The benzene layers were combined, washed with 20 mL water, dried over $MgSO_4$, filtered and concentrated. The residue was then taken up in 10 mL 2:1 pentane/$Et_2O$ and filtered. The solids were washed with 2:1 pentane/$Et_2O$ and the combined organic solution was concentrated. Radial chromatography (2:1 pentane/$Et_2O$ as the eluent) provided 34 mg of the bislactone 37, quite pure by TLC ($R_f$=0.22) and $^1$H-NMR.

3-Amino-4,7,9-trimethylbislactone (38) (See Scheme 7)

N-Cbz-Threoninebislactone 37 (34 mg, 0.097 mmol) was dissolved in 10 mL of methanol in a 500 mL Parr bottle and purged with nitrogen. To this solution was added 10 mg of Pd (black) and the mixture was shaken at 45 psi hydrogen pressure for 1 hr. The catalyst was filtered and the solvent was evaporated to give the free amine 38 (20 mg, 100%). This amine was pure enough ($^1$H-NMR), and was used as such without further purification.

3-Benzyl-4-hydroxy-5-methylbutyrolactone (40) (See Scheme 8)

Pentanoic acid 39 (Shimano et al., *Tetrahedron Lett.* 1998, 39, 4363) (1.8 g, 5.23 mmol) was dissolved in 30 mL of methanol in a 500 mL Parr bottle and purged with nitrogen. To this solution was added 150 mg of 10% Pd on carbon followed by 6 drops of conc. HCl. The mixture was shaken at 50 psi hydrogen pressure for 3 hr. The catalyst was filtered through diatomaceous earth and the solution concentrated. The residue was taken up in 30 mL $CH_2Cl_2$ and washed with water (1×10 mL) . The solution was dried over $MgSO_4$, filtered, and concentrated. Crude $^1$H-NMR and GC/MS revealed expected butyrolactone 40 and 4-methylanisole in a 4:1 ratio (v/v). This material (60% purity by GC) was used directly in the next reaction.

3-Benzyl-5-methylbutenolide 41 (See Scheme 8)

3-Benzyl-4-hydroxy-5-methylbutyrolactone 40, (60% purity, 1.7 g, 8.25 mmol), was dissolved in 25 mL $CH_2Cl_2$ and cooled to 0° C. The solution was stirred while triethylamine (2.3 mL, 16.5 mmol), DMAP (500 mg, 4.13 mmol) and p-toluenesulfonyl chloride (9.0 mmol, 1.7 g) were added sequentially. The reaction was warmed to room temperature and stirred 30 hr. The reaction was diluted with 50 mL $Et_2O$ and washed with 5% $NaHCO_3$ (25 mL). The solution was dried over $MgSO_4$, filtered and concentrated. The residue was purified via radial chromatography using 2:1 pentane/$Et_2O$ as the eluent to yield 677 mg of the butenolide 41 (>95% purity by GC and $^1$H-NMR).

cis-3-Benzyl-5-methylbutyrolactone 42 (See Scheme 8)

3-Benzyl-5-methylbutenolide 41 (677 mg, 3.60 mmol) was dissolved in 30 mL of EtOAc in a 500 mL Parr bottle and purged with nitrogen. To this solution was added 300 mg of 10% Pd/C and the mixture was shaken at 45 psi hydrogen pressure overnight. The catalyst was filtered and the solvent was evaporated. The residue was purified via radial chromatography using 2:1 pentane/$Et_2O$ as the eluent to give 484 mg of a colorless oil (71% yield of material pure by 1H-NMR in $CDCl_3$ and by GC).

2-Benzylpentyldithiane 43 (See Scheme 8)

cis-3-Benzyl-5-methylbutyrolactone 42 (550 mg, 2.89 mmol) was dissolved in 15 mL of $Et_2O$ and cooled to −78° C. Diisobutylalmuminum hydride (1.0 M in hexanes, 3.47 mmol, 3.5 mL) was added dropwise and the solution was stirred at −78° C. for 2 hrs. Methanol (3.3 mL) was added over 15 min and the reaction was stirred at −78° C. for an additional 30 min. Sodium potassium tartrate (1.65 g in 5 mL of water) was added and the reaction was allowed to warm to room temperature and stirred overnight. The layers were separated and the aqueous layer was extracted with $Et_2O$ (2×10 mL). The combined ethereal layers were washed with satd. $NaHCO_3$ and brine (1×10 mL). The solution was dried over $MgSO_4$, filtered, and concentrated. The crude lactol (555 mg) was dissolved in 5 mL of $CH_2Cl_2$ and cooled to 0° C. 1,3-Propanedithiol (3.46 mmol, 0.35 mL) was added followed by 0.37 mL (2.89 mmol) of boron trifluoride etherate. The reaction was allowed to warm to room temperature and stirred overnight. Saturated $NaHCO_3$ was added (20 mL) and the mixture stirred 1 hr. The layers were separated and the aqueous layer extracted with $CH_2Cl_2$ (2×10 mL). The combined organic layers were washed with brine (1×20 mL), dried over $MgSO_4$, filtered, and concentrated. The residue was purified via radial chromatography using 3:1 hexane/EtOAc as the eluent to give 560 mg of a yellow oil (69% yield of material pure by $^1$H-NMR and GC) identified as dithiane 43.

Serinedithiane 44 (See Scheme 8)

2-Benzylpentyldithiane 43 (560 mg, 1.99 mmol) was dissolved in 5 mL of DMF and cooled to 0° C. DMAP (0.29 mmol, 36 mg) was added followed by EDCI, (0.57 g, 2.98 mmol). N-t-BOC-O-benzyl-(L)-serine (760 mg, 2.58 mmol) was then added followed by warming to room temperature and stirring at room temperature overnight. The reaction was poured into a rapidly stirring mixture of 10 mL ice cold 0.5 N HCl and 20 mL 20% ether/hexanes and stirred 10 min. The layers were separated and the aqueous layer extracted with 20% ether/hexanes (1×10 mL). The combined organic layers were washed with 0.5 N HCl (20 mL) and brine (2×20 mL). The solution was dried over $MgSO_4$, filtered, and concentrated. The resulting residue was kept under high vacuum (45° C. @ 0.1 torr) to constant weight to give 1.06 g of a nearly colorless heavy oil identified as dithiane 44 (TLC $R_f$=0.3, 3:1 hexanes/EtOAc).

N-t-BOC-O-Benzylserinecarboxylic Acid 45 (See Scheme 8)

Serinedithiane 44 (1.06 g, 1.90 mmol) was dissolved in 20 mL of a 9:1 $CH_3CN/H_2O$ mixture at room temperature. [Bis(trifluoroacetoxy)iodo]benzene (1.2 g, 2.82 mmol) was added and the reaction stirred for 10 minutes. Saturated $NaHCO_3$ was added (40 mL) and the solution extracted with $Et_2O$ (3×40 mL). The ethereal layer was dried over $MgSO_4$, filtered and concentrated. The aldehyde was sufficiently pure (TLC, GC/MS, $^1$H-NMR) for use directly in the next reaction. The crude aldehyde was taken up in 30 mL (9.70 mmol) of $CrO_3$ reagent (made from 1 g $CrO_3$, 30 mL of $CH_3CO_2H$ and 1 mL pyridine) and stirred at room temperature overnight. The solution was diluted with 60 mL cold water and extracted with $Et_2O$ (3×60 mL). The organic layer was washed with 2×60 mL brine, dried over $MgSO_4$, filtered and concentrated. The residue was taken up in 100 mL 2:1 heptane/EtOAc and evaporated. The residue was purified via radial chromatography using 1.5:1 heptane/EtOAc containing 2% $CH_3CO_2H$ as the eluent. The carboxylic acid (536 mg) looked quite pure by TLC and $^1$H-NMR with two t-BOC rotamers evident in $CDCl_3$ but not in acetone-$d_6$.

N-t-BOC-Serinebislactone 47 (See Scheme 8)

N-t-BOC-O-Benzylserinecarboxylic acid 45 (536 mg, 1.11 mmol) was dissolved in 15 mL of EtOAc in a 500 mL Parr bottle and purged with nitrogen. To this solution was added 390 mg of 10% Pd/C and the mixture was shaken at 50 psi hydrogen pressure for 17 hr. The catalyst was filtered through diatomaceous earth and the solvent was evaporated to give the hydroxyacid 46 (440 mg). The crude hydroxyacid 46 was dissolved in 23 mL benzene and triphenylphosphine (0.34 g, 1.28 mmol) was added at room temperature. Diisopropylazodicarboxylate (DIAD, 0.25 mL, 1.28 mmol) was added dropwise and the reaction was stirred at room temperature overnight. The solution was concentrated and the resulting residue was applied to a small (4 in) gravity column and eluted with 2:1 hexanes/EtOAc. The eluent from the silica gel column was further purified by radial chromatography using 2:1 pentane/ether as the eluent. Product fractions were evaporated to give 132 mg of a yellow oil identified as N-t-BOC-serinebislactone 47 (TLC $R_f$=0.32, quite pure by $^1$H-NMR).

3-Amino-7-Benzyl-9-Methylbislactone 48 (See Scheme 8)

N-t-BOC-Serinebislactone 47 (132 mg, 0.35 mmole) was stirred in 3 mL of trifluoroacetic acid for 30 minutes and the reaction was concentrated on a rotary evaporator. The residue was dried under high vacuum (0.05 mm) overnight. The trifluoroacetic acid salt of amine 48 (0.35 mmol) was quite pure by $^1$H-NMR, and was used as such without further purification.

3-(3-Chlorophenoxy)aniline

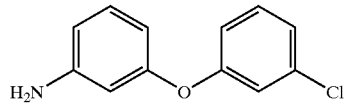

To a stirred solution of potassium t-butoxide (12.3 g) in DMSO (100 mL) was added at once 3-chlorophenol (12.86 g). The resulting solution was stirred for 5 minutes at room temperature, then 3-fluoronitrobenzene (12.70 g) was added all at once. The resulting dark mixture was heated at 120° C. for 12 hours, cooled to room temperature then poured into water (700 mL). The resulting mixture was extracted with ether (2×200 mL). The organic fraction was washed with 2N NaOH (100 mL), then with water (100 mL). After drying (MgSO$_4$), the solvent was evaporated and the resulting dark oil was distilled to give 3-(3-chlorophenoxy)nitrobenzene as a yellow oil, b.p. 135–140° C. at 0.05 mm.

A mixture of 3-(3-chlorophenoxy)nitrobenzene (14 g), and 5% Pt on sulfided carbon (1.25 g) in EtOAc (150 mL) was subjected to a hydrogen atmosphere (initial pressure=50 psi) on a Parr shaker. After 4 hours, the mixture was thoroughly degassed (hydrogen replaced with nitrogen), dried (MgSO$_4$), and filtered (#50 Whatman paper). The solvent was evaporated to give a pale yellow oil (12 g) which was >96% pure by GC. $^1$H-NMR (CDCl$_3$) and GC/MS (m/e=219, 221) were consistent with 3-(3-chlorophenoxy)aniline.

3-(4-Trifluoromethylphenoxy)aniline

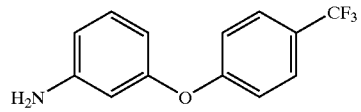

To a stirred solution of 3-hydroxyaniline (6.55 g) and 4-fluorobenzotrifluoride (9.85 g) in DMSO (50 mL) was added in one portion potassium tert-butoxide (7.86 g). The resulting dark solution was heated for 4 hours at 95° C., cooled to room temperature, then poured into water (600 mL). The mixture was extracted with ether (3×125 mL). The organic phase was washed with 2N sodium hydroxide (2×75 mL) and water (100 mL), dried (MgSO$_4$) and the solvent evaporated to give a dark oil. This oil was distilled to give the title aniline as a colorless oil (8.7 g), b.p. 110–112° C. at 0.15 mm.

4-(4-Trifluoromethylphenylthio)aniline

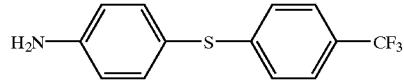

To a stirred solution of 4-fluorobenzotrifluoride (9.85 g) and 4-aminothiophenol (7.51 g) in DMSO (60 mL), cooled in an ice bath, was added in one portion potassium t-butoxide (6.73 g). The resulting mixture was stirred at 0° C. for 10 minutes, then at 60° C. overnight. After cooling, the mixture was poured into water (600 mL) and the resulting mixture extracted with ether (2×200 mL). The organic phase was washed with 2N sodium hydroxide (50 mL), then with water (50 mL). After drying (MgSO$_4$), the solvent was evaporated to give a brown solid. Recrystallization from hexane gave the title aniline as a yellow solid, m.p. 97–99° C.

4-(3-Trifluoromethylbenzyl)aniline

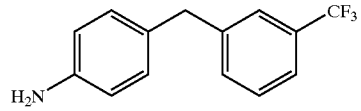

A Grignard reagent was prepared by adding a solution of 4-bromo-N,N-bis-(trimethylsilyl)aniline (9.48 g) in dry THF (75 mL) to a stirred mixture of magnesium turnings (1.09 g) in dry THF (10 mL). A second solution of the catalyst, Li$_2$CuCl$_4$ (0.33 g), was prepared by adding CuCl$_2$ (0.20 g) and LiCl (0.13 g) to dry THF (25 mL) and stirring until a homogeneous solution resulted. This catalyst solution was then added to a solution of 3-trifluormethylbenzyl bromide (7.17 g) in dry THF (75 mL). The orange-red solution was cooled in an ice bath (N$_2$ atmosphere) and the above Grignard solution (previously cooled in an ice bath) was rapidly transferred via cannula into it. After stirring for 15 minutes at 0° C., the mixture was stirred overnight at room temperature. The reaction mixture was quenched by the addition of saturated NH$_4$Cl solution (25 mL). The organic phase was separated, dried (MgSO$_4$) and the solvent evaporated to give a dark oil (11 g). To this oil was added 4 N HCl (50 mL), and the resulting mixture stirred at room temperature for 3 hours. The mixture was made basic by the careful addition of solid sodium carbonate, then extracted with ether (3×100 mL). The organic phase was dried (MgSO$_4$) and the solvent evaporated. EtOAc (100 mL) was added and the solution decanted from some insoluble material. Again the solvent was evaporated and the residue chromatographed (silica gel, 3:1 hexane/EtOAc). The second eluate was collected to give an orange oil, which darkened rapidly. The NMR (CDCl$_3$) and GC/MS (m/e=251) were consistent with the title compound. This material was converted to the HCl salt to give a brown solid.

4-(3-Trifluoromethylbenzoyl)aniline

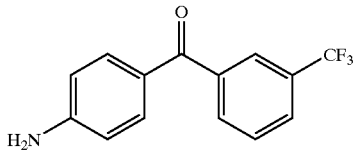

A stirred solution of 4-bromo-N,N-bis-(trimethylsilyl) aniline (9.24 g) in dry THF (100 mL) was cooled to −78° C. under an argon atmosphere. To this was slowly added a 2.5 M solution of n-butyllithium in hexane (12 mL). After the addition was complete, the reaction mixture was stirred at −78° C. for 10 minutes, then a solution of N-methyl-N-methoxy-3-trifluoromethylbenzamide (6.8 g) in dry THF (25 mL) was added dropwise. After the addition was complete, the mixture was stirred at −78° C. for 1 hour, then the cooling bath removed and the reaction temperature allowed to warm to 10° C. The reaction was quenched by the addition of saturated NH$_4$Cl solution (50 mL), then water (10 mL). The organic phase was separated, dried (MgSO$_4$) and the solvent evaporated to give a yellow liquid (12 g). This was taken up in ether (100 mL), and 4N HCl (100 mL) added. The resulting mixture was stirred for 30 minutes at room temperature, during which time a solid separated. This solid was filtered, washed with several portions of ether, then carefully added to a stirred, saturated NaHCO$_3$ solution (100 mL). The resulting mixture was extracted with ether (2×100 mL), the organic phase dried (MgSO$_4$), and the solvent evaporated to give a yellow-white solid (5.7 g). Recrystallization from methanol/water gave a white solid, m.p. 130–131° C. Spectral data were consistent with the title compound.

Ethyl 2-amino-5-(4-trifluoromethylphenoxy) benzoate

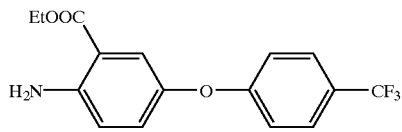

To a mechanically stirred solution of potassium t-butoxide (15.71 g) in DMSO (75 mL) was added in one portion 5-hydroxyanthranilic acid (10.2 g). The mixture was stirred at room temperature under an argon atmosphere for 10 minutes, then 4-fluorobenzotrifluoride (11.16 g) was added, and the resulting mixture stirred and heated at 75–80° C. overnight. After cooling, the mixture was poured into water (600 mL) and the pH adjusted to approximately 2.5. The resulting solid was filtered, washed with several portions of water, then recrystallized from methanol/water (charcoal) to give a tan solid (13.5 g), m.p. 165–167° C. This solid was taken up in anhydrous ethanol (250 mL) and conc. sulfuric acid (15 mL) was carefully added. The resulting mixture was heated at reflux for 24 hours, then most of the ethanol evaporated. The residue was carefully added to ice water (600 mL), the resulting mixture made basic by the slow addition of 50% NaOH solution, and then extracted with ether (2×150 mL). The organic phase was washed with water (100 mL) then saturated NaCl solution (50 mL). After drying (MgSO$_4$), the solvent was evaporated to give a yellow oil of about 98% GC purity. GC/MS indicated a parent of ion m/e=325, consistent with the title compound.

2-Aminobenzonorbornane

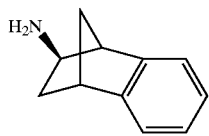

To a stirred solution of benzonorbornene (2.84 g) in dry THF (8 mL) cooled to 0° C. under an argon atmosphere was added rapidly a 1M solution of borane in THF (6.7 mL). The solution was stirred for 10 minutes at 0° C. then at room temperature for 90 minutes. The reaction mixture was again cooled to 0° C. and hydroxylamine-O-sulfonic acid (1.58 g) was added in one portion. The ice bath was removed and the reaction mixture was stirred at room temperature for 2 hours. 1N HCl (25 mL) and ether (20 mL) were added and stirring continued for 10 minutes. The phases were separated and the organic phase discarded. The aqueous phase was made basic by the careful addition of 50% NaOH solution, then extracted with ether (3×30 mL). The organic phase was dried (MgSO$_4$) and the solvent evaporated to give a yellow liquid (1.35 g) which was 98% pure as judged from GC. The NMR (CDCl$_3$) and GC/MS (m/e =159) were consistent with the title compound.

Scheme 9

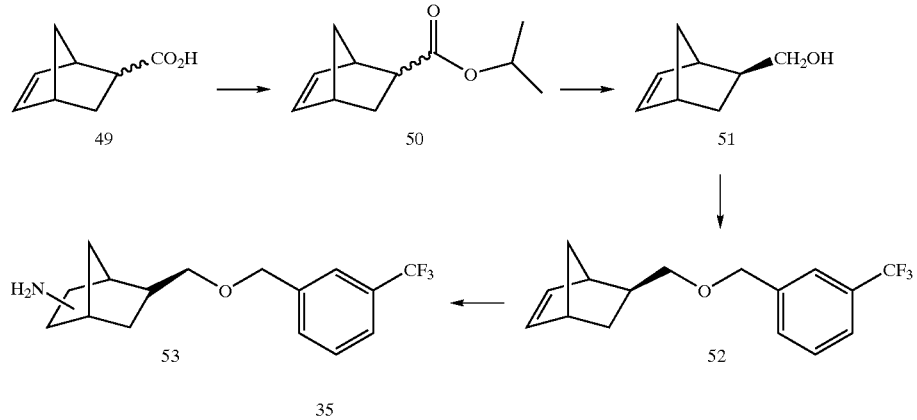

Preparation of mixture of (3-trifluoromethylbenzyloxymethyl)norbonylamines 53

Preparation of this mixture is depicted in Scheme 9. Thus, a mixture of exo- and endo-norbornenecarboxylic acids 49 (~1:4 ratio) (7.0 g), 2-iodopropane (12.8 g) and potassium carbonate (10.4 g) in DMSO (40 mL) was stirred and heated at 55° C. overnight. After cooling the mixture was diluted with water (125 mL), then extracted with pentane. The organic phase was dried (MgSO$_4$) and the solvent evaporated to give a colorless oil (8.2 g). This oil was added to a solution of sodium 2-propoxide (3.6 g) in 2-propanol (100 mL) and the resulting mixture heated at reflux for 16 hours. Removal of the 2-propanol, dilution with water (200 mL), and pentane extraction gave the norbornene isopropyl ester 50 as a 52:48 exo to endo mixture. This was separated into pure isomers via chromatography (silica gel, 95:5 hexane/EtOAc). The exo isomer of 50 (4.0 g) was dissolved in ether (50 mL), cooled to 0° C., and a 1M solution of lithium aluminum hydride in ether (14 mL) was slowly added. After the addition was complete, the mixture was heated at reflux for 1 hour. After cooling, the reaction was quenched by the sequential addition of water (0.53 mL), 15% NaOH solution (0.53 mL), then water (1.59 mL). The resulting mixture was dried (MgSO$_4$), filtered, and the solvent evaporated to give the exo-alcohol 51 (2.7 g) as a colorless liquid. The GC/MS (m/e=124) was consistent with the assigned structure.

To a stirred mixture of potassium hydride (1.0 g) in dry THF (25 mL) was carefully added a solution of 51 (2.7 g) in THF (10 mL). After the addition was complete, the mixture was stirred at room temperature for 30 minutes, then 3-trifluoromethylbenzylbromide (5.98 g) was added all at once (exothermic reaction). The reaction was heated at reflux for 2 hours, cooled, then poured into water (150 mL). Ether extraction (2×75 mL), drying (MgSO$_4$) and solvent evaporation gave a yellow oil, which was purified via chromatography (silica gel, 97:3 hexane/acetone) to give pure 52 as a colorless oil (5.2 g). NMR (CDCl$_3$) and GC/MS (m/e=282) were consistent with the structure of 52.

Conversion of 52 to the diastereomeric mixture of amines 53 was accomplished via the borane/hydroxylamine-O-sulfonic acid procedure described earlier (20% yield).

3-(3-Pyridyl)-1-propanamine

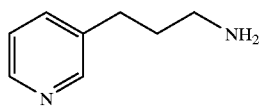

This amine was obtained by initially converting 3-(3-pyridyl)-1-propanol to the corresponding chloride following the procedure of B. Jursic et al., *Synthesis*, 1988, (11), 868, then transforming this chloride to the amine via the procedure of D. J. Dumas et al., *J. Org. Chem.*, 1988, 53, 4650.

3-[[5-(Trifluoromethyl)-2-pyridyl]oxy]-1-propanamine

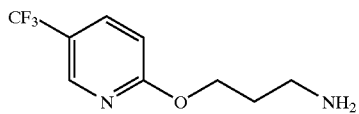

2-Fluoro-5-trifluoromethylpyridine (1.831 g, 11 mmol) was dissolved in anhydrous THF (15 mL) with stirring under nitrogen and cooled to 0° C. in an ice bath. To this was added dropwise over 30 minutes a solution of 3-amino-1-propanol (0.76 mL, 10 mmol) in anhydrous THF (15 mL) and 1M potassium tert-butoxide in THF (10 mL, 10 mmol). The yellow solution was allowed to stir and warm to room temperature in the ice bath overnight. The reaction mixture was poured into water (75 mL) and extracted with ether (2×50 mL). The organic phase was washed with brine (50 mL), dried (Na$_2$SO$_4$), filtered and evaporated under vacuum to a yellow liquid, which was nearly pure by NMR and MS, and was used as such without further purification.

(+)-Trans-1-hydroxy-2-aminocyclopentane Hydrobromide

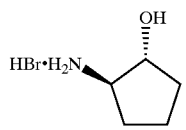

(+)-trans-1-Benzyloxy-2-aminocyclopentane hydrobromide (8.2 g, 42.8 mmol) was treated with 40% HBr (60 mL). After stirring for 3 days, the solution was concentrated in vacuo to provide 7.09 g (91%) of the hydrobromide salt as an orange solid which was pure by $^1$H-NMR (DMSO-d$_6$).

2,3-Dihydro-2,2-dimethyl-1H-inden-1-amine

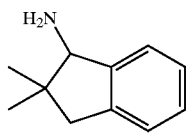

This amine was prepared according to the procedure of world patent WO 9927783.

Scheme 10

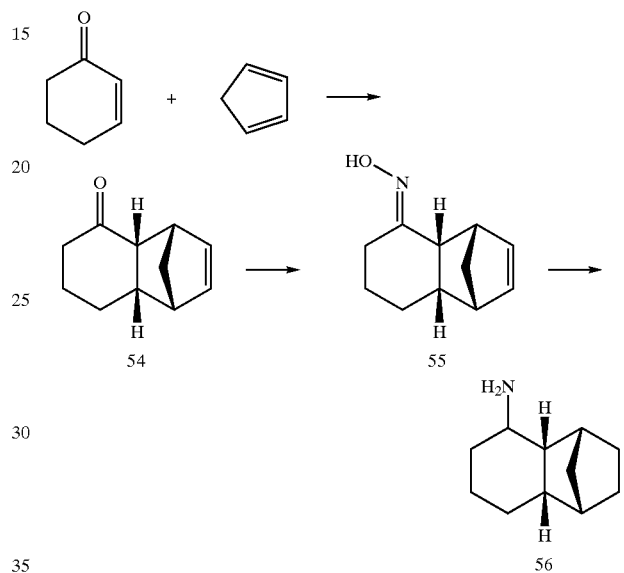

10-Amino-endo-2,5-methanobicyclo[4.4.0]dec-3-ene (56)

This compound was prepared as shown in Scheme 10. Thus, aluminum chloride (700 mg, 5.2 mmol) was added to a solution of 2-cyclohexen-1-one (2.0 g, 20.8 mmol) in toluene (200 mL). After 40 min, freshly distilled cyclopentadiene (13.7 g, 208 mmol) was added and heated to 100° C. for 2 hours. After cooling, the mixture was diluted with Et$_2$O (300 mL) and washed with satd. NaHCO$_3$ (2×150 mL) and brine (100 mL). The combined organic layers were dried (MgSO$_4$), filtered and concentrated. The residue was purified via flash chromatography using 50:1 hexanes:Et$_2$O as the eluent, to provide the endo (1.74 g) and exo (943 mg) isomers of 2,5-methanobicyclo[4.4.0]dec-3-en-10-one (54), which were pure by $^1$H-NMR and GC/MS.

Sodium acetate (1.79 g, 21.8 mmol) was added portionwise to a solution of endo-2,5-methanobicyclo[4.4.1]dec-3-en-10-one (54) (1.61 g, 9.9 mmol) and hydroxylamine hydrochloride (758 mg, 10.9 mmol) in methanol (33 mL), and stirred overnight at room temperature. The reaction was quenched with H$_2$O and extracted with ether (2×50 mL). The combined organic layers were dried (MgSO$_4$), filtered and concentrated to provide endo-2,5-methanobicyclo[4.4.0]dec-3-en-10-one oxime (55) as a pasty residue, pure by $^1$H-NMR and GC/MS.

endo-2,5-Methanobicyclo[4.4.1]dec-3-en-10-one oxime (55) (500 mg, 2.79 mmol) was dissolved in EtOAc (25 mL) and 10t Pd/C (50 mg) was added. After 3 hours under H$_2$ (40 psi), the suspension was filtered through Celite® and concentrated. The resulting residue was dissolved in EtOH (25 mL) and charged with Raney®-Ni (1.0 g). The suspension was saturated with NH$_3$ and pressurized with H$_2$ (45 psi). After 6 hours the suspension was filtered through Celite®, diluted with EtOAc (100 mL), and washed with satd. NaHCO$_3$ (100 mL ). The combined organic layers were dried over MgSO$_4$, filtered and concentrated. $^1$H-NMR and GC/MS revealed the title amine 56 as a 2:1 mixture of diastereomers (418 mg).

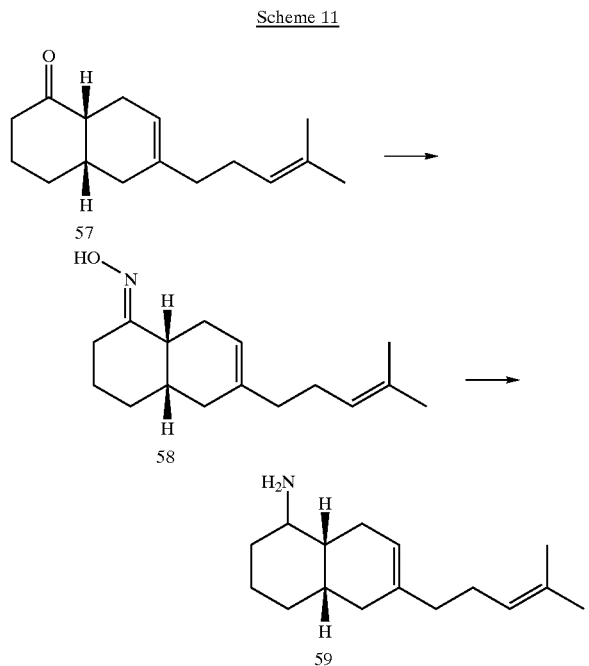

Scheme 11

10-Amino-4-(4'-methylpent-3'-enyl)-bicyclo[4.4.0]dec-3-ene (59)

Preparation of this compound was accomplished as shown in Scheme 11. Thus, aluminum chloride (700 mg, 5.2 mmol) was added to a solution of 2-cyclohexen-1-one (2.0 g, 20.8 mmol) in toluene (100 mL). After 40 min, myrcene (17 g, 125 mmol) was added and heated to 100° C. for 2 hours. After cooling, the mixture was diluted with Et$_2$O (300 mL) and washed with satd. NaHCO$_3$ (2×150 mL) and brine (100 mL). The combined organic layers were dried over MgSO$_4$, filtered and concentrated. The residue was purified via flash chromatography using 50:1 hexanes:Et$_2$O as the eluent to provide 4-(4'-methylpent-3'-enyl)-bicyclo[4.4.0]dec-3-en-10-one (57) (2.55 g), which was pure by $^1$H-NMR and GC/MS.

Sodium acetate (1.73 g, 21 mmol) was added portionwise to a solution of 4-(4'-methylpent-3'-enyl)-bicyclo[4.4.0]dec-3-en-10-one (57) (2.23 g, 9.6 mmol) and hydroxylamine hydrochloride (733 mg, 10.5 mmol) in methanol (32 mL), and stirred overnight at room temperature. The reaction was quenched with H$_2$O and extracted with ether (2×50 mL). The combined organic layers were dried over MgSO$_4$l filtered and concentrated. This gave 4-(4'-methylpent-3'-enyl)-bicyclo[4.4.0]dec-3-en-10-one oxime (58) as a pasty residue, pure by $^1$H-NMR and GC/MS.

4-(4'-Methylpent-3'-enyl)-bicyclo[4.4.0]dec-3-en-10-one oxime (600 mg, 2.42 mmol) was dissolved in EtOH (25 mL) and charged with Raney®-Ni (1.0 g). The suspension was saturated with NH$_3$ and pressurized with H$_2$ (45 psi). After 6 hours, the suspension was filtered through Celite®, diluted with EtOAc (100 mL), and washed with satd. NaHCO$_3$ (100 mL). The combined organic layers were dried over MgSO$_4$, filtered and concentrated. $^1$H-NMR and GC/MS were indicative of the pure title amine (550 mg).

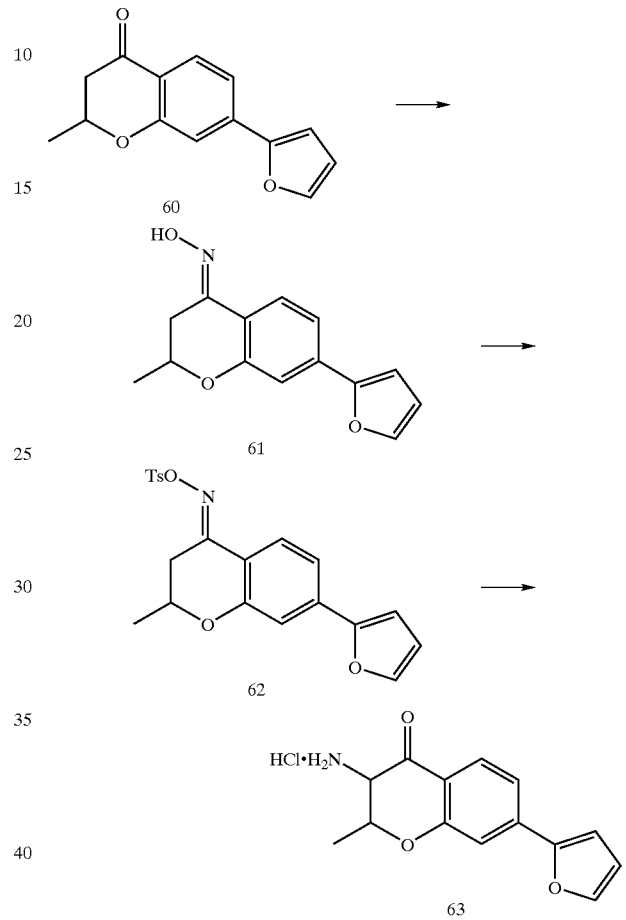

Scheme 12

2-Amino-7-furyl-3-methyl-4-chromanone Hydrochloride (63)

This amine hydrochloride salt was prepared as shown in Scheme 12. Thus, 7-trifluoromethanesulfonate-3-methyl-4-chromanone (3.0 g, 9.7 mmol) (prepared according to the procedure of K. Koch, and M. S. Biggers, *J. Org. Chem.* 1994, 59, 1216) was added to a solution of 2-(tributylstannyl)furan (3.79 g, 10.6 mmol), Pd(PPh$_3$)$_4$ (223 mg, 0.19 mmol), LiCl (1.23 g, 29.0 mmol), and two crystals of 2,6-di-t-butyl-4-methylphenol in 1,4-dioxane (50 mL), and heated to reflux for 12 hours. After cooling, the mixture was quenched with satd. NH$_4$Cl (40 mL) and extracted with Et$_2$O (2×50 mL). The combined organic layers were dried over MgSO$_4$, filtered and concentrated. The residue was purified via flash chromatography using 20:1 hexanes:EtOAc as the eluent to provide 7-furyl-3-methyl-4-chromanone (60) (1.78 g) as a yellow solid, m.p. 94–95° C.

Sodium acetate (395 mg, 4.82 mmol) was added portionwise to a solution of 7-furyl-3-methyl-4-chromanone (60) (500 mg, 2.19 mmol) and hydroxylamine hydrochloride (167 mg, 2.41 mmol) in methanol (5 mL), and stirred overnight at room temperature. The reaction was quenched with H₂O and extracted with ether (2×25 mL). The combined organic layers were dried over MgSO₄, filtered and concentrated to give 7-furyl-3-methyl-4-chromanone oxime (61) as a white solid, m.p. 175–177° C.

Toluenesulfonyl chloride (397 mg, 2.08 mmol) was added to a 0° C. solution of 7-furyl-3-methyl-4-chromanone oxime (61) (461 mg, 1.89 mmol) and pyridine (0.5 mL) in CH₂Cl₂ (10 mL). After 6 hours, the mixture was diluted with CH₂Cl₂ (30 mL) and washed with 59 HCl (20 mL). The organic layer was dried over MgSO₄, filtered and concentrated. The residue was purified via flash chromatography using 5:1 hexanes:EtOAc as the eluent, to provide 7-furyl-3-methyl-4-chromanone O-(toluenesulfonyl)-oxime (62) (429 mg) as a pink solid, m.p. 163–164° C. (dec).

An ethanolic solution of sodium ethoxide (0.35 mL, 2.87 M, 1.0 mmol) was added to a stirred solution of 7-furyl-3-methyl-4-chromanone-O-(toluenesulfonyl)-oxime (62) (410 mg, 1.0 mmol) in benzene (4 mL). After 18 hours, 3N HCl (6 mL) was added and the layers were separated. The organic phase was further extracted with 3N HCl (2×10 mL), and the combined aqueous extracts were concentrated to provide the crude title compound 63 as an orange solid (388 mg), which was used as is without further purification.

Scheme 13

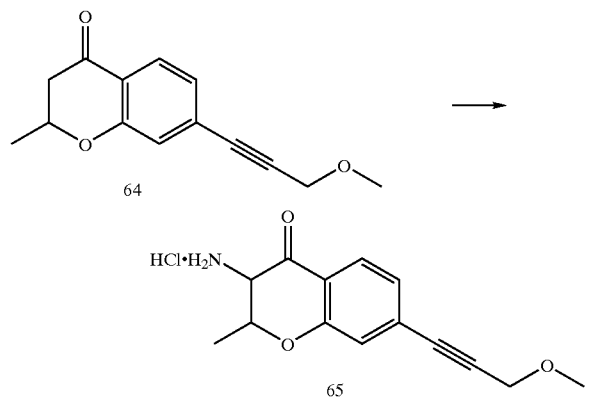

2-Amino-7-(3'-methoxypropynyl)-3-methyl-4-chromanone Hydrochloride (65)

This amine hydrochloride was prepared as shown in Scheme 13. Thus, 7-trifluoromethanesulfonate-3-methyl-4-chromanone (3.10 g, 10 mmol) (prepared according to the procedure of K. Koch and M. S. Biggers, *J. Org. Chem.* 1994, 59, 1216) was added to a solution of methyl propargyl ether (1.05 g, 15 mmol), (Ph₃P)₄Pd (210 mg, 0.30 mmol), and Et₃N (6 mL) in DMF (30 mL) and heated at 70° C. for 1 hour. After cooling, the mixture was quenched with satd. NH₄Cl (40 mL) and extracted with Et₂O (2×50 mL). The combined organic layers were dried over MgSO₄, filtered and concentrated. The residue was purified via flash chromatography using 9:1 hexanes-EtOAc as the eluent to provide 7-(3'-methoxypropynyl)-3-methyl-4-chromanone (64) (1.40 g) as a white solid, m.p. 60–63° C.

Conversion of 64 to the title compound 65 was accomplished in the same manner as described above for 2-amino-7-furyl-3-methyl-4-chromanone hydrochloride.

Scheme 14

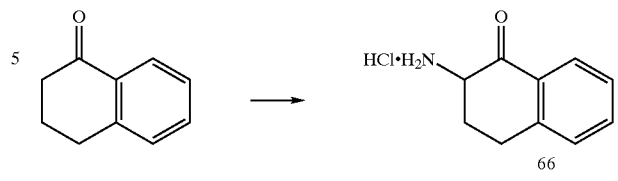

2-Amino-α-tetralone Hydrochloride (66)

This compound was obtained from α-tetralone as shown in Scheme 14, by the same procedure described above for 2-amino-7-furyl-3-methyl-4-chromanone hydrochloride.

Scheme 15

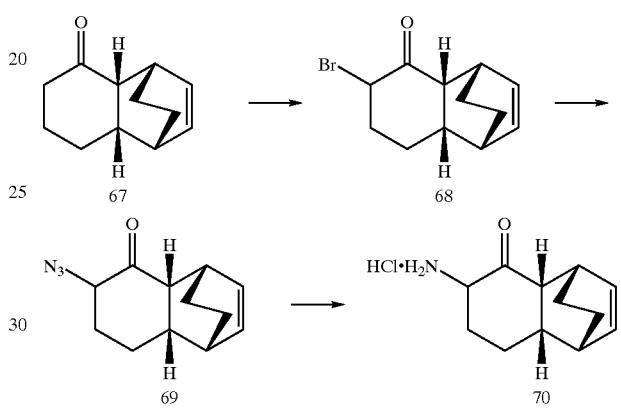

2-Amino-endo-6,9-ethanobicyclo[4.4.0]dec-7-enone Hydrochloride (70)

This amine hydrochloride was prepared as shown in Scheme 15. Thus, aluminum chloride (700 mg, 5.2 mmol) was added to a solution of 2-cyclohexen-1-one (2.0 g, 20.8 mmol) in toluene (100 mL). After 40 min, cyclohexadiene (8.3 g, 104 mmol) was added and heated to 100° C. for 2 hours. Upon cooling, the mixture was diluted with Et₂O (300 mL) and washed with satd. NaHCO₃ (2×150 mL) and brine (100 mL). The combined organic layers were dried over MgSO₄, filtered and concentrated. The residue was purified via flash chromatography using 50:1 hexanes-Et₂O as the eluent to provide endo-2,5-ethanobicyclo[4.4.0]dec-7-en-10-one (67) (2.77 g), which was pure by ¹H-NMR and GC/MS.

A solution of endo-2,5-ethanobicyclo[4.4.0]dec-7-en-10-one (67) (2.17 g, 12.3 mmol) in THF (20 mL) was added to a −78° C. solution of LDA (6.7 mL, 2.0M in THF, 13.5 mmol) in THF (30 mL). After 45 min, trimethylsilyl chloride (2.0 g, 18.5 mmol) was added, and the mixture was slowly warmed to 0° C. The mixture was diluted with satd. NaHCO₃ solution (30 mL), extracted with Et₂O (2×30 mL), dried (MgSO₄) and concentrated. The residue was dissolved in THF (60 mL), and N-bromosuccinimide (2.6 g, 14.7 mmol) was added portionwise. After 30 min, the mixture was diluted with saturated NH₄Cl solution (30 mL) and extracted with Et₂O (2×40 mL). The combined organic layers were dried (MgSO₄) and concentrated. The residue was purified via flash chromatography using 33:1 hexanes-Et₂O as the eluent to provide 2-bromo-endo-6,9-ethanobicyclo[4.4.0]dec-7-enone (68) (1.44 g) as a light yellow oil, which was pure by ¹H-NMR and GC/MS.

Sodium azide (280 mg, 4.3 mmol) was added to a solution of 2-bromo-endo-6,9-ethanobicyclo[4.4.0]dec-7-enone (68) (850 mg, 3.9 mmol) in DMF (20 mL). After 2 hours, the mixture was diluted with water (30 mL) and extracted with Et$_2$O (2×40 mL). The combined organic layers were dried (MgSO$_4$) and concentrated. The residue was purified via flash chromatography using 20:1 hexanes:Et$_2$O as the eluent to provide 2-azido-endo-6,9-ethanobicyclo[4.4.0]dec-7-enone (69) (469 mg) as an oil, which was pure by $^1$H-NMR.

Triphenylphosphine (486 mg, 1.85 mmol) was added to a solution of 2-azido-endo-6,9-ethanobicyclo[4.4.0]dec-7-enone (69) (310 mg, 1.42 mmol) in THF (10 mL) and water (1 mL). After stirring for 12 hours, the mixture was diluted with 6N HCl (10 mL) and the layers separated. The organic phase was extracted with 6N HCl (2×5 mL), and the combined aqueous layers were concentrated to dryness to give the desired title compound 70 as a thick orange oil (500 mg), whose $^1$H-NMR (DMSO-d$_6$) was consistent with the assigned structure.

Isopropyl endo-2-aminonorbornane-5-carboxylate (71) and Isopropyl endo-2-aminonorbornane-6-carboxylate (72)

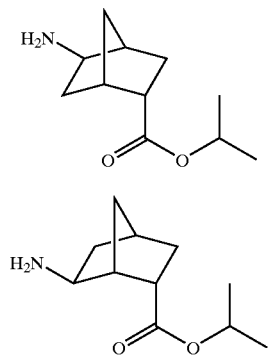

These amines were prepared from isopropyl norborn-2-ene-5-carboxylate in the same manner as described earlier (see Scheme 9).

General Procedure for Reductive Amination of Ketones to Amines

Ketone (1 mmol), ammonium acetate (20 mmol) and 3A molecular sieves (2.8 equivalents by weight) were mixed in anhydrous methanol in a dry flask under nitrogen atmosphere. Sodium cyanoborohydride (4 mmol) was added and the resulting mixture was stirred at room temperature until the disappearance of starting ketone as indicated by TLC analysis. Methanol was stripped off from the reaction mixture under vacuum, and the residue dissolved in 6N HCl. After stirring for 15 min, the non-basic materials were removed by extraction with diethyl ether. The pH of the aqueous phase was carefully raised to ~8 using 50% aqueous NaOH, and the amine was extracted with EtOAc (3 times). The EtOAc extracts were combined, washed with brine, dried (Na$_2$SO$_4$), filtered and concentrated to afford the corresponding amine. The crude amine was generally pure and used without further purification.

General Procedure for BOC-Deprotection of Amines

To an ice-cold solution of BOC-protected amine (1 mmol) in dry CH$_2$Cl$_2$ (1 mL) were added triethylsilane (0.5 mL) and trifluoroacetic acid (1 mL). Progress of the reaction was monitored by disappearance of the starting material (5 minutes to 1.5 hours). The reaction mixture was diluted with toluene and concentrated. The residue was dissolved in water (10 mL) and EtOAc (20 mL), the pH was adjusted to ~8 (aqueous NaHCO$_3$), and the organic phase separated. The aqueous phase was extracted with EtOAc (2×15 mL). The organic phases were combined, washed with brine, dried (Na$_2$SO$_4$), filtered and concentrated to give the amine.

Preparation of Amines 73 and 74

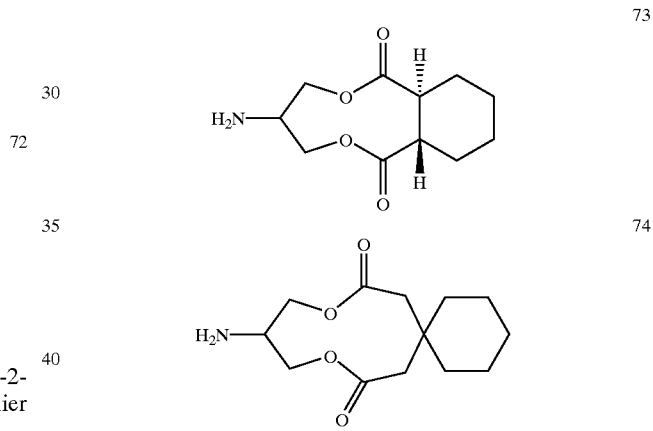

These amines were prepared from the corresponding known ketodilactones (*J. Org. Chem.* 1998, 63, 9889–94) via the standard reductive amination conditions described above. $^1$H, $^{13}$C NMR and IR spectra were consistent with the assigned structures.

Scheme 16

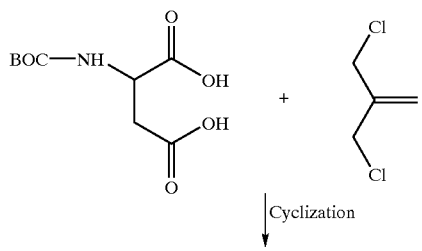

Cyclization

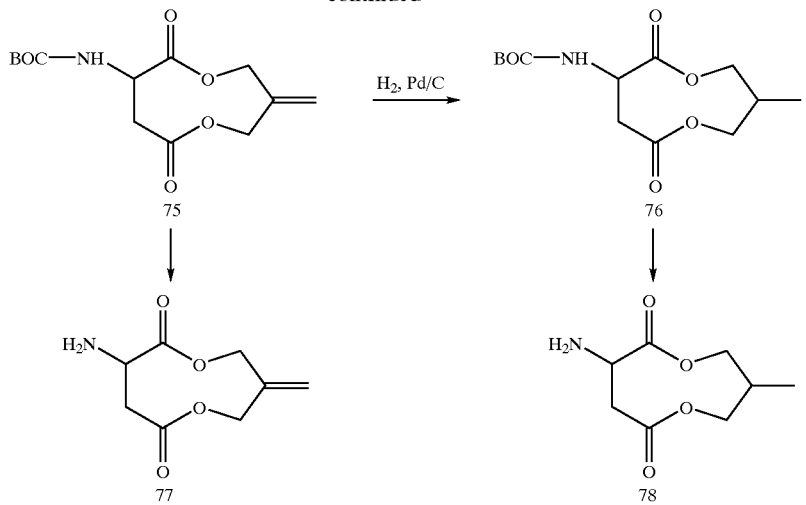

Preparation of the Amines 77 and 78

Preparation of these amines is shown in Scheme 16. The macrodilactone 75 was prepared according to the procedure of *J. Org. Chem.* 1998, 63, 9889–94. Thus, N-t-BOC-aspartic acid (2.33 g) was reacted with 2-chloromethyl-3-chloropropene (1.25 g) and $Cs_2CO_3$ (7.0 g) in DMF (1000 mL) under the standard macrolactonization conditions reported in the above reference to give 1.12 g (40% yield) of 75 as a glassy solid. Mass spectrum (EI-) indicated [M-1]+ at (m/e) 284, while the $^1H$, $^{13}C$ NMR and IR spectra were consistent with the structure of 75.

To a solution of the alkene 75 (288 mg, 1.01 mmol) in dry EtOAc (6 mL) was added 10% Pd/carbon (60 mg). The resulting mixture was purged with nitrogen and stirred under 45 psi hydrogen pressure in a Parr hydrogenator for 2.5 h. The reaction mixture was purged with nitrogen, filtered and concentrated. The residue, upon purification by flash column chromatography (silica gel, 7:3 mixture of hexane-EtOAc), afforded 91 mg (32% yield) of the reduced product 76. $^1H$, $^{13}C$-NMR and IR spectra were consistent with the structure 76.

Removal of the BOC protecting group from 75 and 76, following the general BOC-deprotection procedure described earlier, gave the corresponding amines 77 and 78 respectively. $^1H$, $^{13}C$-NMR and IR spectra were consistent with the assigned structures.

Scheme 17

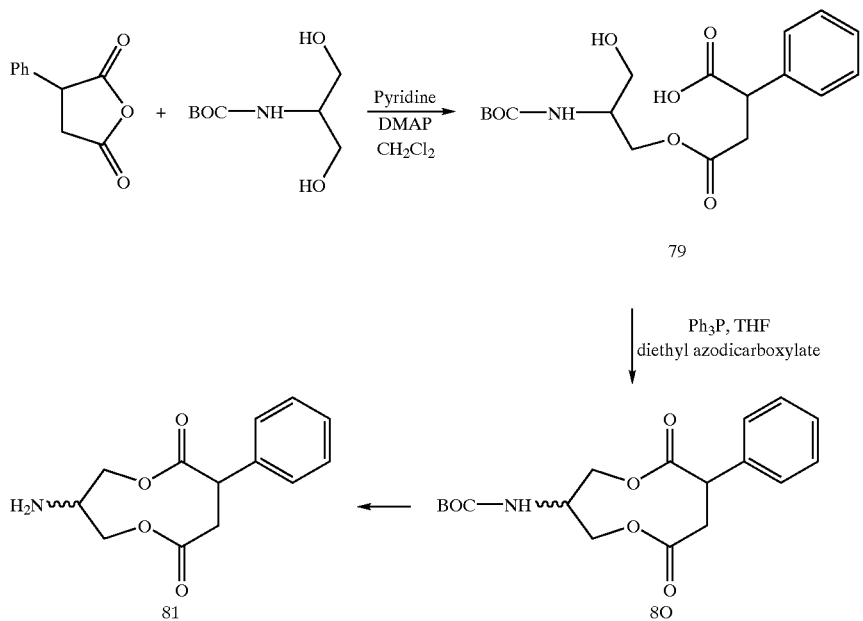

Synthesis of the Phenyl Dilactone 81

To an ice-cold (0° C.), well-stirred solution of phenyl-succinic acid (0.923 g, 5.2 mmol) and DMAP (0.064 g, 0.52 mmol) in dry $CH_2Cl_2$ (55 mL) was added dropwise under nitrogen a solution of BOC-serinol (*Synthesis* 1998, 1113–1118) (1.0 g, 5.2 mmol) over 30 minutes. The resulting mixture was slowly warmed to room temperature, stirred for an additional 12 hours, diluted with CH$_2$Cl$_2$ (40 mL), and extracted with saturated aqueous sodium bicarbonate (3×10 mL). The basic extracts were combined, carefully acidified with 2N HCl, and extracted with EtOAc (3×20 mL). The combined EtOAc extract was washed with brine, dried (Na$_2$SO$_4$), filtered and concentrated to give a white foam (1.7 g). $^1$H-NMR indicated a 1:1 diastereomeric mixture of the acids 79.

To a well-stirred ice-cold suspension of acids 79 (1.00 g, 2.72 mmol) and triphenylphosphine (786 mg, 3.0 mmol) in dry THF (122 mL) was added a solution of diethyl azodicarboxylate (0.52 g, 3.0 mmol) in THF (55 mL) drop-wise over 3 hours. The resulting mixture was slowly warmed to room temperature, stirred for an additional 5 hours, and concentrated to about 5 mL. The residual mixture was diluted with EtOAc (50 mL) and water (20 mL). The organic phase was separated, washed with aqueous NaHCO$_3$ (10 mL), brine (10 mL), dried (Na$_2$SO$_4$), filtered and concentrated to give an oily residue. Purification by flash chromatography (silica gel, hexanes) afforded 228 mg (22% yield) of a 1:1 mixture of dilactones 80, m.p.=161–162° C. Mass spectrum (EI) indicated M+ at m/e 349.

Removal of the BOC protecting group under the standard BOC deprotection conditions described earlier gave the amine 81.

Scheme 18

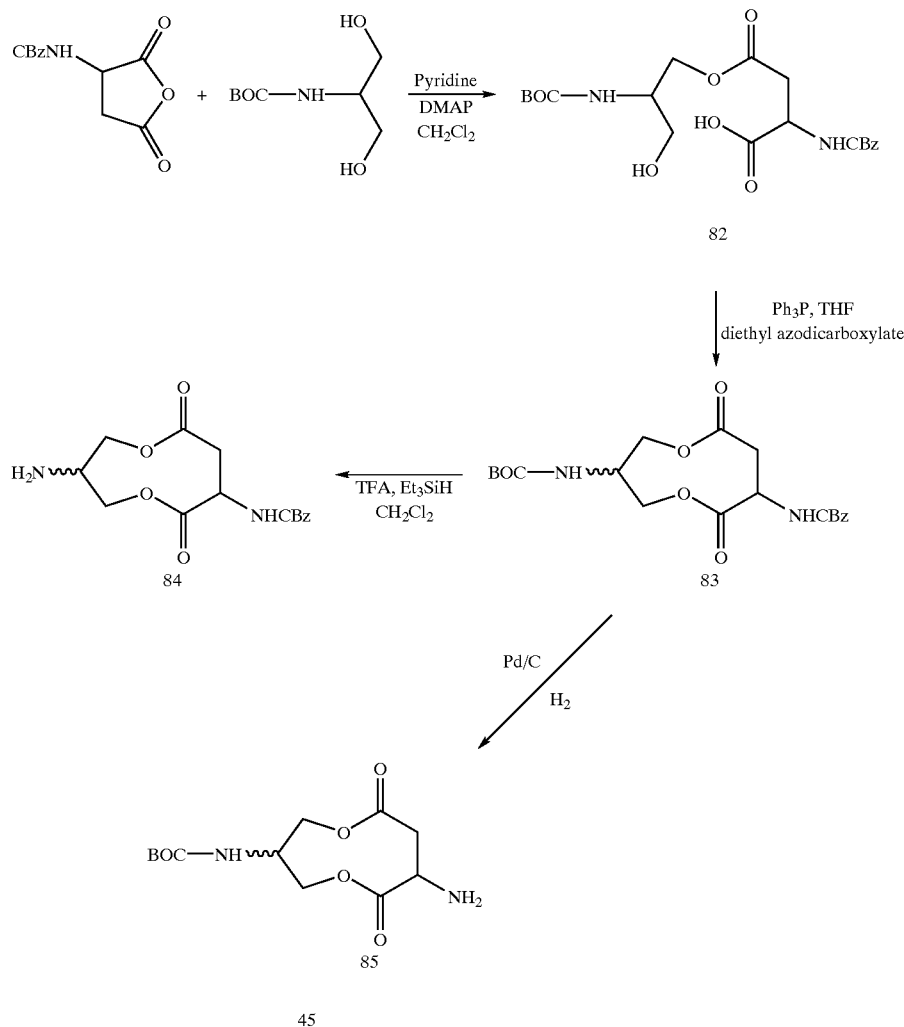

Synthesis of the Dilactoneamines 84 AND 85

To a stirred solution of serinol (3.0 g, 15.7 mmol), pyridine (1.24 g, 0.98 mol) and DMAP (0.19 g, 1.57 mmol) in dry CH$_2$Cl$_2$ (140 mL) was added dropwise a solution of N-CBZ aspartic anhydride (3.52 g, 14.13 mmol) in dry THF (20 mL). After stirring for 2 h at room temperature, the reaction mixture was concentrated to a volume of about 10 mL and diluted with EtOAc (100 mL) and water (30 mL). The pH was adjusted to 8.5 (aqueous NaHCO$_3$), and the aqueous phase was separated, acidified with 2N HCl to pH 3, and extracted with EtOAc (3×20 mL). The combined organic extract was washed with brine, dried (Na$_2$SO$_4$), filtered and concentrated to give 5.8 g of 82 as a foamy white material. $^1$H-NMR spectra indicated that it was quite pure and contained a mixture of diastereomers.

To a solution of triphenylphosphine (3.60 g, 13.75 mmol) and 1,3-diisopropylcarbodiimide (2.80 g, 13.75 mmol) in dry THF (1.15 L) was added dropwise over 3 hours a solution of the acid 82 (5.5 g, 12.5 mmol) in dry THF (100 mL). The resulting mixture was stirred for an additional 6 hours, concentrated in vacuum to a volume of about 20 mL, and diluted with ether (200 mL) and water (100 mL). The organic phase was separated and washed with 5% aqueous NaHCO$_3$ and brine, dried (Na$_2$SO$_4$), filtered and concentrated in vacuum. The oily residue was purified by flash column chromatography to afford 1.3 g (23 % yield) of the desired dilactones 83. Mass spectrum (ES−) indicated an m/e of 421 (M−1)+. $^1$H, $^{13}$C-NMR and IR spectra were consistent with the structure 83.

Dilactone 83 was deprotected under standard BOC deprotection conditions to give the amine 84.

To a solution of the N-CBz-protected dilactone 83 (200 mg, 0.47 mmol) in EtOAc (10 mL) was added 10% Pd/C (40 mg), and the resulting mixture was stirred under a balloon pressure of hydrogen gas for 12 hours. The reaction mixture was purged with N$_2$, filtered through a sintered glass funnel, and concentrated to give the amine 85 (126 mg). This crude amine was used without further purification.

Preparation of the Amines 86 and 88

1,5,5-trimethyl-3-oxo-1-cyclohexylcarboxylic acid (M. S. Ziegler and R. M. Herbst, *J. Org. Chem.* 1951, 16, 920) was coupled to N-Methyl-2-phenylethylamine using the standard HOAt, EDCI and DMAP-mediated coupling conditions to give (N-methyl-N-(2-phenylethyl)]-1,5,5-trimethyl-3-oxo-1-cyclohexylcarboxamide as a pale yellow oil. Mass spectrum indicated the parent ion at m/e 301. $^1$H and $^{13}$C-NMR spectra were consistent with this structure.

Amine 89 was prepared from this ketone according to the general procedure of world patent WO 9927783, by converting to the corresponding N-hydroxyoxime followed by hydrogenation in the presence of Raney® Ni. $^1$H-NMR of the amine indicated a 1:1 mixture of diastereomers.

Scheme 19

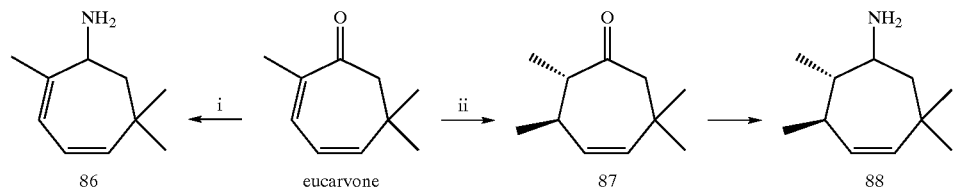

86    eucarvone    87    88

Key: i. NH$_4$Cl, Et$_3$N, Ti(O-i-Pr)$_4$, 14h then NaBH$_4$; ii. Me$_3$Al, cat. CuBr, THF Syntheses of 2,6,6-trimethyl-2,4-cycloheptadienylamine (86) and 2,3,6,6-tetramethyl-3-cycloheptenone (87), which is the precursor to the amine 88, are shown in Scheme 19. Thus, eucarvone (*Can. J. Chem.* 1974, 52, 1352) was readily converted to the corresponding amine 86 using the titanium isopropoxide/NaBH$_4$/Et$_3$N-mediated reductive amination procedure described in *Synlett* 1999, 1781. Cu(I)-catalyzed Michael addition of trimethylaluminum to eucarvone, using the procedure described in *Tetrahedron* 1995, 51, 743–754, gave 2,3,5,5-tetramethyl-3-cycloheptenone (87). The latter was converted to 2,3,5,5-tetramethyl-2-cycloheptenylamine (88) according to the general procedure of world patent WO 9927783.

N-methyl-N-(2-phenylethyl)-(1,5,5-trimethyl-3-aminocyclohexyl)carbamide (89)

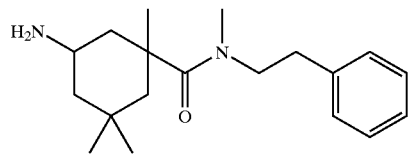

89

3-(3,3-Dimethylbutoxycarbonyl)-3,5,5-trimethylcyclohexylamine (90)

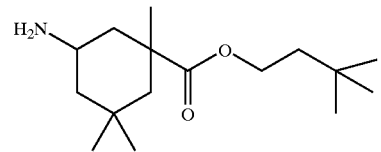

90

1,5,5-trimethyl-3-oxo-1-cyclohexylcarboxylic acid (3.0 g) (M. S. Ziegler and R. M. Herbst, *J. Org. Chem.* 1951, 16, 920) was treated with 3,3-dimethylpentanol (1.84 g), DMAP (2.21 g) and 1,3-diisopropylcarbodiimide (2.17 g) in CH$_2$Cl$_2$ (80 mL) under standard coupling conditions to give 2.41 g (55% yield) of 3-(3,3-dimethylbutoxycarbonyl)-3,5,5-trimethylcyclohexanone. Mass spectrum (EI) indicated parent ion at m/e 268.

This ketone was converted to the title amine 90 according to the general procedure of world patent WO 9927783, by converting to the corresponding oxime followed by hydrogenation in the presence of Raney® Ni. $^1$H-NMR of the amine 90 indicated a 1:1 mixture of diastereomers.

Scheme 20

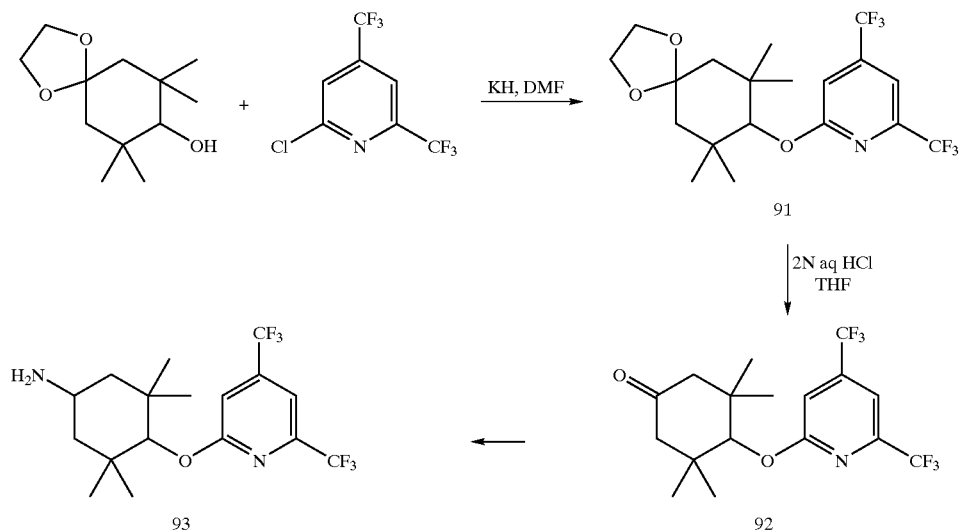

4-(4,6-Bis-trifluoromethyl-2-pyridyl)oxy-3,3,5,5-tetramethylcyclohexylamine (93)

Synthesis of this amine is shown in Scheme 20. Thus, 4-hydroxy-3,3,5,5-tetramethylcyclohexyl-1,1-ethylene glycol acetal (900 mg, 4.2 mmol) was dissolved in dry DMF (8.4 mL), the mixture was cooled to 0° C., and 35% (wt) oil suspension of KH (591 mg, 5.04 mmol) was added. After stirring the mixture for 1 hour, a solution of 2-chloro-4,6-bis-trifluoromethyl-2-pyridine (1.48 g, 6.3 mmol) in DMF (2 mL) was added dropwise. The mixture was stirred at 0° C. for 1 hour, then at room temperature for 12 hours, and carefully quenched with ammonium chloride. Diethyl ether (100 mL) was added, and the organic phase was separated, washed with brine, dried (MgSO$_4$) and concentrated to a dark brown solid. Recrystallization from hot hexanes yielded 950 mg (53% yield) of 4-(4,6-bis-trifluoromethyl-2-pyridyl)oxy-3,3,5,5-tetramethylcyclohexyl-1,1-ethyleneglycolacetal (91), m.p.=105–106° C.

The acetal 91 (900 mg) was dissolved in a 1:1:1 mixture (30 mL) of THF, dioxane and 2N HCl, and the resulting solution was stirred at room temperature for 12 hours, when GC indicated complete disappearance of the starting material. The mixture was diluted with water and diethyl ether (50 mL each), the organic phase was separated, washed with brine, dried (Na$_2$SO$_4$) and concentrated to give an oily residue. This residue was chromatographed on silica gel (hexane-EtOAc, 5:1) to give 712 mg (96% yield) of ketone 92 as a colorless oil. Mass spectrum (EI) indicated parent ion m/e of 383.

Reductive amination of 92 to the title amine 93 was accomplished according to the general procedure of world patent WO 9927783.

Scheme 21

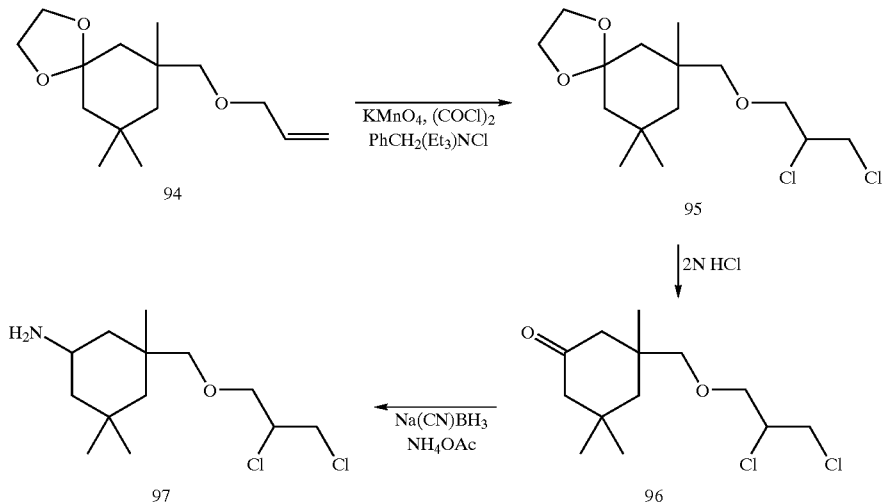

3-(2,3-Dichloropropyloxy)methyl-3,5,5-trimethylcyclohexylamine (97)

Synthesis of the amine 97 is shown in Scheme 21. Dichlorination of the alkene 94, according to the procedure of *Tetrahedron Lett.* 1991, 32, 1831–4, yielded the acetal 95. The latter (500 mg) was dissolved in a 1:1 mixture of THF and 2N HCl. The resulting solution was stirred at room temperature for 1 hour, when TLC indicated that the starting material had disappeared. The mixture was diluted with EtOAc and water (30 mL each), and the organic phase was separated and washed with brine, dried ($Na_2SO_4$), filtered and concentrated to give 383 mg of ketone 96 as an oil. $^1$H-NMR was consistent with a diasteromeric mixture of isomers. Reductive amination following the standard procedure described earlier afforded the title amine 97.

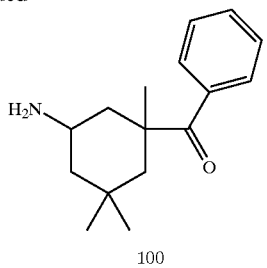

100

3-Benzoyl-3,5,5-trimethylcyclohexlamine (100)

Preparation of this amine is shown in Scheme 22. 3-Cyano-3,5,5-tetramethylcyclohexyl-1,1-ethyleneglycolacetal (98) (World Patent WO 9927783), upon reaction with phenyllithium followed by acid hydrolysis, afforded the diketone 99, which was converted to the title aminoketone 100 according the procedure of the above patent.

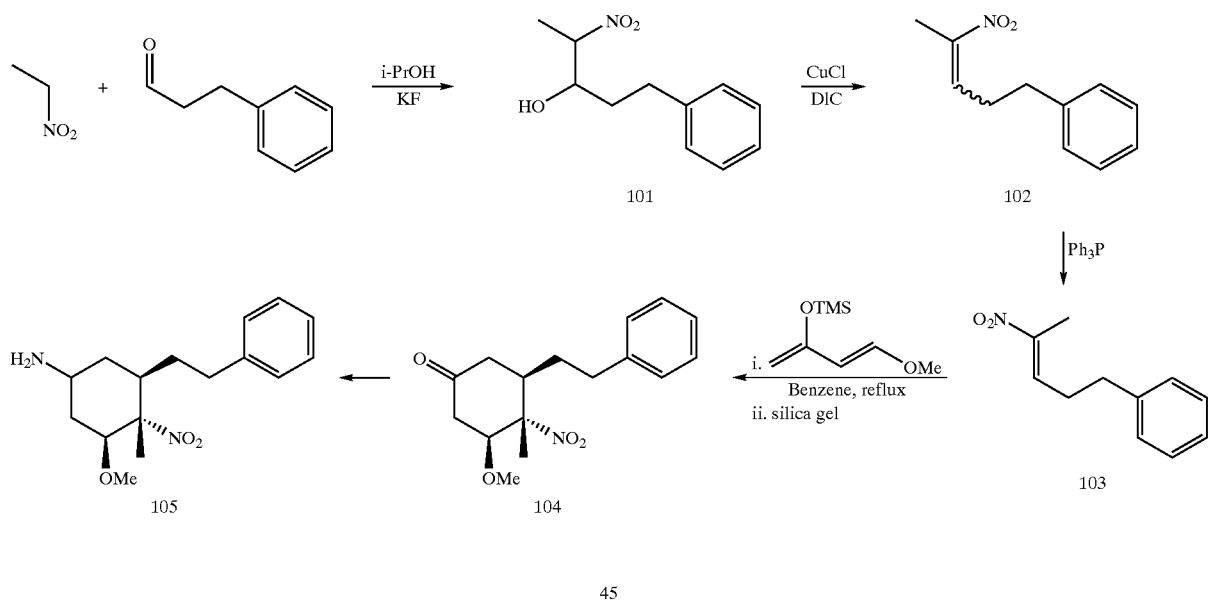

5β-(2-Phenylethyl)-3β-methoxy-4β-methyl-4-nitro-cyclohexylamine (105)

Preparation of the amine 105 is shown in Scheme 23. Condensation of nitroethane with dihydrocinnamaldehyde, according to the procedure of *Bull. Chem. Soc. Jap.* 1968, 41, 1441, gave the corresponding nitro alcohol 101. Dehydration of 101, according to the procedure of *Synthesis*, 1982, 1017, followed by polymer supported triphenylphosphine-mediated isomerization (*Tetrahedron Lett.* 1998, 39, 811–812), gave the alkene 103. Diels-Alder cycloaddition of 103 to Danishefsky's diene, according to the procedure of *Tetrahedron Lett.* 2000, 41, 1717, yielded the ketone 104. The ketone 104 was converted to the amine 105 according to the standard procedure of World Patent WO 9927783.

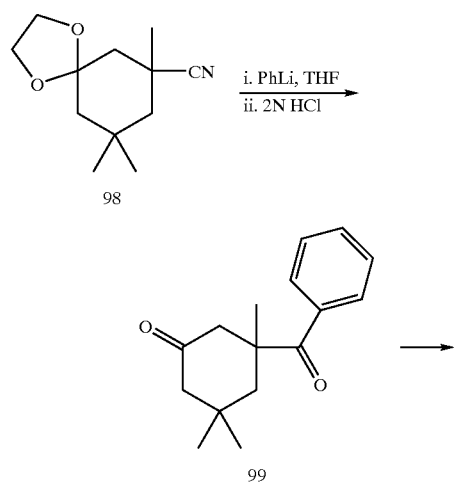

Scheme 24

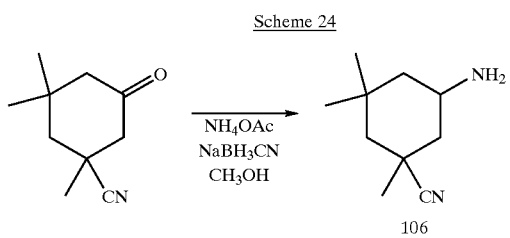

3-Cyano-3,5,5-trimethylcyclohexylamine (106)

This compound was prepared (Scheme 24) by reductive amination of 3-cyano-3,5,5-trimethylcyclohexanone according to the standard reductive amination procedure described above. The mass spectrum (EI) indicated parent ion m/e of 167.

Scheme 25

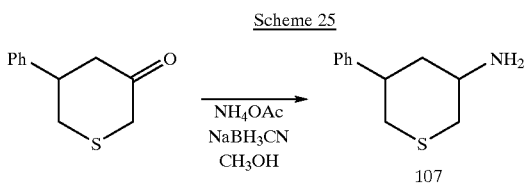

3-Amino-5-phenylthiopyran (107)

This compound was prepared as shown in Scheme 25. Thus, to 0.96 g (5 mmol) of 5-phenyl-3-thiopyranone (P. T. Lansbury, et al., *J. Am. Chem. Soc.* 1970, 92, 5649) in 50 mL of anhydrous methanol was added 7.7 g (100 mmol) of ammonium acetate and 6.5 g of 3A molecular sieves. After stirring 30 minutes at room temperature, 1.25 g (20 mmol) of sodium cyanoborohydride was added portionwise. After stirring 16 hours, the mixture was gravity filtered, and the methanol was evaporated under vacuum. The residue was partitioned between ice/HCl and ether. The acidic aqueous phase was extracted twice more with ether, then it was made basic with ice and 50% NaOH aqueous. The mixture was extracted with $CH_2Cl_2$, dried ($MgSO_4$), and evaporated to give 0.19 g (20%) of the title compound. GC/MS showed 100% purity with a molecular ion of 193.

Scheme 26

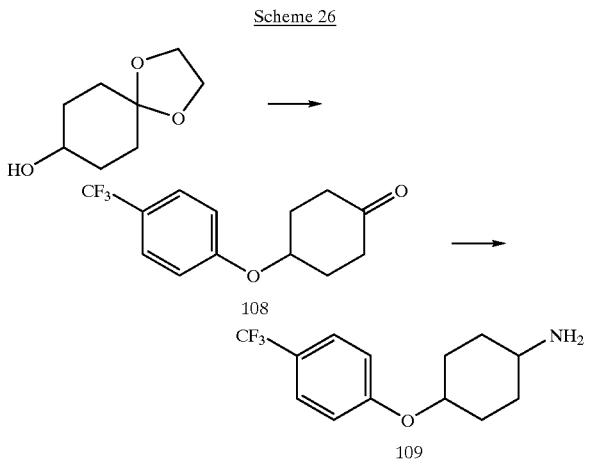

4-(4-Trifluoromethyl)phenoxycyclohexylamine (109)

This compound was prepared according to Scheme 26. To a stirred solution of sodium hydride (1.2 g, 0.05 mol) in 50 mL of DMF was added dropwise over 10 minutes a solution of 1,4-dioxaspiro[4.5]decan-8-ol (7.5 g, 0.047 mol) in 15 mL of DMF. The mixture was stirred at ambient temperature for 30 minutes. 4-Fluorobenzotrifluoride (7.71 g, 0.047 mol) was added all at once and the reaction stirred at room temperature for 2 hours and then overnight at 70° C. The reaction mixture was poured into cold water (700 mL) and the solution made slightly acidic by the addition of 1N HCl. The mixture was filtered and the aqueous filtrate extracted with hexane (2×150 mL). The filtered solid was dissolved in the hexane extracts and washed with water (50 mL). The solution was dried over $MgSO_4$, filtered and concentrated to afford a white solid. This solid was recrystallized from methanol/water to give the pure ketal (8.6 g, 61%).

Silica gel (30 g) was suspended in 150 mL of $CH_2Cl_2$. To this suspension was added dropwise over 5 minutes 7 mL of a 12% HCl solution in water. The mixture was stirred vigorously to prevent clumping. A solution of the above ketal (8.0 g, 26.49 mmol) dissolved in 75 mL $CH_2Cl_2$ was added and the reaction was stirred for 3 hours. The mixture was then filtered and the silica gel pad was washed with 500 mL $CH_2Cl_2$. The solvent was evaporated to afford 5.8 g (86%) of 4-(4-trifluorophenoxy)cyclohexanone (108).

Reductive amination of ketone 108 according to the standard reductive amination procedure described above, gave the title compound 109.

Scheme 27

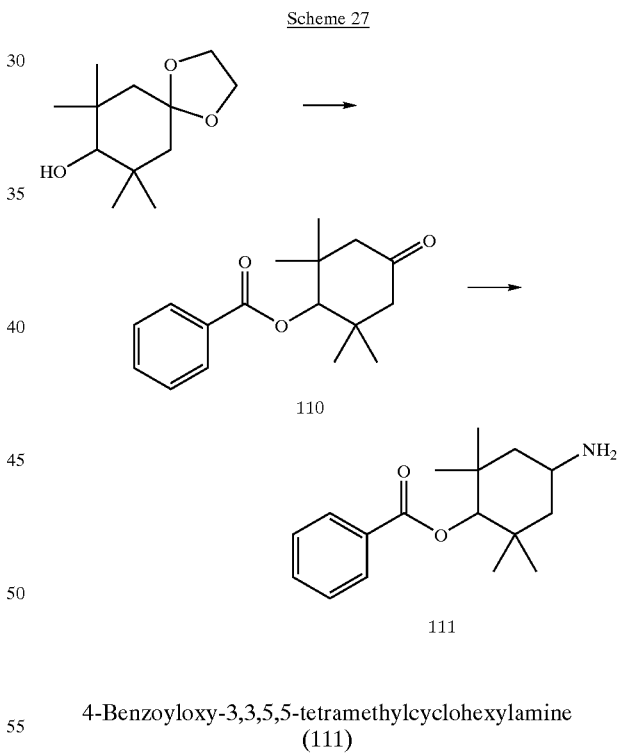

4-Benzoyloxy-3,3,5,5-tetramethylcyclohexylamine (111)

This compound was prepared following the procedure of Scheme 27. To a stirred solution of 7,7,9,9-tetramethyl-1,4-dioxaspiro[4.5]decan-8-ol (0.37 g, 1.73 mmol) in 6 mL of THF cooled to 0° C. was added n-BuLi (2.5M in hexanes, 1.73 mmol, 0.7 mL) dropwise. The reaction was stirred for 10 min. Benzoyl chloride (1.73 mmol, 0.2 mL) was then added, and the reaction was allowed to warm to room temperature and stirred overnight. The reaction mixture was poured into 50 mL 0.5N NaOH and extracted with ether (3×20 mL). The ethereal layer was dried over $MgSO_4$, filtered and concentrated. The residue was purified by radial chromatography using 4:1 hexane-EtOAc as the eluent. Thus obtained was 0.55 g (~100%) of the benzoyloxyketal.

Silica gel (2.2 g) was suspended in 10 mL of CH$_2$Cl$_2$. To this suspension was added dropwise over 5 minutes 0.5 mL of a 12% HCl solution in water. The mixture was stirred vigorously to prevent clumping. A solution of the above benzoyloxy ketal dissolved in 5 mL CH$_2$Cl$_2$ was added and the reaction was stirred for 3 hours. The mixture was then filtered and the silica gel pad was washed with 100 mL CH$_2$Cl$_2$. The solvent was evaporated to afford 0.46 g (90%) of the benzoyloxycyclohexanone 110 as a clear oil.

To a stirred solution of the benzoyloxycyclohexanone 110 (0.46 g, 1.68 mmol) in 4 mL of methanol was added all at once a solution of hydroxylamine hydrochloride (0.23 g, 3.25 mmol) and potassium acetate (0.32 g, 3.25 mmol) in 4 mL of water. The reaction was stirred at room temperature overnight. Water (20 mL) was added and the resulting mixture extracted with ether (3×10 mL). The ether extracts were combined, washed with saturated NaHCO$_3$ (1×20 mL) and brine (1×15 mL). The ethereal layer was dried over MgSO$_4$, filtered and concentrated to give the desired oxime (0.39 g, 80%) as a mixture of E and Z isomers.

Raney® Nickel (0.8 g wet weight, Aldrich Chemical Co.) in a 500 mL Parr pressure bottle was washed with water (3×20 mL) then ethanol (3×20 mL), the wash solvent being decanted each time. To this washed catalyst was added a solution of the oxime (0.39 g, 1.35 mmol) in anhydrous ethanol (30 mL). Some heating of this solution was required for dissolution. The resulting mixture was saturated with ammonia by bubbling ammonia gas through the solution for 1 minute. This solution was placed under a hydrogen atmosphere (initial hydrogen pressure=50 psi) on a Parr shaker and shaken for 7 hours. The reaction mixture was then filtered through a pad of Celite® and the solvent was evaporated to yield a nearly colorless liquid (0.37 g, quantitative yield). The proton NMR and GC/MS were consistent with this material being a diastereomeric (4:1 ratio) mixture of the title amine 111. This material was used as is with no additional purification.

Scheme 28

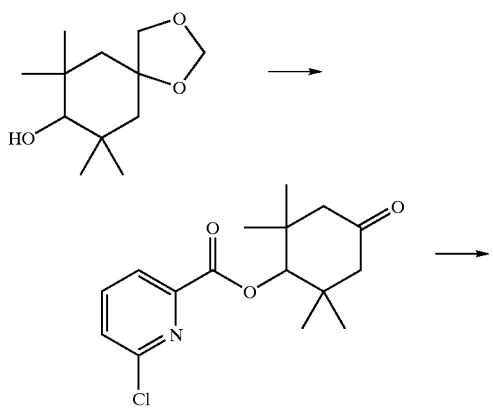

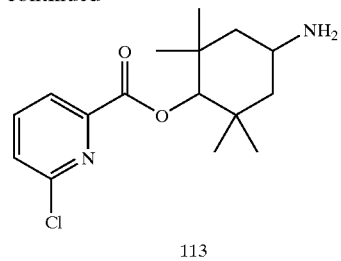

113

4-Amino-2,2,6,6-tetramethylcyclohexyl-6-chloro-2-pyridinecarboxylate (113)

This compound was synthesized as shown in Scheme 28. To a stirred solution of 7,7,9,9-tetramethyl-1,4-dioxaspiro[4.5]decan-8-ol (0.32 g, 1.50 mmol) in 5 mL of THF cooled to 0° C. was added n-BuLi (2.5M in hexanes, 1.50 mmol, 0.6 mL) dropwise. The mixture was stirred for 10 minutes. 6-Chloropicolinoyl chloride (1.50 mmol, 0.26 g) was then added as a solution in 1 mL THF and then the reaction was allowed to warm to room temperature. The solution solidified, so an additional 5 mL of THF was added and the reaction stirred overnight. The reaction mixture was poured into 40 mL 0.5N NaOH and extracted with ether (3×20 mL). The ethereal layer was dried over MgSO$_4$, filtered and concentrated. Proton NMR revealed the expected product together with starting material in 1.6:1 ratio. These compounds could not be separated by silica gel chromatography so the mixture was carried on to the next step and purified there.

Silica gel (1.4 g) was suspended in 10 mL of CH$_2$Cl$_2$. To this suspension was added dropwise over 5 minutes 0.3 mL of a 12% HCl solution in water. The mixture was stirred vigorously to prevent clumping. A solution of the above mixture dissolved in 5 mL CH$_2$Cl$_2$ was added and the reaction was stirred for 3 hours. The mixture was then filtered and the silica gel pad was washed with 100 mL CH$_2$Cl$_2$. The solvent was evaporated to afford an oil. Precipitation of the desired picolinic ester 112 was effected by adding 10 mL of 4:1 hexane-EtOAc solution. The resulting solid was filtered and washed with 10 mL of 4:1 hexane-EtOAc. The hexane-EtOAc washings were combined and evaporated to yield an oil. The above procedure was repeated 3 times to afford the picolinic ester 112 as a white solid (214 mg, 46% for two steps). Proton NMR and GC/MS showed the desired product in >95% purity.

A mixture of this ester (200 mg, 0.65 mmol), titanium(IV) isopropoxide (1.30 mmol, 0.38 mL), ammonium chloride (1.30 mmol, 70 mg) and triethylamine (1.30 mmol, 0.18 mL) in absolute ethanol (10 mL) was stirred under nitrogen at ambient temperature for 12 hours. Sodium borohydride (0.97 mmol, 40 mg) was then added and the resulting mixture was stirred for an additional 8 hours at ambient temperature. The reaction was then quenched by pouring into aqueous ammonia (20 mL, 2.0 M), and the resulting solution was extracted with ether (3×20 mL). The combined ether extracts were extracted with 2N HCl (2×20 mL) to separate the non-basic materials. The acidic solution was washed once with ether (20 mL), and then treated with aqueous sodium hydroxide (2N) to pH 10–12, and extracted with EtOAc (3×20 mL). The combined EtOAc washings were dried over MgSO$_4$, filtered and concentrated to afford an oil. This material was consistent with a 6:1 diastereomeric mixture of the title cyclohexylamines. Proton NMR and GC/MS showed the desired product in ~75% purity. This mixture of amines was used as is without further purification.

trans-2-Thiomethylcyclohexylamine

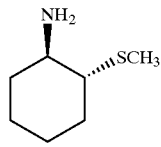

This amine was prepared from cyclohexene using the azasulfenylation technology of B. M. Trost and T. Shibata, *J. Am. Chem. Soc.* 1982, 104, 3225.

Scheme 29

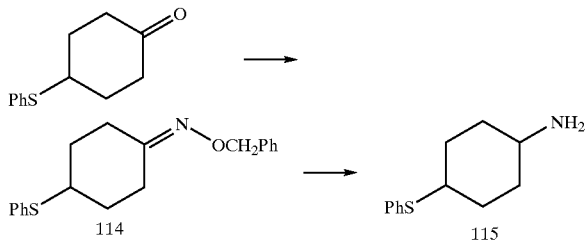

4-Phenylthiocyclohexylamine (115)

This compound was prepared following the procedure shown in Scheme 29. To stirred solution of 4-phenylthiocyclohexanone (V. K. Yadav and D. A. Jeyaraj, *J. Org. Chem.* 1998, 63, 3474) (1.20 g, 5.83 mmol) in 20 mL of methanol was added all at once a solution of benzyloxyamine hydrochloride (1.80 g, 11.22 mmol) and potassium acetate (1.10 g, 11.22 mmol) in 20 mL of water. The reaction was stirred at room temperature overnight. Water (60 mL) was added and the resulting mixture extracted with ether (3×40 mL). The ether extracts were combined, washed with satd. NaHCO$_3$ (1×50 mL) and brine (1×40 mL). The ethereal layer was dried over MgSO$_4$, filtered and concentrated to give an oil. This material was purified via radial chromatography (9:1 hexane-EtOAc) to afford the corresponding O-benzyloxime 114 (1.72 g, 95%) as a mixture of E and Z isomers.

Lithium aluminum hydride (5.08 mmol, 0.19 g) was suspended in 10 mL of anhydrous ether and cooled to 0° C. The O-benzyloxime 114, dissolved in 5 mL of ether, was added dropwise, and the reaction was allowed to warm to room temperature and stirred for 4 hours. Excess lithium aluminum hydride was destroyed by careful, simultaneous addition of water (0.2 mL) and 1N NaOH (0.2 mL). The mixture was filtered and the salts washed with 50 mL of ether. The solvent was evaporated to afford 0.62 g (93%) of the title amine 115 as an oil. Proton NMR and GC/MS revealed the product to be a 1.3:1 ratio of diastereomeric amines in >95% purity.

Scheme 30

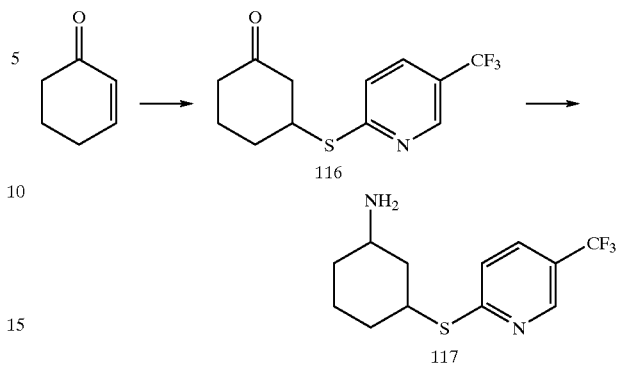

3-{[3-(Trifluoromethyl)-2-pyridinyl]sulfanyl}-cyclohexylamine (117)

This amine was prepared following the method shown in Scheme 30. To a stirred solution of 2-cyclohexen-1-one (0.44 mL, 4.58 mmol) and 2-mercapto-5-trifluoromethylpyridine (0.82 g, 4.58 mmol) in 20 mL CH$_2$Cl$_2$ at ambient temperature was added bismuth trichloride (60 mg, 0.18 mmol). The reaction was stirred at room temperature overnight and concentrated. The residue was purified via radial chromatography using 4:1 hexane-EtOAc as the eluent to afford 1.12 g (89%) of the conjugate addition product 2-(3-oxo-cyclohexylthio)-5-trifluoromethylpyridine (116).

To a stirred solution of 116 (0.26 g, 0.95 mmol) in 3 mL of methanol was added all at once a solution of benzyloxyamine hydrochloride (0.29 g, 1.83 mmol) and potassium acetate (0.18 g, 1.83 mmol) in 3 mL of water. The reaction was stirred at room temperature overnight. Water (10 mL) was added and the resulting mixture extracted with ether (3×10 mL). The ether extracts were combined, washed with saturated NaHCO$_3$ (1×15 mL) and brine (1×15 mL). The ethereal layer was dried over MgSO$_4$, filtered and concentrated to give an oil. This material was purified via radial chromatography (9:1 hexane-EtOAc) to afford the separated oximes (0.32 g, 89%). The E-isomer (R$_f$=0.33) and Z-isomer (R$_f$=0.25) showed consistent proton NMR and GC/MS spectral characteristics.

Lithium aluminum hydride (1.33 mmol, 50 mg) was suspended in 3 mL of anhydrous ether and cooled to 0° C. The combined oximes, dissolved in 1 mL of ether, was added dropwise and the reaction was allowed to warm to room temperature and stirred for 4 hours. Excess lithium aluminum hydride was destroyed by careful, simultaneous addition of water (50 μL) and 1N NaOH (50 μL). The mixture was filtered and the salts washed with ether to a volume of 100 mL. The ether solution was extracted with 2N HCl (2×50 mL) to separate the non-basic materials. The acidic aqueous solution was washed once with ether (50 mL), then treated with aqueous sodium hydroxide (2M) to pH 10–12, and extracted with ether (3×50 mL). The ethereal layer was dried over MgSO$_4$, filtered and concentrated to afford 121 mg (52%) of the desired title amine 117 as an oil. Proton NMR and GC/MS revealed the product to be a 1.3:1 ratio of diastereomeric amines in >95% purity.

Scheme 31

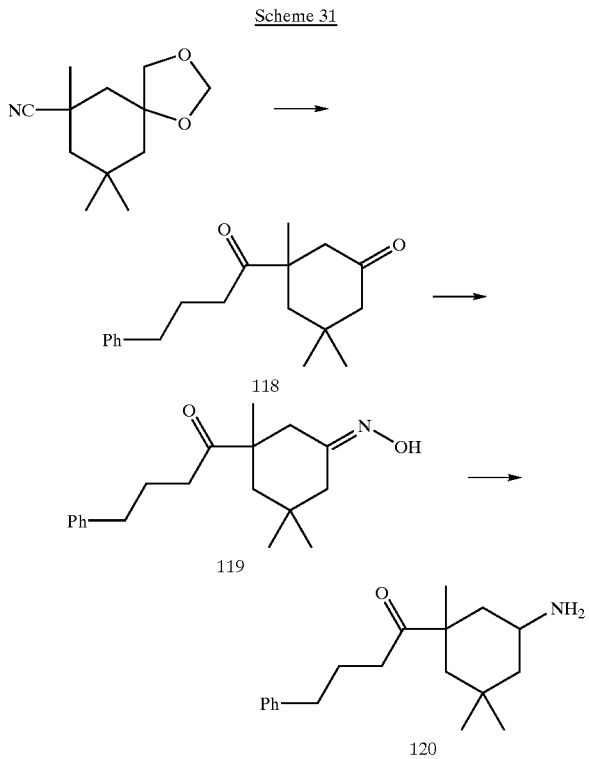

1-(5-Amino-1,3,3-trimethylcyclohexyl)-4-phenyl-1-butanone (120)

Synthesis of this amine was accomplished by the method depicted in Scheme 31. A suspension of naphthalene (1.23 g, 9.57 mmol) and lithium granules (67 mg, 9.57 mmol) in 10 mL of THF at ambient temperature was stirred overnight under nitrogen. This lithium naphthalide solution was cooled to −60° C. and phenyl 3-phenylpropyl sulfide (1.1 g, 4.78 mmol) was added. The reaction was warmed to −20° C. to ensure complete reaction and then recooled to −60° C. A solution of 7-cyano-7,9,9-trimethyl-1,4-dioxaspiro[4.5]decane (0.5 g, 2.39 mmol) in 5 mL THF was added and the solution warmed to 0° C. and stirred for 2 hours at that temperature. The reaction was quenched by the addition of 10 mL of saturated ammonium chloride solution and then treated with 2N HCl to pH ~4 and stirred at room temperature overnight. The mixture was extracted with ether (3×30 mL), dried over MgSO$_4$, filtered and evaporated. The residue was purified via radial chromatography using 6:1 hexane-EtOAc as the eluent. Thus obtained was a 1:3 mixture of 3-(2-oxo-4-phenylbutyl)-3,5,5-trimethylcyclohexanone 118 (136 mg, R$_f$=0.18) and its ketal (509 mg, R$_f$=0.33), the product of an incomplete hydrolysis. The total yield for the addition of 1-lithio-3-phenylpropane to the nitrile was calculated to be 85%.

Silica gel (1.82 g) was suspended in 10 mL of CH$_2$Cl$_2$. To this suspension was added dropwise over 5 minutes 0.41 mL of a 12% HCl solution in water. The mixture was stirred vigorously to prevent clumping. A solution of the above ketal dissolved in 2 mL CH$_2$Cl$_2$ was added and the reaction was stirred for 3 hours. The mixture was then filtered and the silica gel pad was washed with 50 mL CH$_2$Cl$_2$. The solvent was evaporated to afford 0.48 g (100%) of 3-(1-oxo-4-phenylbutyl)-3,5,5-trimethylcyclohexanone (118) as a clear oil consistent with its NMR and GC/MS properties.

To a stirred solution of this bis-ketone (0.62 g, 2.17 mmol) in 7 mL of methanol was added all at once a solution of hydroxylamine hydrochloride (0.16 g, 2.28 mmol) and sodium acetate (0.25 g, 3.03 mmol) in 7 mL of water. The reaction was stirred at room temperature for 1 hour. Water (20 mL) was added and the resulting mixture extracted with ether (3×20 mL). The ether extracts were combined, washed with saturated NaHCO$_3$ (1×20 mL) and brine (1×20 mL). The ethereal layer was dried over MgSO$_4$, filtered and concentrated to give the desired mono-oxime 119 (0.57 g, 87%) as a mixture of E and Z isomers.

Raney® Nickel (0.8 g wet weight, Aldrich Chemical Co.) in a 500 mL Parr pressure bottle was washed with water (3×20 mL) then ethanol (3×20 mL), the wash solvent being decanted each time. To this washed catalyst was added a solution of the oxime 119 (0.57 g, 1.89 mmol) in anhydrous ethanol (40 mL). The resulting mixture was saturated with ammonia by bubbling ammonia gas through the solution for 1 minute. This solution was placed under a hydrogen atmosphere (initial hydrogen pressure=50 psi) on a Parr shaker and shaken for 7 hours. The reaction mixture was then filtered through a pad of Celite® and the solvent was evaporated to yield an oil (0.43 g, 80%). Analysis by GC/MS showed a 1:1 diastereomeric mixture of the title amines 120, along with a minor unidentified byproduct. This mixture of amines was used directly as is without further purification.

Scheme 32

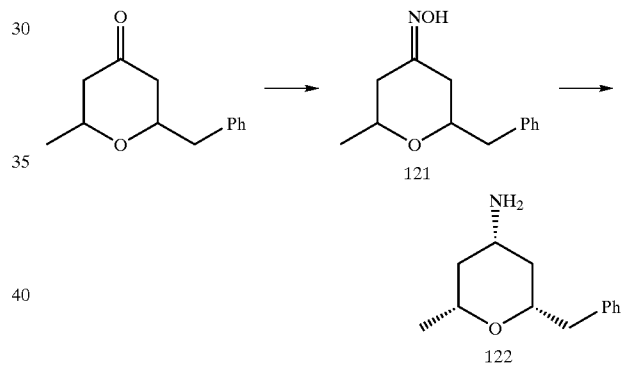

2-Benzyl-6-methyl-4-pyranylamine (122)

This amine was prepared according to Scheme 32. To 0.37 g (1.8 mmol) of 2-benzyl-6-methyl-4-pyranone (G. Piancatilli, et. al., *Synthesis*, 1982, 248) was added 0.22 g (3.1 mmol) of hydroxylamine hydrochloride and 0.16 g (2 mmol) of sodium acetate in 10 mL of methanol. After stirring overnight, the mixture was partitioned between CH$_2$Cl$_2$ and water. The organic phase was dried and evaporated. The oily residue solidified upon standing at room temperature to give 0.4 g (99%) of the desired oxime 121 as a Z/E isomer mixture 1:1 by GC/MS with a molecular ion of 219, and that was used as is in the reduction reaction below.

To 0.4 g of 2-benzyl-6-methyl-4-pyranone oxime (121) (1.8 mmol) in 50 mL of 95% ethanol was added 0.8 g (wet weight) of Raney® nickel that had been washed with water 3 times and ethanol 3 times. The mixture was placed under 41 psig of hydrogen in a Parr Shaker for 32 hours. After venting, the mixture was gravity filtered and evaporated under vacuum. The residue was partitioned between CH$_2$Cl$_2$ and aqueous sodium carbonate solution. The organic phase was dried and evaporated under vacuum to give 0.19 g of a mixture of the desired title amine 122 plus oxime 121 in a 2:1 mixture by GC/MS analysis. The mixture was used as is without further separation.

1-Benzoyl-4-aminopiperidine

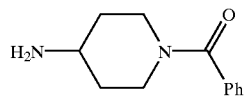

This compound was prepared by the method of Bhattacharyya, et al., *SynLett,* 1999, 11, 1781.

Scheme 33

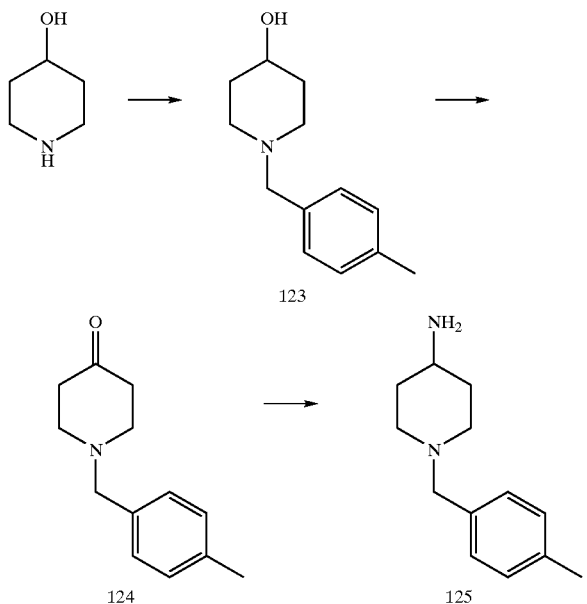

1-(4-Methylbenzyl)-4-piperidinylamine (125)

Synthesis of this compound was accomplished according to Scheme 33. To 5.05 g (50 mmol) of 4-hydroxypiperidine and 7.08 g (50 mmol) of p-methylbenzyl chloride in 25 mL of tert-butanol was added excess solid potassium carbonate, and the mixture was heated on a steam bath for 3 h. The mixture was cooled to room temperature and partitioned between ether and water. The organic phase was extracted with cold dilute HCl, and the acidic aqueous phase was extracted with ether twice. The aqueous phase was made basic with ice and 50% aqueous NaOH and extracted with ether. The ether phase was washed with dilute aqueous sodium bicarbonate solution, brine, dried, and evaporated under vacuum to give 5.3 g (52%) of 1-(4-methylbenzyl)-4-hydroxypiperidine (123) as an oil. GC/MS showed 100% purity with a molecular ion of 205.

To 2.8 mL (32 mmol) of oxalyl chloride in 75 mL of $CH_2Cl_2$ at $-78°$ C. was added 4.6 mL (64 mmol) of DMSO. To this mixture was added 5.3 g (26 mmol) of 1-(4-methylbenzyl)-4-piperidinol 123 in 10 mL of $CH_2Cl_2$, and the mixture was stirred 5 min in the cold. The mixture was quenched with 18 mL (129 mmol) of triethylamine and allowed to come to room temperature, and saturated aqueous ammonium chloride was added. The organic phase was washed with water and brine, dried, and evaporated to give 4.27 g (81%) of 1-(4-methylbenzyl)-4-piperidinone (124), which was used as is without further purification. GC/MS showed 100% purity with a molecular ion of 203.

To 4.25 g (21 mmol) of 1-(4-methylbenzyl)-4-piperidinone 124 in 200 mL of anhydrous methanol was added 32.2 g (420 mmol) of ammonium acetate and 25 g of 3A molecular sieves. After stirring 30 min, 5.25 g (84 mmol) of sodium cyanoborohydride was added portionwise. After stirring 16 hours, the mixture was gravity filtered and the methanol evaporated under vacuum. The residue was partitioned between ether and ice/HCl. The acidic aqueous layer was extracted twice with ether, made basic with 50% aqueous NaOH and ice, and extracted with $CH_2Cl_2$ to give 2.1 g (48%) of the title amine 125 as a thick oil. GC/MS showed a molecular ion of 204. The product was used as is without further purification.

Scheme 34

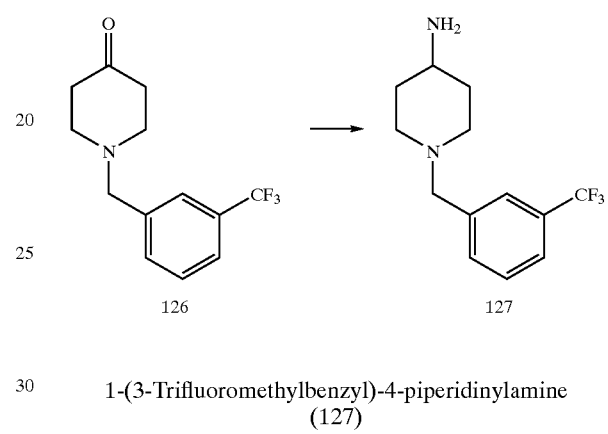

1-(3-Trifluoromethylbenzyl)-4-piperidinylamine (127)

Prepared according to Scheme 34. To 0.8 g (3.1 mmol) of 1-(3-trifluoromethylbenzyl)-4-piperidone [prepared in the same manner as 1-(4-methylbenzyl)-4-piperidinone) 123] in 7 mL of pyridine was added 0.22 g (3.1 mmol) of hydroxylamine hydrochloride, and the mixture was stirred overnight. The mixture was evaporated under vacuum and the residue partitioned between ether and dilute aqueous sodium bicarbonate. The organic phase was dried and evaporated under vacuum to give 0.52 g (62%) of the oxime as an oil, which was used as is in the hydrogenation step below. GC/MS showed a molecular ion of 272.

To 0.5 g (2 mmol) of this oxime in 75 mL of ethanol was added 0.5 g (wet weight) of Raney® nickel that had been washed 3 times each with water and ethanol. Ammonia gas was bubbled into the mixture for several minutes and all was placed under 45 psig of hydrogen in a Parr shaker for 7 hours. The vessel was vented and the mixture gravity filtered. The residue was dissolved in ether, filtered, and evaporated to give 0.43 g (81%) of the title amine 127, which was used as is without further purification. GC/MS indicated a single peak with a molecular ion of 258.

Scheme 35

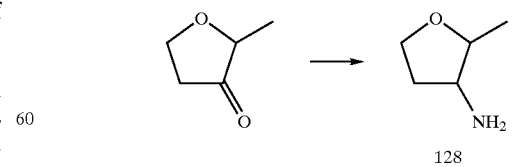

cis/trans-2-Methyl-3-tetrahydrofurylamine (128)

This amine was obtained following the method of Scheme 35. To 1.15 g (10 mmol) of 2-methyltetrahydrofuran-3-one oxime (prepared via standard procedures from commercially available 2-methyltetrahydrofuran-3-one) in 50 mL of methanol was added 1 g (wet weight) of Raney® nickel that had been washed 3 times each with water and ethanol, and placed in a Parr shaker under 44 psig of hydrogen. After 18 hours, the mixture was vented and gravity filtered. The methanol was evaporated under vacuum, and the residue was taken up in ether and dried. The ethereal phase was evaporated under vacuum to give 0.6 g (59%) of the title amine 128 as a cis/trans mixture. The GC/MS showed 41% with a molecular ion of 101 and 59% with a molecular ion of 101. The amine mixture was used as is without further purification.

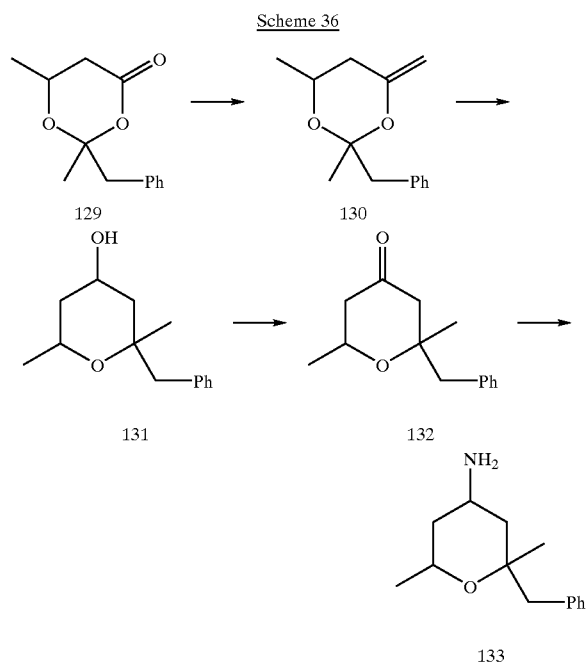

2-Benzyl-2,6-dimethyl-4-pyranylamine (133)

This amine was obtained following the procedure depicted in Scheme 36. To 4.88 g (19.7 mmol) of 3-trimethylsilyoxybutyric acid trimethylsilyl ester in 40 mL of CH$_2$Cl$_2$ at −78° C. was added 2.4 g (18 mmol) of phenylacetone and 1 drop of trimethylsilyl triflate. The mixture was allowed to stand in the cold for 2 days, then was quenched with 0.5 mL of pyridine and allowed to come to room temperature. The organic phase was washed with dilute aqueous sodium bicarbonate solution, dried, and evaporated under vacuum. The residue was distilled under vacuum to give 2.89 g (67%) of 2-benzyl-2,6-dimethyl-4-methylene-1,3-dioxan-4-one (129), b.p. 125–32 @ 0.6 mm. GC/MS showed two isomers, each with a base peak of 134 (phenylacetone).

To 1.5 g (6.8 mmol) of 2-benzyl-2,6-dimethyl-4-methylene-1,3-dioxan-4-one (129) under nitrogen was added 2.9 g (13.9 mmol) of bis-(cyclopentyl)-bis-methyl titanocene in 20 mL dry THF. The mixture was heated at reflux for 16 hours. The reaction mixture was cooled to room temperature and quenched with excess ether. The entire mixture was filtered through a silica gel bed with ether as the eluent. The filtrate was evaporated and chromatographed on silica gel with EtOAc and hexane (1:4) containing 0.2% triethylamine. The product-containing fractions were evaporated and slurried in petroleum ether and filtered under vacuum to give 1.2 g of a solid. GC/MS showed a mixture of approximately 3:1 ratio of 2-benzyl-2,6-dimethyl-4-methylene-1,3-dioxane (130) with a molecular ion of 218, and starting material 129. The mixture was used as is in the rearrangement below.

To 1.2 g (5.5 mmol) of this mixture in 5 mL of toluene under nitrogen was added 10.99 mL (11 mmol) of tri-isobutyl aluminum hydride at −78° C. The reaction was allowed to stand in the cold for 16 hours and then quenched with a few drops of water. The mixture was allowed to come to room temperature, and excess saturated aqueous ammonium chloride was added. The mixture was extracted with excess CH$_2$Cl$_2$, a difficult separation from the aluminum salts. The organic layer was dried and evaporated to give 1.1 g (90%) of 2-benzyl-2,6-dimethyl-4-hydroxypyranol (131) as a 75:25 isomer mixture (by GC/MS).

To 1.1 g (5 mmol) of 131 in 10 mL of CH$_2$Cl$_2$ was added 1.6 g (7.5 mmol) of pyridinium chlorochromate portionwise with magnetic stirring. After 1 hour at room temperature, ether was added and the mixture was filtered through a silica gel bed and washed through with ether. The filtrate was evaporated to give 0.88 g (80%) of 2-benzyl-2,6-dimethyl-4-pyranone (132). GC/MS showed 99% purity with a base peak of 127 (M-benzyl). The isomer mixture was used as is in the reductive amination below.

To 0.88 g (4 mmol) of 132 in 40 mL of anhydrous methanol was added 6.16 g (80 mmol) of ammonium acetate and 5 g of 3A molecular sieves. After stirring 45 min at room temperature, 1.02 g (16 mmol) of sodium cyanoborohydride was added portionwise with magnetic stirring. The mixture was gravity filtered, and the methanol evaporated under vacuum. The residue was partitioned between ether and dilute cold HCl. The aqueous phase was extracted with ether twice, then it was made basic with ice and 50% aqueous NaOH. The product was extracted with CH$_2$Cl$_2$, dried, and evaporated to give 0.43 g (49%) of a two component isomer mixture of the title amine 133. GC/MS showed 58% with a molecular ion of 128 and 42% with a molecular ion of 128.

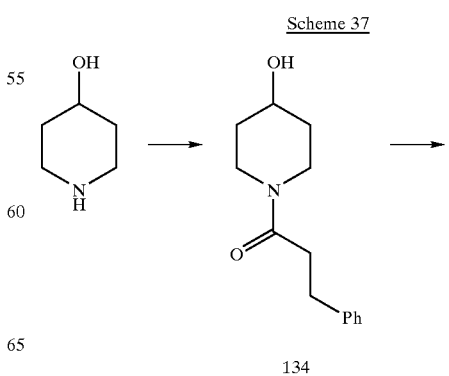

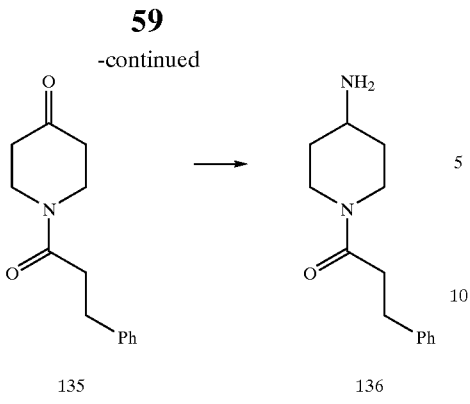

135 → 136

1-(3-Phenylpropionyl)-4-aminopiperidine (136)

This amine was synthesized in accordance with the method of Scheme 37. To 4 g (40 mmol) of 4-hydroxypiperidine in 20 mL of toluene was added phenylpropionyl chloride (derived from 6 g (40 mmol) of phenylpropionic acid in excess thionyl chloride). To the mixture was added excess 2N aqueous NaOH. After stirring 24 hours, the toluene layer was discarded and the aqueous phase was extracted with CH$_2$Cl$_2$, dried, and evaporated under vacuum to give 3.63 g (39%) of 1-(3-phenylpropionyl)-4-hydroxypiperidine (134). GC/MS indicated 100% purity with a molecular ion of 233.

To 1.68 mL of oxalyl chloride (19.2 mmol) in 35 mL of CH$_2$Cl$_2$ at −78° C. was added 2.73 mL (38.5 mmol) of dry DMSO in 5 mL of CH$_2$Cl$_2$. After the addition, 3.6 g (15.4 mmol) of 1-(3-phenylpropionyl)-4-hydroxypiperidine 134 in 5 mL of Cl$_2$Cl$_2$ was added, and the mixture was stirred for 5 min in the cold. 10.73 mL (77 mmol) of triethylamine in 5 mL of CH$_2$Cl$_2$ was added, and the mixture was allowed to come to room temperature. The mixture was quenched with saturated aqueous ammonium chloride solution. The organic phase was washed with water twice, with saturated brine, dried, and evaporated under vacuum to give 3.2 g (89%) of 1-(3-phenylpropionyl)-4-ketopiperidine (135). GC/MS showed 100% purity with a molecular ion of 231.

To 3.2 g (13.8 mmol) of 135 in 125 mL of anhydrous methanol was added 21.3 g of ammonium acetate and 20 g of 3A molecular sieves. After stirring 30 min, 3.47 g (55.2 mmol) of sodium cyanoborohydride was added portionwise with stirring. After 3 hours, the mixture was gravity filtered, and the methanol evaporated under vacuum. The residue was partitioned between ice/HCl and ether. The acidic aqueous phase was extracted twice more with ether. The aqueous phase was made basic with ice and 50% aqueous NaOH. The mixture was extracted with CH$_2$Cl$_2$, dried, and evaporated under vacuum to give 1.5 g (47%) of the title amine 136. GC/MS indicated 100% purity with a molecular ion of 232.

Scheme 38

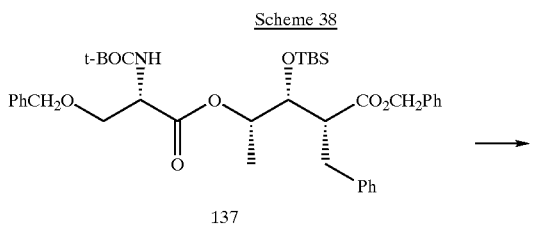

137

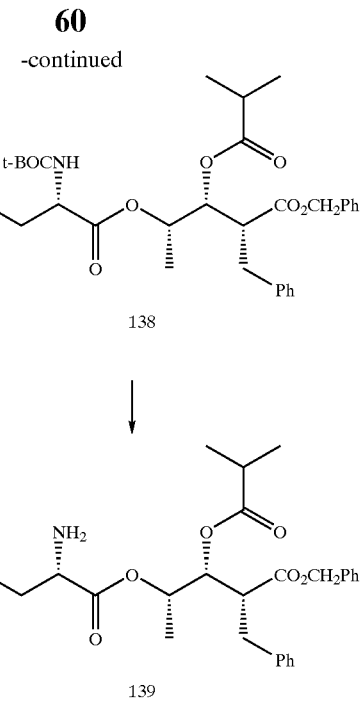

138

↓

139

Preparation of Amine 139

Synthesis of this amine is shown in Scheme 38. A screw cap teflon tube was charged with 137 (M. Shimano et al., Tetrahedron, 1998, 54, 12745) (0.80 g, 1.21 mmol) and 6 mL of pyridine. The solution was cooled to 0° C. and treated with 1.1 mL of HF-pyridine complex and the solution warmed to room temperature and stirred for 17 hours. An additional 1.1 mL of HF-pyridine was then added and the reaction stirred for an additional 30 hours. This mixture was poured into a stirred ice-cold solution of 40 mL 1N HCl and 20 mL 1:1 hexane-diethyl ether. The layers were separated and the aqueous layer was extracted with 1:1 hexane-diethyl ether (2×20 mL). The combined organic layers were washed with ice-cold 1N HCl (1×20 mL) and brine (1×20 mL). The solution was dried over MgSO$_4$, filtered and concentrated. The crude product was purified via radial chromatography (3:1 hexane-EtOAc) to give 282 mg of the hydroxyester (plus a minor impurity) which was carried directly to the next step.

To a stirred solution of the crude hydroxyester (282 mg, 0.48 mmol) in pyridine cooled to 0° C. was added dropwise isobutyryl chloride (0.2 mL, 1.92 mmol). The cooling bath was removed and the mixture stirred for 5 hours. water (2 mL) was added and the mixture stirred an additional 30 minutes. The solution was extracted with ether (3×10 mL). The ethereal layer was washed successively with ice cold 1N HCl (2×10 mL), saturated NaHCO$_3$ (1×10 mL) and brine (1×10 mL). The solution was dried over MgSO$_4$, filtered and concentrated. The crude product was purified via radial chromatography (4:1 hexane-EtOAc) to give 171 mg of the isobutyryl ester 138 (23% overall for two steps).

The BOC group of this ester was removed following the standard BOC-deprotection conditions described earlier to afford the desired amine 139.

Scheme 39

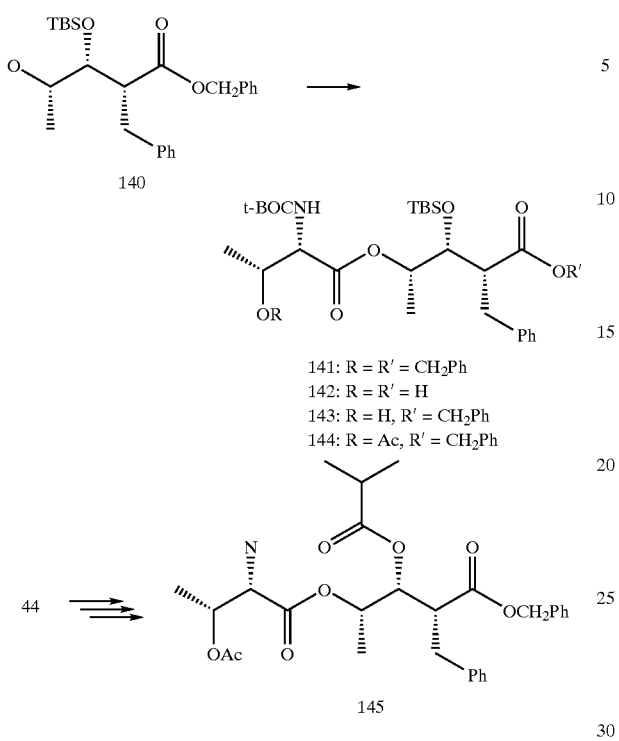

141: R = R' = CH₂Ph
142: R = R' = H
143: R = H, R' = CH₂Ph
144: R = Ac, R' = CH₂Ph

Scheme 40

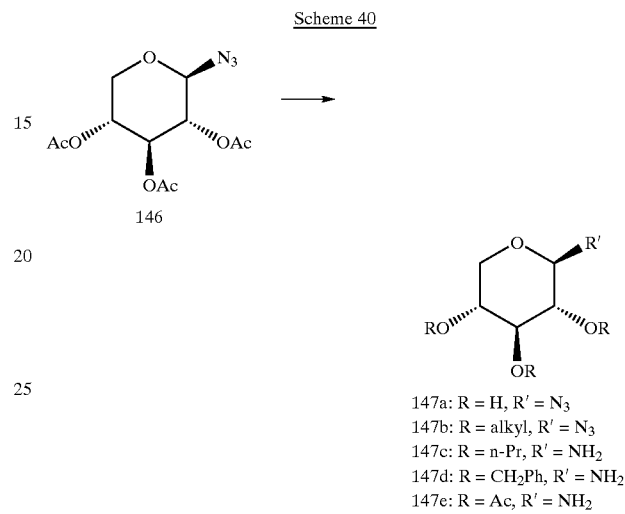

147a: R = H, R' = N₃
147b: R = alkyl, R' = N₃
147c: R = n-Pr, R' = NH₂
147d: R = CH₂Ph, R' = NH₂
147e: R = Ac, R' = NH₂

Preparation of Amine 145

This amine was prepared as depicted in Scheme 39. The hydroxyester 140 (M. Shimano et al., *Tetrahedron*, 1998, 54, 12745) (6.27 mmol) was dissolved in 15 mL DMF and cooled to 0° C. To this solution was added successively DMAP (1.53 g, 12.53 mmol), EDCI (1.8 g, 9.40 mmol) and N-BOC-O-Bn-(L)-threonine (2.52 g, 8.15 mmol). The reaction was warmed to room temperature and stirred overnight. The solution was poured into a rapidly stirred mixture of 30 mL ice cold 0.5N HCl and 50 mL 4:1 hexane-ether. The layers were separated and the aqueous layer was extracted with 4:1 hexane-ether (1×30 mL). The combined organic layers were washed with 0.5N HCl (1×20 mL) and brine (2×20 mL). The solution was dried over MgSO₄, filtered and concentrated. The crude material was chromatographed on silica gel (150 g) using 1.25 L of 3:1 CH₂Cl₂-hexanes to elute anisaldehyde followed by 65:10:25 CH₂Cl₂-ether-hexanes to elute the coupled product 141 (3.95 g, 88%).

A mixture of the benzyl ether 141 (1.32 g, 1.84 mol) and 200 mg 10% Pd/C in 25 mL of EtOAc was shaken in a Parr apparatus under 50 psi of hydrogen pressure for 5 hours. The mixture was filtered through a pad of Celite® and concentrated to afford the hydroxy acid 142 (680 mg, 70%), quite pure by NMR analysis.

To a stirred solution of hydroxyacid 142 (1.54 g, 2.86 mmol) and benzyl bromide (1.5 mL, 12.29 mmol) in 7 mL DMF was added solid sodium bicarbonate (1.2 g, 14.27 mmol). The mixture was stirred at room temperature for 24 hours, then was partitioned between 25 mL water and 10 mL 4:1 hexanes-ether. The layers were separated and the aqueous layer was extracted with 4:1 hexane-ether (2×10 mL). The combined organic layers were washed with 0.1N NaOH (1×10 mL) and water (1×10 mL). The solution was dried over MgSO₄, filtered and concentrated. The crude material was purified via radial chromatography (4:1 hexane-EtOAc) to give 1.04 g (60%) of the hydroxybenzyl ester 143.

To a stirred solution of ester 143 (840 mg, 1.34 mmol) and acetic anhydride (1.0 mL, 10.68 mmol) in 7 mL pyridine was added DMAP (40 mg, 0.67 mmol). The reaction was stirred at room temperature for 4 hours and diluted with 80 mL EtOAc. This solution was washed successively with saturated CuSO₄ (3×30 mL), 1N HCl (1×30 mL), saturated NaHCO₃ (1×30 mL) and brine (1×30 mL). The solution was dried over MgSO₄, filtered and concentrated to yield 0.9 g (100%) of acetate 144, quite pure by spectral analysis. The acetate 144 was converted via similar steps to those described earlier to afford the amine 145.

Preparation of 2,3,4-Tri-O-Alkyl-beta-D-Xylopyranosylamine 147c, d, e

Synthesis of these amines is shown in Scheme 40. To a stirred solution of triacetoxy-2-azidoxylopyranosyl azide 146 (Acros Chemical Co.) in CH₃OH at room temperature was added 1.1 mL (1.06 mmol) of a 1.0 M solution of sodium methoxide in methanol. The reaction was stirred overnight and neutralized with 5×8–100 acidic resin (~0.6 g). The solution was filtered and concentrated. The azidotriol 147a obtained was used directly in the next step.

The crude triol 147a was dissolved in 15 mL DMF, and NaH (60% dispersion, 0.53 g, 13.28 mmol) was added in four portions over 15 minutes. The reaction was stirred for 30 minutes at room temperature, allyl bromide (2.7 mL, 33.20 mmol) was added, and the mixture stirred overnight. Saturated ammonium chloride (10 mL) was carefully added followed by 50 mL of water. The aqueous solution was extracted with EtOAc (3×30 mL). The organic layer was washed successively with water (4×30 mL) and brine (2×30 mL). The solution was dried over MgSO₄, filtered and concentrated. The crude material was purified via radial chromatography (6:1 hexane-EtOAc) to give 753 mg (77%) of the tri-O-n-allyl-2-azidoxylopyranose 147b.

The resulting azide and allyl moieties were reduced by stirring with 150 mg of 10% Pd/C in 40 mL EtOAc under 1 atmosphere of hydrogen for 4 hours. The resulting solution was filtered through a pad of Celite® and evaporated to afford a quantitative yield of the title amine 147c.

The preparation of amine 147d was similar to that of 147c, except using benzyl bromide in the alkylation step, followed by reduction of the azide to the amine as described above.

Similar hydrogenation of azide 146 with 10% Pd/C in EtOAc under 1 atmosphere of hydrogen afforded amine 147e.

Preparation of 2,3,4-Tri-O-Acetyl-Beta-L-Fucopyranosyl Amine (148)

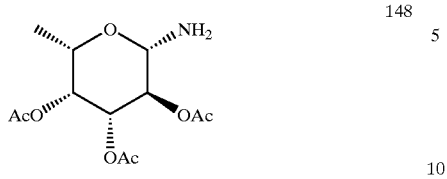

To a solution of 2,3,4-Tri-O-acetyl-beta-L-fucopyranosyl azide (Acros) (750 mg, 2.38 mmol) in 40 mL of EtOAc was added 120 mg of 10% Pd/C. This solution was stirred under an atmosphere of hydrogen gas (1 atm) for 3 hours. The mixture was filtered through a pad of Celite® and the pad was washed with EtOAc (25 mL). The solution was evaporated to afford the desired amine 148 (688 mg, 100%).

Preparation of 1,3,4,6-Tetra-O-Acetyl-2-Amino-2-Deoxy-alpha-D-Glucopyranose (149)

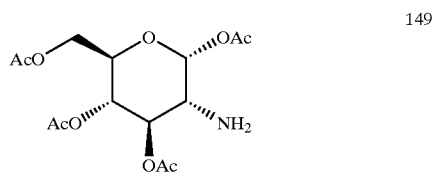

To a solution of 1,3,4,6-tetra-O-acetyl-2-azido-2-deoxy-alpha-D-glucopyranose (TCI-US) (300 mg, 0.80 mmol) in 25 mL of EtOAc was added 180 mg of 10% Pd/C. This solution was stirred under an atmosphere of hydrogen gas (1 atm) for 3 hours. The mixture was filtered through a pad of Celite® and the pad was washed with EtOAc (20 mL). The solution was evaporated to afford the desired amine 149 (282 mg, 100%).

Preparation of Benzyl and Methyl 3-Amino-Trideoxy-L-Arabino-Hexopyranosides 150a and 150b

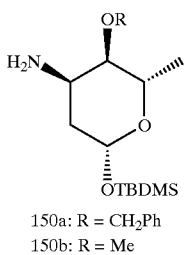

150a: R = CH$_2$Ph
150b: R = Me

These amines were synthesized via the method of L. Daley, et al., *Synth. Commun.* 1998, 28, 61.

Scheme 41

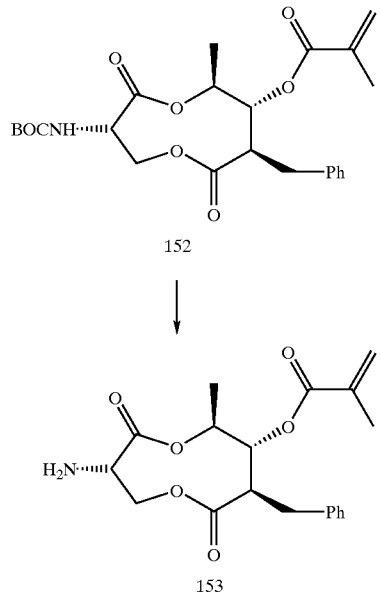

Preparation of Amine 153

This amine was prepared as shown in Scheme 41. [(3S, 7R, 8R, 9S)-7-benzyl-8-hydroxy-9-methyl-2,6-dioxo-[1,5] dioxonane-3-yl]-carbamic acid tert-butyl ester (151) was prepared as described by M. Shimano et al., *Tetrahedron*, 1998, 54, 12745. To a stirred solution of this ester (120 mg, 0.30 mmol) in pyridine (5 mL) was slowly added methacryloyl chloride (0.10 mL, 1.0 mmol) over 5 minutes. The resulting mixture was stirred at room temperature under a N$_2$ atmosphere overnight. The reaction mixture was partitioned between EtOAc (75 mL) and 1N HCl (50 mL). The organic layer was washed with water then saturated NaCl, dried over MgSO$_4$, and concentrated to give a clear oil. This crude oil was chromatographed on silica gel using 30% EtOAc in hexane as eluent to give the acylated intermediate 152 (138 mg) as a clear glass. The BOC group was removed from this intermediate as described in the reference above to give the title amine 153.

Preparation of the Aniline of Antimycin A$_3$ (154)

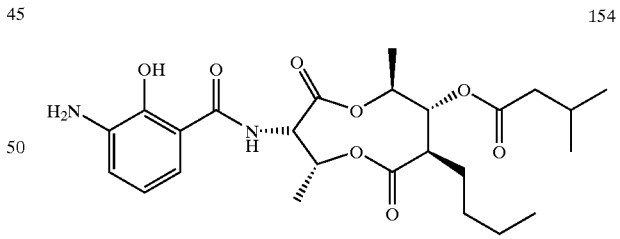

To a stirred solution of Antimycin A$_3$ (25 mg, 0.048 mmol) in 2.5 mL of CH$_2$Cl$_2$ cooled to 0° C., was added pyridine (11 µL) and PCl$_5$ (27 mg, 0.13 mmol). The mixture was refluxed for 1.5 hours, then was cooled to −30° C., and methanol (2.5 mL) was added, and the mixture was allowed to warm to room temperature and stirred overnight. The solution was poured into a 0° C. mixture of 13 mL CH$_2$Cl$_2$ and 13 mL of saturated sodium bicarbonate. The mixture was shaken in a separatory funnel and the layers were separated. The aqueous layer was extracted with CH$_2$Cl$_2$ (2×5 mL) and the combined organic layers were dried (MgSO$_4$), filtered and concentrated to afford the aniline of Antimycin A$_3$.

General Procedures for Coupling of Amines with ortho-Hydroxyheteroaromatic Carboxylic Acids to Generate the Heterocyclic Aromatic Amides 2

Coupling Procedure A: Preparation of N-(2-(4-Chlorophenyl)Ethyl)-3-Hydroxypyridine-2-Carboxamide (233)

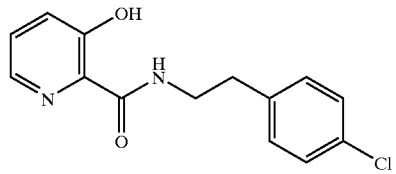

233

A stirred mixture of 3-hydroxypyridine-2-carboxylic acid (1.39 g, 0.01 mol) in dry THF (60 mL) under argon was cooled to −20° C. To this was added all at once a 20% solution of phosgene in toluene (5.1 g, 0.01 mol) and the resulting mixture was stirred for 90 minutes while the temperature slowly rose to 0° C. The reaction mixture was then recooled to −20° C. and a solution of diisopropylethylamine (2.58 g, 0.02 mol) in THF (20 mL) was added dropwise over 30 minutes. After the addition was complete, the mixture was stirred an additional 2 hours as the temperature was slowly brought to 0° C. Stirring was continued at 0° C. overnight. To this stirred mixture was added, all at once, 2-(4-chlorophenyl)ethylamine (1.56 g, 0.01 mol), and the resulting mixture was stirred at room temperature for 6 hours. The mixture was diluted with ether (100 mL), washed with 1N HCl (100 mL), dried (MgSO$_4$) and concentrated to give the title compound as an off-white solid (1.95 g). The mass spectrum showed the expected 3:1 parent ion ratio at m/e 276 and 278.

Coupling Procedure B: Preparation of 3-Hydroxy-4-Methoxy-N-(4-(4-Trifluoromethylphenoxy)Phenyl)-Pyridine-2-Carboxamide (425)

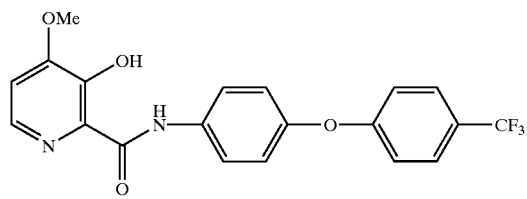

425

To a stirred solution of 4-(4-trifluoromethylphenoxy) aniline (0.20 g, 0.8 mmol) and DMAP (0.10 g, 0.085 mmol) in CH$_2$Cl$_2$ (10 mL) was added all at once a solution of 3-benzyloxy-6-bromo-4-methoxypyridin-2-carbonylchloride (3) (0.29 g, 0.8 mmol) in CH$_2$Cl$_2$ (5 mL). The resulting mixture was stirred overnight at room temperature then poured into 2N HCl (10 mL). The organic layer was separated and the aqueous layer extracted with CH$_2$Cl$_2$ (2×10 mL). The organic layers were combined, dried (MgSO$_4$) and concentrated to give a gummy solid. This solid was taken up in EtOAc (20 mL), and triethylamine (0.80 g, 0.8 mmol) and 5% Pd on carbon (0.10 g) were added. The resulting mixture was subjected to a hydrogen atmosphere (initial pressure=50 psi) on a Parr shaker for 30 minutes. The mixture was filtered, washed with 0.1N HCl (20 mL), dried (MgSO$_4$) and concentrated to give the title compound as an off-white solid (0.14 g), m.p.=122–129° C.

Coupling Procedure C: Preparation of N-(4-Cyclohexylphenyl)-3-Hydroxypyridine-2-Carboxamide

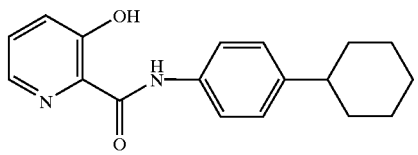

To a stirred solution of 3-hydroxypyridine-2-carboxylic acid (obtained from 16 by catalytic hydrogenation in the presence of Pd/C as described earlier) (0.42 g, 3 mmol) and 4-cyclohexylaniline (0.35 g, 2 mmol) in dry DMF (5 mL) were successively added 1-hydroxybenzotriazole (0.48 g), EDCI (0.65 g) and N-methylmorpholine (1.41 g). An additional amount of DMF (5 mL) was added and the reaction mixture stirred at room temperature overnight. The mixture was poured into water (200 mL), then extracted with EtOAc (2×75 mL). The organic extracts were combined, washed with water (100 mL), and saturated NaCl solution (50 mL), dried (MgSO$_4$) and concentrated. The crude oil which solidified upon standing was chromatographed on silica gel (4:1 petroleum ether-EtOAc) to give the title compound (0.42 g) as a tan solid, m.p. 91–93° C.

Modification of Heterocyclic Aromatic Amides to Other Heterocyclic Aromatic Amides Preparation of 4-Hydroxythiophene-N-(3,3,5,5-Tetramethylcyclohexyl)-3-Carboxamide (554)

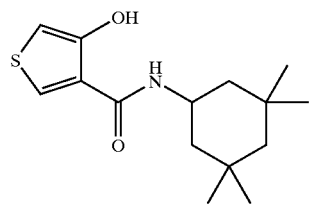

554

4-Methoxythiophenecarboxylic acid and 3,3,5,5-tetramethylcyclohexylamine were coupled together following general coupling procedure C described earlier, to give 4-methoxythiophene-N-(3,3,5,5-tetramethylcyclohexyl)-3-carboxamide.

A solution of 500 mg of this methoxythiopheneamide in 15 mL of chloroform under a drying tube was stirred in a Dry Ice-acetone bath for 5 minutes. To this solution was added dropwise over 15 minutes a solution of 940 mg of boron tribromide (2 equivalents) in 10 mL of chloroform. Stirring was continued while the reaction mixture warmed to room temperature, and then overnight. The reaction mixture was then placed in a cold water bath, and 15 mL of water was added dropwise. After stirring 15 minutes, the mixture was diluted with 50 mL of CH$_2$Cl$_2$ and the organic layer separated. The water layer was washed with 50 mL of CH$_2$Cl$_2$. The combined organic extracts were washed with 25 mL of water and saturated salt solution and dried. The extract was filtered and concentrated. The residue was chromatographed on silica gel using CH$_2$Cl$_2$-5% EtOAc as eluent, to give 310 mg of the title compound as tan crystals, m.p. 170–174° C. A sample was recrystallized from petroleum ether-EtOAc to yield tan needles, m.p. 171–173° C.

Scheme 42

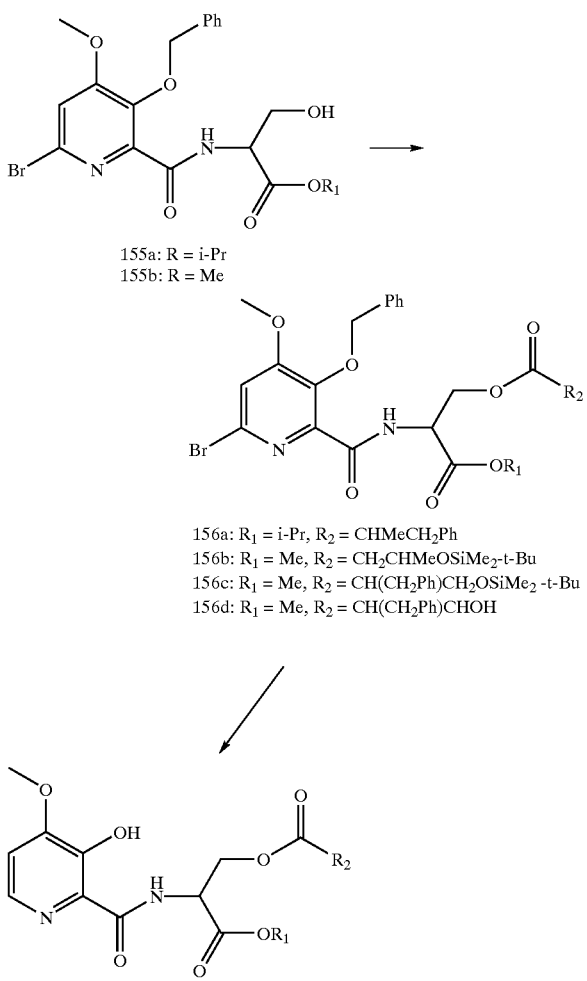

155a: R = i-Pr
155b: R = Me

156a: R₁ = i-Pr, R₂ = CHMeCH₂Ph
156b: R₁ = Me, R₂ = CH₂CHMeOSiMe₂-t-Bu
156c: R₁ = Me, R₂ = CH(CH₂Ph)CH₂OSiMe₂-t-Bu
156d: R₁ = Me, R₂ = CH(CH₂Ph)CHOH

Preparation of Coupled Intermediates 156a–d

These intermediates were prepared as depicted in Scheme 42.

To a stirred solution of the isopropyl ester of (±)-serine hydrochloride (2.75 g) and triethylamine (3.55 g) in CH₂Cl₂ (75 mL) was added over a five minute period a solution of 3-benzyloxy-6-bromo-4-methoxypyridin-2-carbonylchloride (3) (5.32 g) in CH₂Cl₂ (15 mL). The mixture was stirred for 30 minutes at room temperature, then poured into 1N HCl (75 mL). The organic layer was separated, washed with water (25 mL), dried (Na₂SO₄) and the solvent evaporated to give a yellow gum (6.7 g). This material could be recrystallized from ether/hexane to give 155a as a white solid, m.p. 100–103° C. A similar procedure starting from the methyl ester of (±)-serine hydrochloride afforded the methyl ester intermediate 155b.

To a stirred solution of 155a (1.17 g) triethylamine (0.31 g), and DMAP (0.06 g) in CH₂Cl₂ (25 mL) was added in one portion α-methylhydrocinnamoyl chloride (0.46 g). The resulting mixture was stirred for 4 hours at room temperature, then poured into 2N HCl (15 mL). The organic phase was separated, washed with iN NaOH (15 mL), dried (MgSO₄) and the solvent evaporated to give 156a as a yellow oil (1.45 g). The NMR (CDCl₃) was consistent with this oil being a 1:1 mixture of diastereomers.

A solution of 3-(t-butyldimethylsilyloxy)butyryl chloride (3.55 g) (prepared from the corresponding t-butyldimethylsilyl ester by the method of A. Wissner and C. V. Grudzinskas, *J. Org. Chem.,* 1978, 43, 3972), in CH₂Cl₂ (10 mL) was added rapidly to a cold (0° C.), stirred solution of 155b (6.6 g) and DMAP (0.18 g) in dry pyridine (25 mL). The reaction mixture was stirred for 15 minutes at 0° C. then at room temperature for three hours. After dilution with ether (200 mL), the mixture was extracted with water (2×100 mL), dried (MgSO₄) and the solvent evaporated. Toluene (25 mL) was added to the residue and again the solvent evaporated. The yellow oily residue was purified via chromatography (silica gel, 7:3 hexane/acetone) to give 156b as a mixture of diastereomers.

To a stirred solution of 2-benzyl-3-(t-butyldimethylsilyloxy)propionic acid (7.36 g) (N. P. Peet, N. L. Lentz, M. W. Dudley, A. M. L. Ogden, D. E. McCarty, and M. M. Racke, *J. Med. Chem.,* 1993, 36, 4015), in DMF (20 mL) was added all at once t-butyldimethylsilyl chloride (4.52 g), then imidazole (4.1 g), and the resulting mixture stirred at room temperature for 24 hours. The mixture was diluted with water (300 mL) then extracted with pentane (3×100 mL). The pentane phase was washed with water, dried (Na₂SO₄), and the solvent evaporated to give a colorless oil (9.5 g). The NMR (CDCl₃) was consistent with this being a mixture of diastereomers. This ester (4.1 g) was converted to the corresponding acid chloride by the method of N. P. Peete, et al., *J. Org. Chem.,* 1978, 43, 3972. This acid chloride was condensed with 155b (4.4 g) as described above to give after silica gel chromatography (4:1 hexane/acetone) the desired 156c as a mixture of diastereomers.

To a stirred solution of 156c (4.5 g) in methanol (35 mL) was added conc. HCl (1.5 mL). The resulting mixture was stirred at room temperature for 30 minutes, diluted with water (200 mL), then extracted with CH₂Cl₂ (2×100 mL). The organic phase was dried (MgSO₄), and the solvent evaporated. The residue was purified via silica gel chromatography (7:3 hexane/acetone) to give 156d as a pale yellow gum (2.8 g). The NMR (CDCl₃) showed it to be a mixture of diastereomers.

156a–d were converted to the corresponding deprotected heterocyclic aromatic amides by hydrogenation in the presence of Pd/C as described earlier.

Scheme 43

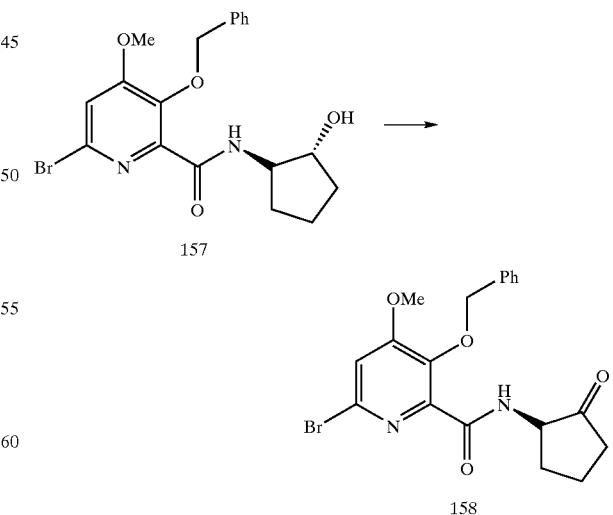

Preparation of Intermediate 158

Synthesis of this intermediate is shown in Scheme 43. Amide 157 was prepared from (+)-trans-1-Hydroxy-2- aminocyclopentane hydrobromide (7.09 g, 38.9 mmol) and 3-benzyloxy-6-bromo-4-methoxypyridin-2-carbonylchloride (3) (13.8 g, 38.9 mmol) in $CH_2Cl_2$ (150 mL), following general coupling procedure B, and purified by flash chromatography using 1:1 hexanes-EtOAc as eluent. This gave 157 (13.4 g) as a white solid, m.p. 56–57° C.

Dimethylsufoxide (7.4 mL, 104.1 mmol) was added slowly to a −78° C. solution of oxalyl chloride (4.54 mL, 52.08 mmol) in $CH_2Cl_2$ (100 mL), followed by a solution of amide 157 (10.46 g, 24.8 mmol) in $CH_2Cl_2$ (25 mL). After 30 min, $Et_3N$ was added and the solution slowly warmed to room temperature. The mixture was poured into satd. $NH_4Cl$ (100 mL) and extracted with $CH_2Cl_2$ (2×100 mL). The combined organic layers were washed with brine, dried and the solvent evaporated. The residue was purified via column chromatography, using 1:1 EtOAc-hexane as the eluent, to give the ketone 158 (9.64 g, 94%), pure by GC/MS and $^1$H-NMR.

Both 157 and 158 were converted to the corresponding deprotected heterocyclic aromatic amides by hydrogenation in the presence of Pd/C as described earlier.

cedure C, afforded 1,3-diol 159 as a colorless oil, pure by $^1$H, $^{13}$C-NMR and IR spectra.

1,3-diol 159 (1 mmol) was condensed with the appropriate carbonyl compound (2 mmol) or the corresponding dimethyl acetal (2 mmol) by refluxing in benzene (20 mL/mmol) in the presence of a catalytic amount of p-toluenesulfonic acid (0.1 mmol) in a Dean-Stark setup.

Thus, condensation of 159 and 1,3,3-trimethoxypropane gave the acetal 160a as a 2:1 mixture of syn and anti diastereomers. Mass spectrum (ES) indicated [M+] at (m/e) 495 and 497. $^1$H-, $^{13}$C-NMR and IR spectra were consistent with the structure 160a.

Condensation of 159 and 2-methyl-3-(4-tert-butyl) phenylpropanone gave the acetal 160b as a 3:1 mixture of syn and anti diastereomers. Mass spectrum (ES) indicated [M+] at (m/e) 597. $^1$H, $^{13}$C-NMR and IR spectra were consistent with the structure 160b.

Condensation of 159 and dihydro-β-ionone gave the acetal 160c as a 2:1 mixture of syn and anti diastereomers. Mass spectrum (EI) indicated [M+] at (m/e) 587. $^1$H, $^{13}$C-NMR and IR spectra were consistent with the structure 160c.

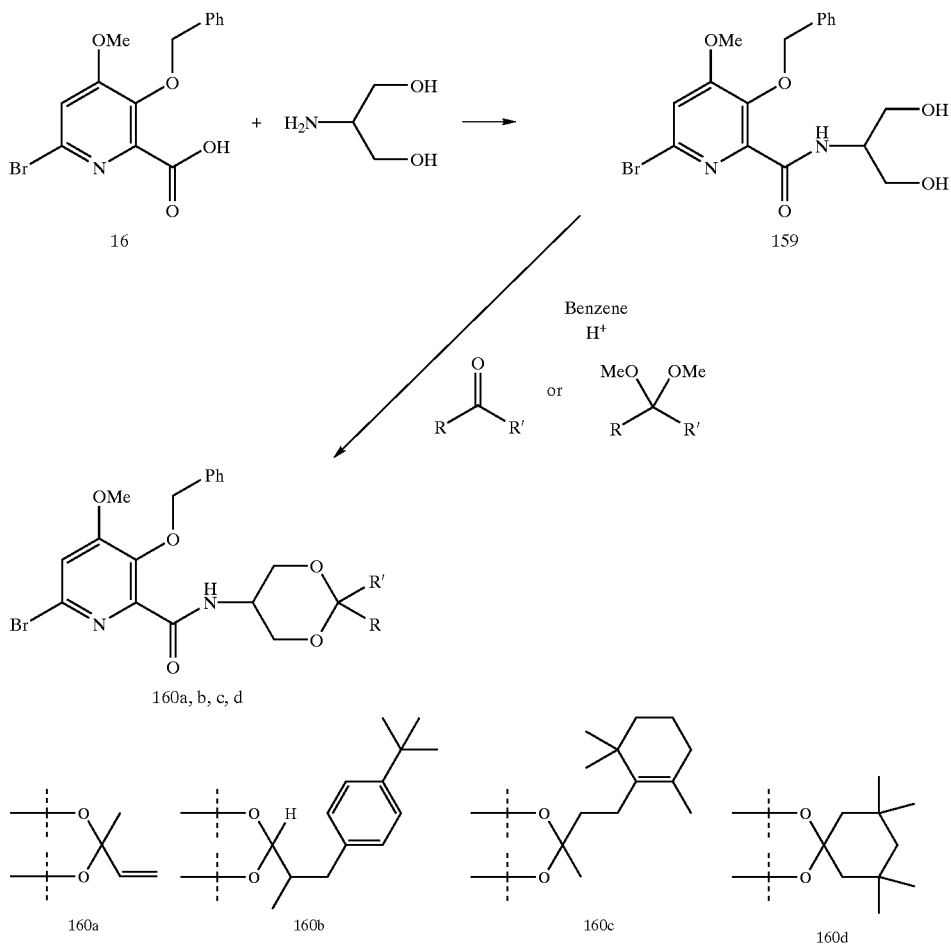

Preparation of Intermediates 160a–d

These intermediates were prepared as depicted in Scheme 44. Coupling of serinol with 3-benzyloxy-6-bromo-4-methoxypicolinic acid (16) following general coupling pro- Condensation of 159 and 3,3,5,5-tetramethylcyclohexanone gave the acetal 160d, consistent by $^1$H, $^{13}$C-NMR and IR spectra.

Intermediates 160a–d were converted to the corresponding deprotected heterocyclic aromatic amides by hydrogenation in the presence of Pd/C as described earlier.

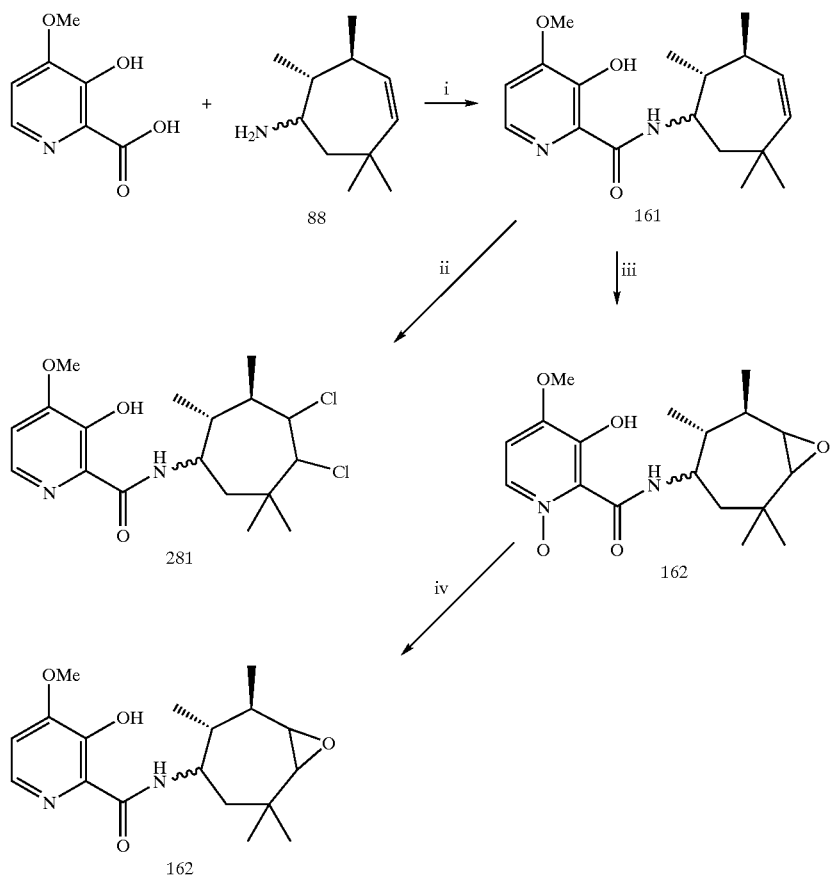

Key: i. EDAC, HOAt, DMAP, DMF, 6h; ii. KMnO₄, Bn(Et₃)NCl, (COCl)2; iii. m-CPBA, CH₂Cl₂; iv. H₂, Pd/C Preparation of Compounds 280 and 281

Scheme 45 describes the preparation of these compounds. Thus, 2,3,6,6-tetramethyl-2-cycloheptenylamine was first coupled to 2-hydroxy-3-methoxy-2-picolinic acid using standard coupling procedure C, to give intermediate 161. Dichlorination of compound 161 according to the procedure of *Tetrahedron Lett.* 1991,32, 1831–1834, afforded the dichloro derivative 281. Standard m-CPBA oxidation of 161 in CH₂Cl₂ led to the N-oxide-containing epoxy analog 162, which upon treatment with H₂ (45 psi) and 10% Pd/C under standard catalytic hydrogenation conditions formed compound 280.

Scheme 46

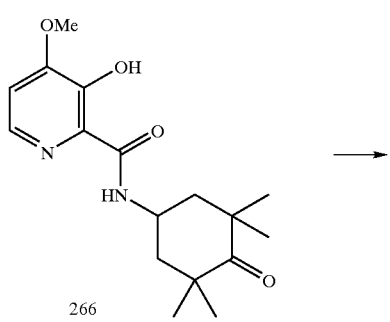

-continued

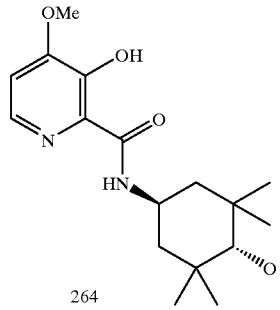

Preparation of trans-4-Hydroxy-3,3,5,5-Tetramethylpicolinamide (264)

This compound was prepared as shown in Scheme 46. To a stirred solution of keto-picolinamide 266 (56 mg, 0.18 mmol) in 2 mL of methanol was added sodium borohydride (20 mg, 0.53 mmol). The reaction was stirred for 5 hours and the methanol evaporated. The crude material was diluted with 5 mL water and extracted with EtOAc (3×5 mL). The organic layer was washed with water (1×5 mL) and brine (1×5 mL). The solution was dried over MgSO₄, filtered and concentrated. NMR and GC anaylses were consistent with the title compound 264 with trans stereochemistry in 95% purity.

Scheme 47

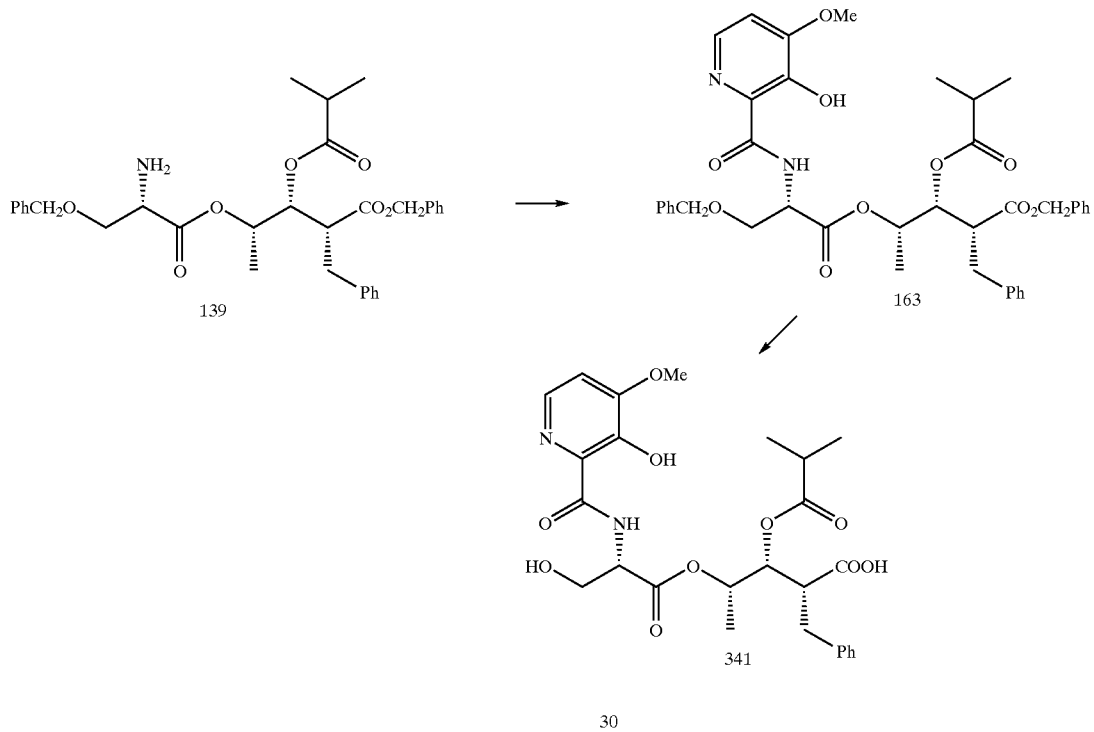

Preparation of Compound 341

Preparation of this compound is depicted in Scheme 47. The benzyl ester precursor 139 (Scheme 38) (33 mg, 0.046 mmol) was dissolved in 10 mL of EtOAc and 110 mg of Pearlman's catalyst was added. The mixture was shaken in a Parr apparatus under 50 psi of hydrogen pressure for 12 hours. The solution was then filtered and concentrated. The residue was then dissolved in a minimal amount of ether and petroleum ether was added until a precipitate formed. The solid was collected by filtration and dried to give the title compound 341.

Preparation of N-(3-Hydroxy-4-Methoxy-2-Pyridylcarbonyl)-2-Amino-2-Deoxy-alpha-D-Glucopyranose (334)

1,3,4,6-Tetra-O-acetyl-2-amino-2-deoxy-alpha-D-glucopyranose (151) and 3-hydroxy-4-methoxypicolinic acid were coupled together using standard coupling procedure C. To a solution of the resulting picolinamide (0.19 g, 0.38 mmol) in 6 mL of methanol was added lithium hydroxide monohydrate (0.92 mmol, 40 mg). The reaction mixture was stirred at room temperature overnight. The solution was neutralized by the addition of DOWEX® 5×8–100 acidic resin (0.5 g). The mixture was filtered and concentrated to afford the title compound (110 mg, 88%).

Scheme 48

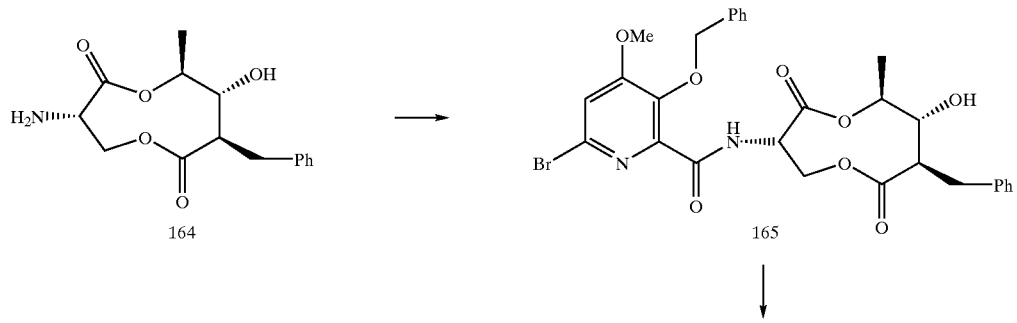

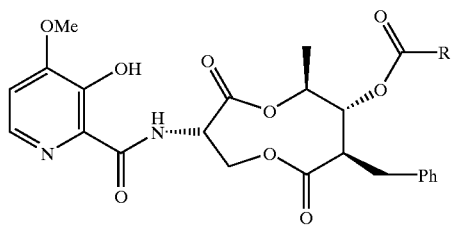

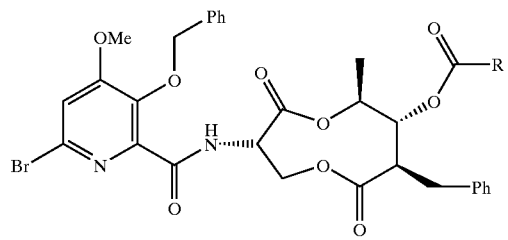

166a: R = c-Pr
166b: R = i-PrNH
166c: R = i-PrO

General Preparation of Exocyclic Ester 166a, Carbamate 166b, and Carbonate 166c

These compounds were generally prepared as depicted in Scheme 48, starting with amine 164, prepared according to the procedures of M. Shimano, et al., *Tetrahedron*, 1998, 54, 12745. This amine was coupled with 3-benzyloxy-6-bromo-4-methoxypicolinic acid 16 following standard coupling procedure C described earlier, then the resulting intermediate 165 was reacted with the appropriate carboxylic acid chloride, alkyl isocyanate, or alkyl chloroformate in the presence of base to afford the desired protected ester 166a, carbamate 166b, or carbonates 166c, respectively. Deprotection of these compounds following the procedures described earlier using $H_2$ in the presence of Pd/C afforded the desired ester, carbamate, or carbonate. The above steps were used to prepare other analogous esters, carbamates, and carbonates.

Preparation of 166a

To a stirred solution of 165 (180 mg, 0.29 mmol) in pyridine (10 mL) was added slowly cyclopropanecarbonyl chloride (0.45 mL, 5 mmol) over 5 minutes. The mixture was allowed to stir under a $N_2$ atmosphere at room temperature overnight. The resulting mixture was poured into 1N HCl (30 mL) and extracted with EtOAc (2×75 mL). The organic layers were combined and washed with water (25 mL) then saturated NaCl (25 mL), dried over $MgSO_4$, and concentrated to give an orange oil. The crude oil was chromatographed on silica gel using a 30% to 50% EtOAc in hexane gradient as eluent to give the title compound 166a (100 mg) as a clear oil.

Preparation of 166b

To a stirred solution of 165 (200 mg, 0.33 mmol) in $CH_2Cl_2$ (5 mL) was added triethylamine (2 drops), DMAP (1 mg), and isopropyl isocyanate (0.2 mL, 2 mmol). The resulting mixture was stirred under a nitrogen atmosphere at room temperature overnight. The reaction mixture was poured into 1N HCl (25 mL) and extracted with EtOAc (2×50 mL). The organic layers were combined and washed with water then saturated NaCl, dried over $MgSO_4$, and concentrated to give a pink foam. The crude foam was chromatographed on silica gel using a 30% to 50% EtOAc in hexane gradient as eluent to give the title compound 166b (90 mg) as a white solid.

Preparation of 166c

A stirred solution of 165 (180 mg, 0.29 mmol) in pyridine (5 mL) and $CH_2Cl_2$ (5 mL) was cooled to 0° C. in an ice bath under a nitrogen atmosphere. Isopropyl chloroformate (1M in toluene, 5 mL) was slowly added to the cooled mixture over 1 minute. The ice bath was removed and the mixture was stirred at room temperature overnight. The reaction mixture was partitioned between 1N HCl (25 mL) and EtOAc (75 mL). The organic layer was washed with water then saturated NaCl, dried over $MgSO_4$, and concentrated to give a clear oil. The crude oil was chromatographed on silica gel using a 30% to 50% EtOAc in hexane gradient as eluent to give the title compound 166c (80 mg) as a clear oil.

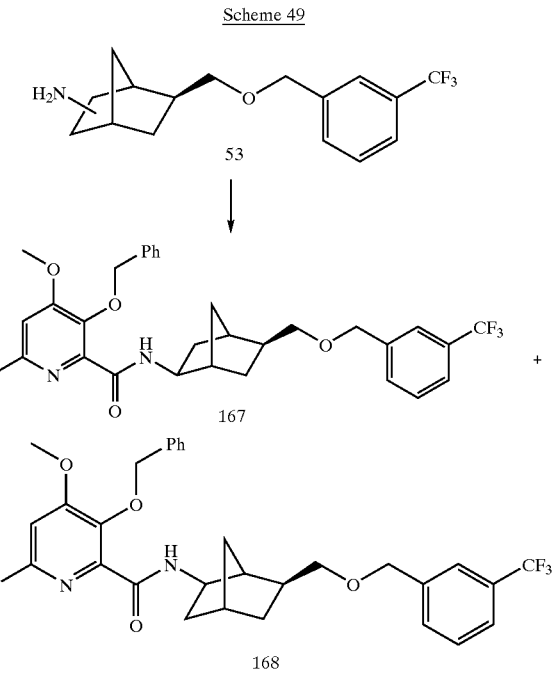

Preparation of Intermediates 167 and 168

The diastereomeric mixture of amines 53 obtained as described earlier (Scheme 9) was coupled with acid chloride 3 via the general coupling procedure A previously described (Scheme 49), to give a mixture of diastereomers 167 and 168. These were separated by careful silica gel chromatography (85:15 hexane/acetone) to give pure 167 and 168 each in about 35% yield. These were deprotected with $H_2$ in the presence of Pd/C as described earlier.

Table I illustrates additional compounds of Formula I made from appropriate starting materials by the above described procedures.

Fungicide Utility

The compounds of the present invention have been found to control fungi, particularly plant pathogens and wood decaying fungi. When employed in the treatment of plant fungal diseases, the compounds are applied to the plants in a disease inhibiting and phytologically acceptable amount. Application may be performed before and/or after the infection with fungi on plants. Application may also be made through treatment of seeds of plants, soil where plants grow, paddy fields for seedlings, or water for perfusion. Other application may be made via wood treatment to control the destruction of wood and/or wood products.

As used herein, the term "disease inhibiting and phytologically acceptable amount", refers to an amount of a compound of the present invention which kills or inhibits the plant pathogen and prevents, eradicates, or arrests plant disease for which control is desired, but is not significantly toxic to the plant. This amount will generally be from about 1 to 1000 ppm, with 10 to 500 ppm being preferred. The exact concentration of compound required varies with the fungal disease to be controlled, the type of formulation employed, the method of application, the particular plant species, climate conditions, and other factors. A suitable application rate is typically in the range from about 50 to about 1000 grams per hectare (g/Ha).

The compounds of the invention may also be used to protect stored grain and other non-plant loci from fungal infestation.

The following experiments were performed in the laboratory to determine the fungicidal efficacy of the compounds of the invention.

Biological Evaluation of Inhibition of in vitro Fungal Growth

Culture Conditions: Suspensions of fungal conidia or mycelial fragments are prepared in sterile potato dextrose broth (Difco) for *Magnaporthe grisea* (*Pyricularia oryzae*—PYRIOR), *Rhizoctonia solani* (RHIZSO), *Mycosphaerella graminicola* (*Septoria tritici*—SEPTTR), *Stagonospora nodorum* (*Leptosphaeria nodorum*—LEPTNO), *Ustilago maydis* (USTIMA), and in rye seed broth for *Phytophthora infestans* (PHYTIN). The suspensions are pipetted into sterile 96 well microtiter plates containing samples of the experimental fungicides dissolved in dimethylsulfoxide. The concentration of the fungicide varies from 0.001 to 100 ppm with the final solvent concentration not exceeding 1% of the medium. The fungi are allowed to grow for various time intervals at 24 to 30° C. until the wells become turbid from the growth of the fungi in control wells containing only the solvent. At that time growth inhibition is determined by visual inspection of each well and the percent inhibition of growth as compared to the solvent treated controls is determined.

In Table II, a "+" indicates that the test material gave at least 80% growth inhibition and a "−" indicates less than 80% growth inhibition of the designated pathogen when incorporated into the growth medium at a concentration of 25 ppm. A blank space indicates not tested.

Biological Evaluation of Control of in vivo Whole Plant Fungal Infection

Compound formulation was accomplished by dissolving technical materials in acetone, with serial dilutions then made in acetone to obtain desired concentrations. Final treatment volumes were obtained by adding 9 volumes 0.05% aqueous Tween-20 or 0.01% Triton X-100, depending upon the pathogen.

Downy Mildew of Grape (*Plasmopara viticola*—PLASVI) (24 Hour Protectant): Vines (cultivar Carignane) were grown from seed in a soilless peat-based potting mixture ("Metromix") until the seedlings were 10–20 cm tall. These plants were then sprayed to run-off with the test compound at a rate of 100 ppm. After 24 hours the test plants were inoculated by spraying with an aqueous sporangia suspension of *Plasmopara viticola,* and kept in a dew chamber overnight. The plants were then transferred to the greenhouse until disease developed on the untreated control plants.

Late Blight of Tomato (*Phytophthora infestans*—PHYTIN) (24 Hour Protectant): Tomatoes (cultivar Rutgers) were grown from seed in a soilless peat-based potting mixture ("Metromix") until the seedlings were 10–20 cm tall. These plants were then sprayed to run-off with the test compound at a rate of 100 ppm. After 24 hours the test plants were inoculated by spraying with an aqueous sporangia suspension of Phytophthora infestans, and kept in a dew chamber overnight. The plants were then transferred to the greenhouse until disease developed on the untreated control plants.

Brown Rust of Wheat (*Puccinia recondita*—PUCCRT) (24 Hour Protectant): Wheat (cultivar Yuma) was grown in a soilless peat-based potting mixture ("Metromix") until the seedlings were 10–20 cm tall. These plants were then sprayed to run-off with the test compound at a rate of 100 ppm. After 24 hours the test plants were inoculated by spraying with an aqueous spore suspension of *Puccinia recondita,* and kept in a dew chamber overnight. The plants were then transferred to the greenhouse until disease developed on the untreated control plants.

Powdery Mildew of Wheat (*Erysiphe graminis*—ERYSGT) (24 Hour Protectant): Wheat (cultivar Monon) was grown in a soilless peat-based potting mixture ("Metromix") until the seedlings were 10–20 cm tall. These plants were then sprayed to run-off with the test compound at a rate of 100 ppm. After 24 hours the test plants were inoculated by dusting with conidia from powdery mildew infected wheat plants. The plants were then transferred to the greenhouse until disease developed on the untreated control plants.

Leaf Blotch of Wheat (*Septoria tritici*—SEPTTR) (24 Hour Protectant): Wheat (cultivar Yuma) was grown in a soilless peat-based potting mixture ("Metromix") until the seedlings were 10–20 cm tall. These plants were then sprayed to run-off with the test compound at a rate of 100 ppm. After 24 hours the test plants were inoculated by spraying with an aqueous spore suspension of *Septoria tritici,* and kept in a dew chamber overnight. The plants were then transferred to the greenhouse until disease developed on the untreated control plants.

Glume Blotch of Wheat (*Leptosphaeria nodorum*—LEPTNO) (24 Hour Protectant): Wheat (cultivar Yuma) was grown in a soilless peat-based potting mixture ("Metromix") until the seedlings were 10–20 cm tall. These plants were then sprayed to run-off with the test compound at a rate of 100 ppm. After 24 hours the test plants were inoculated by spraying with an aqueous spore suspension of *Leptosphaeria nodorum,* and kept in a dew chamber overnight. The plants were then transferred to the greenhouse until disease developed on the untreated control plants.

In Table II, a "++" indicates that the test material gave at least 75–100% control of fungal infection when compared to disease incidence on untreated plants, a "+" indicates that the test material gave 25–74% control of fungal infection, and a "−" indicates <25% control of fungal infection of the designated pathogen at a concentration of 100 ppm. A blank space indicates not tested.

TABLE 1

| Compound Number | Molecular Structure | Appearance | Molecular Ion (M) | Melting Point (° C.) |
|---|---|---|---|---|
| 201 | 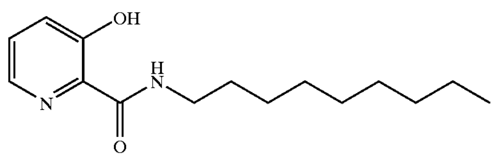 | Yellow oil | 264 | |
| 202 | 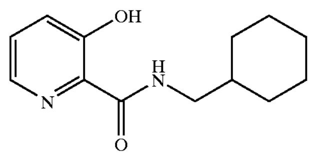 | Pale yellow oil | 234 | |
| 203 | 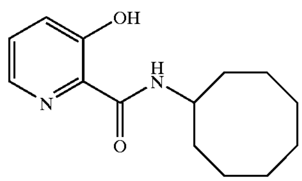 | Pale yellow solid | | 63–64 |
| 204 | 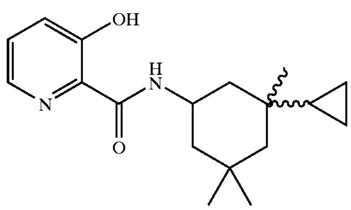 | White solid | 302 | |
| 205 | 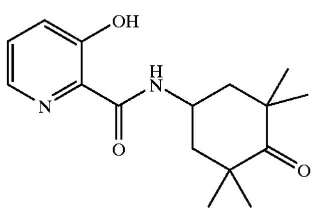 | White solid | 290 | |
| 206 | 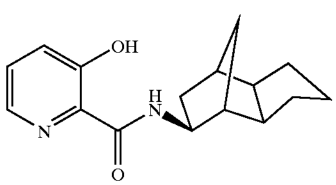 | Oily white solid | 272 | |
| 207 | 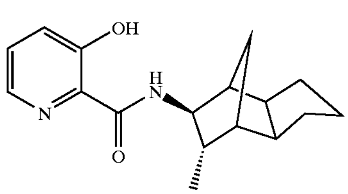 | Yellow oil | 286 | |
| 208 | 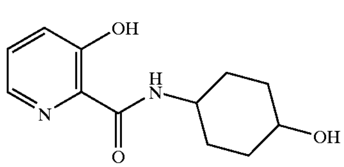 | Colorless thin needles | | 112–115 |

TABLE 1-continued

| Compound Number | Molecular Structure | Appearance | Molecular Ion (M) | Melting Point (° C.) |
| --- | --- | --- | --- | --- |
| 209 | 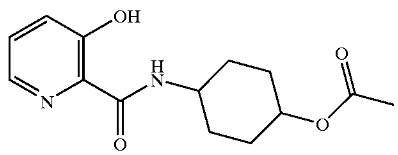 | Colorless crystals | | 123–126 |
| 210 | 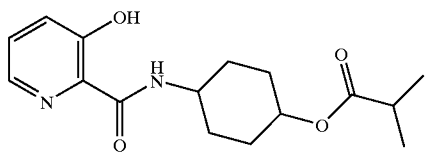 | Colorless crystals | | 139–142 |
| 211 | 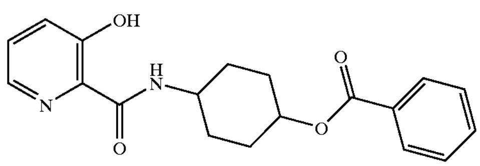 | Colorless crystals | | 154–157 |
| 212 | 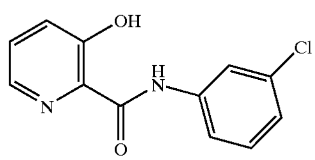 | White solid | | 131–132 |
| 213 | 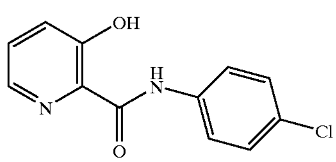 | Tan solid | 248, 250 | |
| 214 | 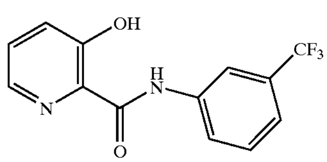 | Yellow solid | 282 | |
| 215 | 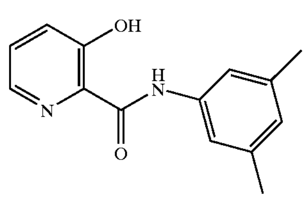 | Orange-white solid | 242 | |
| 216 | 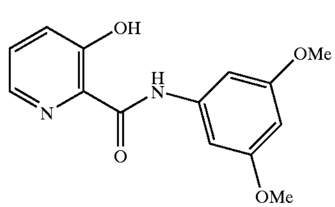 | Off-white solid | | 127–129 |

TABLE 1-continued
| Compound Number | Molecular Structure | Appearance | Molecular Ion (M) | Melting Point (° C.) |
|---|---|---|---|---|
| 217 | 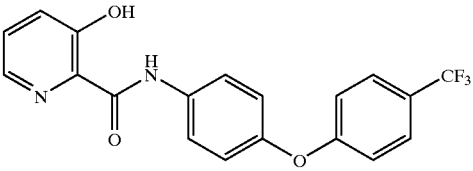 | Tan solid | | 131–133 |
| 218 | 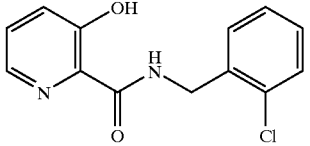 | Off-white solid | | 97–99 |
| 219 | 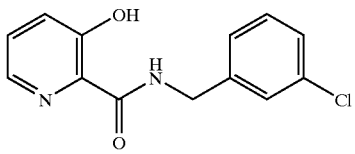 | Off-white solid | | 65–67 |
| 220 | 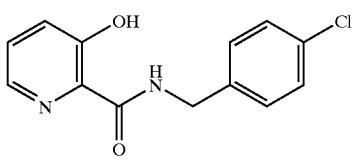 | Off-white solid | | 95–97 |
| 221 | 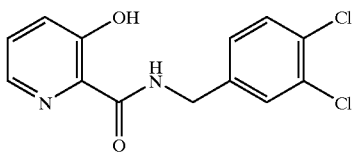 | White solid | | 100–101 |
| 222 | 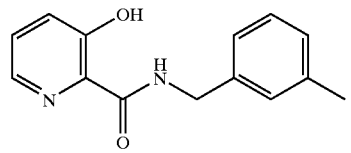 | Pale yellow oil | 242 | |
| 223 | 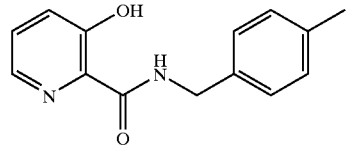 | White solid | | 83–84 |
| 224 | 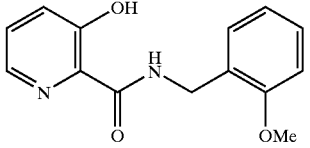 | White solid | | 75–76 |
| 225 | 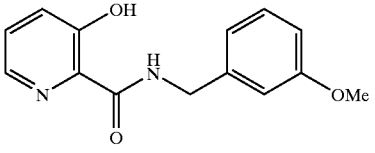 | White solid | | 41–43 |

TABLE 1-continued
| Compound Number | Molecular Structure | Appearance | Molecular Ion (M) | Melting Point (° C.) |
|---|---|---|---|---|
| 226 | 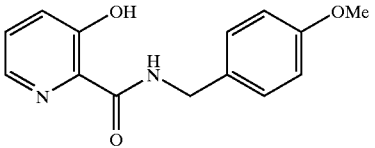 | White solid | | 96–97 |
| 227 | 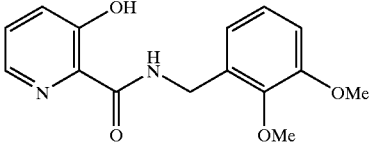 | White solid | | 78–79 |
| 228 | 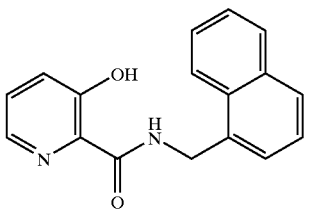 | White solid | | 106–109 |
| 229 | 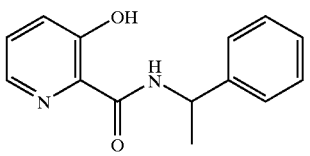 | White solid | | 89–91 |
| 230 | 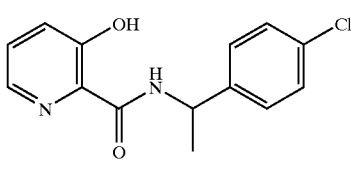 | Yellow oil | | |
| 231 | 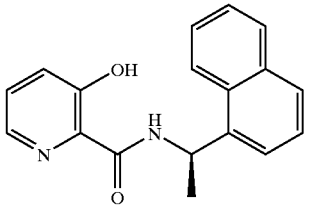 | Orange oil | 292 | |
| 232 | 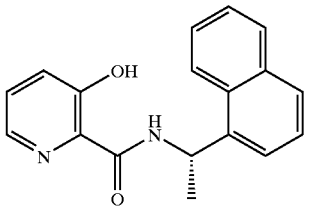 | Orange oil | 292 | |
| 233 | 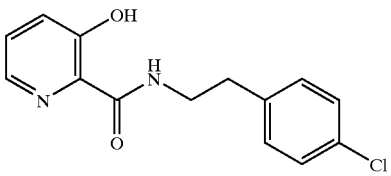 | Off-white solid | 276, 278 | |

TABLE 1-continued

| Compound Number | Molecular Structure | Appearance | Molecular Ion (M) | Melting Point (° C.) |
| --- | --- | --- | --- | --- |
| 234 | 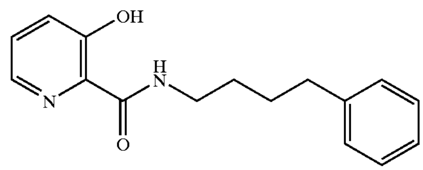 | Yellow oil | 270 | |
| 235 | 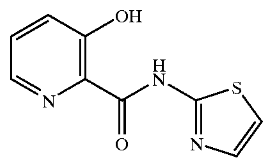 | Brown solid | 221 | |
| 236 | 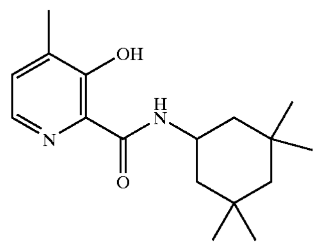 | Colorless crystals | | 42–45 |
| 237 | 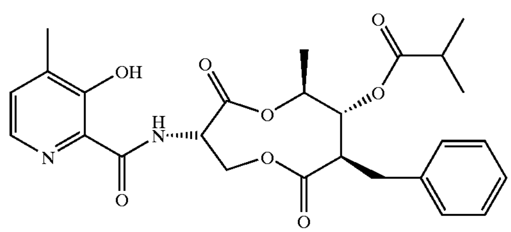 | Colorless solid | | 122–134 |
| 238 | 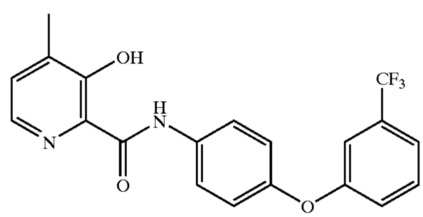 | Colorless needles | | 105–107 |
| 239 | 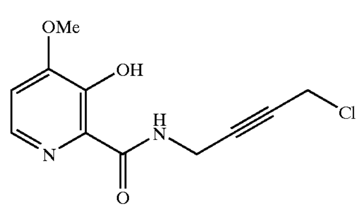 | Off-white fluffy crystals | 254, 256 | |
| 240 | 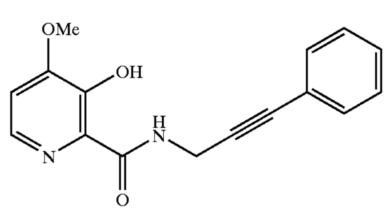 | Yellow fluffy crystals | 282 | |

TABLE 1-continued
| Compound Number | Molecular Structure | Appearance | Molecular Ion (M) | Melting Point (° C.) |
|---|---|---|---|---|
| 241 | 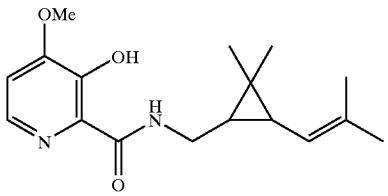 | Tan solid | 304 | |
| 242 | 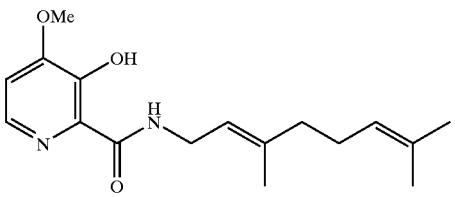 | Gold syrup | 304 | |
| 243 | 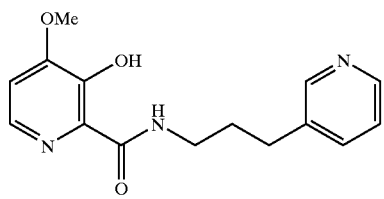 | Brown powder | 287 | |
| 244 | 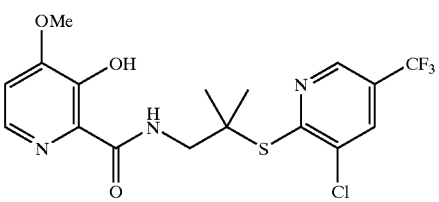 | Yellow gum | 436 | |
| 245 | 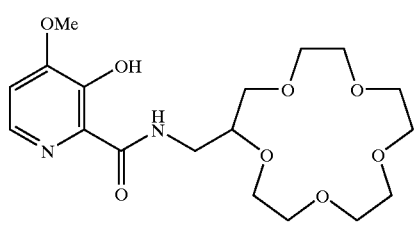 | Colorless oil | | |
| 246 | 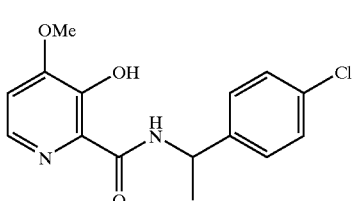 | Off-white solid | | 140–142 |
| 247 | 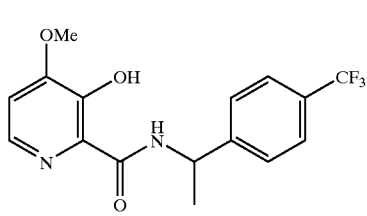 | Pale yellow solid | 340 | |

TABLE 1-continued

| Compound Number | Molecular Structure | Appearance | Molecular Ion (M) | Melting Point (° C.) |
| --- | --- | --- | --- | --- |
| 248 | 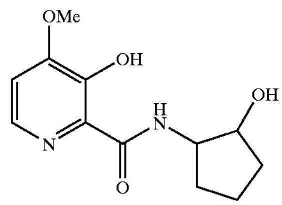 | Yellow oil | M + 1 253 | |
| 249 | 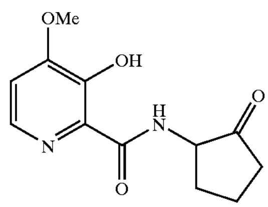 | Thick yellow oil | 250 | |
| 250 | 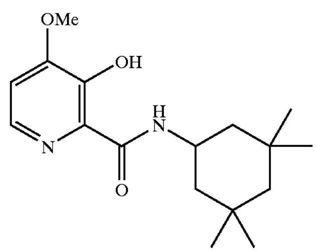 | Off-white solid | | 140–106 |
| 251 | 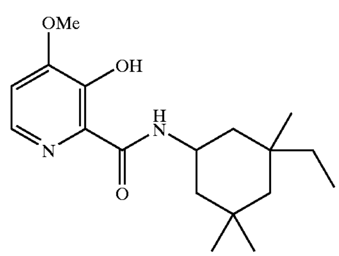 | Amber oil | | |
| 252 | 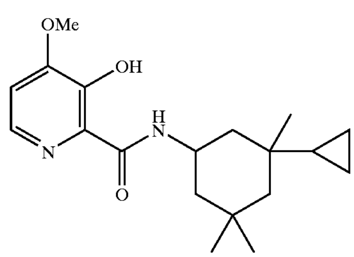 | Yellow gel | | |
| 253 | 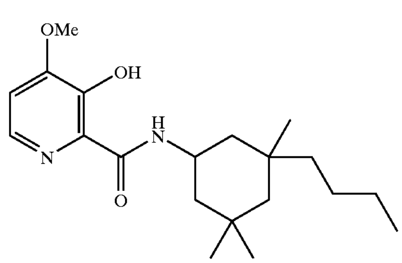 | Clear gel | | |

TABLE 1-continued

| Compound Number | Molecular Structure | Appearance | Molecular Ion (M) | Melting Point (° C.) |
|---|---|---|---|---|
| 254 | 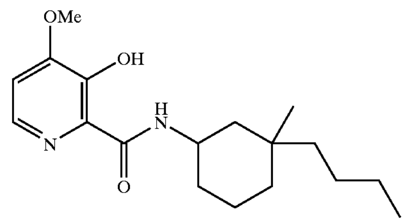 | Yellow gel | | |
| 255 | 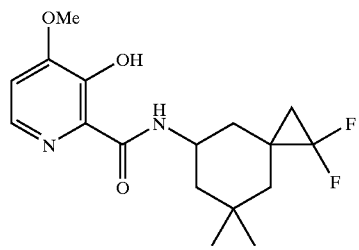 | White powder | 340 | |
| 256 | 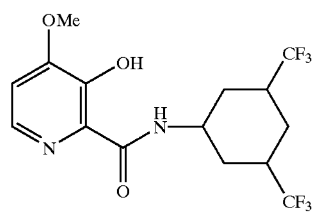 | White solid | | |
| 257 | 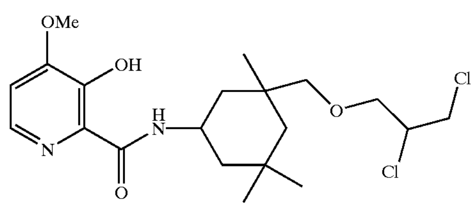 | Oil | 433 | |
| 258 | 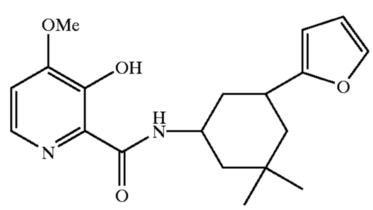 | Gum | M + 1 345 | |
| 259 | 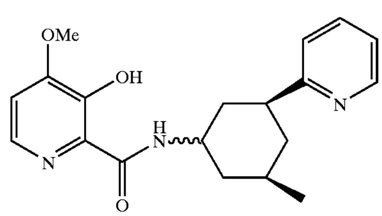 | Gum | M + 1 341 | |
| 260 | 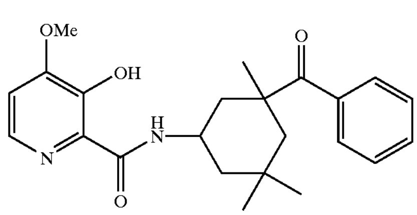 | White solid | 396 | 147–149 |

TABLE 1-continued

| Compound Number | Molecular Structure | Appearance | Molecular Ion (M) | Melting Point (° C.) |
|---|---|---|---|---|
| 261 | 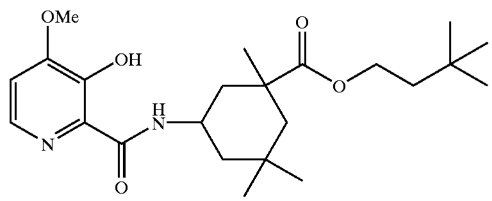 | Pale yellow oil | M + 1 421 | |
| 262 | 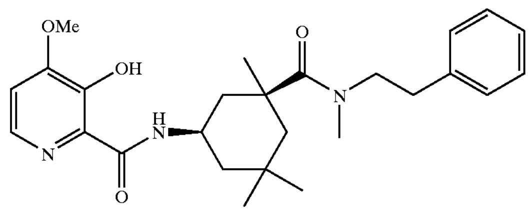 | White solid | M + 1 454 | 59–60 |
| 263 | 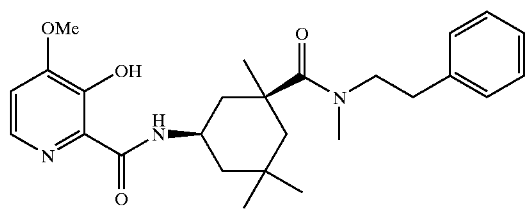 | Off-white foam | M + 1 454 | |
| 264 | 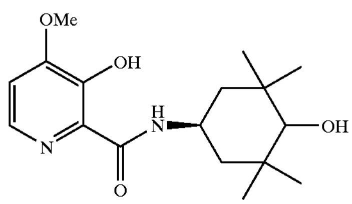 | White solid | 322 | |
| 265 | 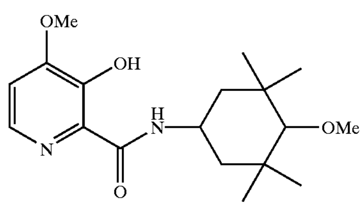 | Yellow oil | | |
| 266 | 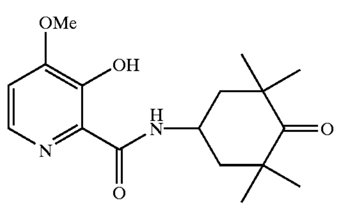 | White solid | 362 | |
| 267 | 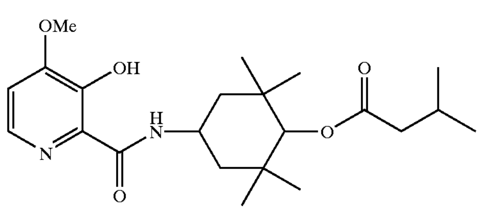 | White foam | | |

TABLE 1-continued

| Compound Number | Molecular Structure | Appearance | Molecular Ion (M) | Melting Point (° C.) |
|---|---|---|---|---|
| 268 | 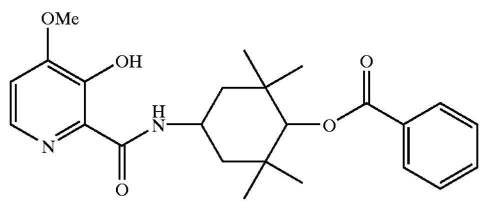 | White solid | 426 | 175–200 |
| 269 | 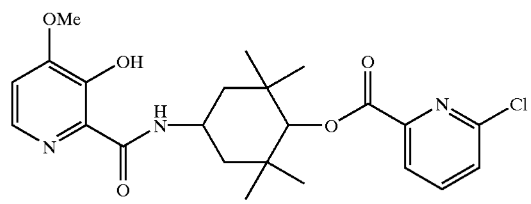 | White solid | 461 | 55–65 |
| 270 | 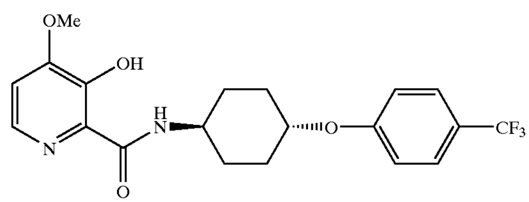 | Off-white solid | | 168–172 (Dec) |
| 271 | 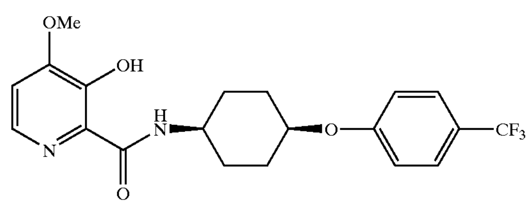 | Off-white solid | | 181–183 (Dec) |
| 272 | 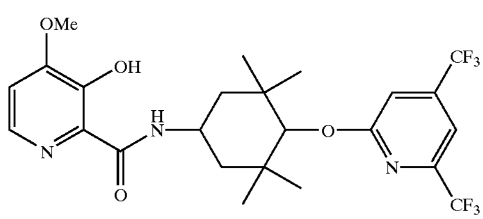 | Off-white solid | 535 | |
| 273 | 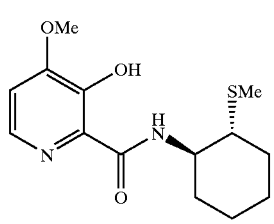 | White solid | 297 | 113–115 |
| 274 | 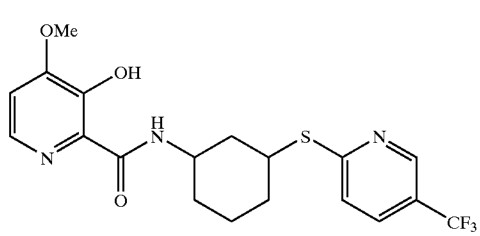 | White solid | 427 | |

TABLE 1-continued
| Compound Number | Molecular Structure | Appearance | Molecular Ion (M) | Melting Point (° C.) |
|---|---|---|---|---|
| 275 | 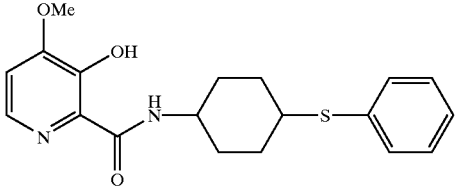 | Yellow gel | 358 | |
| 276 | 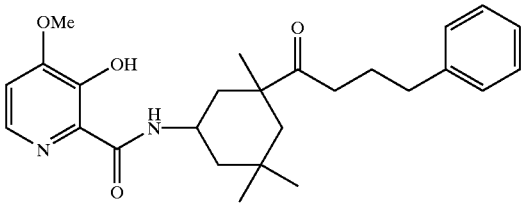 | Colorless gel | 438 | |
| 277 | 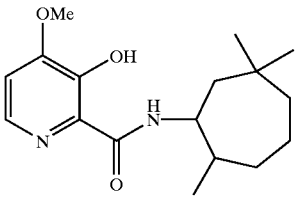 | Gum | 306 | |
| 278 | 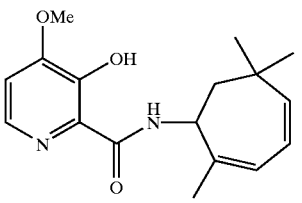 | Pale yellow oil | 302 | |
| 279 | 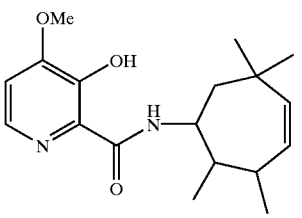 | Gum | 318 | |
| 280 | 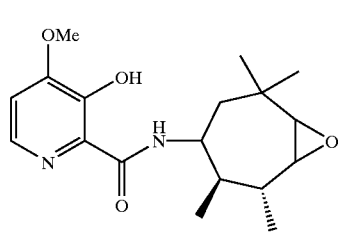 | White foam | 334 | |
| 281 | 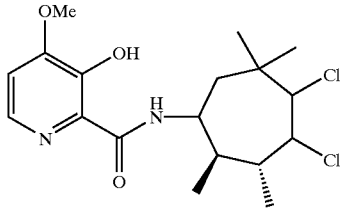 | White foam | M − 1 388 | |

TABLE 1-continued

| Compound Number | Molecular Structure | Appearance | Molecular Ion (M) | Melting Point (° C.) |
|---|---|---|---|---|
| 282 | 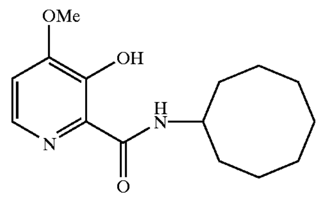 | Pale yellow oil | 278 | |
| 283 | 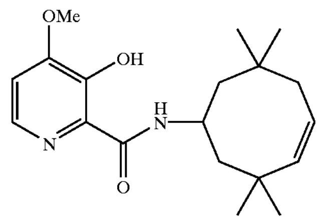 | Clear oil | | |
| 284 | 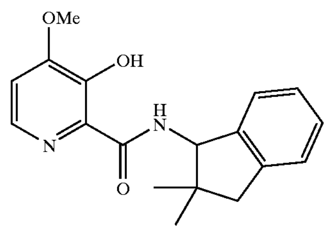 | Solid | | 122–128 |
| 285 | 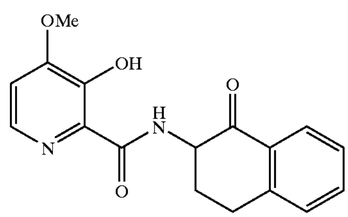 | Tan solid | | 174–179 |
| 286 | 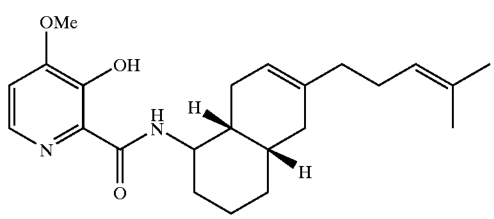 | Thick colorless oil | 384 | |
| 287 | 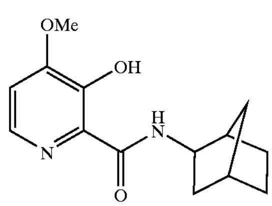 | White solid | 262 | |
| 288 | 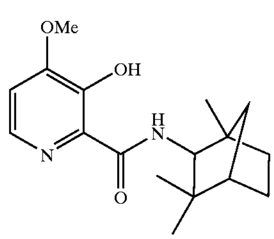 | Pale yellow solid | 304 | |

TABLE 1-continued

| Compound Number | Molecular Structure | Appearance | Molecular Ion (M) | Melting Point (° C.) |
|---|---|---|---|---|
| 289 | | Pale yellow gum | 384 | |
| 290 | 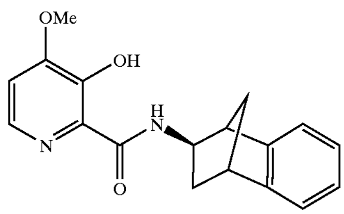 | White solid | 310 | |
| 291 | 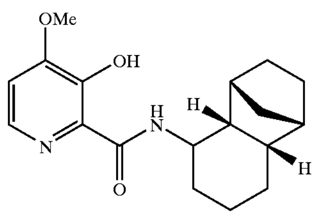 | Dark brown oil | 316 | |
| 292 | 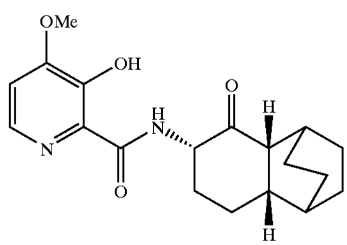 | Pasty yellow solid | 344 | |
| 293 | 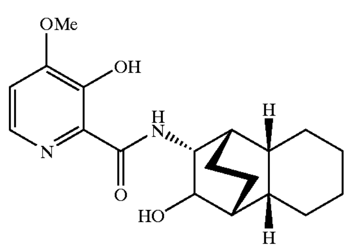 | White solid | | 143–160 (Dec) |
| 294 | 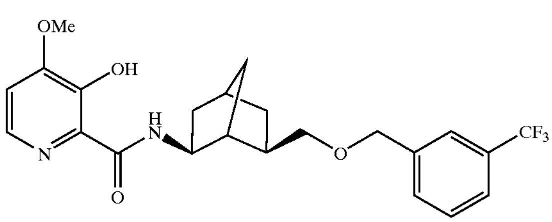 | Yellow gum | 450 | |

TABLE 1-continued

| Compound Number | Molecular Structure | Appearance | Molecular Ion (M) | Melting Point (° C.) |
| --- | --- | --- | --- | --- |
| 295 | OMe, OH, pyridine-C(O)NH-norbornyl-CH₂-O-CH₂-C₆H₄-CF₃ | Colorless gum | 450 | |
| 296 | OMe, OH, pyridine-C(O)NH-norbornyl-CH₂-O-CH₂-C₆H₄-CF₃ | Colorless gum | 450 | |
| 297 | OMe, OH, pyridine-C(O)NH-norbornyl-CH₂-O-CH₂-C₆H₄-CF₃ | Yellow gum | 450 | |
| 298 | OMe, OH, pyridine-C(O)NH-norbornyl-C(O)O-iPr (two structures shown) | Yellow gum | 348 | |
| 299 | OMe, OH, pyridine-C(O)NH-norbornyl(phenyl)-C(O)O-iPr (Mixture) | Pale yellow gum | 439 | |

TABLE 1-continued

| Compound Number | Molecular Structure | Appearance | Molecular Ion (M) | Melting Point (° C.) |
|---|---|---|---|---|
| 300 | 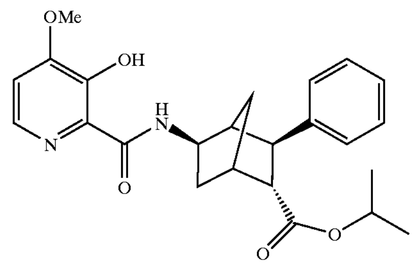 | White solid | 439 | |
| 301 | 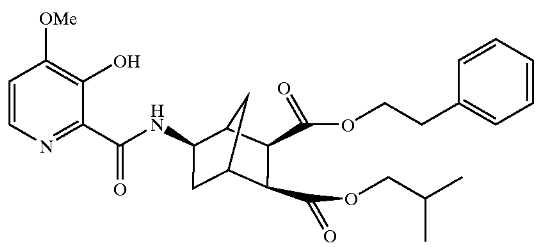 | Colorless gum | 510 | |
| 302 | 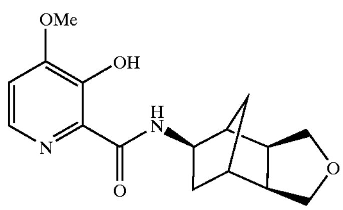 | White solid | 304 | |
| 303 | 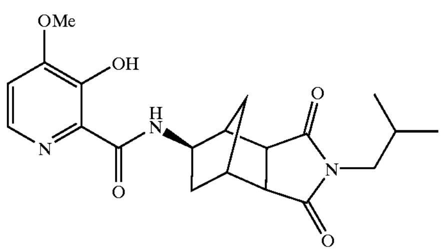 | White foamy solid | 401 | |
| 304 | 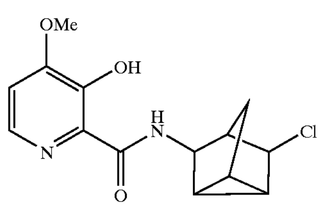 | Brown glass | 294, 296 | |
| 305 | 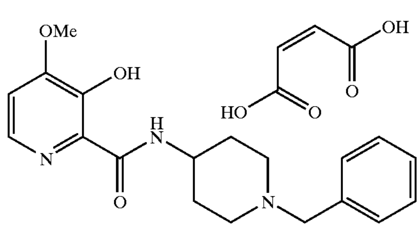 | White solid | | 145–147 |

TABLE 1-continued

| Compound Number | Molecular Structure | Appearance | Molecular Ion (M) | Melting Point (° C.) |
| --- | --- | --- | --- | --- |
| 308 | (4-methoxy-3-hydroxy-pyridine-2-carboxamide, N-[1-(4-methylbenzyl)piperidin-4-yl]) | White solid | 356 | 150–152 |
| 307 | (4-methoxy-3-hydroxy-pyridine-2-carboxamide, N-[1-(3-trifluoromethylbenzyl)piperidin-4-yl], bis maleate) | White solid | | 168–170 |
| 308 | (4-methoxy-3-hydroxy-pyridine-2-carboxamide, N-(1-benzoylpiperidin-4-yl)) | Amber glass | 356 | |
| 309 | (4-methoxy-3-hydroxy-pyridine-2-carboxamide, N-[1-(3-phenylpropanoyl)piperidin-4-yl]) | Sticky oil | 384 | |
| 310 | (4-methoxy-3-hydroxy-pyridine-2-carboxamide, N-(5-methyltetrahydrofuran-3-yl)) | Glass | 252 | |
| 311 | (4-methoxy-3-hydroxy-pyridine-2-carboxamide, N-(6-benzyl-2-methyltetrahydropyran-4-yl), HBr salt) | White solid | 356 | 156–158 |

TABLE 1-continued

| Compound Number | Molecular Structure | Appearance | Molecular Ion (M) | Melting Point (° C.) |
|---|---|---|---|---|
| 312 | 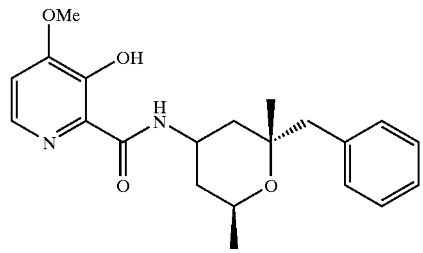 | Oil | 370 | |
| 313 | 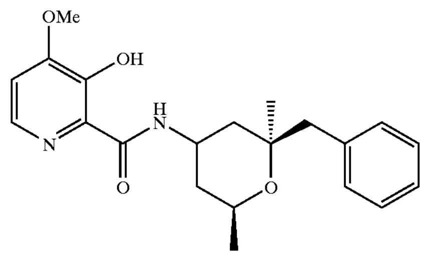 | Oil | 370 | |
| 314 | 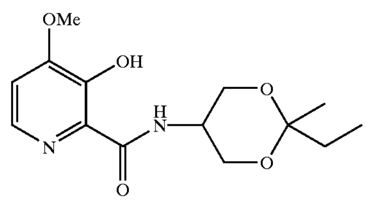 | Light brown gum | 296 | |
| 315 | 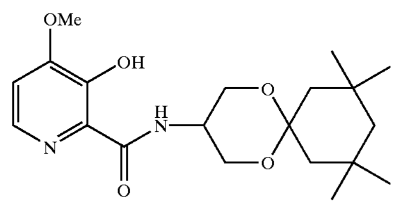 | White solid | 379 | |
| 316 | 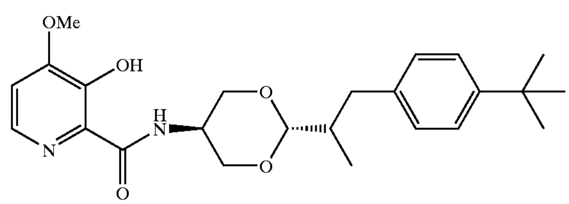 | White solid | M + 1 429 | |
| 317 | 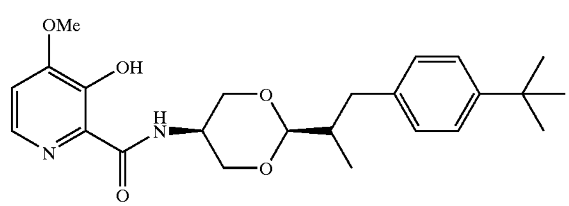 | | 428 | |
| 318 | 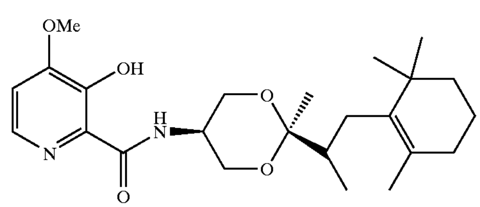 | Gum | 418 | |

TABLE 1-continued

| Compound Number | Molecular Structure | Appearance | Molecular Ion (M) | Melting Point (° C.) |
| --- | --- | --- | --- | --- |
| 319 | 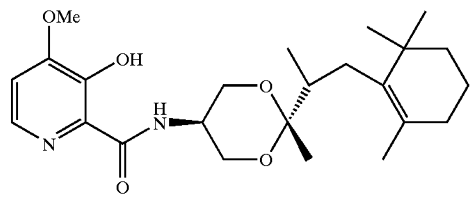 | White solid | 418 | 139–140 |
| 320 | 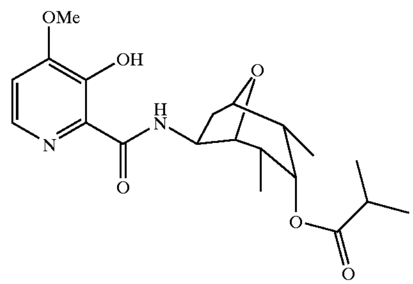 | White solid | | 108.5–109.5 |
| 321 | 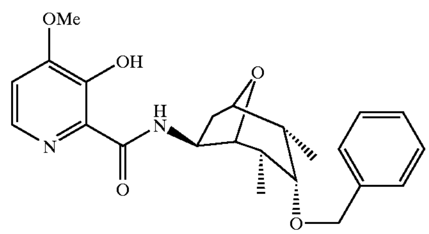 | Yellow glass | 412 | |
| 322 | 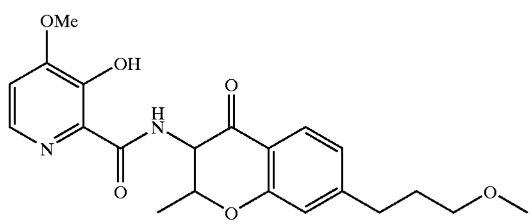 | Yellow sticky solid | 400 | |
| 323 | 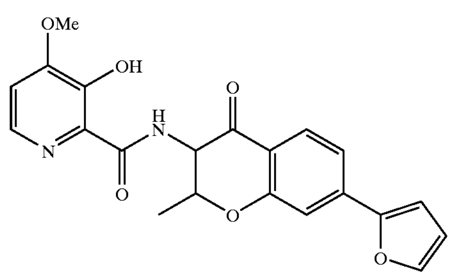 | Yellow sticky solid | 394 | |
| 324 | 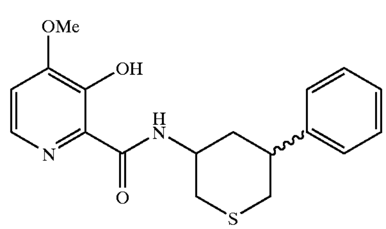 | White solid | 345 | 141–143 |

TABLE 1-continued
| Compound Number | Molecular Structure | Appearance | Molecular Ion (M) | Melting Point (° C.) |
|---|---|---|---|---|
| 325 | 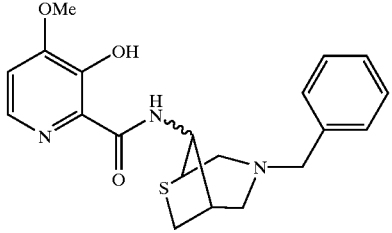 | Glass | 398 | |
| 326 | 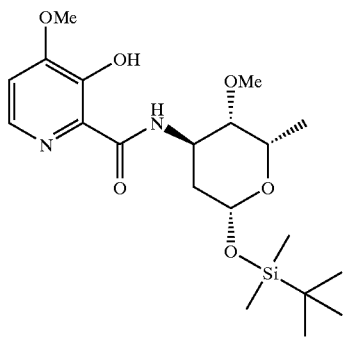 | Clear gel | | |
| 327 | 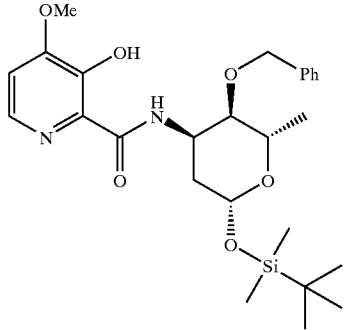 | Clear gel | | |
| 328 | 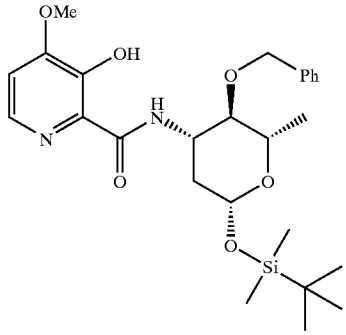 | Off white solid | | |
| 329 | 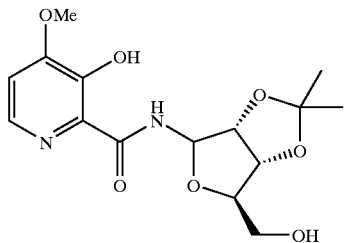 | White solid | | |

TABLE 1-continued

| Compound Number | Molecular Structure | Appearance | Molecular Ion (M) | Melting Point (° C.) |
|---|---|---|---|---|
| 330 | 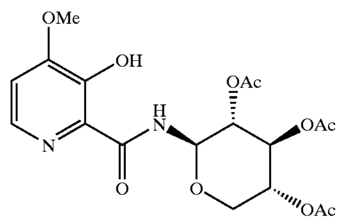 | White solid | | |
| 331 | 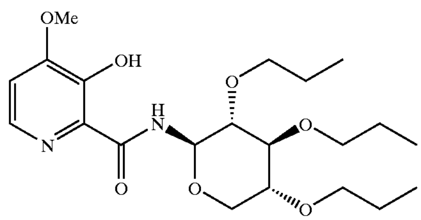 | White solid | | |
| 332 | 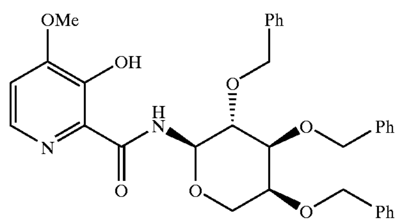 | White solid | | |
| 333 | 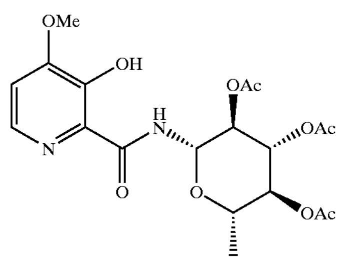 | White solid | | |
| 334 | 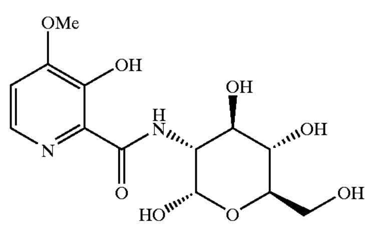 | Yellow solid | | |
| 335 | 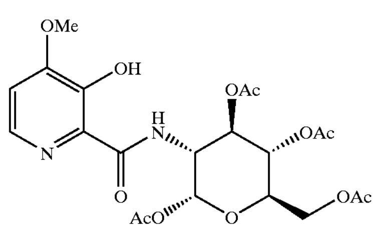 | White solid | | |

TABLE 1-continued

| Compound Number | Molecular Structure | Appearance | Molecular Ion (M) | Melting Point (° C.) |
| --- | --- | --- | --- | --- |
| 336 | 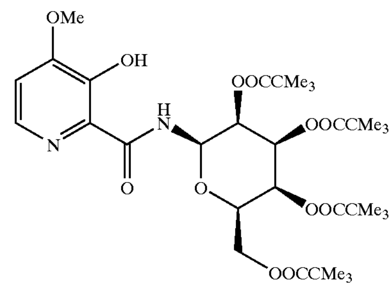 | White solid | | |
| 337 | 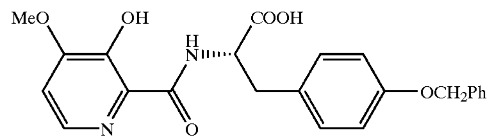 | White solid | M + 1 423 | |
| 338 | 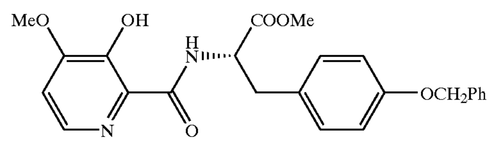 | Tan oily solid | M + 1 437 | |
| 339 | 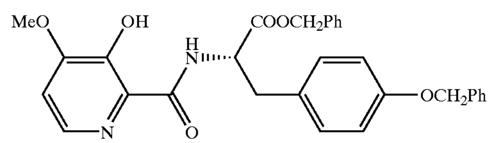 | White waxy solid | M + 1 513 | |
| 340 | 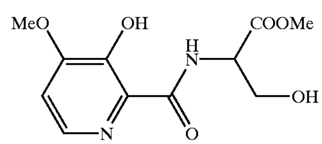 | Tacky solid | 270 | |
| 341 | 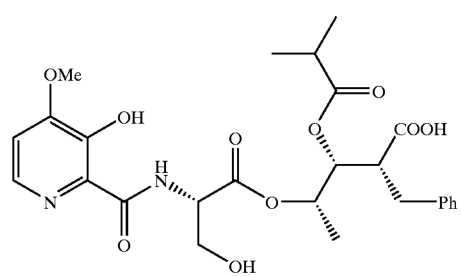 | Brown oil | | |
| 342 | 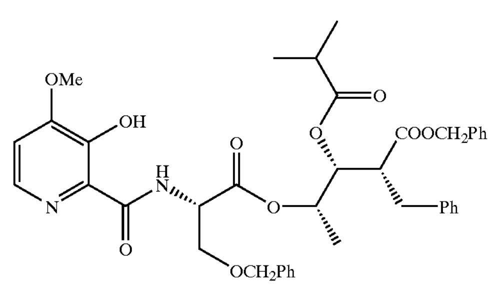 | Clear oil | | |

TABLE 1-continued

| Compound Number | Molecular Structure | Appearance | Molecular Ion (M) | Melting Point (° C.) |
| --- | --- | --- | --- | --- |
| 343 | 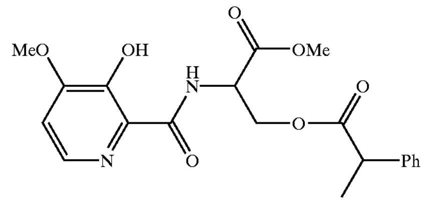 | Pale yellow gum | M + 1 403 | |
| 344 | 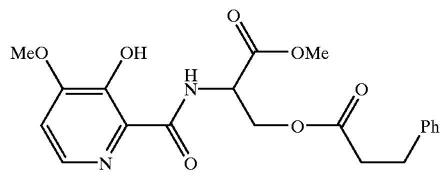 | Pale yellow gum | M + 1 403 | |
| 345 | 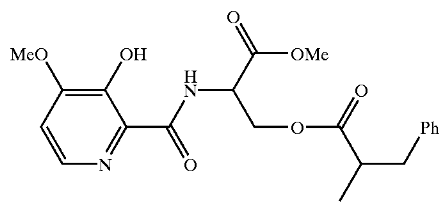 | Amber gum | M + 1 417 | |
| 346 | 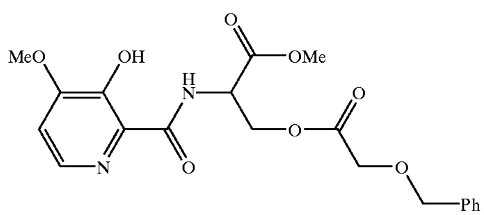 | Pale yellow oil | M + 1 419 | |
| 347 | 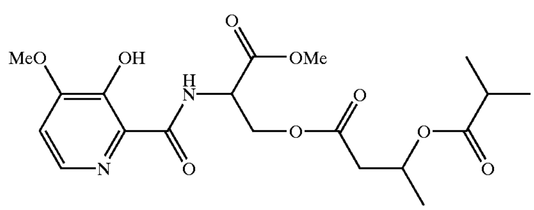 | Pinkish gum | M + 1 427 | |
| 348 | 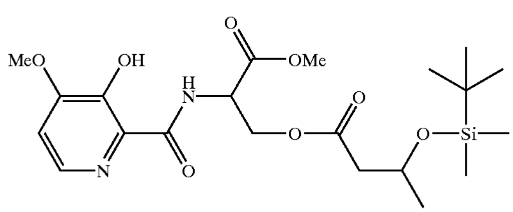 | Pinkish gum | M + 1 469 | |
| 349 | 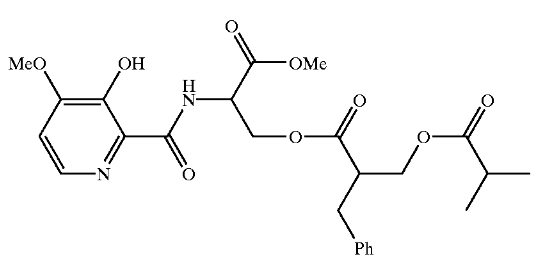 | Pale yellow gum | M + 1 503 | |

TABLE 1-continued

| Compound Number | Molecular Structure | Appearance | Molecular Ion (M) | Melting Point (° C.) |
| --- | --- | --- | --- | --- |
| 350 | 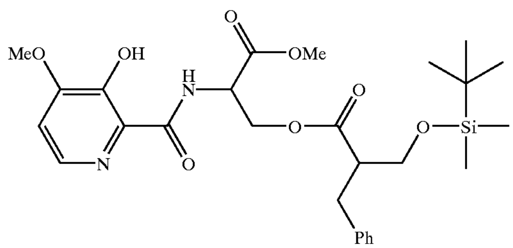 | Amber gum | M + 1 447 | |
| 351 | 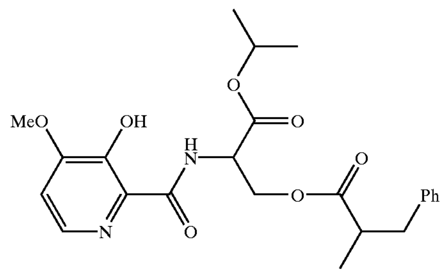 | Pale yellow gum | M + 1 445 | |
| 352 | 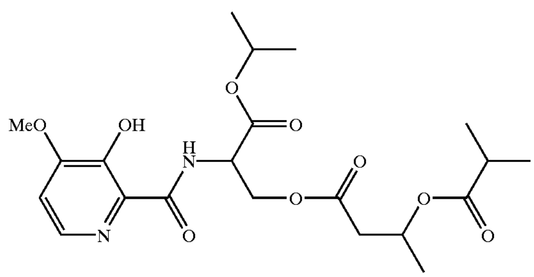 | Amber gum | 454 | |
| 353 | 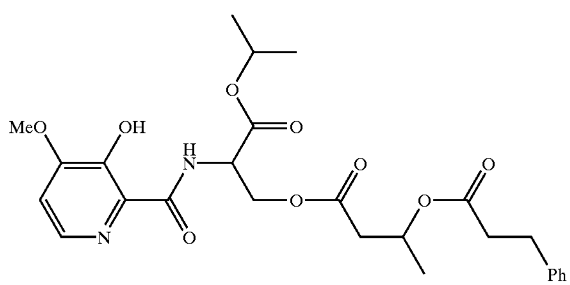 | Yellow gum | 516 | |
| 354 | 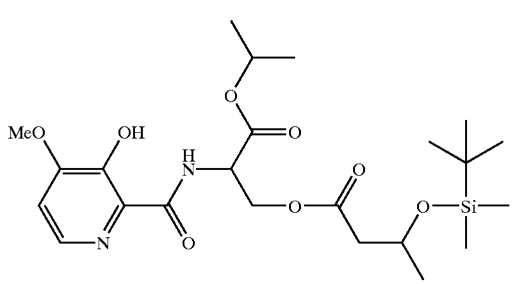 | Yellow gum | M + 1 499 | |

TABLE 1-continued

| Compound Number | Molecular Structure | Appearance | Molecular Ion (M) | Melting Point (° C.) |
| --- | --- | --- | --- | --- |
| 355 | 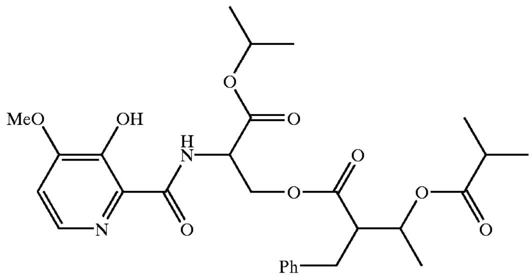 | Yellow gum | M + 1 545 | |
| 356 | 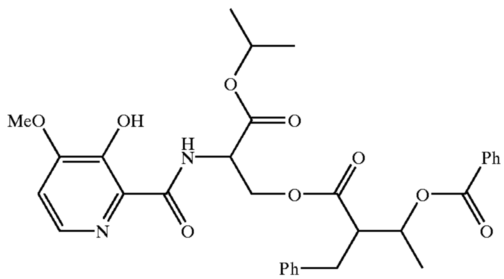 | Pale yellow gum | M + 1 579 | |
| 357 | 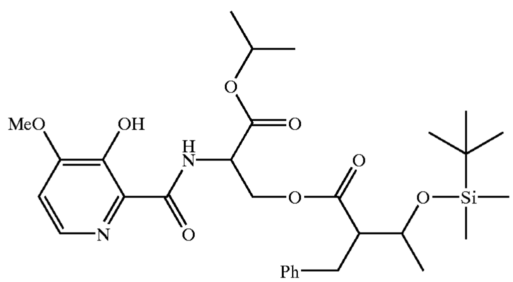 | Yellow gum | M + 1 589 | |
| 358 | (Either S, S or S, R diastereomer) | Pale yellow gum | 516 | |
| 359 | (Either S, S or S, R diastereomer) | Pale yellow gum | 516 | |

TABLE 1-continued

| Compound Number | Molecular Structure | Appearance | Molecular Ion (M) | Melting Point (° C.) |
|---|---|---|---|---|
| 360 | 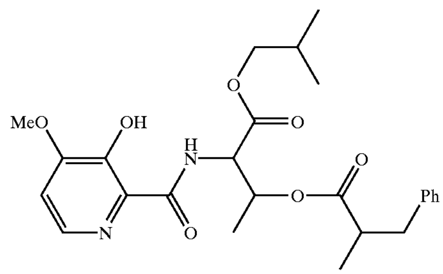 | Yellow gum | 472 | |
| 361 | 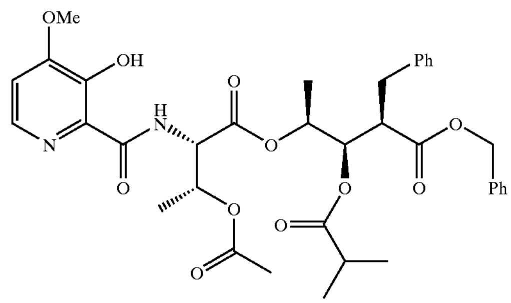 | Yellow oil | | |
| 362 | 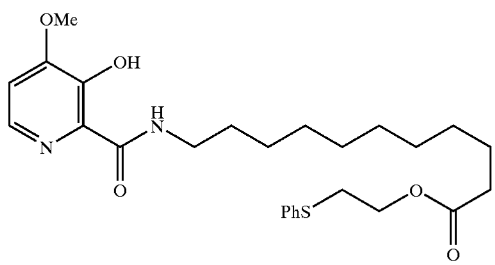 | Yellow oil | M + 1 489 | |
| 363 | 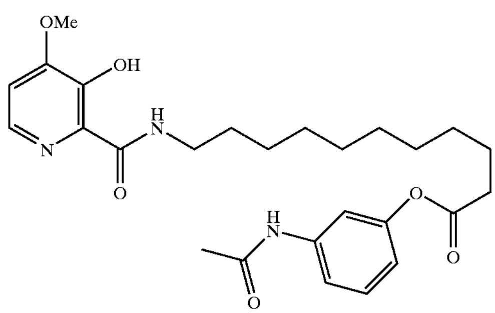 | Yellow oil | M + 1 486 | |
| 364 | 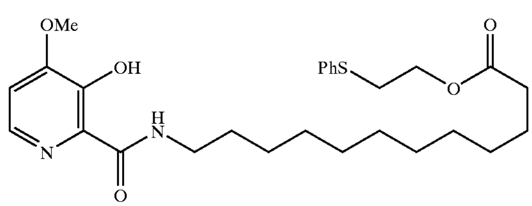 | Yellow oil | M + 1 503 | |

TABLE 1-continued

| Compound Number | Molecular Structure | Appearance | Molecular Ion (M) | Melting Point (° C.) |
|---|---|---|---|---|
| 365 | 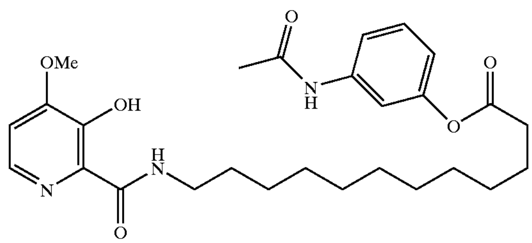 | Yellow oil | | |
| 366 | 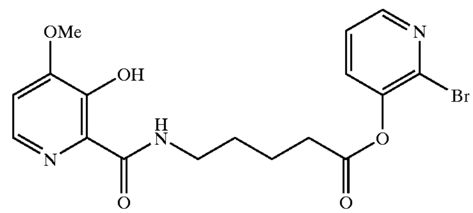 | Yellow oil | | |
| 367 | 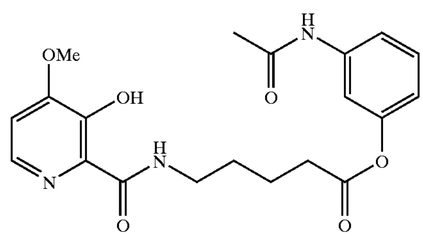 | Yellow oil | | |
| 368 | 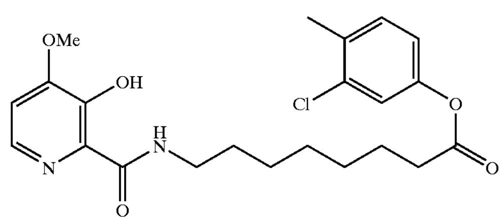 | Yellow oil | M + 1 435 | |
| 369 | 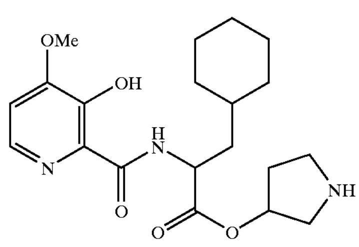 | Yellow oil | | |
| 370 | 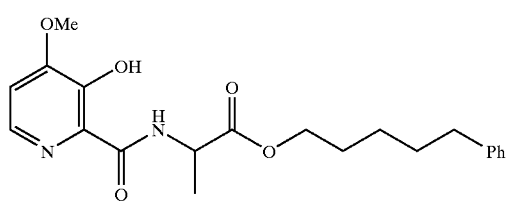 | Yellow oil | M + 1 387 | |

TABLE 1-continued

| Compound Number | Molecular Structure | Appearance | Molecular Ion (M) | Melting Point (° C.) |
| --- | --- | --- | --- | --- |
| 371 | 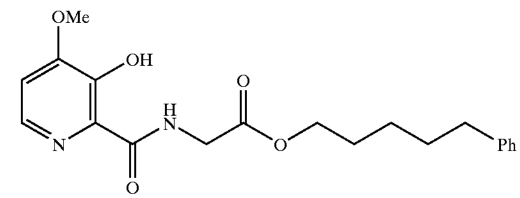 | Yellow oil | M + 1 373 | |
| 372 | 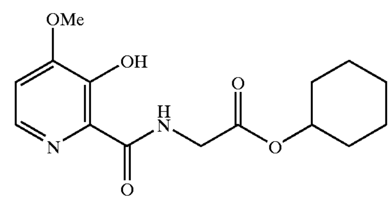 | Yellow oil | | |
| 373 | 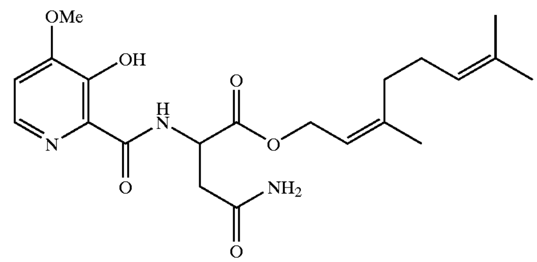 | Yellow oil | | |
| 374 | 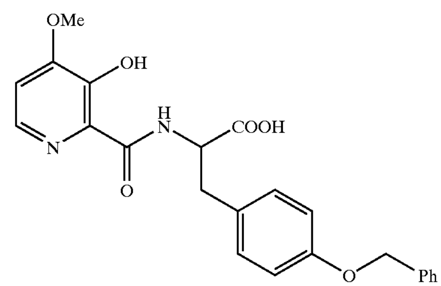 | Yellow oil | M + 1 423 | |
| 375 | 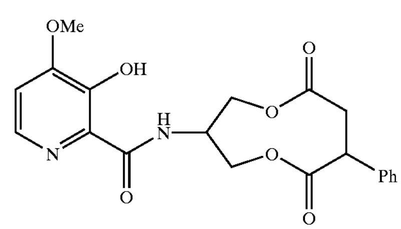 | White solid | 400 | |
| 376 | 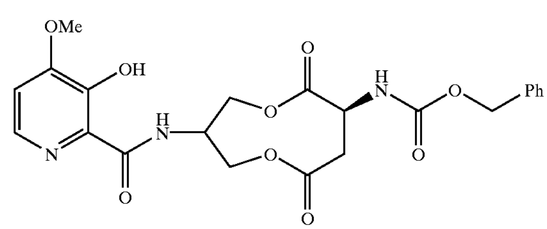 | Pale yellow solid | 473 | 190–192 |

TABLE 1-continued

| Compound Number | Molecular Structure | Appearance | Molecular Ion (M) | Melting Point (° C.) |
| --- | --- | --- | --- | --- |
| 377 | 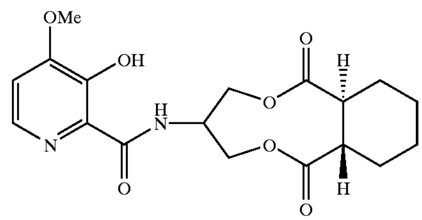 | White solid | M + 1 379 | 234–235 |
| 378 | 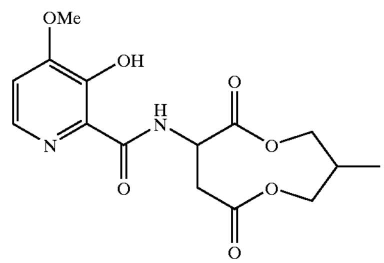 | Solid | 338 | |
| 379 | 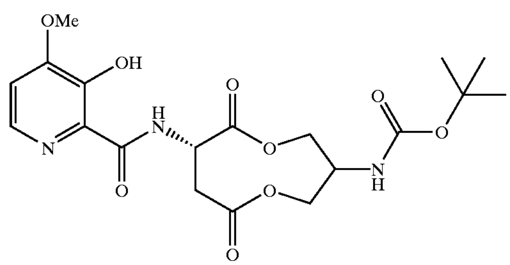 | Pale yellow solid | 439 | 118–121 |
| 380 | 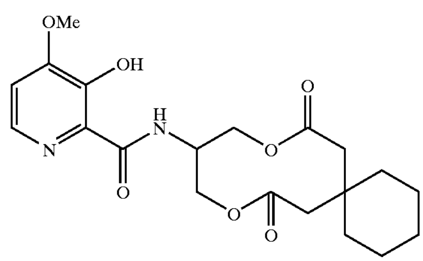 | White solid | 405 | 107–108 |
| 381 | 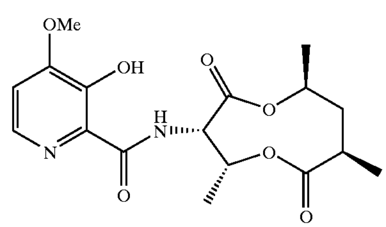 | White solid | | |
| 382 | 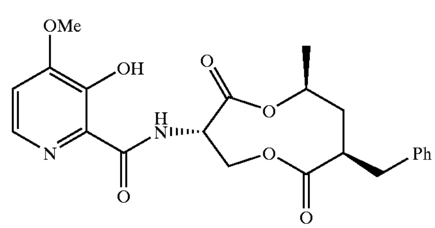 | White solid | | |

TABLE 1-continued

| Compound Number | Molecular Structure | Appearance | Molecular Ion (M) | Melting Point (° C.) |
|---|---|---|---|---|
| 383 | 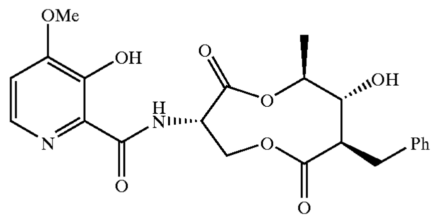 | White solid | 444 | |
| 384 | 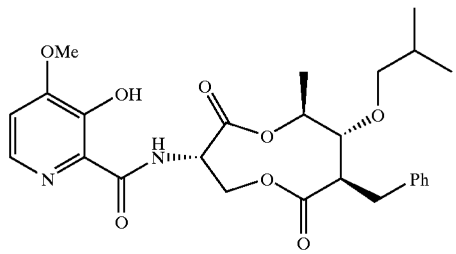 | White solid | | 172–174 |
| 385 | 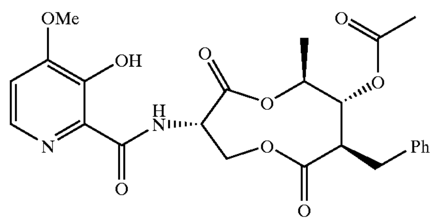 | Ivory solid | | 194–196 |
| 386 | 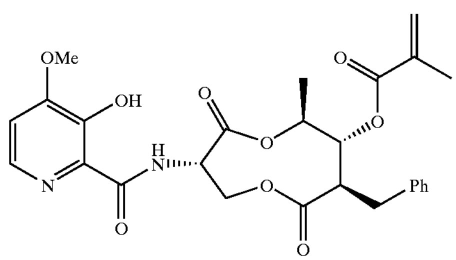 | Clear oil | 512 | |
| 387 | 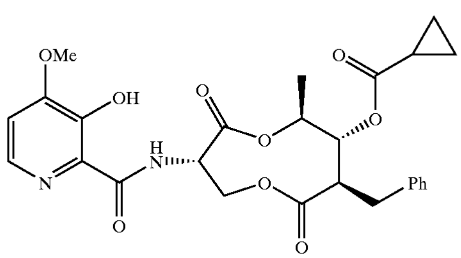 | Off-white foam | 512 | |
| 388 | 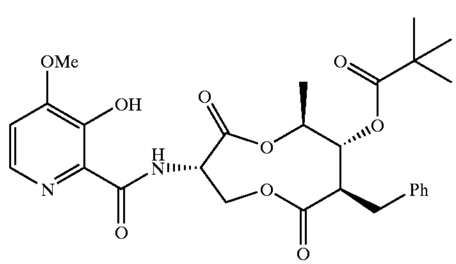 | White solid | | 212–214 |

TABLE 1-continued

| Compound Number | Molecular Structure | Appearance | Molecular Ion (M) | Melting Point (° C.) |
|---|---|---|---|---|
| 389 | 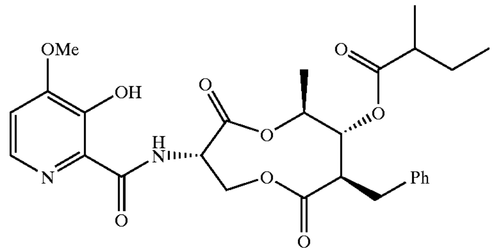 | Off-white foam | | |
| 390 | 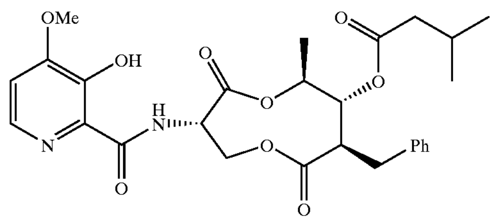 | Yellow solid | | |
| 391 | 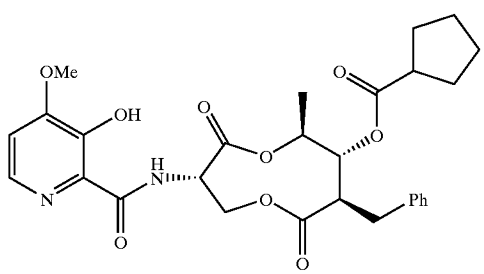 | Tan foam | 540 | |
| 392 | 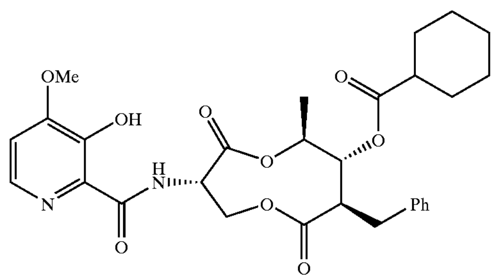 | Clear oil | | |
| 393 | 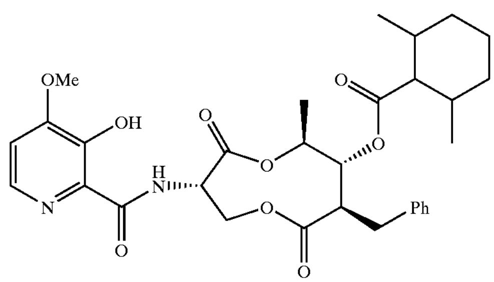 | Yellow glass | | |
| 394 | 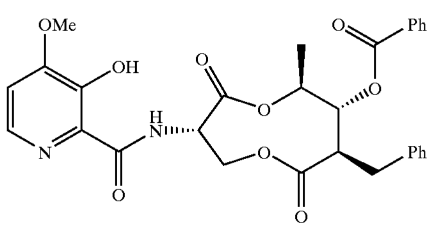 | Pale yellow solid | | 181–185 |

TABLE 1-continued
| Compound Number | Molecular Structure | Appearance | Molecular Ion (M) | Melting Point (° C.) |
|---|---|---|---|---|
| 395 | 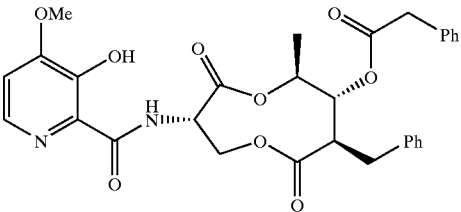 | Yellow solid | 582 | |
| 396 | 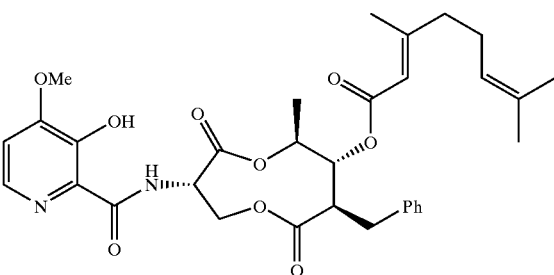 | White foam | M + 1 595 | |
| 397 | 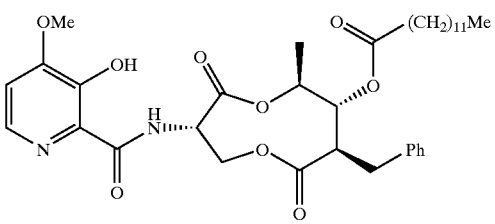 | Yellow solid | | |
| 398 | 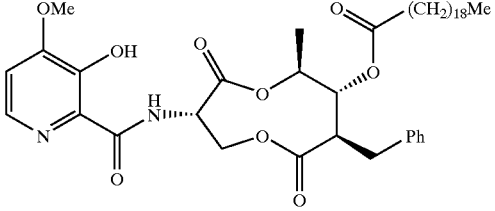 | White solid | | |
| 399 | 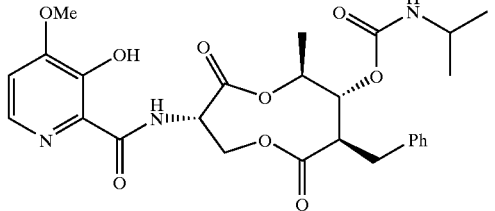 | White foam | M + 1 530 | |
| 400 | 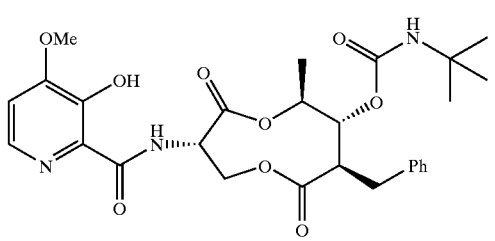 | White solid | | |

TABLE 1-continued

| Compound Number | Molecular Structure | Appearance | Molecular Ion (M) | Melting Point (° C.) |
|---|---|---|---|---|
| 401 | 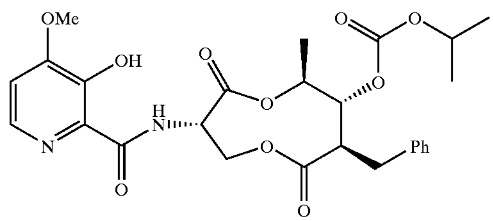 | White gummy solid | 530 | |
| 402 | 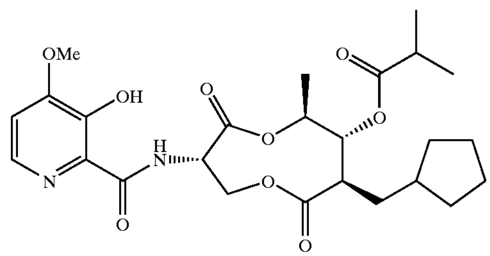 | Off-white solid | | 182–184 |
| 403 | 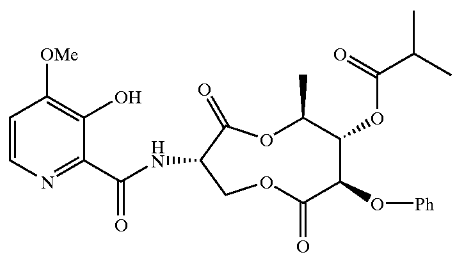 | White solid | | 194–195 |
| 404 | 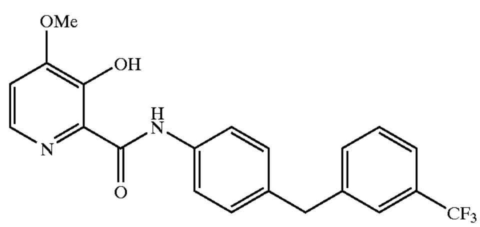 | White solid | | 126–127 |
| 405 | 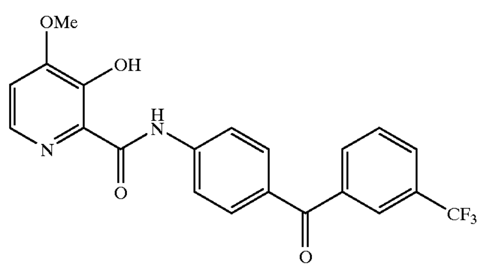 | Pale yellow solid | 416 | |
| 406 | 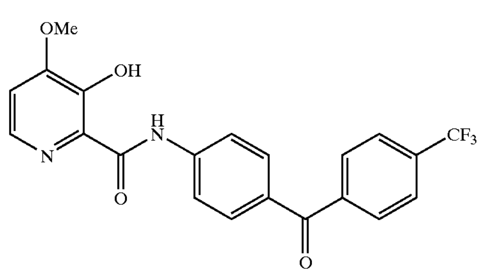 | Off-white solid | 416 | |

TABLE 1-continued

| Compound Number | Molecular Structure | Appearance | Molecular Ion (M) | Melting Point (° C.) |
| --- | --- | --- | --- | --- |
| 407 | 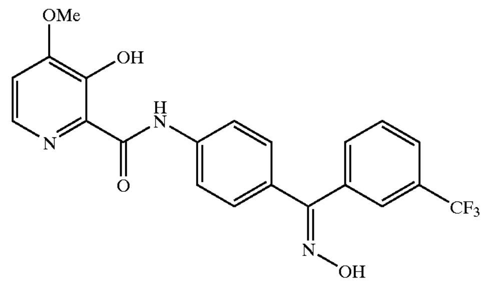 | Off-white solid | 431 | |
| 408 | 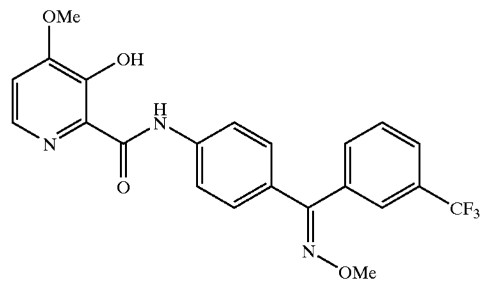 | White solid | M + 1 446 | |
| 409 | 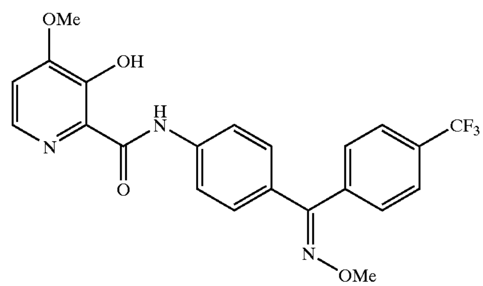 | White solid | 445 | |
| 410 | 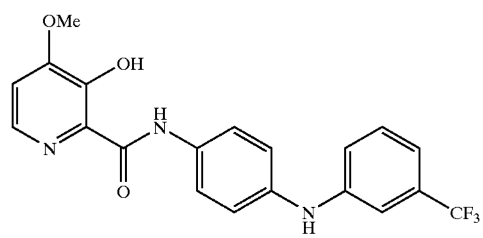 | Yellow solid | | 204–205 |
| 411 | 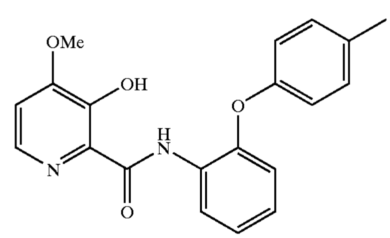 | Off-white solid | 350 | |
| 412 | 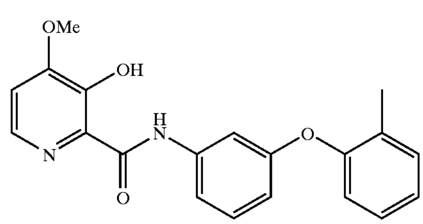 | Off-white solid | 350 | |

TABLE 1-continued

| Compound Number | Molecular Structure | Appearance | Molecular Ion (M) | Melting Point (° C.) |
|---|---|---|---|---|
| 413 | 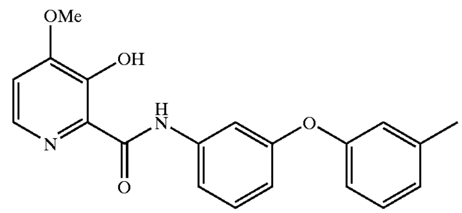 | Off-white solid | 350 | |
| 414 | 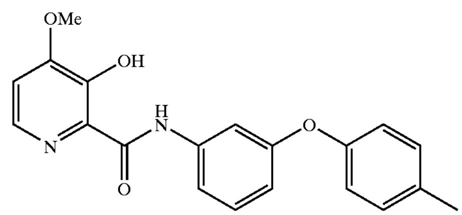 | Off-white solid | 350 | |
| 415 | 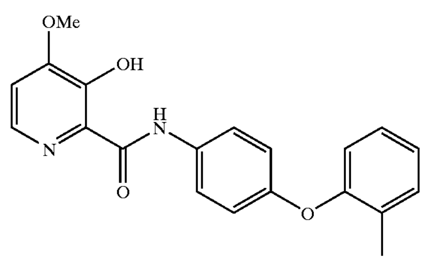 | Off-white solid | 350 | |
| 416 | 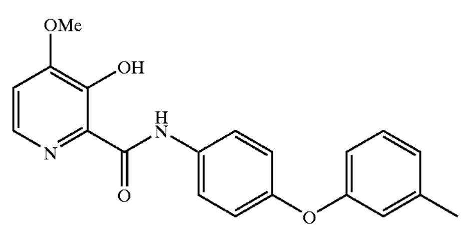 | Off-white solid | 350 | |
| 417 | 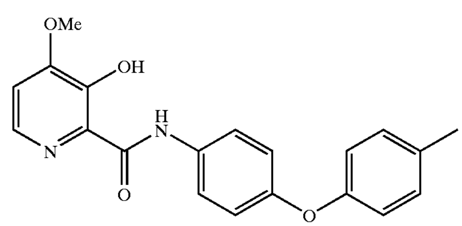 | Off-white solid | 350 | |
| 418 | 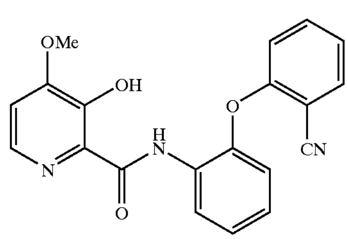 | Off-white solid | 361 | |

TABLE 1-continued

| Compound Number | Molecular Structure | Appearance | Molecular Ion (M) | Melting Point (° C.) |
|---|---|---|---|---|
| 419 | 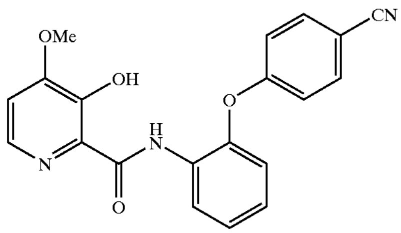 | Off-white solid | 361 | |
| 420 | 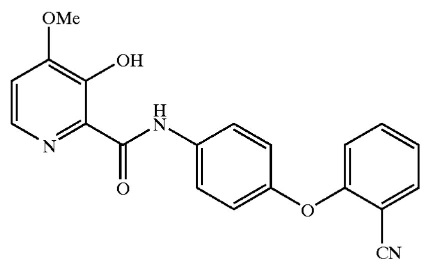 | Off-white solid | 361 | |
| 421 | 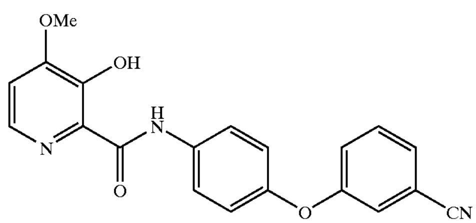 | Off-white solid | 361 | |
| 422 | 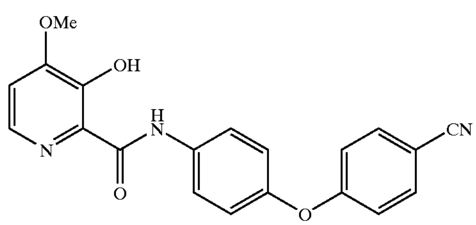 | Off-white solid | 361 | |
| 423 | 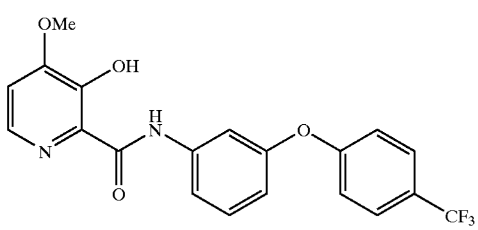 | Pale yellow solid | | |
| 424 | 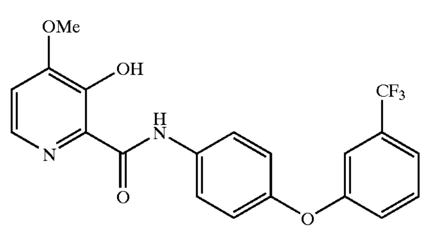 | Off-white solid | 404 | |

TABLE 1-continued

| Compound Number | Molecular Structure | Appearance | Molecular Ion (M) | Melting Point (° C.) |
|---|---|---|---|---|
| 425 | 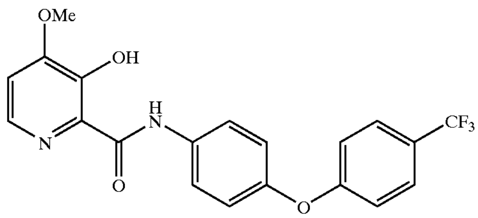 | Off-white solid | 404 | |
| 426 | 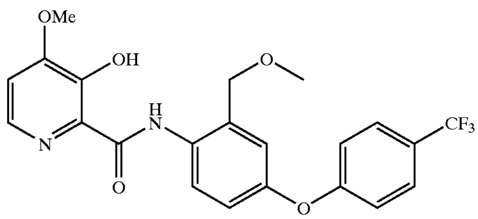 | White solid | | 125–127 |
| 427 | 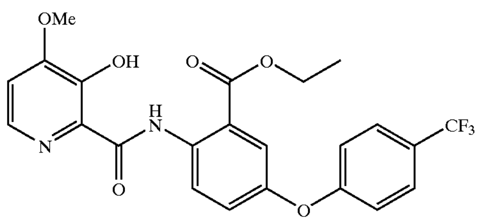 | White solid | | 145–147 |
| 428 | 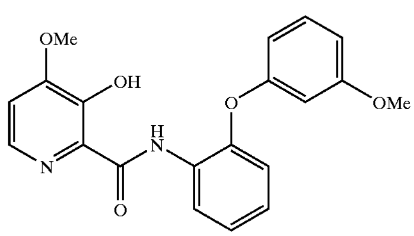 | Off-white solid | 366 | |
| 429 | 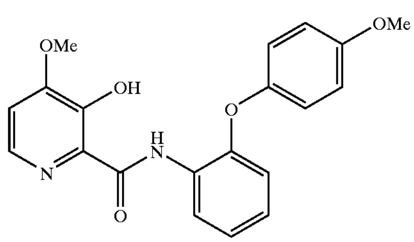 | Off-white solid | 366 | |
| 430 | 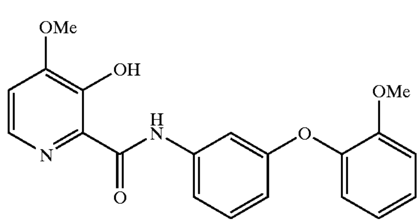 | Off-white solid | 366 | |

TABLE 1-continued
| Compound Number | Molecular Structure | Appearance | Molecular Ion (M) | Melting Point (° C.) |
|---|---|---|---|---|
| 431 | 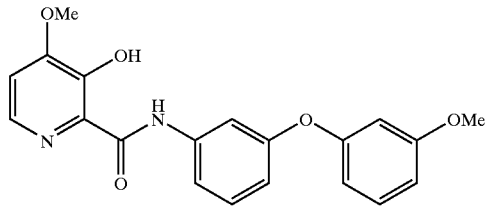 | Off-white solid | 366 | |
| 432 | 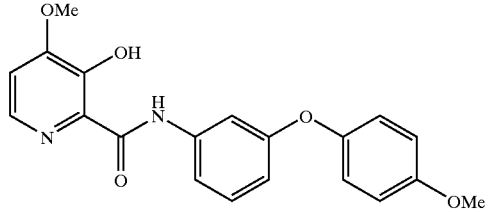 | Off-white solid | 366 | |
| 433 | 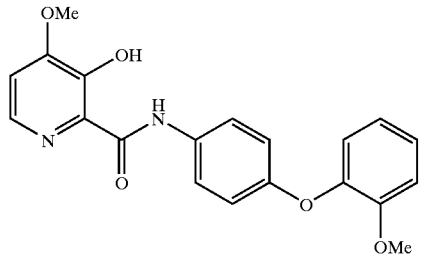 | Off-white solid | 366 | |
| 434 | 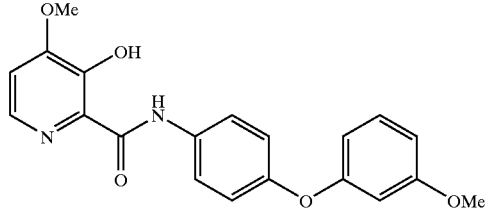 | Off-white solid | 366 | |
| 435 | 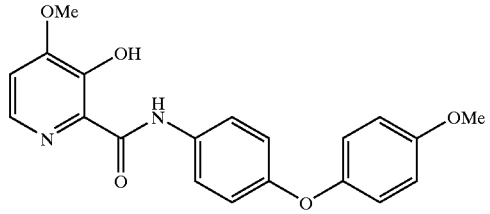 | Off-white solid | 366 | |
| 436 | 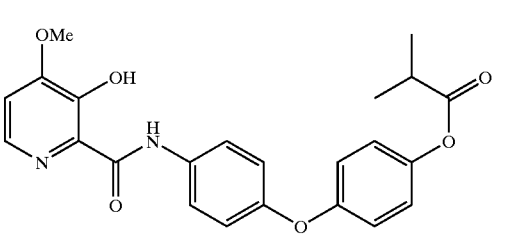 | White solid | 370, 372 | 109–110.5 |

TABLE 1-continued

| Compound Number | Molecular Structure | Appearance | Molecular Ion (M) | Melting Point (° C.) |
| --- | --- | --- | --- | --- |
| 437 | 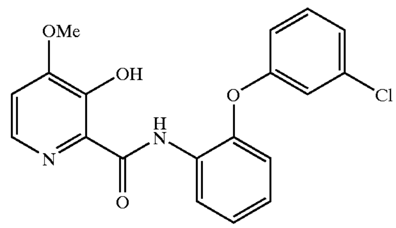 | Off-white solid | 370, 372 | |
| 438 | 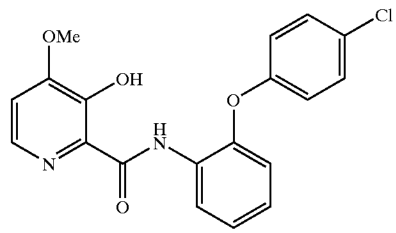 | Off-white solid | 370, 372 | |
| 439 | 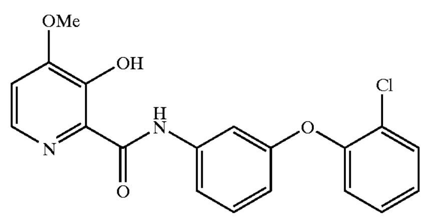 | Off-white solid | 370, 372 | |
| 440 | 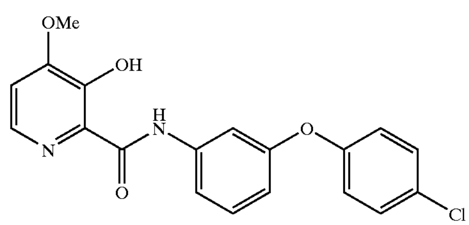 | Off-white solid | 370, 372 | |
| 441 | 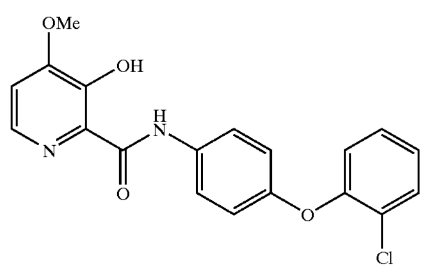 | Off-white solid | 370, 372 | |
| 442 | 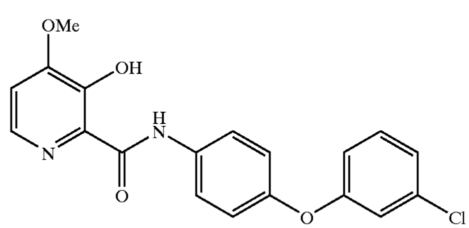 | Off-white solid | 370, 372 | |

TABLE 1-continued

| Compound Number | Molecular Structure | Appearance | Molecular Ion (M) | Melting Point (° C.) |
| --- | --- | --- | --- | --- |
| 443 | 4-methoxy-3-hydroxy-N-[4-(4-chlorophenoxy)phenyl]pyridine-2-carboxamide | Off-white solid | 370, 372 | |
| 444 | 4-methoxy-3-hydroxy-N-[3-(4-trifluoromethylphenylthio)phenyl]pyridine-2-carboxamide | White solid | | 133–134 |
| 445 | 4-methoxy-3-hydroxy-N-[4-(3-trifluoromethylphenylthio)phenyl]pyridine-2-carboxamide | Yellow solid | | 167–169 |
| 446 | 4-methoxy-3-hydroxy-N-[4-(4-trifluoromethylphenylthio)phenyl]pyridine-2-carboxamide | White solid | 420 | |
| 447 | 4-methoxy-3-hydroxy-N-[4-(3-trifluoromethylbenzyloxy)phenyl]pyridine-2-carboxamide | White solid | 418 | |
| 448 | 4-methoxy-3-hydroxy-N-[4-(4-trifluoromethylbenzyloxy)phenyl]pyridine-2-carboxamide | White solid | 418 | |

TABLE 1-continued

| Compound Number | Molecular Structure | Appearance | Molecular Ion (M) | Melting Point (° C.) |
|---|---|---|---|---|
| 449 | 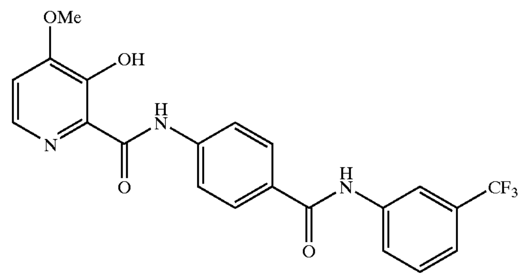 | Off-white solid | 431 | |
| 450 | 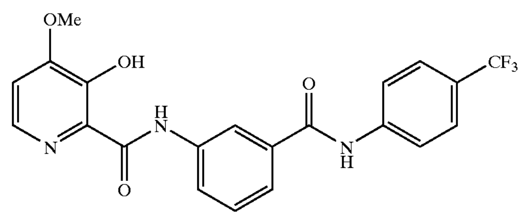 | White solid | | >260 |
| 451 | 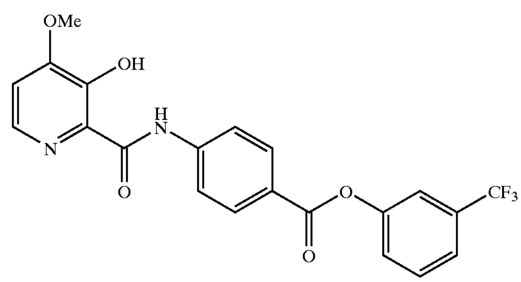 | Off-white solid | M + 1 433 | 196 (Dec) |
| 452 | 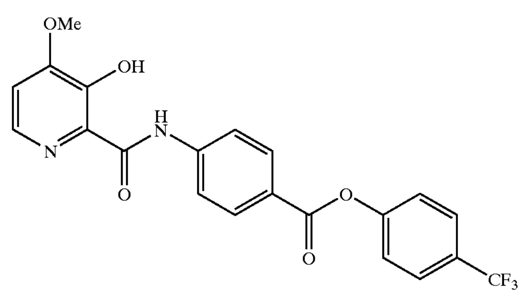 | Off-white solid | 432 | |
| 453 | 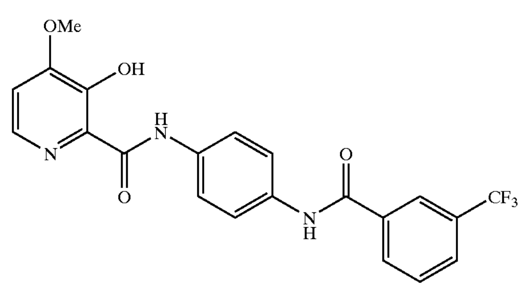 | Yellow solid | | 240–242 |

TABLE 1-continued
| Compound Number | Molecular Structure | Appearance | Molecular Ion (M) | Melting Point (° C.) |
|---|---|---|---|---|
| 454 | 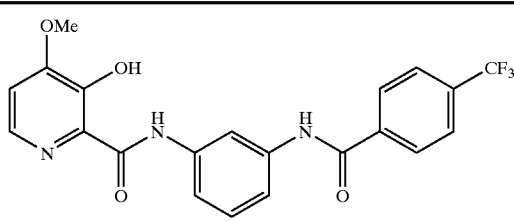 | Off-white solid | | 240–242 |
| 455 | 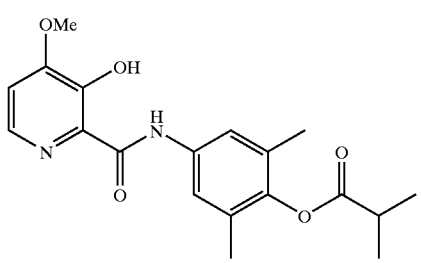 | White solid | 368 | |
| 456 | 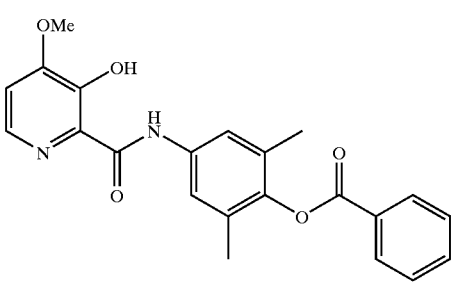 | White solid | 392 | |
| 457 | 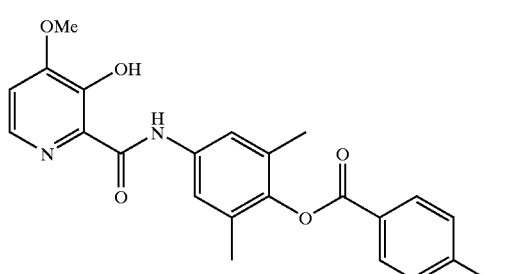 | Off-white solid | 460 | |
| 458 | 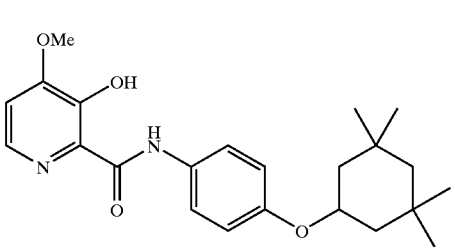 | Off-white solid | | 141–142 |
| 459 | 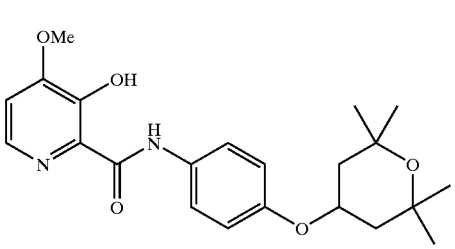 | Off-white solid | | 161–183 |

TABLE 1-continued

| Compound Number | Molecular Structure | Appearance | Molecular Ion (M) | Melting Point (° C.) |
|---|---|---|---|---|
| 460 | 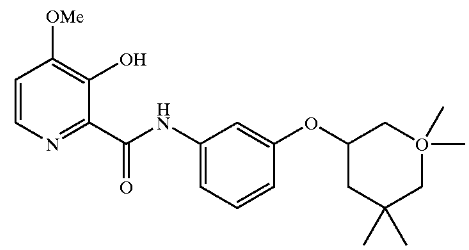 | White solid | | 149–153 |
| 461 | 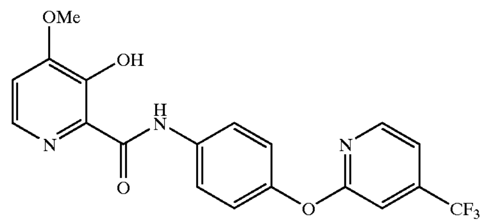 | White solid | | 169–171 |
| 462 | 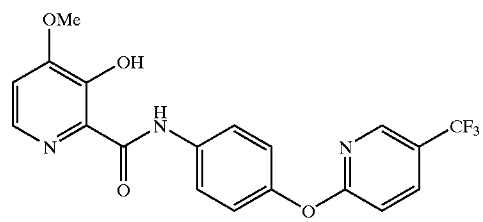 | White solid | | 141–143 |
| 463 | 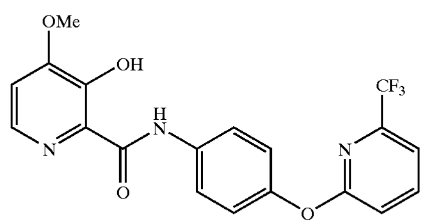 | White solid | | 140–141.5 |
| 464 | 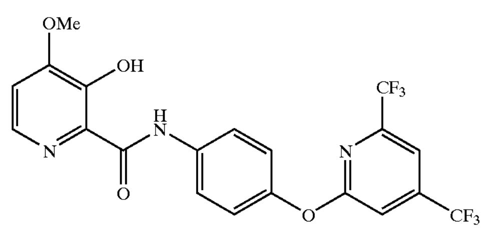 | White solid | | 179–181 |
| 465 | 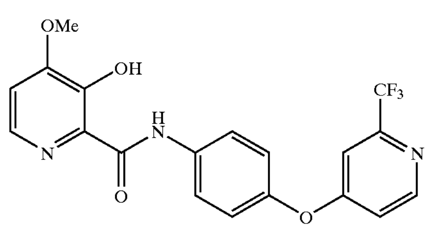 | White solid | | 160–162 |

TABLE 1-continued

| Compound Number | Molecular Structure | Appearance | Molecular Ion (M) | Melting Point (° C.) |
| --- | --- | --- | --- | --- |
| 466 | 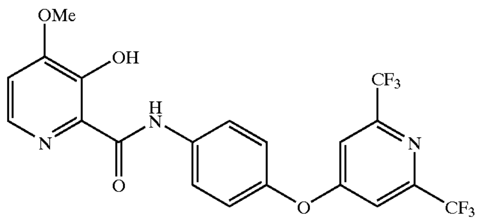 | White solid | | 198–200 |
| 467 | 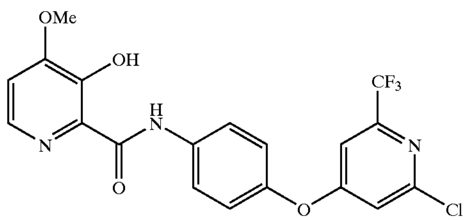 | Pale yellow solid | | 198–201 |
| 468 | 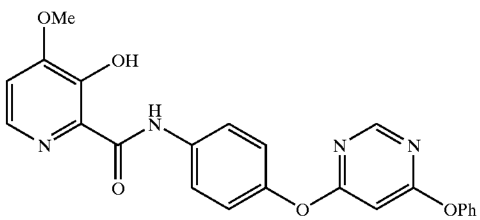 | White solid | 430 | |
| 469 | 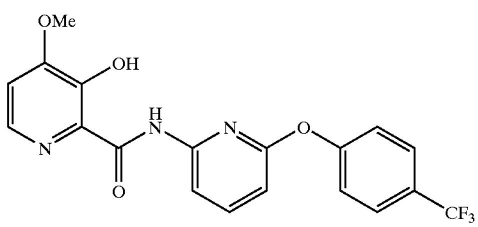 | White solid | | 149–151 |
| 470 | 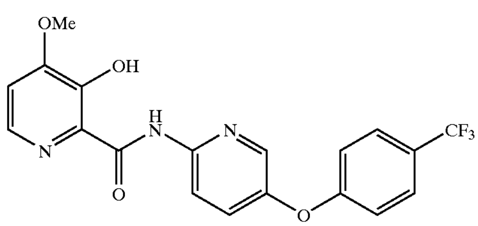 | White solid | | 173–175 |
| 471 | 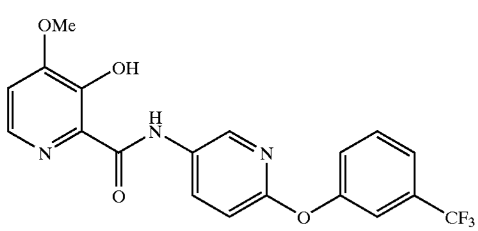 | White solid | | 193–195 |

TABLE 1-continued

| Compound Number | Molecular Structure | Appearance | Molecular Ion (M) | Melting Point (° C.) |
|---|---|---|---|---|
| 472 | 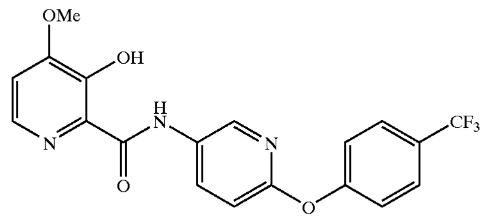 | White solid | M + 1 406 | |
| 473 | 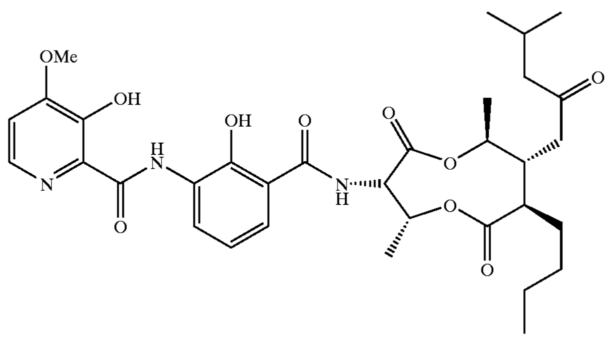 | Yellow solid | 812 | |
| 474 | 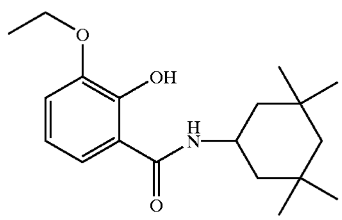 | Colorless crystals | | 107–110 |
| 475 | 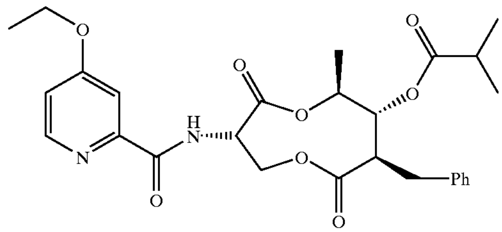 | Yellow solid | | 168–172 |
| 476 | 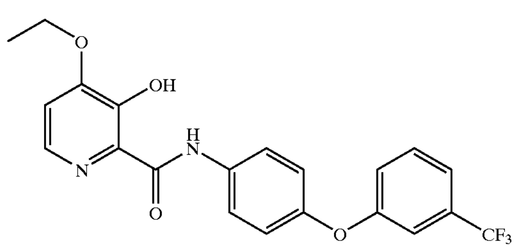 | Tan crystals | | 118–121 |
| 477 | 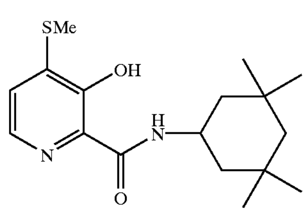 | Yellow gum | 322 | |

TABLE 1-continued

| Compound Number | Molecular Structure | Appearance | Molecular Ion (M) | Melting Point (° C.) |
| --- | --- | --- | --- | --- |
| 478 | 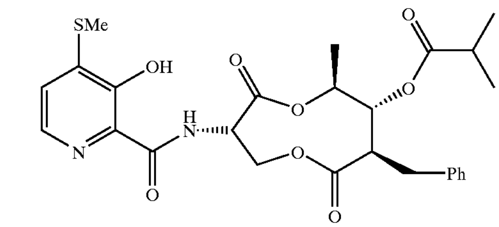 | Light yellow solid | | 184–187 |
| 479 | 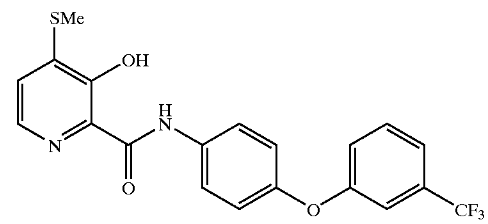 | Light yellow solid | | 129–132 |
| 480 | 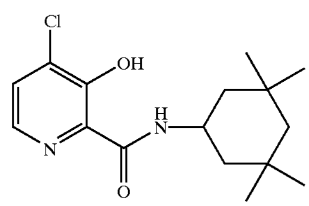 | Gummy tan solid | 310, 312 | |
| 481 | 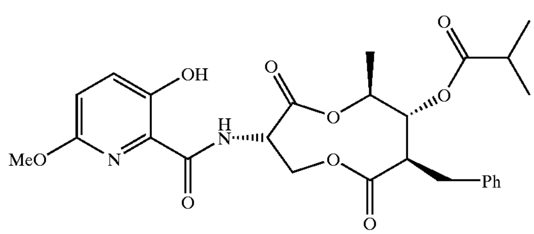 | Glass | 514 | |
| 482 | 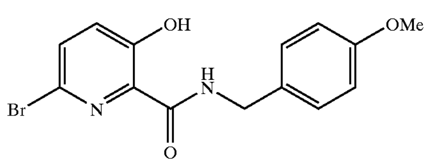 | White solid | | |
| 483 | 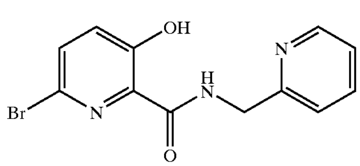 | Solid | | 124–126 |
| 484 | 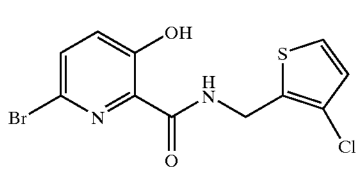 | White solid | | |

TABLE 1-continued

| Compound Number | Molecular Structure | Appearance | Molecular Ion (M) | Melting Point (° C.) |
| --- | --- | --- | --- | --- |
| 485 | 6-bromo-3-hydroxy-N-((1,2,3,4-tetrahydronaphthalen-1-yl)methyl)picolinamide | Yellow solid | | 140–142 |
| 486 | 6-bromo-3-hydroxy-N-(1-(4-methoxyphenyl)ethyl)picolinamide | Off-white solid | | 111–113 |
| 487 | 6-bromo-N-(1-(4-chlorophenyl)ethyl)-3-hydroxypicolinamide | White solid | | |
| 488 | 6-bromo-3-hydroxy-N-(1-(4-(trifluoromethyl)phenyl)ethyl)picolinamide | White solid | | |
| 489 | 6-bromo-3-hydroxy-N-(1-(4-pentylphenyl)ethyl)picolinamide | Yellow gum | | |
| 490 | 6-bromo-3-hydroxy-N-(1-(4-phenoxyphenyl)ethyl)picolinamide | Light-yellow Oil | 412, 414 | |
| 491 | 6-bromo-3-hydroxy-N-(1,2-diphenylethyl)picolinamide | Yellow gum | 395, 398 | |
| 492 | 6-bromo-3-hydroxy-N-(2-(3-(trifluoromethyl)phenoxy)phenyl)picolinamide | White solid | 452, 454 | |

TABLE 1-continued
| Compound Number | Molecular Structure | Appearance | Molecular Ion (M) | Melting Point (° C.) |
|---|---|---|---|---|
| 493 | 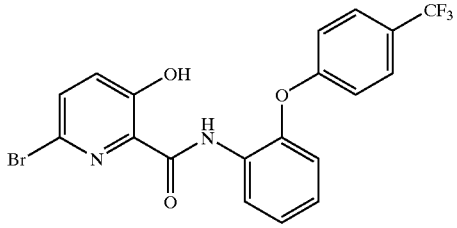 | White solid | 452, 454 | |
| 494 | 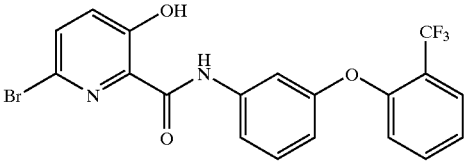 | White solid | 452, 454 | |
| 495 | 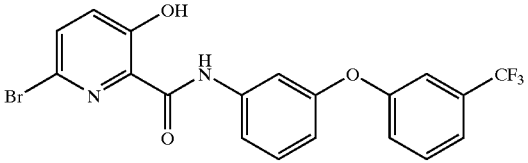 | Orange gum | 452, 454 | |
| 496 | 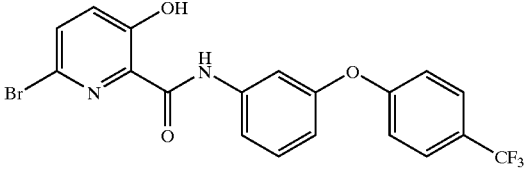 | White solid | 452, 454 | |
| 497 | 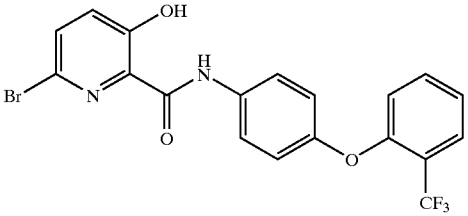 | Orange whitesolid | 452, 454 | |
| 498 | 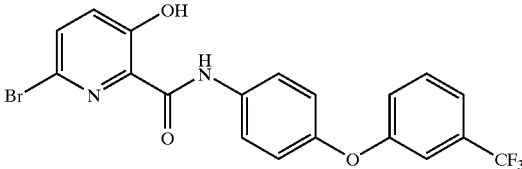 | White Solid | 452, 454 | |
| 499 | 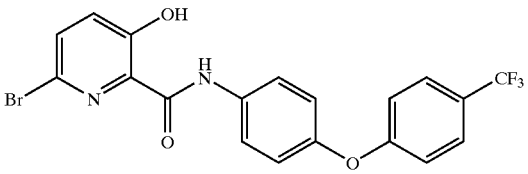 | White Solid | 452, 454 | |

TABLE 1-continued
| Compound Number | Molecular Structure | Appearance | Molecular Ion (M) | Melting Point (° C.) |
|---|---|---|---|---|
| 500 | 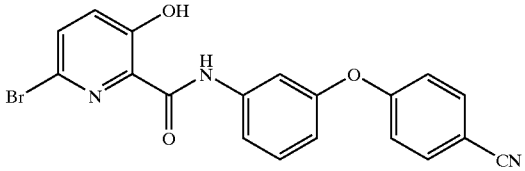 | White Solid | 409, 411 | |
| 501 | 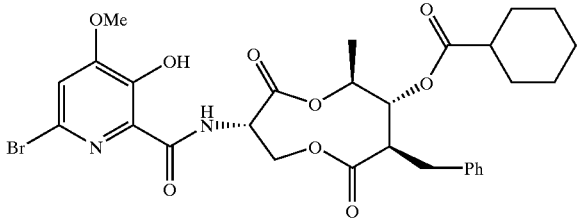 | White foam | M − 2 631 | |
| 502 | 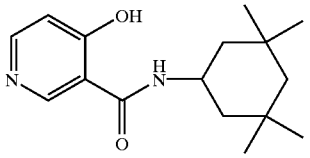 | Off-white solid | | 232–235 (Dec) |
| 503 | 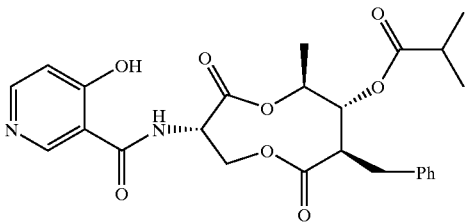 | White solid | | 213–215 (Dec) |
| 504 | 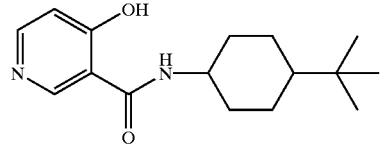 | Grey solid | | 70–78 |
| 505 | 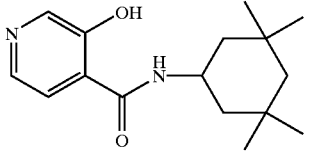 | Dark tar | | |
| 506 | 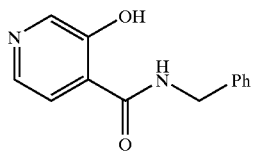 | Dark tar | | |
| 507 | 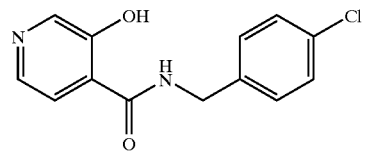 | Dark tar | | |

TABLE 1-continued

| Compound Number | Molecular Structure | Appearance | Molecular Ion (M) | Melting Point (° C.) |
| --- | --- | --- | --- | --- |
| 508 | 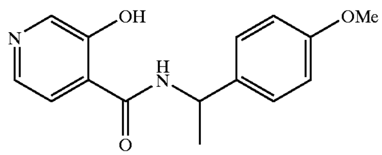 | Dark tar | 272 | |
| 509 | 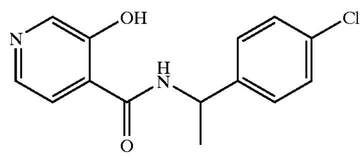 | Dark tar | 276, 278 | |
| 510 | 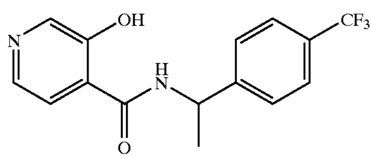 | Dark tar | 310 | |
| 511 | 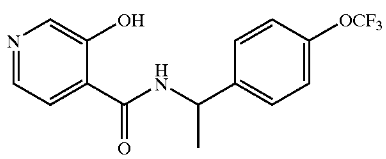 | Dark tar | 326 | |
| 512 | 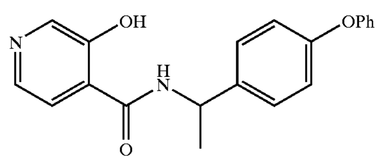 | Dark tar | | |
| 513 | 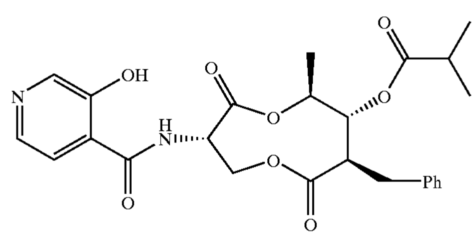 | Tan glass | 485 | |
| 514 | 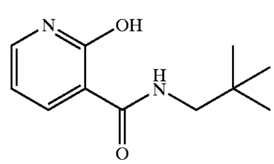 | White solid | | 180–181 |
| 515 | 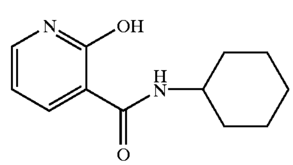 | Light-tan solid | | 190–192 |
| 516 | 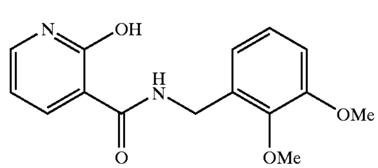 | Off-white crystals | | 193–194 |

TABLE 1-continued

| Compound Number | Molecular Structure | Appearance | Molecular Ion (M) | Melting Point (° C.) |
|---|---|---|---|---|
| 517 | 2-hydroxy-N-(3,4-dichlorobenzyl)nicotinamide | White crystals | | 229–230 |
| 518 | 2-hydroxy-N-[2-(4-chlorophenyl)ethyl]nicotinamide | White solid | | 219–221 |
| 519 | 2-hydroxy-N-(1,2-diphenylethyl)nicotinamide | Tannish-white solid | | 190–192 |
| 520 | 2-hydroxy-N-(2-phenoxyphenyl)nicotinamide | Light-yellow needles | | 234–235 |
| 521 | 2-hydroxy-N-(3-phenoxyphenyl)nicotinamide | Light-tan crystals | | 200–201 |
| 522 | 2-hydroxy-N-(4-phenoxyphenyl)nicotinamide | White crystals | | 223–224 |
| 523 | 2-hydroxynicotinamide macrocyclic derivative | White solid | | 188–190 (Dec) |
| 524 | 6-methyl-2-hydroxy-N-(3,3,5,5-tetramethylcyclohexyl)nicotinamide | Colorless needles | | 307–308 |

TABLE 1-continued

| Compound Number | Molecular Structure | Appearance | Molecular Ion (M) | Melting Point (° C.) |
|---|---|---|---|---|
| 525 | 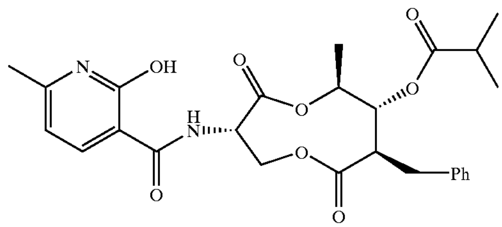 | Colorless crystals | | 247–250 |
| 526 | 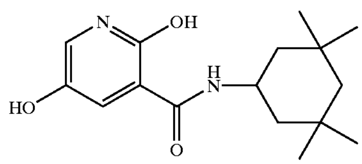 | Grey solid | | 320–327 |
| 527 | 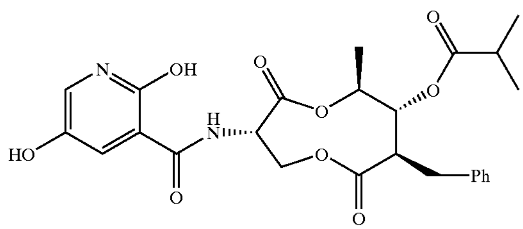 | Grey solid | | 120–130 |
| 528 | 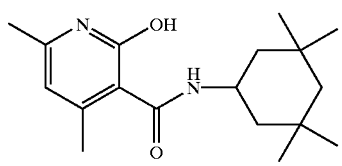 | Colorless needles | | 286–288 |
| 529 | 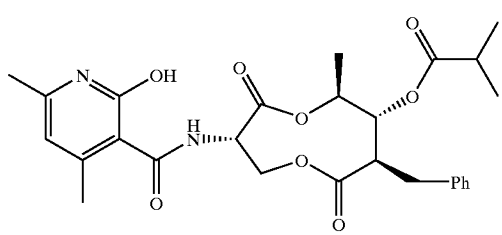 | Colorless solid | 512 | |
| 530 | 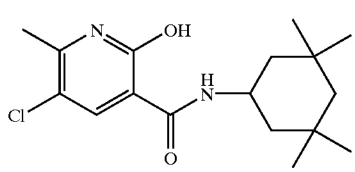 | Colorless crystals | | 329–331 |
| 531 | 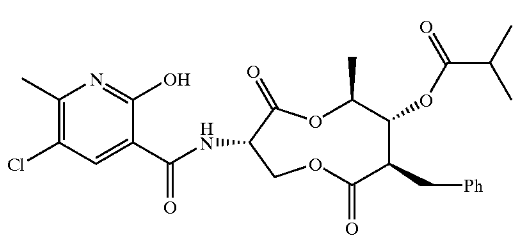 | Colorless solid | | 103–108 |

TABLE 1-continued

| Compound Number | Molecular Structure | Appearance | Molecular Ion (M) | Melting Point (° C.) |
|---|---|---|---|---|
| 532 | 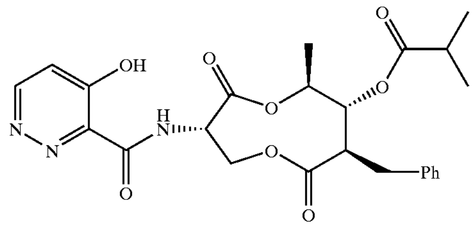 | White solid | | 233 (Dec) |
| 533 | 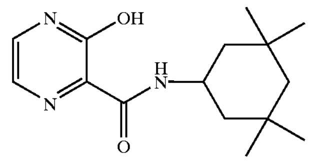 | Bright yellow plates | | 248–250 (Dec) |
| 534 | 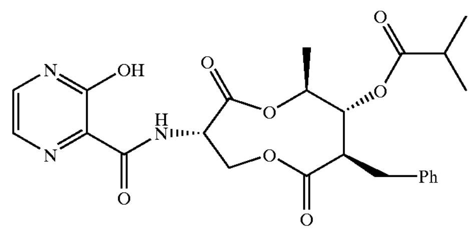 | Yellow solid | M + 1 484 | |
| 535 | 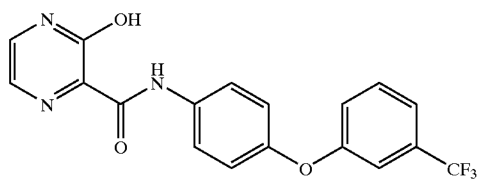 | Yellow solid | | 239–243 (Dec) |
| 536 | 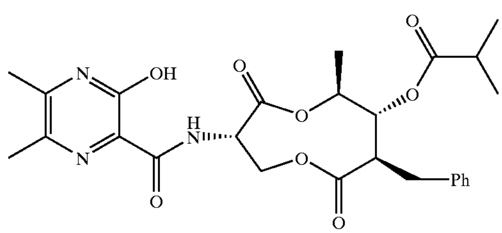 | Off-white solid | | 80–83 |
| 537 | 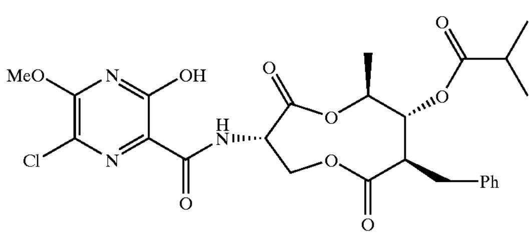 | Tan solid | | 84–86 |
| 538 | 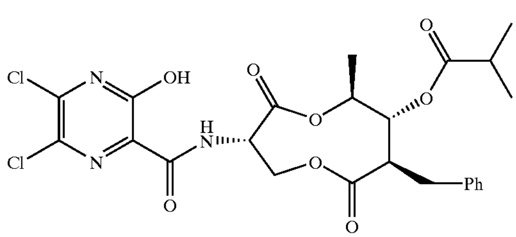 | Beige solid | | 108–110 |

TABLE 1-continued

| Compound Number | Molecular Structure | Appearance | Molecular Ion (M) | Melting Point (° C.) |
|---|---|---|---|---|
| 539 | 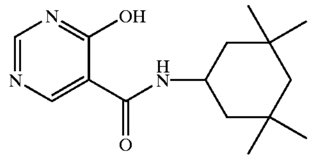 | White solid | | 263–265 |
| 540 | 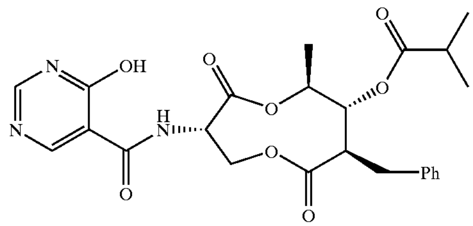 | white solid | | 195 (Dec) |
| 541 | 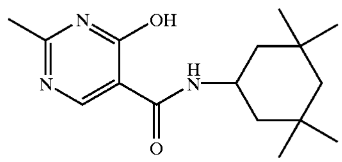 | White crystalline solid | | >300 |
| 542 | 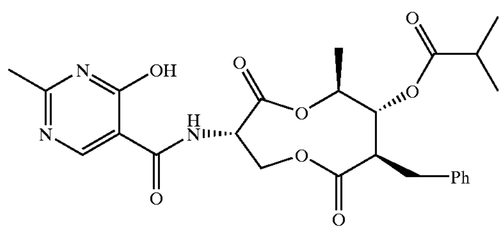 | Clear solid | | 220 (Dec) |
| 543 | 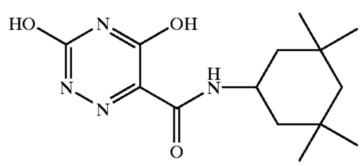 | Tan solid | | 283–285 |
| 544 | 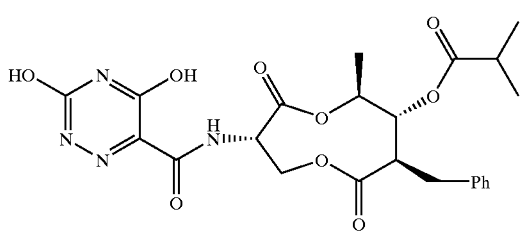 | Colorless glass | M + 1 503<br>M − 1 501 | |
| 545 | 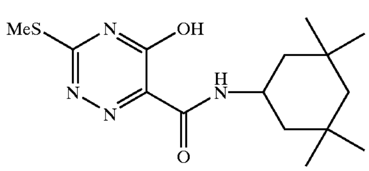 | Colorless solid | | 265–268 |
| 546 | 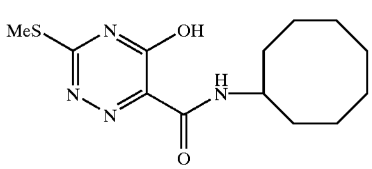 | Yellow crystals | | 208–213 |

TABLE 1-continued

| Compound Number | Molecular Structure | Appearance | Molecular Ion (M) | Melting Point (° C.) |
| --- | --- | --- | --- | --- |
| 547 | 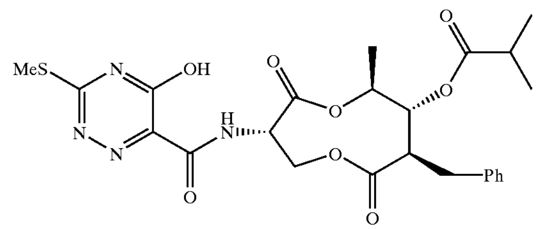 | Yellow-brown solid | M + 1 533 | |
| 548 | 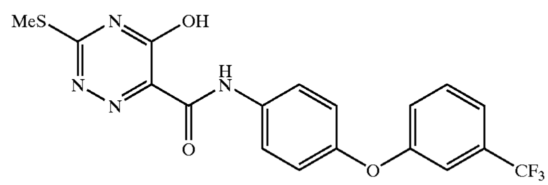 | Yellow solid | | 261–265 |
| 549 | 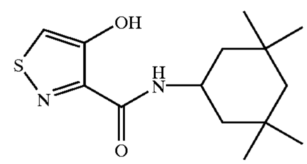 | Colorless needles | | 121–125 |
| 550 | 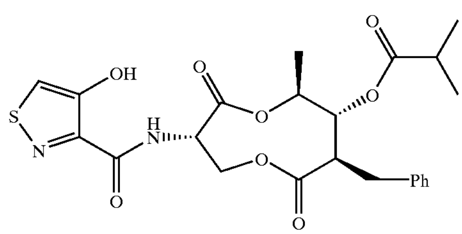 | Colorless glass | M + 1 491 | |
| 551 | 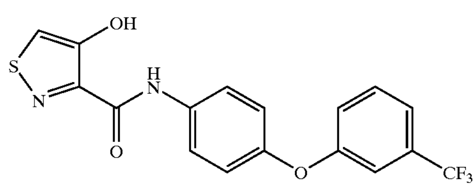 | Yellow solid | 380 | |
| 552 | 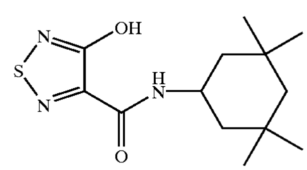 | Yellow solid | | 96–102 |
| 553 | 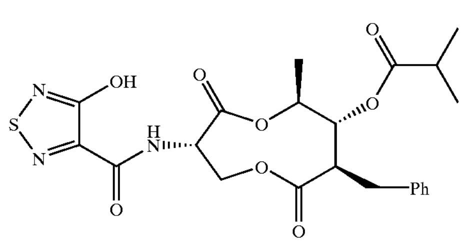 | Glassy solid | M + 1 492 | |

TABLE 1-continued

| Compound Number | Molecular Structure | Appearance | Molecular Ion (M) | Melting Point (° C.) |
|---|---|---|---|---|
| 554 | 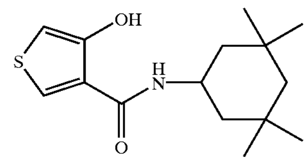 | Tan crystals | | 170–174 |
| 555 | 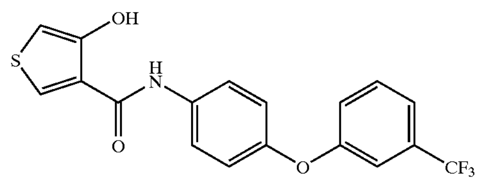 | Brown gum | 379 | |
| 556 | 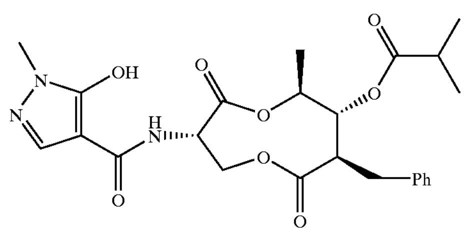 | White solid | | 195 (Dec) |
| 557 | 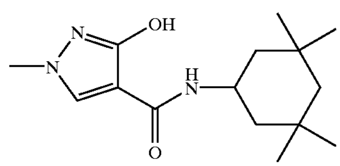 | White solid | | 205–208 |
| 558 | 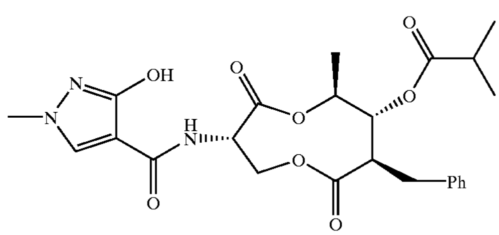 | White solid | | 199–205 |
| 559 | 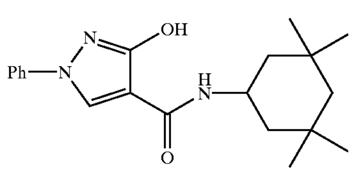 | White solid | | 215–217 |
| 560 | 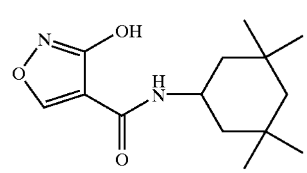 | Light brown solid | | 186–188 |

TABLE 1-continued

| Compound Number | Molecular Structure | Appearance | Molecular Ion (M) | Melting Point (° C.) |
|---|---|---|---|---|
| 561 | 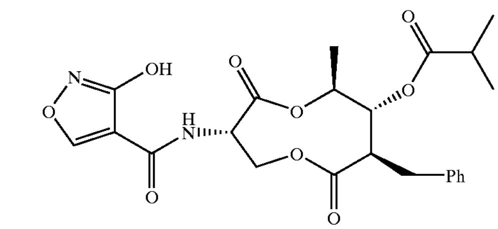 | Brown glassy solid | | 115–117 |
| 562 | 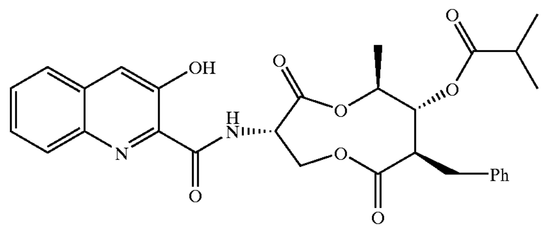 | Off-white solid | | 163–165 |
| 563 | 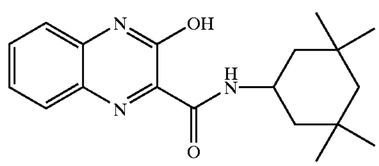 | Yellow solid | | >300 |

TABLE 2

| Compound Number | ERYSGT in vivo 1 Day Protectant | LEPTNO in vivo 1 Day Protectant | PHYTIN in vivo 1 Day Protectant | PLASVI in vivo 1 Day Protectant | PUCCRT in vivo 1 Day Protectant | SEPTTR in vivo 1 Day Protectant | LEPTNO in vitro Growth Inhibition | PHYTIN in vitro Growth Inhibition | PYRIOR in vitro Growth Inhibition | RHIZSO in vitro Growth Inhibition | SEPTTR in vitro Growth Inhibition | USTIMA in vitro Growth Inhibition |
|---|---|---|---|---|---|---|---|---|---|---|---|---|
| 201 | − | − | − | − | − | − | − | − | + | − | − | − |
| 202 | − | − | − | − | − | − | − | + | + | − | − | − |
| 203 | | | | | | | + | − | + | + | + | − |
| 204 | − | − | − | − | − | + | − | − | − | − | − | − |
| 205 | − | − | − | + | − | − | − | − | − | − | − | − |
| 206 | − | − | − | − | − | − | + | − | + | + | + | − |
| 207 | − | − | − | − | − | − | + | − | + | − | + | − |
| 208 | − | − | + | − | + | − | − | − | − | − | − | − |
| 209 | − | − | − | − | − | + | − | − | − | − | − | − |
| 210 | − | − | − | − | − | + | − | − | − | − | − | − |
| 211 | − | + | − | − | − | + | − | − | − | − | − | − |
| 212 | − | − | − | + | − | − | − | − | + | − | − | − |
| 213 | − | − | + | + | ++ | − | − | + | − | − | + | − |
| 214 | − | − | − | + | − | − | − | − | − | − | − | − |
| 215 | − | − | − | − | − | − | − | − | − | − | + | − |
| 216 | − | − | − | − | − | − | − | + | − | − | − | − |
| 217 | + | − | − | − | − | − | − | − | − | − | − | − |
| 218 | − | − | − | + | − | − | + | + | + | + | − | + |
| 219 | − | − | − | + | − | − | + | + | + | + | + | + |
| 220 | − | − | + | + | − | − | + | + | + | + | + | + |
| 221 | − | − | − | − | − | − | − | + | + | − | + | − |
| 222 | − | − | − | − | + | − | − | − | − | − | − | − |
| 223 | − | − | − | + | − | − | + | + | + | − | − | + |
| 224 | − | − | − | − | − | − | − | + | − | − | − | − |
| 225 | − | − | − | − | − | − | − | + | − | − | − | − |
| 226 | + | − | − | − | − | − | − | + | − | − | − | − |
| 227 | − | − | − | − | − | − | − | + | − | − | − | − |
| 228 | − | − | + | − | − | − | − | − | − | − | − | − |
| 229 | − | − | − | − | − | − | − | + | − | − | + | − |
| 230 | − | + | − | − | − | + | + | + | + | − | + | − |
| 231 | − | − | − | + | − | − | − | − | + | − | − | − |
| 232 | + | − | − | − | − | − | − | + | − | − | + | − |
| 233 | − | − | − | + | − | + | + | + | + | − | + | + |

TABLE 2-continued

| Compound Number | ERYSGT in vivo 1 Day Protectant | LEPTNO in vivo 1 Day Protectant | PHYTIN in vivo 1 Day Protectant | PLASVI in vivo 1 Day Protectant | PUCCRT in vivo 1 Day Protectant | SEPTTR in vivo 1 Day Protectant | LEPTNO in vitro Growth Inhibition | PHYTIN in vitro Growth Inhibition | PYRIOR in vitro Growth Inhibition | RHIZSO in vitro Growth Inhibition | SEPTTR in vitro Growth Inhibition | USTIMA in vitro Growth Inhibition |
|---|---|---|---|---|---|---|---|---|---|---|---|---|
| 234 | − | − | − | + | − | + | + | + | + | − | − | − |
| 235 | − | − | − | − | − | − | + | + | + | + | + | + |
| 236 | − | − | − | − | − | − | + | − | − | − | − | − |
| 237 | − | + | − | − | ++ | + | − | − | − | − | − | − |
| 238 | − | + | − | − | − | − | − | − | − | − | − | − |
| 239 | − | + | − | + | + | + | − | − | − | − | − | − |
| 240 | − | + | − | ++ | − | ++ | − | − | − | − | − | − |
| 241 | − | + | − | + | + | + | − | + | − | + | − | − |
| 242 | − | − | − | − | − | + | + | + | + | + | + | + |
| 243 | − | + | − | − | + | + | − | − | − | − | − | − |
| 244 | − | + | − | − | − | − | + | − | + | − | + | − |
| 245 | − | + | − | + | − | + | − | − | − | − | − | − |
| 246 | + | ++ | − | − | − | + | − | − | − | − | − | − |
| 247 | − | + | − | + | − | + | + | − | − | − | + | − |
| 248 | − | + | − | − | − | − | − | − | − | − | − | − |
| 249 | − | + | − | − | − | + | − | − | − | − | − | − |
| 250 | − | + | + | − | + | − | + | + | − | − | − | − |
| 251 | − | ++ | + | + | ++ | ++ | + | + | − | − | + | − |
| 252 | − | + | + | − | + | + | + | + | + | + | + | − |
| 253 | − | + | − | − | + | + | + | + | + | − | + | − |
| 254 | − | + | − | − | + | + | + | + | + | − | + | − |
| 255 | − | ++ | − | − | + | + | − | − | − | − | + | − |
| 256 | + | + | − | − | + | + | − | − | − | − | − | − |
| 257 | − | ++ | − | + | + | + | + | + | − | − | + | + |
| 258 | − | + | − | − | − | + | + | + | − | − | + | − |
| 259 | − | + | + | + | + | + | − | − | − | − | − | − |
| 260 | − | + | − | + | − | + | + | − | − | − | − | − |
| 261 | − | + | + | + | + | + | + | + | − | − | + | − |
| 262 | − | + | − | + | − | + | − | − | − | − | − | − |
| 263 | − | + | − | − | − | − | − | − | − | − | − | − |
| 264 | − | − | − | − | + | + | − | − | − | − | − | − |
| 265 | + | + | − | + | − | + | − | − | − | − | − | − |
| 266 | − | + | − | − | − | + | − | − | − | − | − | − |
| 267 | − | + | − | ++ | + | − | + | + | − | − | − | + |
| 268 | − | + | − | ++ | + | + | + | + | − | − | − | − |
| 269 | − | − | − | ++ | + | + | − | − | − | − | − | − |
| 270 | + | ++ | + | + | + | + | + | − | + | + | + | + |
| 271 | − | + | + | + | − | + | + | + | + | + | + | + |
| 272 | − | + | − | − | − | ++ | − | − | − | − | + | − |
| 273 | − | + | − | + | − | + | − | − | − | − | − | − |
| 274 | − | ++ | − | + | ++ | + | + | + | + | + | + | − |
| 275 | − | + | − | − | − | + | + | − | − | + | + | − |
| 276 | − | ++ | − | + | + | + | + | − | − | − | − | − |
| 277 | − | + | − | − | − | ++ | + | − | − | − | + | − |
| 278 | − | + | − | + | + | + | − | − | − | − | − | − |
| 279 | + | + | + | − | − | + | + | + | − | − | + | − |
| 280 | − | + | + | + | + | + | − | − | − | − | − | − |
| 281 | + | + | + | ++ | + | + | − | + | + | − | − | − |
| 282 | − | + | − | − | + | + | − | − | − | − | − | − |
| 283 | − | + | − | − | + | ++ | − | − | − | − | − | − |
| 284 | − | + | − | − | + | + | − | − | − | − | − | − |
| 285 | − | + | − | − | − | + | − | − | − | + | − | − |
| 286 | − | + | − | + | − | − | + | − | − | + | − | − |
| 287 | − | + | − | + | + | + | − | − | − | + | − | − |
| 288 | − | + | − | + | − | + | − | − | − | + | − | − |
| 289 | + | + | − | ++ | + | ++ | − | − | + | + | + | − |
| 290 | + | ++ | − | ++ | ++ | + | + | − | + | + | + | − |
| 291 | − | + | − | − | − | − | + | − | − | + | − | − |
| 292 | − | ++ | − | − | + | + | + | − | − | − | − | − |
| 293 | − | + | − | − | − | + | − | − | − | − | − | − |
| 294 | − | ++ | − | + | − | + | + | − | + | + | + | − |
| 295 | − | + | − | + | + | ++ | − | − | + | + | + | − |
| 296 | − | + | − | − | − | − | + | − | + | + | − | − |
| 297 | − | + | − | + | − | + | + | − | + | + | + | − |
| 298 | − | + | − | + | + | + | − | − | − | + | − | − |
| 299 | − | + | − | ++ | + | − | + | − | − | + | − | − |
| 300 | − | + | − | ++ | − | − | + | − | − | + | − | − |
| 301 | − | + | − | − | + | + | + | − | + | − | − | − |
| 302 | − | + | − | + | − | + | − | − | − | − | − | − |
| 303 | − | + | + | ++ | − | + | − | − | − | − | − | − |
| 304 | − | + | − | + | − | ++ | − | − | − | + | − | − |
| 305 | − | − | ++ | − | − | − | − | − | − | − | − | − |

TABLE 2-continued

| Compound Number | ERYSGT in vivo 1 Day Protectant | LEPTNO in vivo 1 Day Protectant | PHYTIN in vivo 1 Day Protectant | PLASVI in vivo 1 Day Protectant | PUCCRT in vivo 1 Day Protectant | SEPTTR in vivo 1 Day Protectant | LEPTNO in vitro Growth Inhibition | PHYTIN in vitro Growth Inhibition | PYRIOR in vitro Growth Inhibition | RHIZSO in vitro Growth Inhibition | SEPTTR in vitro Growth Inhibition | USTIMA in vitro Growth Inhibition |
|---|---|---|---|---|---|---|---|---|---|---|---|---|
| 306 | − | − | − | + | − | + | − | − | − | − | − | − |
| 307 | + | − | − | − | − | − | − | − | − | − | − | − |
| 308 | + | − | − | + | − | + | − | − | − | − | − | − |
| 309 | + | + | − | − | − | − | − | − | − | − | − | − |
| 310 | + | − | − | + | − | − | − | − | − | − | − | − |
| 311 | − | + | − | − | + | ++ | − | − | − | − | − | − |
| 312 | + | + | − | − | − | + | − | − | − | − | − | − |
| 313 | + | + | − | − | + | + | − | − | − | − | − | − |
| 314 | − | + | − | + | − | − | − | − | − | − | − | − |
| 315 | − | + | − | − | − | − | − | − | − | − | − | − |
| 316 | − | + | − | + | ++ | − | + | − | + | − | − | + |
| 317 | − | − | + | + | ++ | − | − | − | − | − | − | − |
| 318 | − | + | + | + | + | + | + | + | − | + | + | − |
| 319 | + | − | − | + | ++ | + | − | − | − | − | − | − |
| 320 | − | + | − | − | − | + | − | − | − | − | − | − |
| 321 | − | − | − | − | + | − | − | − | − | − | − | − |
| 322 | + | + | − | − | + | + | + | − | − | + | − | − |
| 323 | − | ++ | − | − | + | ++ | + | − | + | + | + | − |
| 324 | + | ++ | − | + | + | + | + | + | − | + | + | + |
| 325 | − | + | − | + | − | − | − | − | − | − | − | − |
| 326 | − | + | − | − | − | ++ | − | − | − | − | − | − |
| 327 | − | + | + | − | − | ++ | − | − | − | − | − | − |
| 328 | − | + | − | + | − | + | − | + | − | − | − | − |
| 329 | − | + | − | − | + | + | − | − | − | − | − | − |
| 330 | − | − | − | + | − | − | − | − | − | − | − | − |
| 331 | − | + | − | − | − | − | − | − | + | − | − | − |
| 332 | − | + | − | − | − | + | − | − | − | − | − | − |
| 333 | − | + | − | − | + | + | − | − | − | − | − | − |
| 334 | − | + | − | − | − | − | − | − | − | − | − | − |
| 335 | − | + | + | − | − | − | − | − | − | − | − | − |
| 336 | − | + | − | − | − | + | − | − | − | − | − | − |
| 337 | − | ++ | − | − | + | − | − | − | − | − | − | − |
| 338 | − | ++ | − | − | ++ | + | − | − | − | − | − | + |
| 339 | − | ++ | − | − | ++ | ++ | − | − | − | − | − | − |
| 340 | + | + | − | − | − | − | − | − | − | − | − | − |
| 341 | − | − | − | − | − | + | − | − | − | − | − | − |
| 342 | + | + | − | − | ++ | + | − | − | − | − | − | + |
| 343 | + | + | − | − | − | − | − | − | − | − | − | − |
| 344 | − | + | − | − | − | + | + | − | − | − | − | − |
| 345 | − | − | − | + | + | − | − | − | − | − | − | − |
| 346 | − | − | − | + | + | + | − | − | + | − | − | − |
| 347 | − | + | − | − | + | − | − | − | − | − | − | − |
| 348 | − | + | − | − | + | + | − | − | − | − | − | − |
| 349 | − | − | − | + | ++ | − | − | − | − | − | − | − |
| 350 | − | ++ | − | − | ++ | − | − | − | − | − | − | − |
| 351 | − | + | − | + | ++ | − | − | − | − | − | − | + |
| 352 | − | − | − | + | + | − | − | − | − | − | − | − |
| 353 | − | − | − | + | ++ | − | − | − | − | − | − | − |
| 354 | + | − | − | − | ++ | − | − | − | − | − | − | − |
| 355 | − | − | − | + | + | − | − | − | − | − | − | − |
| 356 | − | + | − | + | + | + | − | − | − | − | − | − |
| 357 | − | + | − | + | ++ | − | − | − | − | − | − | − |
| 358 | − | + | − | − | + | + | − | − | − | − | − | − |
| 359 | − | + | − | + | ++ | ++ | − | − | − | − | − | − |
| 360 | − | ++ | − | + | + | + | − | − | − | − | − | − |
| 361 | − | + | − | + | ++ | − | − | + | + | − | + | − |
| 362 |  |  |  |  |  |  | − | − | + | − | − | − |
| 363 |  |  |  |  |  |  | − | − | + | − | − | − |
| 364 |  |  |  |  |  |  | − | − | + | − | − | − |
| 365 |  |  |  |  |  |  | − | − | + | − | − | − |
| 366 |  |  |  |  |  |  | − | + | − | − | − | − |
| 367 |  |  |  |  |  |  | − | + | − | − | − | − |
| 368 |  |  |  |  |  |  | − | − | − | + | − | − |
| 369 |  |  |  |  |  |  | − | − | − | + | − | − |
| 370 |  |  |  |  |  |  | + | − | − | − | − | − |
| 371 |  |  |  |  |  |  | − | − | − | − | + | − |
| 372 |  |  |  |  |  |  | − | − | − | − | + | − |
| 373 |  |  |  |  |  |  | − | − | − | − | + | − |
| 374 |  |  |  |  |  |  | + | − | − | − | − | − |
| 375 | − | + | − | + | − | + | − | − | − | − | − | − |
| 376 | + | + | − | + | − | + | − | − | − | − | − | − |
| 377 | − | + | − | − | − | − | − | + | − | − | − | − |

TABLE 2-continued

| Compound Number | ERYSGT in vivo 1 Day Protectant | LEPTNO in vivo 1 Day Protectant | PHYTIN in vivo 1 Day Protectant | PLASVI in vivo 1 Day Protectant | PUCCRT in vivo 1 Day Protectant | SEPTTR in vivo 1 Day Protectant | LEPTNO in vitro Growth Inhibition | PHYTIN in vitro Growth Inhibition | PYRIOR in vitro Growth Inhibition | RHIZSO in vitro Growth Inhibition | SEPTTR in vitro Growth Inhibition | USTIMA in vitro Growth Inhibition |
|---|---|---|---|---|---|---|---|---|---|---|---|---|
| 378 | − | + | − | − | − | − | − | − | − | − | − | − |
| 379 | + | + | − | + | + | + | − | − | − | − | − | − |
| 380 | + | + | − | + | − | − | − | − | − | − | − | − |
| 381 | − | − | − | − | + | − | + | − | − | − | + | − |
| 382 | − | ++ | − | − | + | + | − | − | − | − | + | − |
| 383 | − | − | − | + | + | − | − | − | − | − | − | − |
| 384 | ++ | ++ | − | − | + | + | + | − | + | − | + | − |
| 385 | − | ++ | + | − | + | + | + | − | − | − | + | − |
| 386 | + | ++ | − | ++ | + | + | + | − | − | − | + | − |
| 387 | + | ++ | − | − | + | + | + | − | + | + | + | + |
| 388 | − | ++ | − | − | + | + | + | − | − | − | + | − |
| 389 | − | ++ | − | − | + | + | + | − | + | − | + | − |
| 390 | − | ++ | − | − | + | + | + | − | − | − | + | − |
| 391 | − | ++ | − | − | + | + | + | − | + | − | + | + |
| 392 | + | ++ | − | − | + | + | + | − | + | − | + | − |
| 393 | − | + | − | − | + | + | + | − | + | − | + | + |
| 394 | − | ++ | − | − | + | + | + | − | − | − | + | − |
| 395 | − | + | − | − | + | + | + | − | − | − | + | + |
| 396 | − | + | − | − | + | + | + | − | + | − | + | − |
| 397 | − | + | − | − | + | + | − | − | − | − | − | − |
| 398 | − | − | − | − | + | − | + | − | + | − | + | − |
| 399 | − | ++ | − | − | + | + | − | − | − | − | − | − |
| 400 | + | ++ | − | + | + | + | − | − | + | − | − | − |
| 401 | − | ++ | − | − | + | + | + | − | + | − | + | + |
| 402 | ++ | ++ | − | + | + | + | + | − | − | − | − | − |
| 403 | − | ++ | − | − | + | + | + | − | − | − | + | − |
| 404 | + | + | − | + | + | + | − | − | − | − | − | + |
| 405 | − | + | − | − | − | − | + | − | − | − | − | − |
| 406 | + | + | − | − | − | + | − | − | − | − | − | − |
| 407 | − | + | − | − | − | + | − | − | − | − | + | − |
| 408 | + | + | − | + | − | + | + | − | − | − | − | − |
| 409 | + | ++ | + | − | + | + | + | + | + | − | + | − |
| 410 | − | + | − | − | − | − | − | − | − | − | − | − |
| 411 | − | − | − | − | − | − | + | − | − | − | + | − |
| 412 | − | − | − | − | + | − | + | − | + | − | + | − |
| 413 | − | − | + | + | + | − | + | − | + | − | + | − |
| 414 | − | − | + | − | + | − | + | − | + | − | + | − |
| 415 | + | − | − | − | + | − | − | − | − | − | + | − |
| 416 | − | − | − | − | + | − | − | − | + | − | + | − |
| 417 | − | ++ | − | − | − | − | − | − | + | − | + | − |
| 418 | − | − | − | − | + | − | − | − | − | − | − | − |
| 419 | − | − | + | − | − | − | − | − | − | − | − | − |
| 420 | − | + | − | − | − | − | − | − | − | − | − | − |
| 421 | − | + | − | − | − | − | − | − | − | − | − | − |
| 422 | − | − | + | − | − | − | − | − | + | − | − | − |
| 423 | − | + | − | − | + | + | − | − | + | − | − | − |
| 424 | + | + | + | + | + | + | + | − | − | − | − | − |
| 425 | − | − | + | − | + | + | + | − | + | + | + | − |
| 426 | + | − | + | + | + | + | + | + | + | + | + | + |
| 427 | − | + | − | + | + | + | − | − | − | − | − | − |
| 428 | − | − | − | − | − | − | − | − | + | − | + | − |
| 429 | − | − | − | − | − | − | − | − | − | − | + | − |
| 430 | − | − | + | − | − | − | − | − | − | − | − | − |
| 431 | − | − | − | − | − | + | + | − | − | − | + | − |
| 432 | − | + | − | − | + | − | + | − | − | − | + | − |
| 433 | − | − | − | − | − | − | − | − | − | − | + | − |
| 434 | + | + | − | − | − | − | + | − | − | − | + | − |
| 435 | − | + | − | − | − | − | − | − | − | − | + | − |
| 436 | − | + | − | − | − | + | − | − | − | − | − | − |
| 437 | − | − | + | − | − | − | − | − | − | − | + | − |
| 438 | − | − | − | − | − | − | + | − | + | − | + | − |
| 439 | − | + | − | − | + | − | − | − | − | − | − | − |
| 440 | − | ++ | − | − | + | + | + | − | + | − | + | − |
| 441 | − | − | − | − | − | − | − | − | − | − | + | − |
| 442 | − | − | + | − | + | − | + | − | + | − | + | − |
| 443 | − | − | − | + | + | − | + | − | − | − | − | − |
| 444 | − | + | − | + | + | + | − | − | − | − | − | − |
| 445 | + | ++ | − | − | + | + | − | − | + | − | + | + |
| 446 | − | − | + | − | − | − | − | − | − | − | − | − |
| 447 | − | + | − | + | − | − | − | − | − | − | − | − |
| 448 | − | ++ | − | − | + | + | − | − | − | − | − | + |
| 449 | − | + | − | − | − | + | − | − | + | + | − | − |

TABLE 2-continued

| Compound Number | ERYSGT in vivo 1 Day Protectant | LEPTNO in vivo 1 Day Protectant | PHYTIN in vivo 1 Day Protectant | PLASVI in vivo 1 Day Protectant | PUCCRT in vivo 1 Day Protectant | SEPTTR in vivo 1 Day Protectant | LEPTNO in vitro Growth Inhibition | PHYTIN in vitro Growth Inhibition | PYRIOR in vitro Growth Inhibition | RHIZSO in vitro Growth Inhibition | SEPTTR in vitro Growth Inhibition | USTIMA in vitro Growth Inhibition |
|---|---|---|---|---|---|---|---|---|---|---|---|---|
| 450 | − | + | − | − | − | + | − | − | − | − | − | − |
| 451 | − | + | − | − | + | − | − | − | + | − | − | − |
| 452 | − | + | − | − | − | + | − | − | − | − | − | − |
| 453 | − | + | − | − | − | + | − | − | − | − | − | − |
| 454 | − | + | − | − | − | + | − | − | − | − | − | − |
| 455 | − | + | − | + | − | + | + | − | − | − | − | + |
| 456 | − | − | − | + | − | + | + | − | − | − | + | − |
| 457 | − | − | − | − | − | + | + | − | − | − | − | − |
| 458 | − | ++ | − | − | + | − | + | − | − | − | − | − |
| 459 | + | ++ | − | − | − | + | + | − | − | − | − | − |
| 460 | + | + | − | − | + | + | − | − | − | − | − | − |
| 461 | − | + | − | − | + | + | − | − | − | − | − | − |
| 462 | − | + | − | − | + | + | − | − | + | − | + | − |
| 463 | − | − | − | − | − | + | − | − | − | − | − | − |
| 464 | − | + | − | − | − | + | − | − | − | − | − | − |
| 465 | − | + | − | − | − | + | − | − | + | − | − | − |
| 466 | − | + | − | − | − | + | + | − | − | − | − | − |
| 467 | + | + | − | − | − | + | + | − | − | − | − | − |
| 468 | − | − | − | − | − | + | − | − | − | − | − | − |
| 469 | − | + | − | − | ++ | + | + | − | + | − | − | − |
| 470 | + | + | − | − | + | + | + | − | + | + | + | − |
| 471 | − | + | − | − | + | + | + | − | − | − | − | − |
| 472 | − | + | − | − | + | + | − | − | + | − | − | − |
| 473 | − | ++ | − | − | + | + | | | | | | |
| 474 | − | + | − | − | + | − | − | − | − | − | − | − |
| 475 | − | ++ | − | − | + | + | + | − | + | − | + | − |
| 476 | − | + | − | − | − | − | − | − | − | − | − | − |
| 477 | − | + | − | − | − | + | − | − | − | − | − | − |
| 478 | − | + | − | + | + | + | − | − | − | − | − | − |
| 479 | − | + | − | − | − | + | − | − | − | − | − | − |
| 480 | − | + | − | − | − | − | − | − | + | − | − | − |
| 481 | − | + | − | − | − | + | − | − | − | − | − | − |
| 482 | − | + | − | − | − | + | − | − | − | − | − | − |
| 483 | − | − | − | − | − | − | + | − | − | − | − | − |
| 484 | − | − | − | − | − | − | − | − | − | − | − | − |
| 485 | − | − | − | + | − | − | − | − | − | − | − | − |
| 486 | − | − | − | − | − | − | − | − | + | − | − | − |
| 487 | − | − | − | − | + | − | − | − | + | − | − | − |
| 488 | − | − | − | + | + | + | − | − | + | − | − | − |
| 489 | − | − | − | − | + | − | − | − | − | − | − | − |
| 490 | − | − | − | + | + | + | − | − | − | − | − | − |
| 491 | − | − | − | + | − | − | − | + | − | − | − | − |
| 492 | − | − | − | − | − | + | − | − | − | − | − | − |
| 493 | − | − | − | − | − | + | − | − | − | − | − | − |
| 494 | − | − | − | − | − | + | − | − | − | − | − | − |
| 495 | + | − | − | − | + | + | − | − | − | − | − | − |
| 496 | − | − | − | − | + | + | − | − | − | − | − | − |
| 497 | − | + | − | − | + | + | − | − | − | − | − | − |
| 498 | − | − | − | − | + | + | − | − | − | − | − | − |
| 499 | − | + | − | + | + | − | − | − | − | − | − | − |
| 500 | − | − | − | − | − | + | − | − | − | − | − | − |
| 501 | − | + | − | − | + | − | + | − | + | − | + | + |
| 502 | − | + | − | + | + | + | − | − | − | − | − | − |
| 503 | + | + | − | + | + | − | + | − | − | − | + | − |
| 504 | − | + | − | − | − | − | + | − | − | − | − | − |
| 505 | − | − | − | + | − | − | − | − | − | − | − | − |
| 506 | − | − | − | + | − | − | − | − | − | − | − | − |
| 507 | − | − | − | + | − | − | − | − | − | − | − | − |
| 508 | − | − | − | + | − | − | − | − | − | − | − | − |
| 509 | − | − | − | + | − | − | − | − | − | − | − | − |
| 510 | − | − | + | − | − | − | − | − | − | − | − | − |
| 511 | − | − | − | + | − | − | − | − | − | − | − | − |
| 512 | − | − | + | + | − | − | − | − | − | − | − | − |
| 513 | − | ++ | − | + | + | − | | | | | | |
| 514 | − | + | − | − | − | − | − | − | − | − | − | − |
| 515 | − | − | − | + | − | + | − | − | − | − | − | − |
| 516 | − | − | − | + | − | − | − | − | − | − | − | − |
| 517 | − | + | − | + | − | − | − | − | − | − | − | − |
| 518 | − | − | + | + | − | − | − | − | − | − | − | − |
| 519 | − | + | − | − | − | − | − | − | − | − | − | − |
| 520 | − | + | − | − | − | − | − | − | − | − | − | − |
| 521 | − | + | + | − | − | − | − | − | − | − | − | − |

TABLE 2-continued

| Compound Number | ERYSGT in vivo 1 Day Protectant | LEPTNO in vivo 1 Day Protectant | PHYTIN in vivo 1 Day Protectant | PLASVI in vivo 1 Day Protectant | PUCCRT in vivo 1 Day Protectant | SEPTTR in vivo 1 Day Protectant | LEPTNO in vitro Growth Inhibition | PHYTIN in vitro Growth Inhibition | PYRIOR in vitro Growth Inhibition | RHIZSO in vitro Growth Inhibition | SEPTTR in vitro Growth Inhibition | USTIMA in vitro Growth Inhibition |
|---|---|---|---|---|---|---|---|---|---|---|---|---|
| 522 | − | ++ | − | − | − | − | − | − | − | − | − | − |
| 523 | + | ++ | + | + | + | + | − | − | − | − | − | − |
| 524 | − | − | − | − | − | + | − | − | − | − | − | − |
| 525 | − | ++ | − | − | + | + | − | − | − | − | − | − |
| 526 | − | + | − | − | − | + | − | − | − | − | − | − |
| 527 | − | − | − | + | + | + | − | − | − | − | − | − |
| 528 | − | − | − | − | − | + | − | − | − | − | − | − |
| 529 | − | + | − | − | + | + | − | − | − | − | − | − |
| 530 | − | + | − | − | + | + | − | − | − | − | − | − |
| 531 | + | + | − | − | − | + | − | − | − | − | − | − |
| 532 | + | + | + | + | + | + | − | − | − | − | − | − |
| 533 | − | + | + | + | + | + | − | − | − | − | − | − |
| 534 | − | ++ | − | ++ | + | + | + | + | + | − | + | − |
| 535 | − | + | − | + | + | + | − | − | − | + | − | − |
| 536 | − | ++ | − | − | + | + | − | − | − | − | + | − |
| 537 | − | ++ | − | + | + | + | − | − | − | − | − | − |
| 538 | − | + | − | + | + | + | − | − | − | − | − | − |
| 539 | − | + | − | − | + | + | − | − | − | − | + | − |
| 540 | − | − | − | − | − | + | − | − | − | − | − | − |
| 541 | − | − | − | − | − | + | − | − | − | − | − | − |
| 542 | − | − | − | − | − | + | − | − | − | − | − | − |
| 543 | − | + | − | − | − | − | − | − | − | − | − | − |
| 544 | − | + | − | − | + | + | − | − | − | − | − | − |
| 545 | − | + | + | + | + | + | − | + | − | − | − | − |
| 546 | − | + | − | + | + | + | − | + | − | − | − | − |
| 547 | − | − | + | + | + | + | − | + | − | − | − | − |
| 548 | − | + | + | + | − | + | − | − | − | − | − | − |
| 549 | − | + | − | + | − | + | − | + | − | − | + | − |
| 550 | + | ++ | − | ++ | + | + | + | + | + | − | + | − |
| 551 | + | + | − | − | − | + | − | − | − | − | − | − |
| 552 | + | − | + | ++ | − | − | + | + | + | + | + | − |
| 553 | + | ++ | ++ | ++ | + | + | + | + | + | + | + | + |
| 554 | − | + | − | − | + | + | + | + | + | − | − | − |
| 555 | − | + | − | − | − | + | + | + | + | + | + | − |
| 556 | − | + | − | − | + | − | − | + | − | − | − | − |
| 557 | − | + | − | ++ | + | + | − | + | − | − | − | − |
| 558 | − | + | − | ++ | + | + | − | − | − | − | − | − |
| 559 | − | + | − | − | + | − | − | − | − | − | − | − |
| 560 | − | + | − | + | + | + | − | − | − | − | − | − |
| 561 | + | − | − | + | + | + | − | − | − | − | − | − |
| 562 | + | − | − | − | − | + | − | − | − | − | − | − |
| 563 | − | + | − | − | − | − | − | − | − | − | − | − |

The compounds of this invention are preferably applied in the form of a composition comprising one or more of the compounds of Formula I with a phytologically-acceptable carrier. The compositions are either concentrated formulations which are dispersed in water or another liquid for application, or are dust or granular formulations which are applied without further treatment. The compositions are prepared according to procedures which are conventional in the agricultural chemical art, but which are novel and important because of the presence therein of the compounds of this invention. Some description of the formulation of the compositions is given to assure that agricultural chemists can readily prepare desired compositions.

The dispersions in which the compounds are applied are most often aqueous suspensions or emulsions prepared from concentrated formulations of the compounds. Such water-soluble, water suspendable, or emulsifiable formulations are either solids, usually known as wettable powders, or liquids, usually known as emulsifiable concentrates, or aqueous suspensions. The present invention contemplates all vehicles by which the compounds of this invention can be formulated for delivery for use as a fungicide. As will be readily appreciated, any material to which these compounds can be added may be used, provided they yield the desired utility without significant interference with activity of the compounds of this invention as antifungal agents.

Wettable powders, which may be compacted to form water dispersible granules, comprise an intimate mixture of the active compound, an inert carrier, and surfactants. The concentration of the active compound is usually from about 10% to about 90% w/w, more preferably about 25% to about 75% w/w. In the preparation of wettable powder compositions, the toxicant products can be compounded with any of the finely divided solids, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier is ground or mixed with the toxicant in a volatile organic solvent. Effective surfactants, comprising from about 0.5% to about 10% of the wettable powder, include sulfonated lignins, naphthalenesulfonates, alkylbenzenesulfonates, alkyl sulfates, and non-ionic surfactants such as ethylene oxide adducts of alkyl phenols.

Emulsifiable concentrates of the compounds of this invention comprise a convenient concentration, such as from about 10% to about 50% w/w, in a suitable liquid. The compounds are dissolved in an inert carrier, which is either a water miscible solvent or a mixture of water-immiscible organic solvents and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used such as, for example, terpenic solvents including rosin derivatives, aliphatic ketones, such as cyclohexanone, and complex alcohols such as 2-ethoxyethanol.

Emulsifiers which can be advantageously employed herein can be readily determined by those skilled in the art and include various nonionic, anionic, cationic, and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines, or fatty acids with ethylene oxide, propylene oxides such as the ethoxylated alkyl phenols, and carboxylic esters solubilized with polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts of sulphated polyglycol ethers, and appropriate salts of phosphated polyglycol ether.

Representative organic liquids which can be employed in preparing the emulsifiable concentrates of the present invention are the aromatic liquids such as xylene, propyl benzene fractions or mixed naphthalene fractions, mineral oils, substituted aromatic organic liquids such as dioctyl phthalate, kerosene, and dialkyl amides of various fatty acids; particularly the dimethyl amides of fatty glycols and glycol derivatives such as the n-butyl ether, ethyl ether, or methyl ether of diethylene glycol, and the methyl ether of triethylene glycol. Mixtures of two or more organic liquids are also often suitably employed in the preparation of the emulsifiable concentrate. The preferred organic liquids are xylene and propyl benzene fractions, with xylene being most preferred. The surface active dispersing agents are usually employed in liquid compositions and in the amount of from 0.1 to 20 percent by weight of the combined weight of the dispersing agent and active compound. The active compositions can also contain other compatible additives, for example, plant growth regulators and other biologically active compounds used in agriculture.

Aqueous suspensions comprise suspensions of water-insoluble compounds of this invention, dispersed in an aqueous vehicle at a concentration in the range from about 5% to about 50% w/w. Suspensions are prepared by finely grinding the compound and vigorously mixing it into a vehicle comprised of water and surfactants chosen from the same types above discussed. Inert ingredients, such as inorganic salts and synthetic or natural gums, may also be added to increase the density and viscosity of the aqueous vehicle. It is often most effective to grind and mix the compound at the same time by preparing the aqueous mixture and homogenizing it in an implement such as a sand mill, ball mill, or piston-type homogenizer.

The compounds may also be applied as granular compositions which are particularly useful for applications to the soil. Granular compositions usually contain from about 0.5% to about 10% w/w of the compound dispersed in an inert carrier which consists entirely or in large part of coarsely divided attapulgite, bentonite, diatomite, clay, or a similar inexpensive substance. Such compositions are usually prepared by dissolving the compound in a suitable solvent and applying it to a granular carrier which has been preformed to the appropriate particle size, in the range of from about 0.5 to about 3 mm. Such compositions may also be formulated by making a dough or paste of the carrier and compound, and crushing, and drying to obtain the desired granular particle Dusts containing the compounds are prepared simply by intimately mixing the compound in powdered form with a suitable dusty agricultural carrier such as, for example, kaolin clay, ground volcanic rock, and the like. Dusts can suitably contain from about 1% to about 10% w/w of the compound.

The active compositions may contain adjuvant surfactants to enhance deposition, wetting, and penetration of the compositions onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5 percent. Suitable adjuvant surfactants include ethoxylated nonyl phenols, ethoxylated synthetic or natural alcohols, salts of the esters of sulphosuccinic acids, ethoxylated organosilicones, ethoxylated fatty amines, and blends of surfactants with mineral or vegetable oils.

The composition may optionally include fungicidal combinations which comprise at least 1% of one or more of the compounds of this invention with another pesticidal compound. Such additional pesticidal compounds may be fungicides, insecticides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds in combination can generally be present in a ratio of from 1:100 to 100:1

The present invention includes within its scope methods for the control or prevention of fungal attack. These methods comprise applying to the locus of the fungus, or to a locus in which the infestation is to be prevented (for example applying to cereal or grape plants), a fungicidal amount of one or more of the compounds of this invention or compositions. The compounds are suitable for treatment of various plants at fungicidal levels while exhibiting low phytotoxicity. The compounds are useful in a protectant or eradicant fashion. The compounds of this invention are applied by any of a variety of known techniques, either as the compounds or as compositions including the compounds. For example, the compounds may be applied to the roots, seeds, or foliage of plants for the control of various fungi without damaging the commercial value of the plants. The materials are applied in the form of any of the generally used formulation types, for example, as solutions, dusts, wettable powders, flowable concentrates, or emulsifiable concentrates. These materials are conveniently applied in various known fashions.

The compounds of this invention have been found to have significant fungicidal effect, particularly for agricultural use. Many of the compounds are particularly effective for use with agricultural crops and horticultural plants, or with wood, paint, leather, or carpet backing.

In particular, the compounds effectively control a variety of undesirable fungi which infect useful plant crops. Activity has been demonstrated for a variety of fungi, including, for example, the following representative fungi species: Downy Mildew of Grape (*Plasmopara viticola*—PLASVI), Late Blight of Tomato (*Phytophthora infestans*—PHYTIN), Apple Scab (*Venturia inaequalis*—VENTIN), Brown Rust of Wheat (*Puccinia recondita*—PUCCRT), Stripe Rust of Wheat (*Puccinia striiformis*—PUCCST), Rice Blast (*Pyricularia oryzae*—PYRIOR), Cercospora Leaf Spot of Beet (*Cercospora beticola*—CERCBE), Powdery Mildew of Wheat (*Ezysiphe graminis*—ERYSGT), Leaf Blotch of Wheat (*Septoria tritici*—SEPTTR), Sheath Blight of Rice (*Rhizoctonia solani*—RHIZSO), Eyespot of Wheat (*Pseudocercosporella herpotrichoides*—PSDCHE), Brown Rot of Peach (*Monilinia fructicola*—MONIFC), and Glume Blotch of Wheat (*Leptosphaeria nodorum*—LEPTNO). It will be understood by those in the art that the efficacy of the compounds of this invention for the foregoing fungi establishes the general utility of the compounds as fungicides.

The compounds of this invention have broad ranges of efficacy as fungicides. The exact amount of the active material to be applied is dependent not only on the specific active material being applied, but also on the particular action desired, the fungal species to be controlled, and the stage of growth thereof, as well as the part of the plant or other product to be contacted with the toxic active ingredient. Thus, all the active ingredients of the compounds of this invention and compositions containing the same, may not be equally effective at similar concentrations or against the same fungal species. The compounds of this invention and compositions are effective in use with plants in a disease inhibiting and phytologically acceptable amount.

What is claimed is:

1. A compound of Formula I:

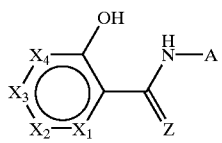

Formula I wherein:

(a)

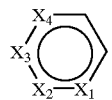

represents a 5- or 6-membered heterocyclic aromatic ring in which
(i) each of $X_1$–$X_4$ is independently O, S, NR', N, CR" or a bond;
(ii) no more than one of $X_1$–$X_4$ is O, S or NR';
(iii) no more than one of $X_1$–$X_4$ is a bond;
(iv) when any one of $X_1$–$X_4$ is S, O or NR', one of the adjacent $X_1$–$X_4$ must represent a bond; and
(v) at least one of $X_1$–$X_4$ must be O, S, NR' or N;
wherein
R' is H, $C_1$–$C_3$ alkyl, $C_2$–$C_3$ alkenyl, $C_2$–$C_3$ alkynyl, hydroxy, acyloxy, $C_1$–$C_6$ alkoxymethyl, $CHF_2$, cyclopropyl or $C_1$–$C_4$ alkoxy; and,
R" is independently H, halogen, cyano, hydroxy, $C_1$–$C_3$ alkyl, $C_1$–$C_3$ haloalkyl, cyclopropyl, $C_1$–$C_3$ alkoxy, $C_1$–$C_3$ haloalkoxy, $C_1$–$C_3$ alkylthio, aryl, $C_1$–$C_3$ NHC(O)alkyl, NHC(O)H, $C_1$–$C_3$ haloalkylthio, $C_2$–$C_4$ alkenyl, $C_2$–$C_4$ haloalkenyl, $C_2$–$C_4$ alkynyl, $C_2$–$C_4$ haloalkynyl or nitro wherein adjacent R" substituents may form a ring or adjacent R' and R" substituents may form a ring;

(b) Z is O, S or $NOR_Z$ in which $R_Z$ is H or $C_1$–$C_3$ alkyl; and
(c) A represents

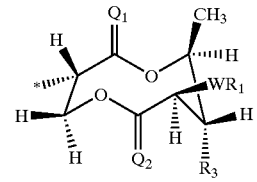

where * = point of attachment in which
$Q_1$, $Q_2$ are O or S;
W is O, $CH_2$, $CHR_6$, or a bond;
$R_1$ is $C_1$–$C_8$ alkyl, $C_2$–$C_8$ alkenyl, $C_2$–$C_8$ alkynyl, $C_3$–$C_8$ cycloalkyl, aryl or heteroaryl;
$R_3$ is H, $R_1$, $OR_1$, $OC(O)OR_1$ or $OC(O)NR_1R_6$;
$R_6$ is independently $C_1$–$C_6$ alkyl, $C_3$–$C_6$ cycloalkyl, $C_2$–$C_5$ alkenyl or $C_2$–$C_5$ alkynyl.

2. A compound according to claim 1 wherein

is selected from the group consisting of pyridine, pyridazine, pyrimidine, pyrazine, pyrrole, pyrazole, imidazole, furan, thiophene, oxazole, isoxazole, thiazole, isothiazole, and thiadiazole.

3. A compound according to claim 2 wherein

is selected from the group consisting of pyridine, pyridazine, pyrimidine, pyrazine, pyrazole, oxazole, isothiazole, thiazole and thiadiazole.

4. A compound according to claim 1 in which Z is O.
5. A compound according to claim 1 in which $X_1$ is N, $X_2$ and $X_3$ are CH and $X_4$ is CH, or COMe, CMe, CCl, COEt, or CSMe.
6. A compound according to claim 5 in which Z is O.
7. A compound according to claim 1 in which $X_1$ is N, $X_2$ is CR", $X_3$ is N, and $X_4$ is CR".
8. A compound according to claim 1 in which $X_1$ is N, $X_2$ is CR", $X_3$ is CR", and $X_4$ is N.
9. A compound according to claim 1 in which $X_1$ is N, $X_2$ is N, $X_3$ is CR", and $X_4$ is CR".
10. A compound according to claim 1 in which $X_1$ is N, $X_2$ is CR", $X_3$ is O, and $X_4$ is a bond.
11. A compound according to claim 1 in which $X_1$ is N, $X_2$ is CR", $X_3$ is S, and $X_4$ is a bond.
12. A compound according to claim 1 in which $X_1$ is N, $X_2$ is NR', $X_3$ is CR", and $X_4$ is a bond.
13. A compound according to claim 1 in which $X_1$ is CR", $X_2$ is CR", $X_3$ is N, and $X_4$ is CR".
14. A compound according to claim 1 in which $X_1$ is N, $X_2$ is S, $X_3$ is a bond, and $X_4$ is CR".
15. A fungicidal composition comprising at least one of compounds according to claim 1 and a phytologically acceptable carrier.

16. A composition according to claim 15 which further comprises at least one other compound selected from the group consisting of insecticides, fungicides, herbicides, nematocides, miticides, arthropodocides, bactericides, and combinations thereof.

17. A method for the control, or prevention of, fungal infestation, wherein said method comprises applying to the locus of the fungus, or the locus in which the infestation is to be controlled, or prevented, a fungicidally effective amount of a compound according to claim 1.

18. A compound of Formula I:

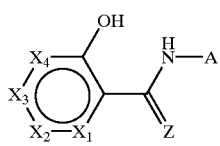

Formula I wherein:
(a)

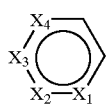

represents a 5- or 6-membered heterocyclic aromatic ring in which
(i) each of $X_1$–$X_4$ is independently O, S, NR', N, CR" or a bond;
(ii) no more than one of $X_1$–$X_4$ is O, S or NR';
(iii) no more than one of $X_1$–$X_4$ is a bond;
(iv) when any one of $X_1$–$X_4$ is S, O or NR', one of the adjacent $X_1$–$X_4$ must represent a bond; and
(v) at least one of $X_1$–$X_4$ must be O, S, NR' or N; wherein
R' is H, $C_1$–$C_3$ alkyl, $C_2$–$C_3$ alkenyl, $C_2$–$C_3$ alkynyl, hydroxy, acyloxy, $C_1$–$C_6$ alkoxymethyl, $CHF_2$, cyclopropyl or $C_1$–$C_4$ alkoxy; and,
R" is independently H, halogen, cyano, hydroxy, $C_1$–$C_3$ alkyl, $C_1$–$C_3$ haloalkyl, cyclopropyl, $C_1$–$C_3$ alkoxy, $C_1$–$C_3$ haloalkoxy, $C_1$–$C_3$ alkylthio, aryl, $C_1$–$C_3$ NHC(O)alkyl, NHC(O)H, $C_1$–$C_3$ haloalkylthio, $C_2$–$C_4$ alkenyl, $C_2$–$C_4$ haloalkenyl, $C_2$–$C_4$ alkynyl, $C_2$–$C_4$ haloalkynyl or nitro wherein adjacent R" substituents may form a ring or adjacent R' and R" substituents may form a ring;
(b) Z is O, S or $NOR_Z$ in which $R_Z$ is H or $C_1$–$C_3$ alkyl; and
(c) A represents

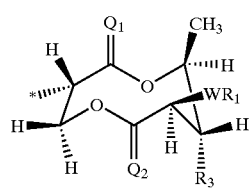

where *=point of attachment
in which
$Q_1$, $Q_2$ are O or S;

W is O, $CH_2$, $CHR_6$, or a bond;
$R_1$ is $C_2$–$C_8$ alkynyl, $C_3$–$C_8$ cycloalkyl, aryl or heteroaryl;
$R_3$ is $OC(O)R_1$;
$R_6$ is independently $C_1$–$C_6$ alkyl, $C_3$–$C_6$ cycloalkyl, $C_2$–$C_6$ alkenyl or $C_2$–$C_5$ alkynyl.

19. A compound according to claim 18 wherein

is selected from the group consisting of pyridine, pyridazine, pyrimidine, pyrazine, pyrrole, pyrazole, imidazole, furan, thiophene, oxazole, isoxazole, thiazole, isothiazole, and thiadiazole.

20. A compound according to claim 19 wherein

is selected from the group consisting of pyridine, pyridazine, pyrimidine, pyrazine, pyrazole, oxazole, isothiazole, thiazole and thiadiazole.

21. A compound according to claim 18 in which Z is O.

22. A compound according to claim 18 in which $X_1$ is N, $X_2$ and $X_3$ are CH and $X_4$ is CH, or COMe, CMe, CCl, COEt, or CSMe.

23. A compound according to claim 22 in which Z is O.

24. A compound according to claim 18 in which $X_1$ is N, $X_2$ is CR", $X_3$ is N, and $X_4$ is CR".

25. A compound according to claim 18 in which $X_1$ is N, $X_2$ is CR", $X_3$ is CR", and $X_4$ is N.

26. A compound according to claim 18 in which $X_1$ is N, $X_2$ is N, $X_3$ is CR", and $X_4$ is CR".

27. A compound according to claim 18 in which $X_1$ is N, $X_2$ is CR", X is O, and $X_4$ is a bond.

28. A compound according to claim 18 in which $X_1$ is N, $X_2$ is CR", $X_3$ is S, and $X_4$ is a bond.

29. A compound according to claim 18 in which $X_1$ is N, $X_2$ is NR', $X_3$ is CR", and $X_4$ is a bond.

30. A compound according to claim 18 in which $X_1$ is CR", $X_2$ is CR", $X_3$ is N, and $X_4$ is CR".

31. A compound according to claim 18 in which $X_1$ is N, $X_2$ is S, $X_3$ is a bond, and $X_4$ is CR".

32. A fungicidal composition comprising at least one of compounds according to claim 18 and a phytologically acceptable carrier.

33. A composition according to claim 32 which further comprises at least one other compound selected from the group consisting of insecticides, fungicides, herbicides, nematocides, miticides, arthropodocides, bactericides, and combinations thereof.

34. A method for the control, or prevention of, fungal infestation, wherein said method comprises applying to the locus of the fungus, or the locus in which the infestation is to be controlled, or prevented, a fungicidally effective amount of a compound according to claim 18.

* * * * *

UNITED STATES PATENT AND TRADEMARK OFFICE
CERTIFICATE OF CORRECTION

PATENT NO.    : 6,521,622 B1
DATED         : February 18, 2003
INVENTOR(S)   : Michael J. Ricks et al.

It is certified that error appears in the above-identified patent and that said Letters Patent is hereby corrected as shown below:

Column 206,
Line 6, should read -- $C_2$-$C_5$ alkenyl or $C_2$-$C_5$ alkynyl. -- rather than "$C_2$-$C_6$ alkenyl or $C_2$-$C_5$ alkynyl."
Line 41, should read -- $X_2$ is CR", $X_3$ is O, and $X_4$ is a bond. -- rather than "$X_2$ is CR", X is O, and $X_4$ is a bond."

Signed and Sealed this

Twenty-second Day of April, 2003

JAMES E. ROGAN
*Director of the United States Patent and Trademark Office*